United States Patent
Briner et al.

(10) Patent No.: US 7,186,715 B2
(45) Date of Patent: Mar. 6, 2007

(54) PIPERAZINE- AND PIPERIDINE-DERIVATIVES AS MELANOCORTIN RECEPTOR AGONISTS

(75) Inventors: Karin Briner, Indianapolis, IN (US); Christopher William Doecke, Indianapolis, IN (US); Vincent Mancuso, Thy-le Chateau (BE); Michael John Martinelli, Zionsville, IN (US); Timothy Ivo Richardson, Indianapolis, IN (US); Roger Ryan Rothhaar, Reelsville, IN (US); Qing Shi, Carmel, IN (US); Chaoyu Xie, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 315 days.

(21) Appl. No.: 10/466,248

(22) PCT Filed: Jan. 23, 2002

(86) PCT No.: PCT/US01/00515

§ 371 (c)(1),
(2), (4) Date: Jul. 11, 2003

(87) PCT Pub. No.: WO02/059107

PCT Pub. Date: Aug. 1, 2002

(65) Prior Publication Data

US 2004/0082590 A1    Apr. 29, 2004

Related U.S. Application Data

(60) Provisional application No. 60/263,471, filed on Jan. 23, 2001.

(51) Int. Cl.
| A61K 31/496 | (2006.01) |
| C07D 401/12 | (2006.01) |
| C07D 401/14 | (2006.01) |
| C07D 403/12 | (2006.01) |
| C07D 403/14 | (2006.01) |

(52) U.S. Cl. .................... 514/233.5; 514/252.11; 514/253.05; 514/254.09; 514/218; 544/121; 544/357; 544/363; 544/373; 540/575

(58) Field of Classification Search ............... 544/363, 544/373, 357, 121; 514/252.11, 233.5, 253.05, 514/254.09
See application file for complete search history.

(56) References Cited

U.S. PATENT DOCUMENTS 6,294,534 B1    9/2001 Nargund et al.

FOREIGN PATENT DOCUMENTS

| WO | WO 94 13696 A | 6/1994 |
| WO | WO 99 55679 A | 11/1999 |
| WO | WO 99 64002 A | 12/1999 |
| WO | WO 00 74679 A | 12/2000 |
| WO | WO 01 70337 A | 9/2001 |
| WO | WO 01 70708 A | 9/2001 |
| WO | WO 02 15909 A | 2/2002 |
| WO | WO 02 059095 | 8/2002 |
| WO | WO 02 059107 | 8/2002 |
| WO | WO 02 059108 | 8/2002 |
| WO | WO 02 070511 | 9/2002 |

OTHER PUBLICATIONS

Sebhat et al. Annual Reports in Medicinal Chemistry, vol. 38, p. 31-40 (2003).*
Campfield et al. Science, vol. 280, p. 1383-1387 (1998).*

* cited by examiner

*Primary Examiner*—Emily Bernhardt
(74) *Attorney, Agent, or Firm*—Soonhee Jang; James B. Myers

(57) ABSTRACT

The present invention relates to melanocortin receptor agonists of formula I, which is useful in the treatment of obesity, diabetes and male and/or female sexual dysfunction (I)

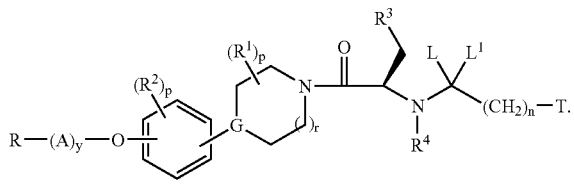

42 Claims, No Drawings

PIPERAZINE- AND PIPERIDINE-DERIVATIVES AS MELANOCORTIN RECEPTOR AGONISTS

REFERENCE TO RELATED APPLICATION

This application is submitted as a United States national phase entry, pursuant to 35 U.S.C. §371, of PCT/US02/00515, filed on 23 Jan. 2002, which claims the benefit of U.S. provisional patent application Ser. No. 60/263,471, filed 23 Jan. 2001.

FIELD OF THE INVENTION

The present invention relates to melanocortin receptor agonists, and more particularly piperazine and piperidine derivatives as melanocortin receptor agonists, which are useful for the treatment or prevention of diseases and disorders responsive to the activation of melanocortin receptors.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are targets of POMC derived peptides involved in the control of food intake and metabolism.

Evidence for the involvement of MC-R in obesity includes: i) the agouti ($A^{vy}$) mouse which ectopically expresses an antagonist of the MC-1R, MC-3R and MC-4R is obese, indicating that blocking the action of these three MC-Rs can lead to hyperphagia and metabolic disorders; ii) MC-4R knockout mice (Huszar et al., *Cell*, 88:131–141, 1997) recapitulate the phenotype of the agouti mouse and these mice are obese; iii) the cyclic heptapeptide MC-1R, MC-3R, MC4R, and MC-5R agonist melanotanin-II (MT-II) injected intracerebroventricularly (ICV) in rodents, reduces food intake in several animal feeding models (NPY, ob/ob, agouti, fasted) while ICV injected SHU-9119 (MC-3R, MC-4R antagonist; MC-1R and MC-5R agonist) reverses this effect and can induce hyperphagia; and iv) chronic intraperitoneal treatment of Zucker fatty rats with an α-NDP-MSH derivative (HP228) has been reported to activate MC-1R, MC-3R, MC-4R and MC-5R and to attenuate food intake and body weight gain over a 12 week period.

Five MC-Rs have thus far been identified, and these are expressed in different tissues. MC-1R was initially characterized by dominant gain of function mutations at the extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. (A. Kask, et al., "Selective antagonist for the melanocortin-4-receptor (HS014) increases food intake in free-feeding rats, *Biochem. Biophys. Res. Commun.*, 245:90–93, 1998). MC-5R is expressed in many tissues including white fat, placenta and exocrine glands. A low level of expression is also observed in the brain. MC-5R knock out mice reveal reduced sebaceous gland lipid production (Chen et al., *Cell*, 91:789–798, 1997).

MC-4R appears to play role in other physiological functions as well, namely controlling grooming behavior, erection and blood pressure. Erectile dysfunction denotes the medical condition of inability to achieve penile erection sufficient for successful intercourse. The term "impotence" is often times employed to describe this prevalent condition. Synthetic melanocortin receptor agonists have been found to initiate erections in men with psychogenic erectile dysfunction (H. Wessells et al., "Synthetic Melanotropic Petide Initiates Erections in Men With Psychogenic Erectile Dysfunction: Double-Blind, Placebo Controlled Crossover Study," *J. Urol.*, 160: 389–393, 1998). Activation of melanocortin receptors of the brain appears to cause normal stimulation of sexual arousal. Evidence for the involvement of MC-R in male and/or female sexual dysfunction is detailed in WO 00/74670.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL is known as Syndrome X.

Spiropiperidine and piperidine derivates have been disclosed in U.S. Pat. No. 6,294,534 B1, WO 01/70337, WO 00/74679 and WO 01/70708 as agonists of melanocortin receptor(s), which can be used for the treatment of diseases and disorders, such as obesity, diabetes and sexual dysfunction.

In view of the unresolved deficiencies in treatment of various diseases and disorders as discussed above, it is an object of the present invention to provide novel piperazine derivatives, which are useful as melanocortin receptor agonists to treat obesity, diabetes, and male and female sexual dysfunction.

SUMMARY OF THE INVENTION

The present invention relates to a compound of novel piperazine or piperidine derivatives as melanocortin receptor agonists as shown formula I:

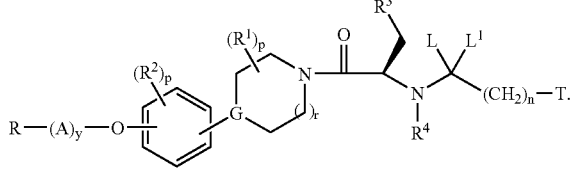

(I)

or a pharmaceutically acceptable salts or stereoisomers thereof, wherein
G is $CR^1$ or N;
A is $C_1$–$C_8$ alkyl or $C_3$–$C_7$ cycloalkyl;
L and $L^1$ are independently: hydrogen or together oxo;
T is:

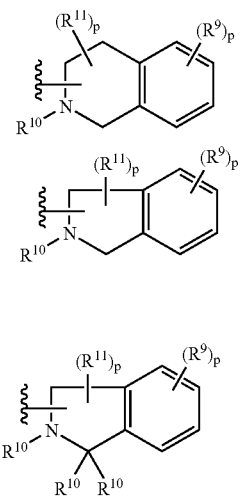

R is: when y is 1;
  $N(R^8)_2$,
  $NR^8COR^8$,
  $NR^8CON(R^8)_2$,
  $NR^8C(O)OR^8$,
  $NR^8C(R^8)=N(R^8)$,
  $NR^8SO_2R^8$ or
  $NR^8SO_2N(R^8)_2$;
R is: when y is 0 or 1;
  heterocyclyl, provided that when y is 0, a heteroatom is not directly connected to oxygen or adjacent to a carbon that connected to oxygen; and
  wherein the heterocyclyl contains at least one nitrogen in the ring and is optionally substituted with one to five substituents independently selected from $R^8$;
$R^1$ is independently:
  hydrogen, $CONH(C_1$–$C_8$ alkyl), $C_1$–$C_8$ alkyl, (D)phenyl, (D)$C_3$–$C_7$ cycloalkyl or oxo, provided that oxo is not attached to the same carbon that attached to nitrogen which forms an amide bond when G is N;
$R^2$ is independently:
  hydrogen,
  halo
  $C_1$–$C_8$ alkyl,
  $C_1$–$C_8$ alkylsulfonyl,
  (D)$C_3$–$C_7$ cycloalkyl or
  $C_1$–$C_4$ haloalkyl;

$R^3$ is independently: aryl or thienyl;
  wherein aryl and thienyl are optionally substituted with one to three substituents selected from the group consisting of:
  cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;
$R^4$ is independently:
  hydrogen, $C_1$–$C_8$ alkyl, $C(O)R^8$, $C(O)OR^8$, $C_3$–$C_7$ cycloalkyl or $(CH_2)_nO(C_1$–$C_8$ alkyl), wherein n is 2–8;
each $R^8$ is independently:
  hydrogen,
  phenyl
  $C_1$–$C_8$ alkyl,
  $C_1$–$C_8$ alkylsulfonyl,
  $C(O)C_1$–$C_8$ alkyl,
  C(O)aryl, wherein aryl being phenyl or naphthyl,
  $SO_2$-aryl, wherein aryl being phenyl or naphthyl,
  (D)$C_3$–$C_7$ cycloalkyl or
  $(CH_2)_nC_1$–$C_4$ haloalkyl, wherein n is 1–8;
each $R^9$ is independently:
  hydrogen,
  hydroxy,
  (D)cyano,
  halo,
  $C_1$–$C_8$ alkyl,
  $C_1$–$C_8$ alkoxy,
  $C_3$–$C_7$ cycloalkyl,
  $C_1$–$C_4$ haloalkyl,
  (D)heterocyclyl
  (D)$C(O)R^8$,
  (D)$C(O)(CH_2)_nN(R^8)_2$,
  $C_1$–$C_8$ alkyl-$N(R^8)_2$,
  (D))$OR^8$,
  (D)$OCOR^8$,
  (D)$OC(O)N(R^8)_2$,
  (D)$N(R^8)_2$,
  (D)$NR^8C(O)R^8$,
  (D)$NR^8C(O)OR^8$,
  (D)$NR^8C(O)N(R^8)_2$,
  (D)$NR^8SO_2R^8$,
  (D)$SR^8$,
  (D)$SOR^8$,
  (D)$SO_2R^8$, or
  (D)$SO_2N(R^8)_2$;
each $R^{10}$ is independently:
  hydrogen, $(C_1$–$C_8)$alkyl, $C(O)C_1$–$C_8$ alkyl, aryl or $C_3$–$C_7$ cycloalkyl;
each $R^{11}$ is independently:
  hydrogen,
  $C_1$–$C_8$ alkyl,
  (D)aryl,
  (D)heteroaryl
  $(CH_2)_nN(R^8)_2$,
  $(CH_2)_nNR^8C(O)C_1$–$C_4$ alkyl,
  $(CH_2)_nNR^8SO_2C_1$–$C_4$ alkyl,
  $(CH_2)_nSO_2N(R^8)_2$,
  $(CH_2)_n[O]_qC_1$–$C_8$ alkyl,
  $(CH_2)_n[O]_q(CH_2)_nNR^8COR^8$,
  $(CH_2)_n[O]_q(CH_2)_nNR^8SO_2R^8$,
  $(CH_2)_n[O]_q$-heterocyclyl or
  $(CH_2)_n[O]_q(C_1$–$C_8$ alkyl)-heterocyclyl; and
  wherein n is 2–8;
each $R^{12}$ is independently:
  hydrogen,
  $C_1$–$C_8$ alkyl,
  (D)$C_3$–$C_7$ cycloalkyl,
  (D)phenyl C(O)C$_1$–C$_8$ allyl,
C(O)phenyl,
SO$_2$C$_1$–C$_8$ alkyl or
SO$_2$-phenyl;
D is a bond or —(CH$_2$)$_n$—;
n is 0–8;
p is 0–4;
q is 0–1;
r is 1–2; and
y is 0–1.

The compounds of the present invention are useful in preventing or treating obesity or diabetes mellitus in a mammal comprising the administration of a therapeutically effective amount of the compound of formula I.

The compounds of the present invention are also useful in preventing or treating male or female sexual dysfunction in mammal, more specifically erectile dysfunction, comprising the administration of a therapeutically effective amount of the compound of formula I.

Also within the scope of the present invention is a pharmaceutical composition or formulation which comprises a pharmaceutical carrier and at least one compound of formula I or its pharmaceutically acceptable salts or stereoisomers thereof.

The present invention further includes a process of making a pharmaceutical composition or formulation comprising a compound of formula I or its pharmaceutically acceptable salt or stereoisomers thereof and a pharmaceutically acceptable carrier.

The present invention further includes a process of preparing a compound of formula I.

DETAILED DESCRIPTION OF THE INVENTION

The present invention relates to melanocortin receptor agonists, and more particularly piperazine and piperidine derivatives as melanocortin receptor agonists. The compounds of present invention are useful for the treatment or prevention of diseases and disorders responsive to the activation of melanocortin receptors, such as obesity, diabetes and sexual dysfunction including erectile dysfunction and female sexual dysfunction.

An embodiment of the present invention is a compound of formula I:

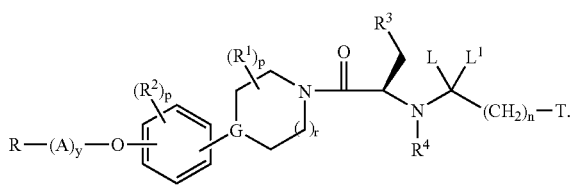

(I)

or a pharmaceutically acceptable salts or stereoisomers thereof, wherein
G is CR$^1$ or N;
A is C$_1$–C$_8$ alkyl or C$_3$–C$_7$ cycloalkyl;
L and L$^1$ are independently: hydrogen or together oxo;

T is:

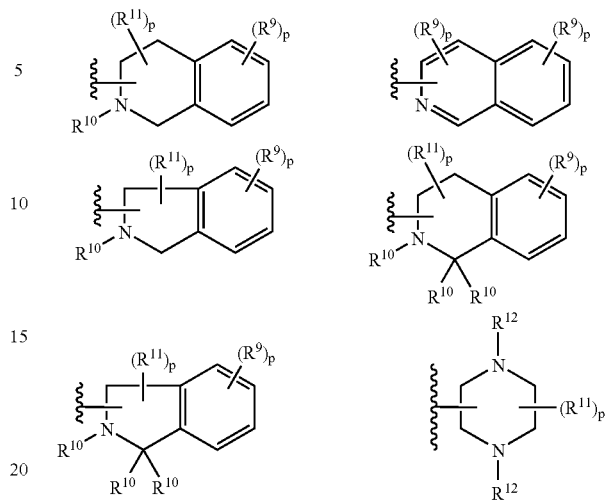

R is: when y is 1;
  N(R$^8$)$_2$,
  NR$^8$COR$^8$,
  NR$^8$CON(R$^8$)$_2$,
  NR$^8$C(O)OR$^8$,
  NR$^8$C(R$^8$)=N(R$^8$),
  NR$^8$SO$_2$R$^8$ or
  NR$^8$SO$_2$N(R$^8$)$_2$;
R is: when y is 0 or 1;
  heterocyclyl, provided that when y is 0, a heteroatom is not directly connected to oxygen or adjacent to a carbon that connected to oxygen; and
  wherein the heterocyclyl contains at least one nitrogen in the ring and is optionally substituted with one to five substituents independently selected from R$^8$;
R$^1$ is independently:
  hydrogen, CONH(C$_1$–C$_8$ alkyl), C$_1$–C$_8$ alkyl, (D)phenyl, (D)C$_3$–C$_7$ cycloalkyl or oxo, provided that oxo is not attached to the same carbon that attached to nitrogen which forms an amide bond when G is N;
R$^2$ is independently:
  hydrogen,
  halo
  C$_1$–C$_8$ alkyl,
  C$_1$–C$_8$ alkylsulfonyl,
  (D)C$_3$–C$_7$ cycloalkyl or
  C$_1$–C$_4$ haloalkyl;
R$^3$ is independently: aryl or thienyl;
  wherein aryl and thienyl are optionally substituted with one to three substituents selected from the group consisting of:
    cyano, halo, C$_1$–C$_8$ alkyl, (D)C$_3$–C$_7$ cycloalkyl, C$_1$–C$_4$ alkoxy, C$_1$–C$_4$ haloalkyl and C$_1$–C$_4$ haloalkyloxy;
R$^4$ is independently:
  hydrogen, C$_1$–C$_8$ alkyl, C(O)R$^8$, C(O)OR$^8$, C$_3$–C$_7$ cycloalkyl or (CH$_2$)$_n$O(C$_1$–C$_8$ alkyl), wherein n is 2–8;
each R$^8$ is independently:
  hydrogen,
  phenyl
  C$_1$–C$_8$ alkyl,
  C$_1$–C$_8$ alkylsulfonyl,
  C(O)C$_1$–C$_8$ alkyl,
  C(O)aryl, wherein aryl being phenyl or naphthyl,
  SO$_2$-aryl, wherein aryl being phenyl or naphthyl, (D)$C_3$–$C_7$ cycloalkyl or
($CH_2$)$_n$$C_1$–$C_4$ haloalkyl, wherein n is 1–8;
each $R^9$ is independently:
  hydrogen,
  hydroxy,
  (D)cyano,
  halo,
  $C_1$–$C_8$ alkyl,
  $C_1$–$C_8$ alkoxy,
  $C_3$–$C_7$ cycloalkyl,
  $C_1$–$C_4$ haloalkyl,
  (D)heterocyclyl
  (D)C(O)$R^8$,
  (D)C(O)($CH_2$)$_n$N($R^8$)$_2$,
  $C_1$–$C_8$ alkyl-N($R^8$)$_2$,
  (D)O$R^8$,
  (D)OCO$R^8$,
  (D)OC(O)N($R^8$)$_2$,
  (D)N($R^8$)$_2$,
  (D)$NR^8$C(O)$R^8$,
  (D)$NR^8$C(O)O$R^8$,
  (D)$NR^8$C(O)N($R^8$)$_2$,
  (D)$NR^8$$SO_2$$R^8$,
  (D)S$R^8$,
  (D)SO$R^8$,
  (D)$SO_2$$R^8$, or
  (D)$SO_2$N($R^8$)$_2$;
each $R^{10}$ is independently:
  hydrogen, ($C_1$–$C_8$)alkyl, C(O)$C_1$–$C_8$ alkyl, aryl or $C_3$–$C_7$ cycloalkyl;
each $R^{11}$ is independently:
  hydrogen,
  $C_1$–$C_8$ alkyl,
  (D)aryl,
  (D)heteroaryl
  ($CH_2$)$_n$N($R^8$)$_2$,
  ($CH_2$)$_n$$NR^8$C(O)$C_1$–$C_4$ alkyl,
  ($CH_2$)$_n$$NR^8$$SO_2$$C_1$–$C_4$ alkyl,
  ($CH_2$)$_n$$SO_2$N($R^8$)$_2$,
  ($CH_2$)$_n$[O]$_q$$C_1$–$C_8$ alkyl,
  ($CH_2$)$_n$[O]$_q$($CH_2$)$_n$$NR^8$CO$R^8$,
  ($CH_2$)$_n$[O]$_q$($CH_2$)$_n$$NR^8$$SO_2$$R^8$,
  ($CH_2$)$_n$[O]$_q$-heterocyclyl or
  ($CH_2$)$_n$[O]$_q$($C_1$–$C_8$ alkyl)-heterocyclyl; and
  wherein n is 2–8;
each $R^{12}$ is independently:
  hydrogen,
  $C_1$–$C_8$ alkyl,
  (D)$C_3$–$C_7$ cycloalkyl,
  (D)phenyl
  C(O)$C_1$–$C_8$ allyl,
  C(O)phenyl,
  $SO_2$$C_1$–$C_8$ alkyl or
  $SO_2$-phenyl;
D is a bond or —($CH_2$)$_n$—;
n is 0–8;
p is 0–4;
q is 0–1;
r is 1–2; and
y is 0–1.

The compound of the present invention as recited above, wherein the heterocyclyl is a 4-, 5- or 6-membered ring containing one nitrogen atom.

The compound of the present invention as recited above, wherein the heterocyclyl is a 6-membered ring containing one nitrogen and one oxygen atom.

The compound of the present invention as recited above, wherein $R^3$ is phenyl optionally para-substituted with fluoro, chloro, bromo, iodo, benzyloxy, methoxy or methyl. The preferred $R^3$ is phenyl para-substituted with chloro, fluoro or methoxy.

The compound of the present invention as recited above, wherein $R^4$ is hydrogen.

The compound of the present invention as recited above, wherein —($CH_2$)$_n$—T is:

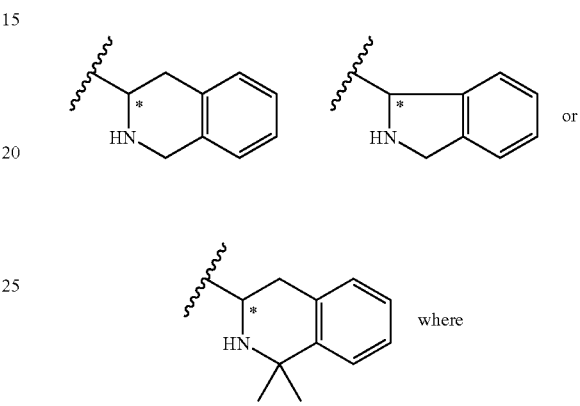

* denotes a chiral carbon atom having a R or S configuration.

The compound of the present invention as recited above, wherein L and $L^1$ are together oxo and the chiral carbon has R configuration.

A preferred embodiment of the present invention provides a compound of formula II,

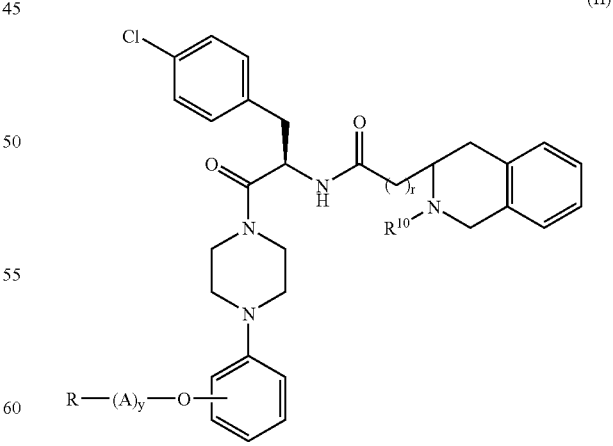

(II)

or a pharmaceutically acceptable salts or stereoisomers thereof.

Yet another preferred embodiment of the present invention provides a compound of formula III,

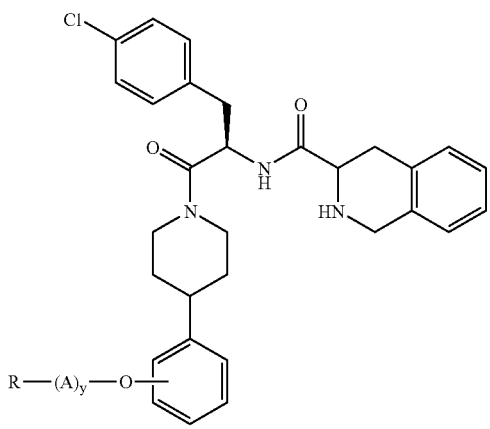

(III)

or a pharmaceutically acceptable salts or stereoisomers thereof.

Yet another preferred embodiment of the present invention provides a compound of formula IV,

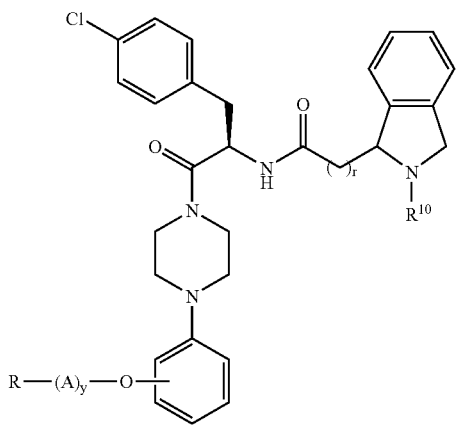

(IV)

or a pharmaceutically acceptable salts or stereoisomers thereof.

Yet another preferred embodiment of the present invention provides a compound of formula V,

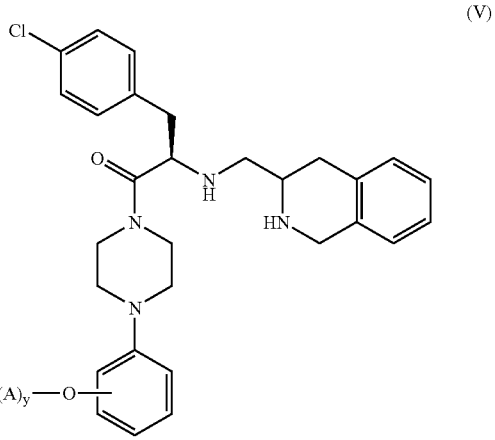

(V)

or a pharmaceutically acceptable salts or stereoisomers thereof.

Yet another preferred embodiment of the present invention provides a compound of formula VI,

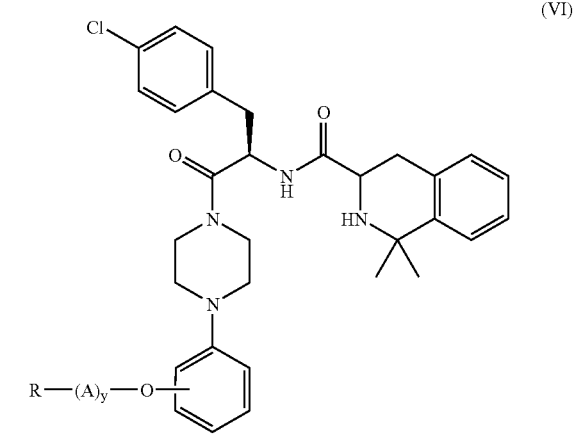

(VI)

or a pharmaceutically acceptable salts or stereoisomers thereof.

The substituents of the compound of present invention as recited above in formula (II) to (VI) are as follows:

A is $C_1$–$C_8$ alkyl or $C_3$–$C_7$ cycloalkyl;
r is 0 or 1;
y is 0 or 1;
D is a bond or —$(CH_2)_n$—;

n is 0–8;

R is: when y is 1;
N(R$^8$)$_2$,
NR$^8$COR$^8$,
NR$^8$CON(R$^8$)$_2$,
NR$^8$C(O)OR$^8$,
NR$^8$C(R$^8$)=N(R$^8$),
NR$^8$SO$_2$R$^8$ or
NR$^8$SO$_2$N(R$^8$)$_2$;

R is: when y is 0 or 1;
heterocyclyl, provided that when y is 0, a heteroatom is not directly connected to oxygen or adjacent to a carbon that connected to oxygen; and
wherein the heterocyclyl contains at least one nitrogen in the ring and are optionally substituted with one to five substituents independently selected from R$^8$;

each R$^8$ is independently:
hydrogen,
phenyl
C$_1$–C$_8$ alkyl,
C$_1$–C$_8$ alkylsulfonyl,
C(O)C$_1$–C$_8$ alkyl,
C(O)aryl, wherein aryl being phenyl or naphthyl,
SO$_2$-aryl, wherein aryl being phenyl or naphthyl,
(D)C$_3$–C$_7$ cycloalkyl or
(CH$_2$)$_n$C$_1$–C$_4$ haloalkyl, wherein n is 1–8;

each R$^{10}$ is independently:
hydrogen, (C$_1$–C$_8$)alkyl, C(O)C$_1$–C$_8$ alkyl, aryl or C$_3$–C$_7$ cycloalkyl.

The compound of present invention as recited above in formula (II)–(VI), wherein O—(A)$_y$—R is attached to ortho position of the phenyl ring.

The compound of present invention as recited above in formula (I)–(VI), wherein the heterocyclyl is a 4-, 5- or 6-membered ring containing one nitrogen atom.

The compound of present invention as recited above in formula (II)–(VI), wherein the nitrogen is substituted with one substituent selected from R$^8$ when y is 0.

The compound of present invention as recited above in formula (II)–(VI), wherein the heterocyclyl is a 6-membered ring containing one nitrogen and one oxygen atom.

The most preferred compounds of the present invention are:

| Name of Compound | Compound |
| --- | --- |
| (N-(1-(4-R-chlorobenzyl)-2-{4-[2-(1-methyl-S-piperidin-3-yloxy)-phenyl]-piperazin-1-yl}-2-oxo-ethyl)-2-(2,3-dihydro-1H-isoindol-1-yl)-aceamide, trihydrochloride | 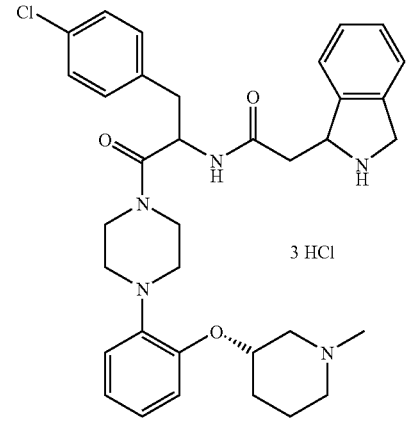 |
| (N-(1-(4-R-chlorobenzyl)-2-oxo-2-{4-[2-(R-piperidin-3-yloxy)-phenyl]-piperazin-1-yl}ethyl)-2-(2,3-dihydro-1H-isoindol-1-yl)-aceamide, trihydrochloride | 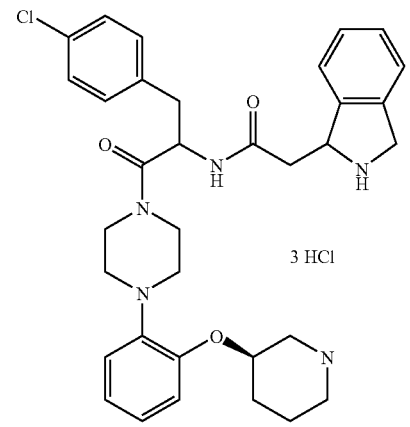 |

-continued

| Name of Compound | Compound |
|---|---|
| 2-(2,3-dihydro-1H-isoindol-1-yl)-N-(1-(4-methoxy-benzyl)-2-{4-[2-(1-methyl-piperidin-3-yloxy)-phenyl]-piperazin-1-yl}-2-oxo-ethyl)-acetamide, trihydrochloride | |

Also encompassed by the present invention is a pharmaceutical composition or formulation, which comprises a pharmaceutical carrier and at least one compound of formula I or its pharmaceutically acceptable salts or stereoisomers thereof. The pharmaceutical composition and or formulation may optionally further include a second active ingredient selected from the group consisting of an insulin sensitizer, insulin mimetic, sulfonylurea, alpha-glucosidase inhibitor, HMG-CoA reductase inhibitor, sequestrant cholesterol lowering agent, beta 3 adrenergic receptor agonist, neuropeptide Y antagonist, phosphodiester V inhibitor, and an alpha 2 adrenergic receptor antagonist.

Yet another aspect of the present invention is a process of making a pharmaceutical composition comprising a compound of formula I or its pharmaceutically acceptable salt or stereoisomers thereof as recited above and a pharmaceutically acceptable carrier.

Yet another aspect of the present invention is a method of preventing or treating obesity or diabetes mellitus in mammal comprising the administration of a therapeutically effective amount of the compound of formula I.

Yet anther aspect of the present invention is a method of preventing or treating male or female sexual dysfunction in mammal, more specifically the male or female sexual dysfunction, comprising the administration of a therapeutically effective amount of the compound of formula I.

Yet another aspect of the present invention is a process for preparing a compound of formula I:

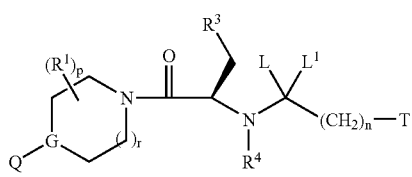

or a pharmaceutically acceptable salts or stereoisomers thereof, wherein
G is $CR^1$ or N;
A is $C_1$–$C_8$ alkyl or $C_3$–$C_7$ cycloalkyl;

—$CLL^1$—$(CH_2)_n$—T is:

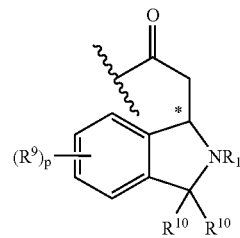

wherein $R_1$ is hydrogen, $C_1$–$C_8$ alkyl, Boc, CBZ, FMOC, phenyl or ($C_1$–$C_8$ alkyl)phenyl;
Q represents a moiety:

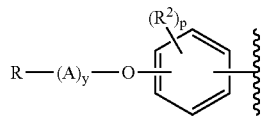

R is: when y is 1;
  $N(R^8)_2$,
  $NR^8COR^8$,
  $NR^8CON(R^8)_2$,
  $NR^8C(O)OR^8$,
  $NR^8C(R^8)=N(R^8)$,
  $NR^8SO_2R^8$ or
  $NR^8SO_2N(R^8)_2$;
R is: when y is 0 or 1;
  heterocyclyl, provided that when y is 0, a heteroatom is not directly connected to oxygen or adjacent to a carbon that connected to oxygen; and
  wherein the heterocyclyl contains at least one nitrogen in the ring and is optionally substituted with one to five substituents independently selected from $R^8$;
$R^1$ is independently:
  hydrogen, $CONH(C_1$–$C_8$ alkyl), $C_1$–$C_8$ alkyl, (D)phenyl, (D)$C_3$–$C_7$ cycloalkyl or oxo, provided that oxo is not attached to the same carbon that attached to nitrogen which forms an amide bond when G is N;
$R^2$ is independently:
  hydrogen,
  halo C₁–C₈ alkyl,
C₁–C₈ alkylsulfonyl,
(D)C₃–C₇ cycloalkyl or
C₁–C₄ haloalkyl;
R³ is independently: aryl or thienyl;
  wherein aryl and thienyl are optionally substituted with one to three substituents selected from the group consisting of:
  cyano, halo, C₁–C₈ alkyl, (D)C₃–C₇ cycloalkyl, C₁–C₄ alkoxy, C₁–C₄ haloalkyl and C₁–C₄ haloalkyloxy;
R⁴ is independently:
  hydrogen, C₁–C₈ alkyl, C(O)R⁸, C(O)OR⁸, C₃–C₇ cycloalkyl or (CH₂)ₙO(C₁–C₈ alkyl), wherein n is 2–8;
each R⁸ is independently:
  hydrogen,
  phenyl
  C₁–C₈ alkyl,
  C₁–C₈ alkylsulfonyl,
  C(O)C₁–C₈ alkyl,
  C(O)aryl, wherein aryl being phenyl or naphthyl,
  SO₂-aryl, wherein aryl being phenyl or naphthyl,
  (D)C₃–C₇ cycloalkyl or
  (CH₂)ₙC₁–C₄ haloalkyl, wherein n is 1–8;
each R⁹ is independently:
  hydrogen,
  hydroxy,
  (D)cyano,
  halo,
  C₁–C₈ alkyl,
  C₁–C₈ alkoxy,
  C₃–C₇ cycloalkyl,
  C₁–C₄ haloalkyl,
  (D)heterocyclyl
  (D)C(O)R⁸,
  (D)C(O)(CH₂)ₙN(R⁸)₂,
  C₁–C₈ alkyl-N(R⁸)₂,
  (D)OR⁸,
  (D)OCOR⁸,
  (D)OC(O)N(R⁸)₂,
  (D)N(R⁸)₂,
  (D)NR⁸C(O)R⁸,
  (D)NR⁸C(O)OR⁸,
  (D)NR⁸C(O)N(R⁸)₂,
  (D)NR⁸SO₂R⁸,
  (D)SR⁸,
  (D)SOR⁸,
  (D)SO₂R⁸, or
  (D)SO₂N(R⁸)₂;
each R¹⁰ is independently:
  hydrogen, (C₁–C₈)alkyl, C(O)C₁–C₈ alkyl, aryl or C₃–C₇ cycloalkyl;
D is a bond or —(CH₂)ₙ—;
n is 0–8;
p is 0–4;
q is 0–1;
r is 1–2; and
y is 0–1.
comprising the steps of:
a) reacting a compound having a structural formula 1,

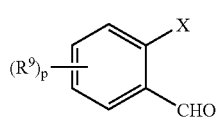
(1)

with CH₂CH=C(O)ORᵃ wherein Rᵃ is hydrogen or C₁–C₈ alkyl and X is halo, in the presence of a catalyst and a base in a suitable organic solvent to give the compound of formula 2,

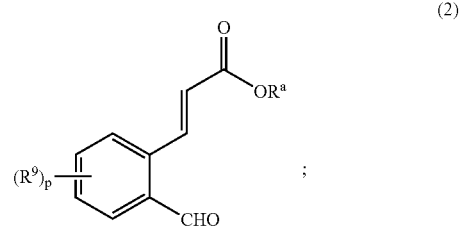
(2)

b) reductively aminating the compound of formula 2 in the presence of amine in an acidic condition to give a compound of formula 3,

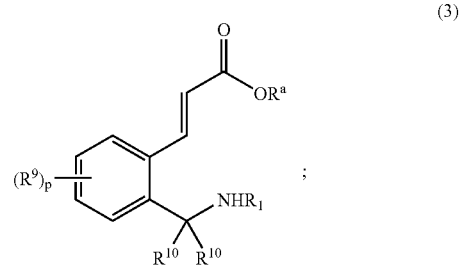
(3)

c) cyclizing the compound of formula 3 by Michael addition to give a compound of formula 4 or stereoisomers thereof,

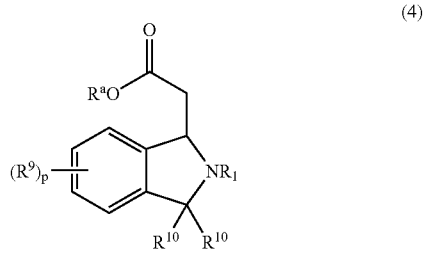
(4)

d) coupling the compound of formula 4 or stereoisomers thereof, wherein Rᵃ of compound 4 is H, with a compound of formula 5,

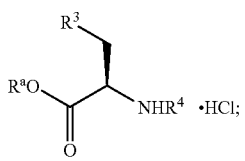
(5)

wherein R^a of compound 5 is $C_1$–$C_8$ alkyl, to give a compound of formula 6;

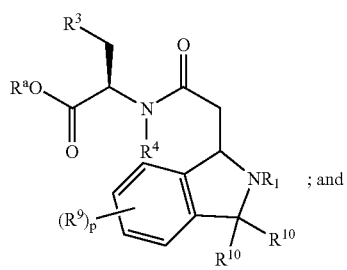
(6)

e) coupling the compound of formula 6, wherein $R^a$ is H, with a compound having a structural,

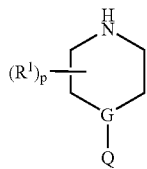

to afford the compound of formula 1.

The process of present invention as recited above, wherein

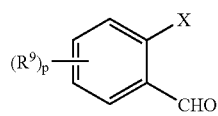

in Step (a) is 2-boromobenzaldehydes.

The process of present invention as recited above, wherein $CH_2CH=C(O)OR$ in Step (a) is methylacrylate.

The process of present invention as recited above, wherein the catalyst in Step (a) is selected from the group consisting of: $Pd(Ph_3P)_2Cl_2$, $Pd(Ph_3P)_4Cl_2$, $Pd(Ph_3P)_4$, $Pd(Ph_3P)_2Cl_2/CuI$, $Pd(OAc)_2/Ph_3P$—$Bu_4NBr$, $Pd(Ph_3P)_4Cl_2/H_2$ and $Pd(OAc)_2/P(O\text{-tol})_3$; and wherein the base in Step (a) is $NR_3$ wherein R is hydrogen or $C_1$–$C_8$ alkyl.

The process of present invention as recited above, wherein the amine in Step (b) is selected from the group consisting of: benzylamine, alpha-methylbenzylamine and $BocNH_2$.

The process of present invention as recited above, wherein the Step (b) further comprises reducing of intermediate imine compound in the presence of reducing agent, the reducing agent being selected from the group consisting of: $NaCNBH_3$, $Na(OAc)_3BH$, $NaBH_4/H+$, and a combination of $Et_3SiH$ and TFA in $CH_3CN$ or $CH_2Cl_2$.

The process of present invention as recited above, wherein the stereoisomer of compound of formula 4 in Step (c) is a compound of formula 4a.

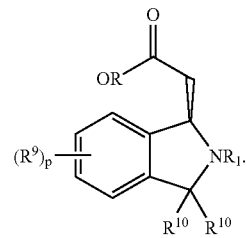
(4a)

The process of present invention as recited above, wherein the compound of formula 4a is prepared by asymmetric hydrogenation of a compound having structural formula,

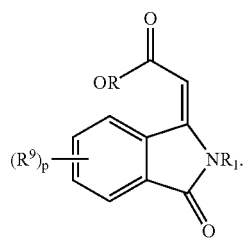

The process of present invention as recited above, wherein the Michael addition in Step (c) is carried out in a basic workup condition.

The process of present invention as recited above, wherein the Step (e) further comprises deprotecting or protecting of the compound of formula (4) at $NR_1$.

Yet another aspect of the present invention is a process for preparing a compound of formula I:

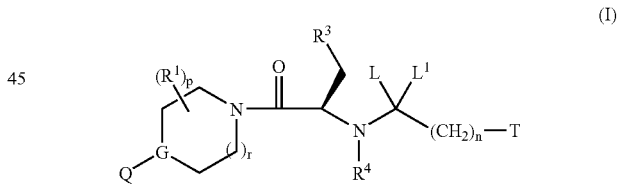
(I)

or a pharmaceutically acceptable salts or stereoisomers thereof, wherein

G is $CR^1$ or N;

A is $C_1$–$C_8$ alkyl or $C_3$–$C_7$ cycloalkyl;

—$CLL^1$—$(CH_2)_n$—T is:

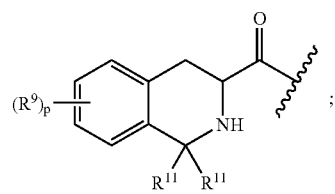

Q represents a moiety:

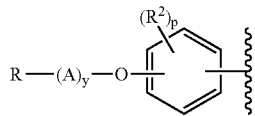

R is: when y is 1;
 $N(R^8)_2$,
 $NR^8COR^8$,
 $NR^8CON(R^8)_2$,
 $NR^8C(O)OR^8$,
 $NR^8C(R^8)=N(R^8)$,
 $NR^8SO_2R^8$ or
 $NR^8SO_2N(R^8)_2$;

R is: when y is 0 or 1;
 heterocyclyl, provided that when y is 0, a heteroatom is not directly connected to oxygen or adjacent to a carbon that connected to oxygen; and
 wherein the heterocyclyl contains at least one nitrogen in the ring and is optionally substituted with one to five substituents independently selected from $R^8$;

$R^1$ is independently:
 hydrogen, $CONH(C_1-C_8$ alkyl), $C_1-C_8$ alkyl, (D)phenyl, $(D)C_3-C_7$ cycloalkyl or oxo, provided that oxo is not attached to the same carbon that attached to nitrogen which forms an amide bond when G is N;

$R^2$ is independently:
 hydrogen,
 halo
 $C_1-C_8$ alkyl,
 $C_1-C_8$ alkylsulfonyl,
 $(D)C_3-C_7$ cycloalkyl or
 $C_1-C_4$ haloalkyl;

$R^3$ is independently: aryl or thienyl;
 wherein aryl and thienyl are optionally substituted with one to three substituents selected from the group consisting of:
 cyano, halo, $C_1-C_8$ alkyl, $(D)C_3-C_7$ cycloalkyl, $C_1-C_4$ alkoxy, $C_1-C_4$ haloalkyl and $C_1-C_4$ haloalkyloxy;

$R^4$ is independently:
 hydrogen, $C_1-C_8$ alkyl, $C(O)R^8$, $C(O)OR^8$, $C_3-C_7$ cycloalkyl or $(CH_2)_nO(C_1-C_8$ alkyl), wherein n is 2–8;

each $R^8$ is independently:
 hydrogen,
 phenyl
 $C_1-C_8$ alkyl,
 $C_1-C_8$ alkylsulfonyl,
 $C(O)C_1-C_8$ alkyl,
 C(O)aryl, wherein aryl being phenyl or naphthyl,
 $SO_2$-aryl, wherein aryl being phenyl or naphthyl,
 $(D)C_3-C_7$ cycloalkyl or
 $(CH_2)_nC_1-C_4$ haloalkyl, wherein n is 1–8;

each $R^9$ is independently:
 hydrogen,
 hydroxy,
 (D)cyano,
 halo,
 $C_1-C_8$ alkyl,
 $C_1-C_8$ alkoxy,
 $C_3-C_7$ cycloalkyl,
 $C_1-C_4$ haloalkyl,
 (D)heterocyclyl
 $(D)C(O)R^8$,
 $(D)C(O)(CH_2)_nN(R^8)_2$,
 $C_1-C_8$ alkyl-$N(R^8)_2$,
 $(D))OR^8$,
 $(D)OCOR^8$,
 $(D)OC(O)N(R^8)_2$,
 $(D)N(R^8)_2$,
 $(D)NR^8C(O)R^8$,
 $(D)NR^8C(O)OR^8$,
 $(D)NR^8C(O)N(R^8)_2$,
 $(D)NR^8SO_2R^8$,
 $(D)SR^8$,
 $(D)SOR^8$,
 $(D)SO_2R^8$, or
 $(D)SO_2N(R^8)_2$;

each $R^{11}$ is independently: hydrogen, $(C_1-C_8)$alkyl,
D is a bond or $-(CH_2)_n-$;
n is 0–8;
p is 0–4;
q is 0–1;
r is 1–2; and
y is 0–1.

comprising the steps of:
a) esterifying a compound of formula 1,

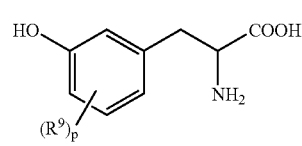

with an alcohol $R^aOH$ to form a compound of formula 2,

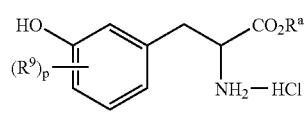

wherein $R^a$ is $C_1-C_4$ alkyl or (D)phenyl;
b) reacting a compound of formula 2 with $R^{11}COR^{11}$ to form a compound of formula 3,

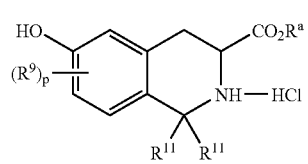

wherein $R^{11}$ is independently hydrogen or $C_1-C_4$ alkyl;
c) reacting a compound of formula 3 with an activating group to form a compound of formula 4,

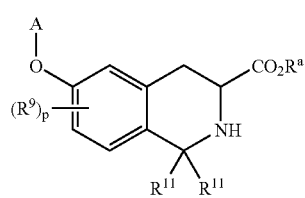

(4)

wherein A is an activating group;

d) deoxygenating the compound of formula 4 by hydrogenation to afford a compound of formula 5,

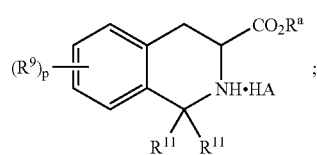

(5)

e) optionally reacting the compound of formula 5 with an inorganic base to form a compound of formula 6,

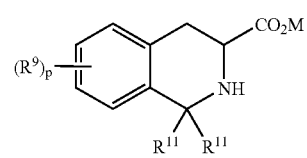

(6)

wherein HA is an acidic and M is a univalent cation;

f) resolving the compound of formula 5 or formula 6 to afford a chiral compound of formula 7,

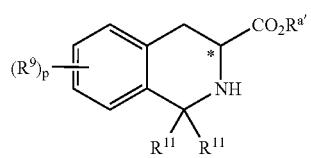

(7)

wherein M is hydrogen and $R^a$ is H or $R^a$;

g) coupling the compound of formula 7 with a compound of formula 8,

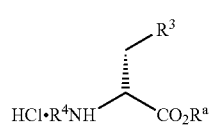

(8)

to afford a compound of formula 9,

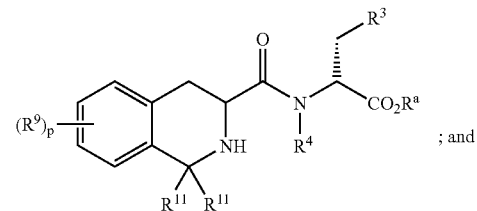

(9)

; and h) coupling the compound of formula 9 with a compound having a formula,

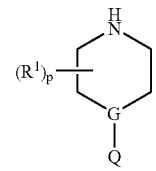

to afford a compound of formula I.

Yet another aspect of the present invention is a process for preparing a compound of formula I,

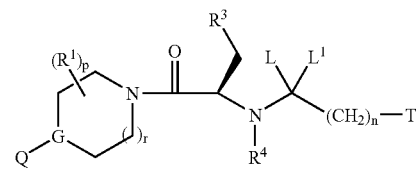

(I)

or a pharmaceutically acceptable salts or stereoisomers thereof, wherein

G is $CR^1$ or N;

A is $C_1$–$C_8$ alkyl or $C_3$–$C_7$ cycloalkyl;

—$CLL^1$—$(CH_2)_n$—T is:

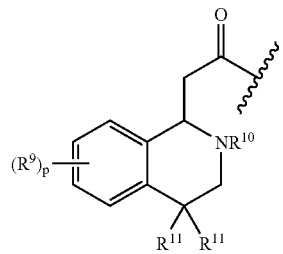

Q represents a moiety:

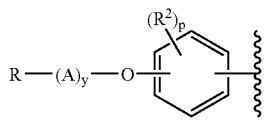

R is: when y is 1;

$N(R^8)_2$,

NR⁸COR⁸,
NR⁸CON(R⁸)₂,
NR⁸C(O)OR⁸,
NR⁸C(R⁸)=N(R⁸),
NR⁸SO₂R⁸ or
NR⁸SO₂N(R⁸)₂;

R is: when y is 0 or 1;
  heterocyclyl, provided that when y is 0, a heteroatom is not directly connected to oxygen or adjacent to a carbon that connected to oxygen; and
  wherein the heterocyclyl contains at least one nitrogen in the ring and is optionally substituted with one to five substituents independently selected from R⁸;

R¹ is independently:
  hydrogen, CONH(C₁–C₈ alkyl), C₁–C₈ alkyl, (D)phenyl, (D)C₃–C₇ cycloalkyl or oxo, provided that oxo is not attached to the same carbon that attached to nitrogen which forms an amide bond when G is N;

R² is independently:
  hydrogen,
  halo
  C₁–C₈ alkyl,
  C₁–C₈ alkylsulfonyl,
  (D)C₃–C₇ cycloalkyl or
  C₁–C₄ haloalkyl;

R³ is independently: aryl or thienyl;
  wherein aryl and thienyl are optionally substituted with one to three substituents selected from the group consisting of:
  cyano, halo, C₁–C₈ alkyl, (D)C₃–C₇ cycloalkyl, C₁–C₄ alkoxy, C₁–C₄ haloalkyl and C₁–C₄ haloalkyloxy;

R⁴ is independently:
  hydrogen, C₁–C₈ alkyl, C(O)R⁸, C(O)OR⁸, C₃–C₇ cycloalkyl or (CH₂)ₙO(C₁–C₈ alkyl), wherein n is 2–8;

each R⁸ is independently:
  hydrogen,
  phenyl
  C₁–C₈ alkyl,
  C₁–C₈ alkylsulfonyl,
  C(O)C₁–C₈ alkyl,
  C(O)aryl, wherein aryl being phenyl or naphthyl,
  SO₂-aryl, wherein aryl being phenyl or naphthyl,
  (D)C₃–C₇ cycloalkyl or
  (CH₂)ₙC₁–C₄ haloalkyl, wherein n is 1–8;

each R⁹ is independently:
  hydrogen,
  hydroxy,
  (D)cyano,
  halo,
  C₁–C₈ alkyl,
  C₁–C₈ alkoxy,
  C₃–C₇ cycloalkyl,
  C₁–C₄ haloalkyl,
  (D)heterocyclyl
  (D)C(O)R⁸,
  (D)C(O)(CH₂)ₙN(R⁸)₂,
  C₁–C₈ alkyl-N(R⁸)₂,
  (D)OR⁸,
  (D)OCOR⁸,
  (D)OC(O)N(R⁸)₂,
  (D)N(R⁸)₂,
  (D)NR⁸C(O)R⁸,
  (D)NR⁸C(O)OR⁸,
  (D)NR⁸C(O)N(R⁸)₂,
  (D)NR⁸SO₂R⁸,
  (D)SR⁸,
  (D)SOR⁸,
  (D)SO₂R⁸, or
  (D)SO₂N(R⁸)₂;

each R¹⁰ is independently:
  hydrogen, (C₁–C₈)alkyl, C(O)C₁–C₈ alkyl, aryl or C₃–C₇ cycloalkyl, or protecting group selected from Boc, CBZ or FMOC;

each R¹¹ is independently: hydrogen or (C₁–C₈)alkyl;

D is a bond or —(CH₂)ₙ—;
n is 0–8;
p is 0–4;
q is 0–1;
r is 1–2; and
y is 0–1.

comprising the steps of:
  a) reacting a compound formula 1:

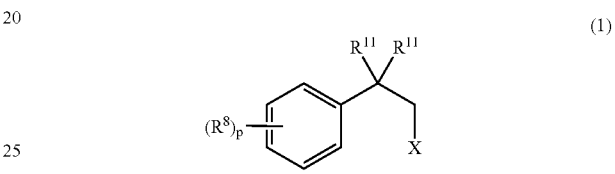

wherein X is halo, and R¹¹ is independently, hydrogen or C1–C4 alkyl, with CNCH₂CO₂Rᵃ wherein Rᵃ is C₁–C₈ alkyl or benzyl to afford a compound of formula 2:

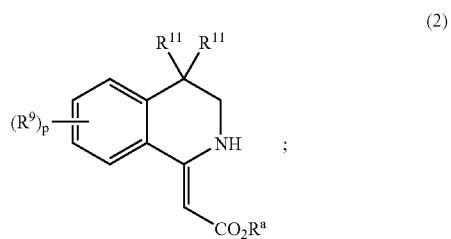

b) protecting the compound of formula 2 to form the compound of formula 3:

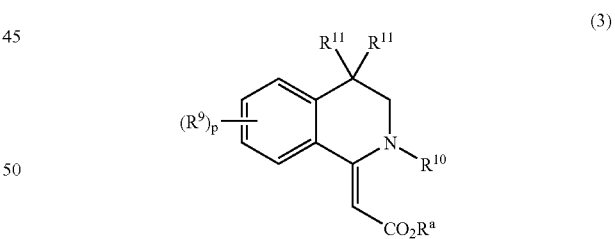

c) hydrogenating the compound of formula 3 to afford a compound of formula 4:

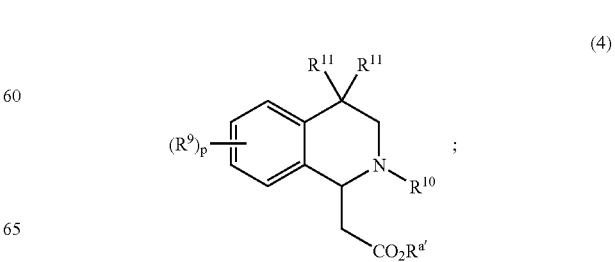

d) coupling the compound of formula 4 wherein $R^{a'}$ is hydrogen or $R^a$, with a compound of formula 5,

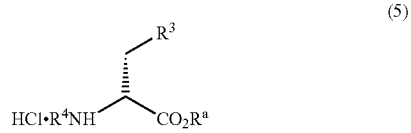

(5)

to afford a compound of formula 6,

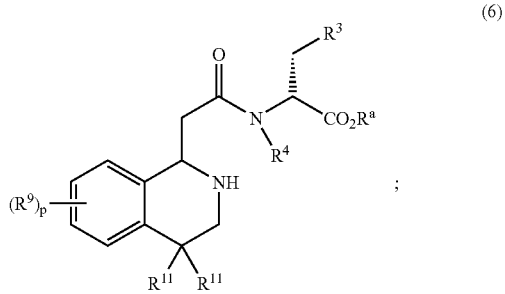

(6)

e) coupling the compound of formula 6 with a compound having a formula,

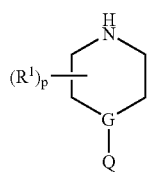

to afford a compound of formula I.

Throughout the instant application, the following terms have the indicated meanings:

The term "alkyl," unless otherwise indicated, refers to those alkyl groups of a designated number of carbon atoms of either a straight or branched saturated configuration. Examples of "alkyl" includes, but are not limited to methyl, ethyl, n-propyl. isopropyl, n-butyl, isobutyl, sec-butyl and t-butyl, pentyl, hexyl, neopenyl, isopentyl and the like.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like.

The term "haloalkyl" is an alkyl group of indicated number of carbon atoms, which is substituted with one to five halo atoms selected from F, Br, Cl, and I. An example of a haloalkyl group is trifluoromethyl.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like.

The term "cycloalkyl" refers to a ring composed of 3 to 7 methylene groups, each of which may be optionally substituted with other hydrocarbon substituents. Examples of cycloalkyl includes, but are not limited to: cyclopropyl, cyclobutyl, cyclopentyl, cyclohexyl and cycloheptyl, and the like.

The term "halo" refers to fluoro, chloro, bromo and iodo.

The term "haloalkyloxy" represents a haloalkyl group of indicated number of carbon atoms attached through an oxygen bridge, such as $OCF_3$.

The term "aryl" refers to phenyl, naphthyl, anthracenyl, phenanthrenyl and the like.

The term "heteroaryl" refers to monocyclic or bicyclic aromatic ring of 5- to 10-carbon atoms containing from one to four heteroatoms selected from O, N, or S. Examples of heteroaryl are, but are not limited to furanyl, thienyl, thiazolyl, imidazolyl, isoxazoyl, oxazoyl, pyrazoyl, pyrrolyl, pyrazinyl, pyridyl, pyrimidyl, and purinyl, cinnolinyl, benzothienyl, benzotriazolyl, benzoxazolyl, quinoline, isoquinoline and the like.

The "heterocyclyl" is defined as a monocyclic, bicyclic, or tricyclic ring of 5 to 14 carbon atoms which are saturated or partially saturated containing from one to four heteroatoms selected from N, O or S. The "heterocyclyl" includes "nitrogen containing heterocyclyl," which contains from one to four nitrogen atoms and optionally further contains one other heteroatom selected from O or S.

A mammal as used in here includes a human and a warm-blooded animal such as a cat, a dog and the like.

The term "composition" or "formulation", as in pharmaceutical composition or formulation, is intended to encompass a product comprising the active ingredient(s), and the inert ingredient(s) that make up the carrier. Accordingly, the pharmaceutical compositions of the present invention encompass any composition made by admixing a compound of the present invention (a compound of formula 1) and a pharmaceutically acceptable carrier.

The term "pharmaceutical" when used herein as an adjective means substantially non-deleterious to the recipient mammal.

The term "unit dosage form" refers to physically discrete units suitable as unitary dosages for human subjects and other non-human animals such as warm-blooded animals each unit containing a predetermined quantity of active ingredient (a compound of formula I) calculated to produce the desired therapeutic effect in association with a suitable pharmaceutical carrier.

The term "treating" or "preventing" as used herein includes its generally accepted meanings, i.e., preventing, prohibiting, restraining, alleviating, ameliorating, slowing, stopping, or reversing the progression or severity of a pathological condition, or sequela thereof as described herein.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, inability to achieve an orgasm. An increase in erectile dysfunction is often associated with age and is generally caused by a physical disease or as a side effect of drug treatment.

"Female sexual dysfunction" encompasses, without limitation, conditions such as a lack of sexual desire and related arousal disorders, inhibited orgasm, lubrication difficulties, and vaginismus.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, beta-hydroxybutyrate, glycollate, maleate, tartrate, methanesulfonate, propanesulfonate, naphthalene-1-sulfonate, naphthalene-2-sulfonate, mandelate and the like salts. Preferred salt form of compound of formula I is an acid addition salts, more specifically hydrochloride salt.

Some of the compounds described herein may exist as tautomers such as ketoenol tautomers. The individual tautomers as well as mixtures thereof are encompassed within the scope of the present invention.

Utility

Compounds of formula I are effective as melanocortin receptor modulators, particularly as agonists of the human MC-4 receptor. As melanocortin receptor agonists, the compounds of formula I are useful in the treatment of diseases, disorders or conditions responsive to the activation of one or more of the melanocortin receptors including, but not limited to, MC-1, MC-2, MC-3, MC4, and MC-5. Diseases, disorders or conditions receptive to treatment with a MC-4 agonist include those mentioned above and those described in WO 00/74679, the teachings of which are herein incorporated by reference. In particular diseases, disorders or conditions receptive to treatment with a MC-4 agonist include obesity or diabetes mellitus, male or female sexual dysfunction, more specifically erectile dysfunction.

When describing various aspects of the present compounds of formula I, the terms "A domain", "B domain" and "C domain" are used below. This domain concept is illustrated below:

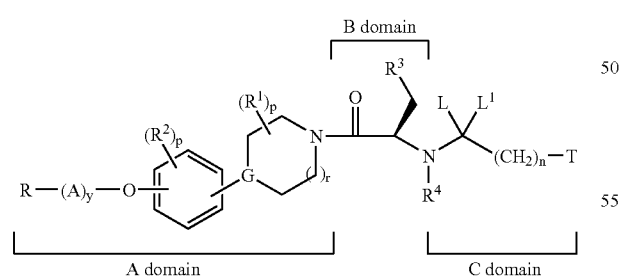

The following listing provides some of examples "A domain", "B domain" and "C domain" of the compound of formula I. These listings are provided as illustrative purposes and as such are not meant to be limiting.

Examples of A Domain:

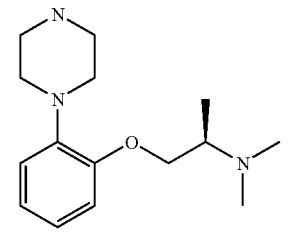

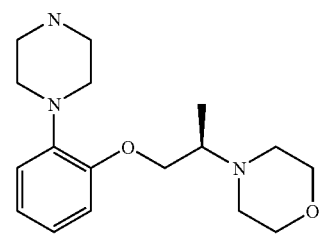

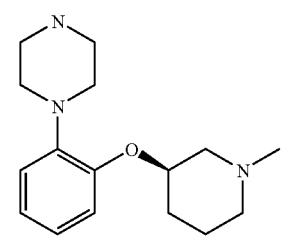

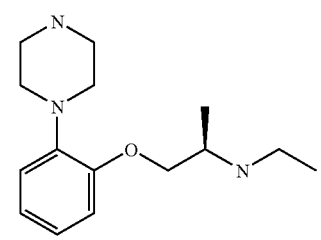

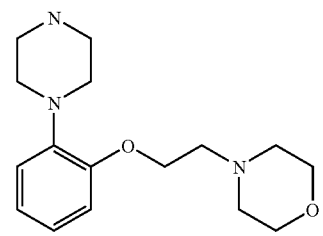

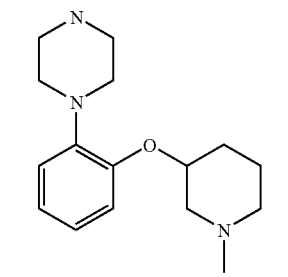

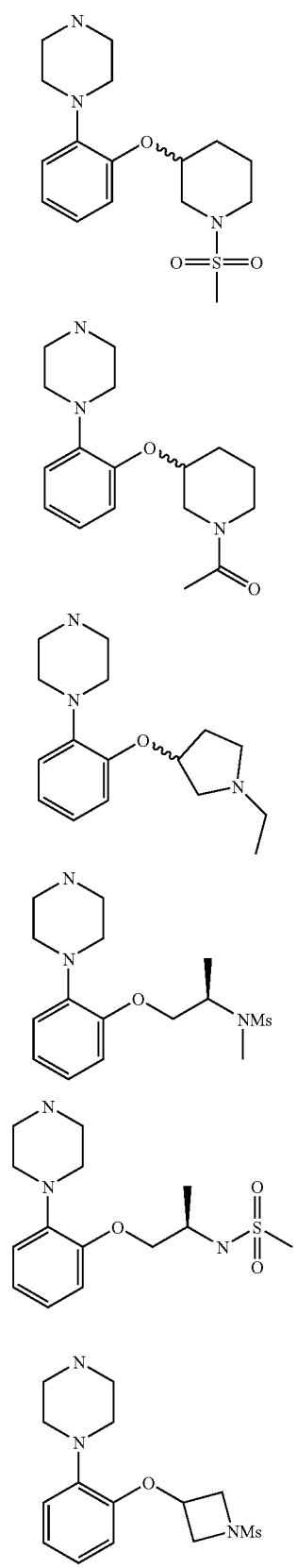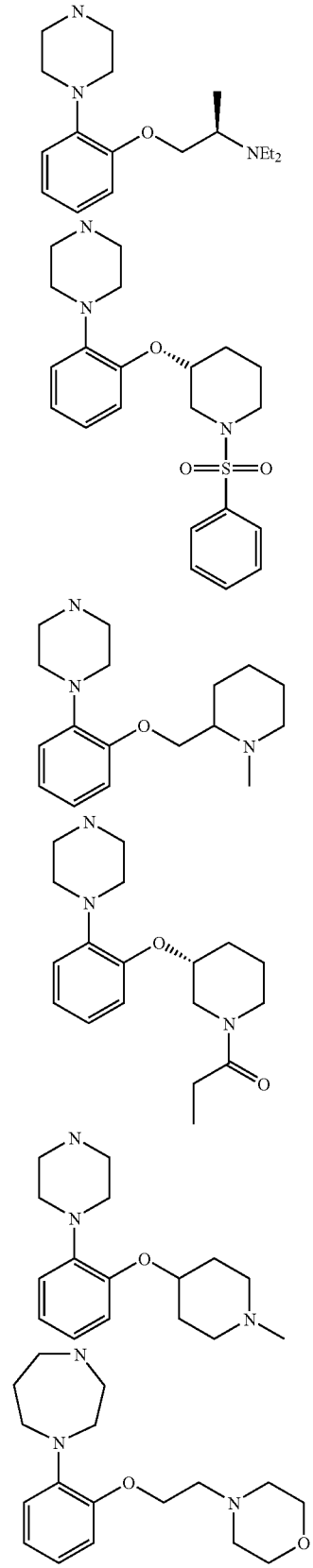

-continued
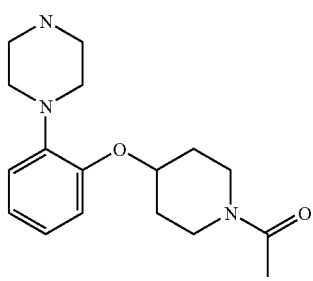
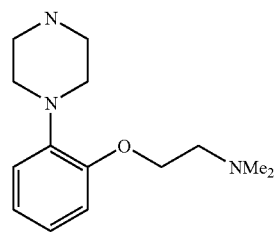
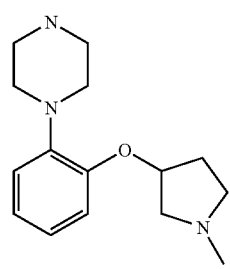
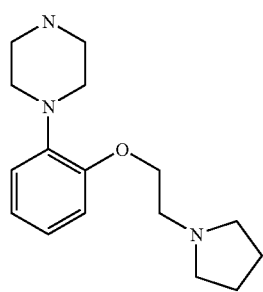
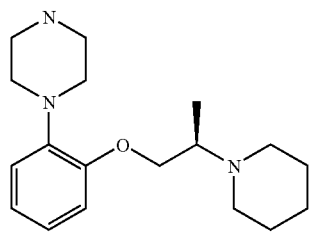
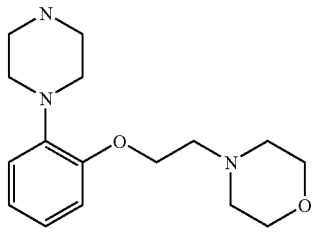
-continued
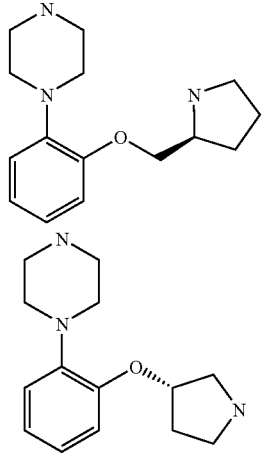
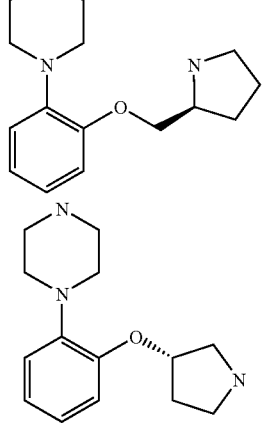
Examples of B Domain:
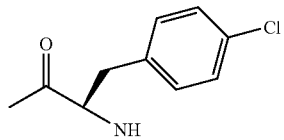
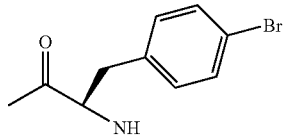
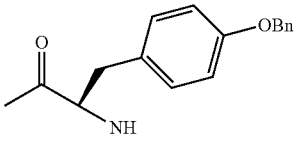
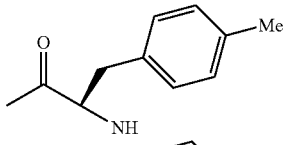
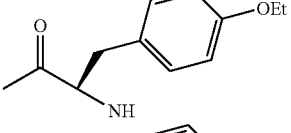
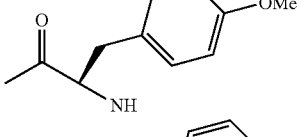
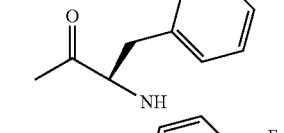
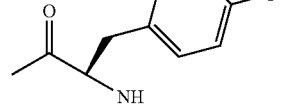

-continued

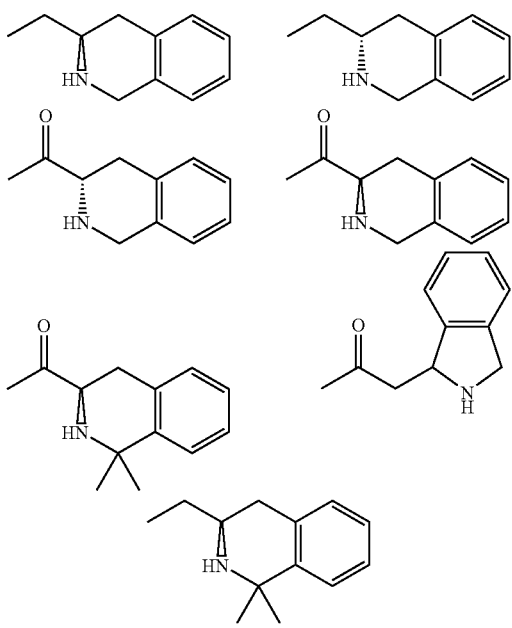

Examples of C Domain:

Formulation

The compound of formula I is preferably formulated in a unit dosage form prior to administration. Accordingly the present invention also includes a pharmaceutical composition comprising a compound of formula I and a suitable pharmaceutical carrier.

The present pharmaceutical compositions are prepared by known procedures using well-known and readily available ingredients. In making the formulations of the present invention, the active ingredient (a compound of formula I) is usually mixed with a carrier, or diluted by a carrier, or enclosed within a carrier, which may be in the form of a capsule, sachet, paper or other container. When the carrier serves as a diluents, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Dosage:

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. Additionally, it would be understood that the therapeutic dosage administered can be determined by the physician in the light of the relevant circumstances.

Generally, an effective minimum daily dose of a compound of formula I is about 1, 5, 10, 15, or 20 mg. Typically, an effective maximum dose is about 500, 100, 60, 50, or 40 mg. The suitable dose may be determined in accordance with the standard practice in the medical arts of "dose titrating" the recipient, which involves administering a low dose of the compound initially and then gradually increasing the does until the desired therapeutic effect is observed.

Route of Administration

The compounds may be administered by a variety of routes including the oral, rectal, transdermal, subcutaneous, topical, intravenous, intramuscular or intranasal routes.

Combination Therapy

Compounds of formula I may be used in combination with other drugs that are used in the treatment of the diseases or conditions for which compounds of formula I are useful. Such other drugs may be administered by a route and in an amount commonly used therefor, contemporaneously or sequentially with a compound of formula I. When a compound of formula I is used contemporaneously with one or more other drugs, a pharmaceutical composition containing such other drugs in addition to the compound of formula I is preferred. Accordingly, the pharmaceutical compositions of the present invention include those that also contain one or more other active ingredients in addition to a compound of formula I. Examples of other active ingredients that may be combined with a compound of formula I, either administered separately or in the same pharmaceutical compositions, include but are not limited to:

(a) insulin sensitizers including (i) PPARγ agonists such as the glitazones (e.g. troglitazone, pioglitazone, englitazone, MCC-555, BRL49653 and the like) and compounds disclosed in WO97/27857, WO 97/28115, WO 97/28137 and WO97/27847; (ii) biguanides such as metformin and phenformin;

(b) insulin or insulin mimetics;

(c) sulfonylureas such as tolbutamide and glipizide;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (iii) nicotinyl alcohol nicotinic acid or a salt thereof, (iv) proliferator-activater receptor α-agonists such as fenofibric acid derivatives (gemfibrozil, clofibrat, fenofibrate and benzafibrate), (v) inhibitors of cholesterol absorption such as β-sitosterol and acyl CoA:

cholesterol acyltransferase inhibitors such as melinamide, (vi) probucol, (vii) vitamin E, and (viii) thyromimetics;
(f) PPARδ agonists such as those disclosed in WO97/28149;
(g) antiobesity compounds such as fenfluramine, dexfenfluramine, phentermine, sibutramine, orlistat, and β-3 adrenergic receptor agonists;
(h) feeding behavior modifying agents such as neuropeptide Y antagonists (e.g. neuropeptide Y5) as disclosed in WO 97/19682, WO 97/20820, WO 97/20821, WO 97/20822 and WO 97/20823;
(i) PPARα agonists as described in WO 97/36579;
(j) PPARγ antagonists as described in WO97/10813;
(k) serotonin reuptake inhibitors, such as fluoxetine and sertraline;
(l) growth hormone secretagogues such as MK-0677; and
(m) agents useful in the treatment of male and/or female sexual dysfunction, such as phosphodiester V inhibitors including sildenafil and ICI-351, and α-2 adrenergic receptor antagonists including phentolamine mesylate; and dopamine-receptor agonists, such as apomorphine.

Biological Assays

A. Binding Assay:

The radioligand binding assay is used to identify competitive inhibitors of $^{125}$I-NDP-α-MSH binding to cloned human MCRs using membranes from stably transfected human embryonic kidney (HEK) 293 cells.

HEK 293 cells transfected with human or rat melanocortinin receptors are grown either as adherent monolayers or suspension culture. Monolayer cells are grown in roller bottle cultures at 37° C. and 5% $CO_2$/air atmosphere in a 3:1 mixture of Dulbecco's modified Eagle medium (DMEM) and Ham's F12 containing 25 mM L-glucose, 100 units/ml penicillin G, 100 microgram/ml streptomyocin, 250 nanogram/ml amphoterin B, 300 microgram/ml genticin and supplemented with 5% fetal bovine serum. Monolayer cells are adapted to suspension culture (Berg et al., *Biotechniques* Vol. 14, No. 6, 1993) and are grown in either spinner or shaker flasks (37° C. and 7.5% $CO_2$/air overlay) in a modified DME/F12 medium containing 0.1 mM $CaCl_2$, 2% equine serum and 100 microgram/ml sodium heparin to prevent cell-cell aggregation. Cells are harvested by centrifugation, washed in PBS, and pellets are stored frozen at −80° C. until membrane preparations.

The cell pellets are resuspended in 10 volumes of membrane preparation buffer (i.e., 1 g pellet to 10 ml buffer) having the following composition: 50 mM Tris pH 7.5 @4° C., 250 mM sucrose, 1 mM $MgCl_2$, Complete® EDTA-free protease inhibitor tablet (Boehringer Mannheim), and 24 micrograms/ml DNase I (Sigma, St. Louis, Mo.). The cells are homogenized with a motor-driven dounce using 20 strokes, and the homogenate is centrifuged at 38,000×g at 4° C. for 40 minutes. The pellets are resuspended in membrane preparation buffer at a concentration of 2.5–7.5 mg/ml and 1 milliliter aliquots of membrane homogenates are quickly frozen in liquid nitrogen and then stored at −80° C.

Solutions of a compound of formula I (300 picomolar to 30 micromolar) or unlabelled NDP-α-MSH (1 picomolar to 100 nanomolar) are added to 150 microliters of membrane binding buffer to yield final concentrations (listed in parantheses). The membrane binding buffer has the following composition: 25 mM HEPES pH 7.5; 10 mM $CaCl_2$; 0.3% BSA). One hundred fifty microliters of membrane binding buffer containing 0.5–5.0 microgram membrane protein is added, followed by 50 nanomolar $^{125}$I-NDP-α-MSH to final concentration of 100 picomolar. Additionally, fifty microliters of SPA beads (5 mg/ml) are added and the resulting mixture is agitated briefly and incubated for 10 hours at r.t. The radioactivity is quantified in a Wallac Trilux Microplate Scintillation counter. $IC_{50}$ values obtained in competition assays are converted to affinity constants ($K_i$ values) using the Cheng-Prusoff equation: $K_i=IC_{50}(1+D/K_d)$.

B. Functional Assay:

Functional cell based assays are developed to discriminate agonists and antagonists.

Agonist Assay: HEK 293 cells stably expressing a human melanocortin receptor (see e.g., Yang, et al., *Mol-Endocrinol.*, 11(3): 274–80, 1997) are dissociated from tissue culture flasks using a trypsin/EDTA solution(0.25%; Life Technologies, Rockville, Md.). Cells are collected by centrifugation and resuspended in DMEM (Life Technologies, Rockville, Md.) supplemented with 1% L-glutamine and 0.5% fetal bovine serum. Cells are counted and diluted to $4.5 \times 10^5$/ml.

A compound of formula I is diluted in dimethylsulfoxide (DMSO) ($3 \times 10^{-5}$ to $3 \times 10^{-10}$ M final concentrations) and 0.05 volume of compound solution is added to 0.95 volumes of cell suspension; the final DMSO concentration is 0.5%. After incubation at 37° C./5% $CO_2$ for 5 hours, cells are lysed by addition of luciferin solution (50 mM Tris, 1 mM $MgCl_2$, 0.2% Triton-X100, 5 mM DTT, 500 micromolar Coenzyme A, 150 micromolar ATP, and 440 micromolar luciferin) to quantify the activity of the reporter gene luciferase, an indirect measurement of intracellular cAMP production.

Luciferase activity is measured from the cell lysate using a Wallac Victor 2 luminometer. The amount of lumen production which results from a compound of formula I is compared to that amount of lumens produced in response to NDP-α-MSH, defined as a 100% agonist, to obtain the relative efficacy of a compound. The $EC_{50}$ is defined as the compound concentration that results in half maximal stimulation, when compared to its own maximal level of stimulation.

Antagonist assay: Antagonist activity is defined as the ability of a compound to block lumen production in response to NDP-α-MSH. Concentration-response curves are generated for NDP-α-MSH in the absence and presence of a fixed concentration of a solution of a compound of formula I (10×$K_i$ from binding assays). Suspensions of MCR-expressing cells are prepared and are incubated with NDP-α-MSH and compound solutions for 5 hours as described above. The assay is terminated by the addition of luciferin reagent and lumen production is quantified. Antagonist potency is determined from the rightward shift of the $EC_{50}$ value in the absence of a compound of formula I using the equation: $K_b$=Concentration of Antagonist/[($EC_{50}$'/$EC_{50}$)−b 1].

Whole Cell cAMP Accumulation Assay

Compound Preparation

In the agonist assay, compounds are prepared as 10 M, and NDP-alpha-MSH (control) as 33.3 μM stock solutions in 100% DMSO. These are serially diluted in 100% DMSO. The compound plate is further diluted 1:200 in compound dilution buffer (HBSS-092, 1 mM Ascorbic Acid, 1 mM IBMX, 0.6% DMSO, 0.1% BSA). The final concentration range being 10 μM–100 pM for compound and 33.33 nM–0.3 pM for control in 0.5% DMSO. Transfer 20 μl from this plate into four PET 96-well plates (all assays are performed in duplicate for each receptor).

Cell Culture and Cell Stimulation

HEK 293 cells stably transfected with the MC3R and MC4R were grown in DMEM containing 10% FBS and 1% Antibiotic/Antimycotic Solution. On the day of the assay the cells were dislodged with enzyme free cell dissociation solution and resuspended in cell buffer (HBSS-092, 0.1% BSA, 10 mM HEPES) at 1×e6 cells/ml. Add 40 µl of cells/well to the PET 96-well plates containing 20 microliter diluted compound and control. Incubate@37° C. in a water bath for 20 minutes. Stop the assay by adding 50 µQuench Buffer (50 mM Na Acetate, 0.25% Triton X-100).

Radioligand Binding Assays

Radioligand binding assays were run in SPA buffer (50 mM Sodium Acetate, 0.1% BSA). The beads, antibody and radioligand were diluted in SPA buffer to provide sufficient volume for each 96-well plate. To each quenched assay well was added 100 microliter cocktail containing 33.33 microliter of beads, 33.33 microliter antibody and 33.33 microliter $^{125}$I-cAMP. This was based on a final concentration of 6.3 mg/ml beads, 0.65% anti-goat antibody and 61 pM of $^{125}$I-cAMP (containing 25000–30000 CPM) in a final assay volume of 210 microliter. The plates were counted in a Wallac MicroBeta counter after a 12-hour incubation.

The data was converted to pmoles cAMP using a standard curve assayed under the same conditions. The data was analyzed using Activity Base software to generate agonist potencies (EC50) and percent relative efficacy data to NDP-alpha-MSH.

C. In vivo Food Intake Models:

1) Daily food intake. Male Long-Evans rats are injected intracerebroventricularly (ICV) with a test compound in 5 microliters of 50% propylene glyco/artificial cerebrospinal fluid one hour prior to onset of dark cycle (12 hours). Food intake is determined by subtracting the food weight remaining after 24 hours from food weight just prior to ICV injection.

2) Acute Calorimetry. Male Long-Evans rats are administered test compound by subcutaneous injection, intramuscular injection, intravenous injection, intraperitoneal injection, ICV injection or by oral gavage between 0 and 5 hours after the onset of the dark cycle. Rats are placed into a calorimetry chamber and the volume of oxygen consumed and volume or carbon dioxide exhaled are measured each hour for 24 hours. Food intake is measured for the 24 hour period as described in C. 1). Locomoter activity is measured when the rat breaks a series of infrared laser beams when in the calorimeter. These measurements permit calculation of energy expenditure, respiratory quotient and energy balance.

3) Food intake in diet induced obese mice. Male C57/B16J mice maintained on a high fat diet (60% fat calories) for 6.5 months from 4 weeks of age are dosed intraperitoneally with a compound of formula I. Food intake and body weight are measured over an eight day period. Biochemical parameters relating to obesity, including leptin, insulin, triglyceride, free fatty acid, cholesterol and serum glucose levels are determined.

D. Rat Ex Copula Assay:

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes about 4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation, animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copulu genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and/or vehicle evaluations are conducted to determine how and if an animal will respond. Some animals have a long duration until the first response while others are non-responders altogether. During this baseline evaluation, latency to first response time, number and type of responses are recorded. The testing time frame is 15 minutes after the first response.

After a minimum of 1 day between evaluations, these same animals are administered a compound of formula I at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICY).

E. Models of Female Sexual Dysfunction:

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna, et al., *Am. J. Physiol.*, (Regulatory Integrative Comp. Physiol 30):R1276–R1285, 1991; McKenna, et al., *Pharm. Bioch. Behav.*, 40:151–156, 1991; and Takahashi, et al., *Brain Res.*, 359:194–207, 1985.

Preparation of the Compounds of the Invention

Preparation of the compounds of the present invention may be carried out via sequential or convergent synthetic routes. The skilled artisan will recognize that, in general, the three domains of a compound of formula I are connected via amide bonds. The B and C domains are optionally connected via a reduced or partially reduced amide bond (e.g., via reductive amination). The skilled artisan can, therefore, readily envision numerous routes and methods of connecting the three domains via standard peptide coupling reaction conditions.

The phrase "standard peptide coupling reaction conditions" means coupling a carboxylic acid with an amine using an acid activating agent such as EDC, dicyclohexylcarbodiimide, and benzotriazol-1-yloxytris (dimethylamino)phosphonium hexafluorophosphate in a inert solvent such as DCM in the presence of a catalyst such as HOBT. The uses of protective groups for amine and carboxylic acids to facilitate the desired reaction and minimize undesired reactions are well documented. Conditions required to remove protecting groups which may be present can be found in Greene, et al., *Protective Groups in Organic Synthesis*, John Wiley & Sons, Inc., New York, N.Y. 1991.

CBZ, Boc or FMOC protecting groups are used extensively in the synthesis, and their removal conditions are well known to those skilled in the art. For example, removal of CBZ groups can he achieved by catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, removal of CBZ can also be achieved by treatment with a solution of hydrogen bromide in acetic acid, or by treatment with a mixture of TFA and dimethylsulfide. Removal of Boc protecting groups is carried out in a solvent such as methylene chloride, methanol or ethyl acetate with a strong acid, such as TFA or HCl or hydrogen chloride gas.

The compounds of formula I, when exist as a diastereomeric mixture, may be separated into diastereomeric pairs of enantiomers by fractional crystallization from a suitable solvent such as methanol, ethyl acetate or a mixture thereof. The pair of enantiomers thus obtained may be separated into individual stereoisomers by conventional means by using an optically active acid as a resolving agent. Alternatively, any enantiomer of a compound of the formula I may be obtained by stereospecific synthesis using optically pure starting materials or reagents of known configuration.

The compounds of the present invention can be prepared according to the procedure of the following schemes and examples, which may further illustrate details for the preparation of the compounds of the present invention. The compounds illustrated in the examples are, however, not to be construed as forming the only genus that is considered as the present invention.

Reaction Scheme 1: Coupling Procedure

Procedure 1

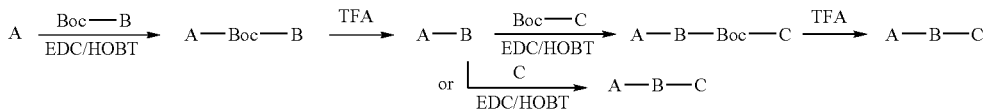

Procedure 2

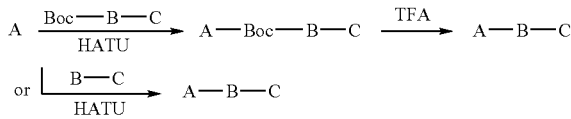

Procedure 3

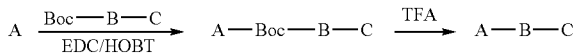

Procedure 4

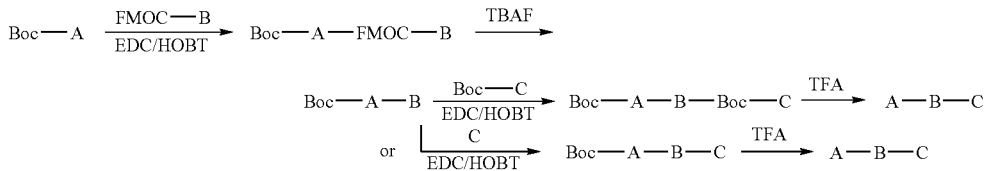

Procedure 5

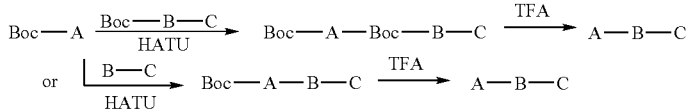

Procedure 6

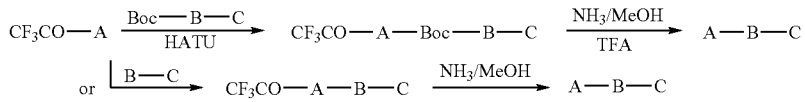

In coupling procedure 1, an appropriate A domain (e.g., piperazine) is coupled to B domain (e.g., D-Boc-p-Cl-Phe-OH) in the presence of EDC/HOBt followed by Boc deprotection in the presence of TFA. The coupled AB compound is then coupled to an appropriate C domain followed by deprotection of Boc group and salt formation. Alternatively, when C domain is not protected with Boc group, the final compound can be obtained without the deprotection step.

In coupling procedure 2, an appropriate A domain (e.g., piperazine) is coupled to an appropriate BC domain in the presence of HATU followed by deprotection of Boc group in the presence of TFA and salt formation. Alternatively, when BC domain is not protected with Boc group, the final compound can be obtained without the deprotection step.

In coupling procedure 3, an appropriate A domain is coupled to an appropriate BC domain in the presence of EDC/HOBT followed by deprotection of Boc group in the presence of TFA and salt formation.

In coupling procedure 4, an appropriate AB domain is coupled to an appropriate C domain in the presence of EDC/HOBT followed by deprotection of Boc group in the presence of TFA and salt formation. Alternatively, when C domain is not protected with Boc group, the final compound can be obtained without the deprotection step.

In coupling procedure 5, an appropriate A domain is coupled to an appropriate BC domain (protected or non-protected BC domain) in the presence of HATU followed by deprotection of Boc group in the presence of TFA and salt formation In coupling procedure 6, an appropriate A domain is coupled to an appropriate BC domain (protected or non-protected BC domain) in the presence of HATU followed by deprotection of $CF_3CO$ group in the presence of $NH_3$/MeOH and salt formation. Coupling procedure 6 is preferred to prepared piperidine derivatives of the present invention.

Alternatively, EDC/HOAT, EDC/HOBT or DCC/HOBT can be used when A domain is coupled with B domain.

Generally, the starting material of Boc-protected piperazine (A domain) can be deprotected in the presence of TFA/$CH_2Cl_2$, HCl/EtOAc, HCl/dioxane, or HCl in MeOH/$Et_2O$ with or without a cation scavenger, such as dimethyl sulfide (DMS) before being subjected to the coupling procedure. It can be freebased before being subjected to the coupling procedure or in some cases used as the salt.

A suitable solvent such as $CH_2Cl_2$, DMF, THF or a mixture of the above solvents can be used for the coupling procedure. Suitable base includes triethyl amine (TEA), diisopropyethyl amine (DIPEA), N-methymorpholine, collidine, or 2,6-lutidine. Base may not be needed when EDC/HOBt is used.

Generally after the reaction is completed, the reaction mixture can be diluted with an appropriate organic solvent, such as EtOAc, $CH_2Cl_2$, or $Et_2O$, which is then washed with aqueous solutions, such as water, HCl, $NaHSO_4$, bicarbonate, $NaH_2PO_4$, phosphate buffer (pH 7), brine or any combination thereof. The reaction mixture can be concentrated and then be partitioned between an appropriate organic solvent and an aqueous solution. The reaction mixture can be concentrated and subjected to chromatography without aqueous workup.

Protecting group such as Boc or CBZ, FMOC, $CF_3CO$ and $H_2$/Pd—C can be deprotected in the presence of TFA/$CH_2Cl_2$, HCl/EtOAc, HCl/dioxane, HCl in MeOH/$Et_2O$, NH3/MeOH, TBAF or $H_2$/Pd—C with or without a cation scavenger, such as thioanisole, ethane thiol and dimethyl sulfide (DMS). The deprotected amines can be used as the resulting salt or are freebased by dissolving in $CH_2Cl_2$ and washing with aqueous bicarbonate or aqueous NaOH. The deprotected amines can also be freebased by SCX ion exchange chromatography.

The compounds of the present invention can be prepared as salt, such as TFA, hydrochloride or succinate salts by using known standard methods.

In the Schemes, Preparations and Examples below, various reagent symbols and abbreviations have the following meanings:

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | dichloromethane |
| DEAD | diethyl azodicarboxylate |
| DIAD | diisopropyl azodicarboxylate |
| DIPEA | diisopropylethylamine |
| DMAP | 4-dimethylamino pyridine |
| DMF | N,N-dimethylformamide |
| DMSO | dimethylsulfoxide |
| eq. | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| FMOC | 9-Flurorenylmethyl carbamate |
| HATU | O-(7-azabenzotriazol-1-yl)-N,N,N',N'-tetramethyluronium hexafluorophosphate |
| HOAT | 1-hydroxy-7-azabenzotriazole |
| HOBT | 1-hydroxybenzotriazole hydrate |
| HPLC | high performance liquid chromatography |
| HRMS | high resolution mass spectroscopy |
| h (hr) | hour(s) |
| LRMS | low resolution mass spectroscopy |
| Me | methyl |
| Ms | methanesulfonyl |
| NMM | 4-methyl morpholine |
| $Pd_2(dba)_3$ | tris(dibenzylideneacetone) dipalladium(0) |
| Ph | phenyl |
| Phe | phenylalanine |
| Pr | propyl |
| r.t. | room temperature |
| TBAF | tetrabutylammonium fluoride |
| TBS | tertbutyldimethylsilyl |
| TFA | trifluoroacetic acid |
| TEA | triethylamine |
| THF | tetrahydrofuran |
| Tic | 1,2,3,4-tetrahydroisoquinoline-3-carboxylic acid |
| TLC | thin-layer chromatography |

Reaction Scheme for Preparation of "A Domain"

The A domains of the present invention, in general, may be prepared from commercially available starting materials via known chemical transformations. The preparation of A domain of the compound of the present invention is illustrated in the reaction scheme 2 below.

Reaction Scheme 2: "A Domains"

1. Mitsunobu followed by Buchwald

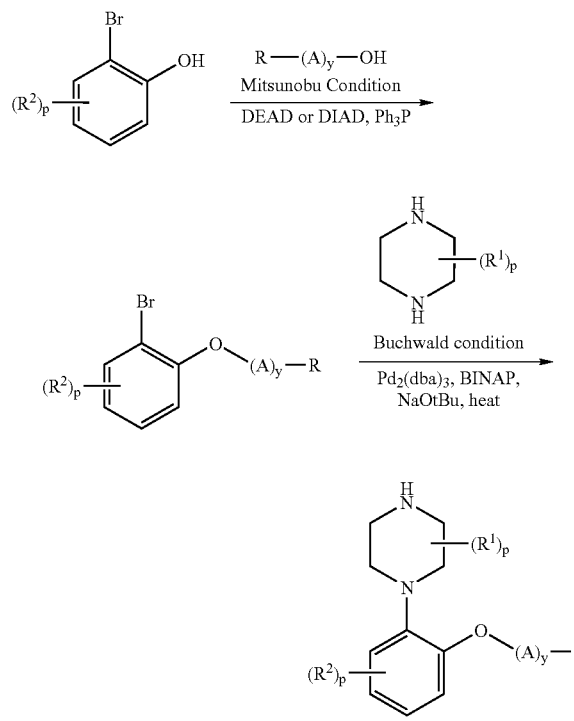

2. SNAr followed by Buchwald

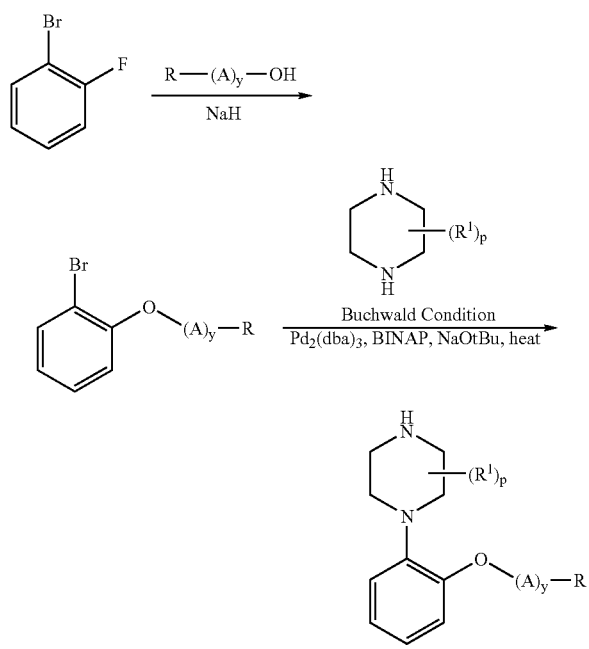

3. Mitsuno

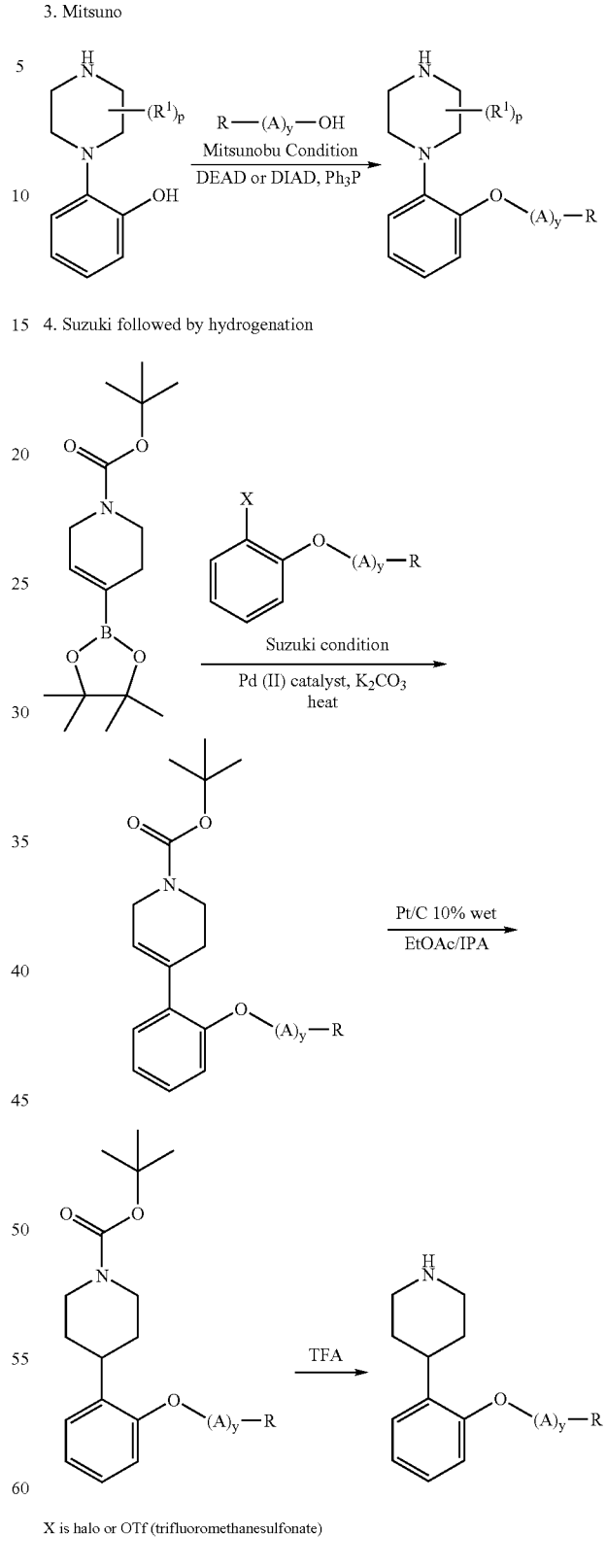

4. Suzuki followed by hydrogenation

X is halo or OTf (trifluoromethanesulfonate)

The present invention also provides a novel process for preparing certain intermediates and/or compounds of the invention as shown in Reaction Schemes 3–5.

Reaction Scheme 3:

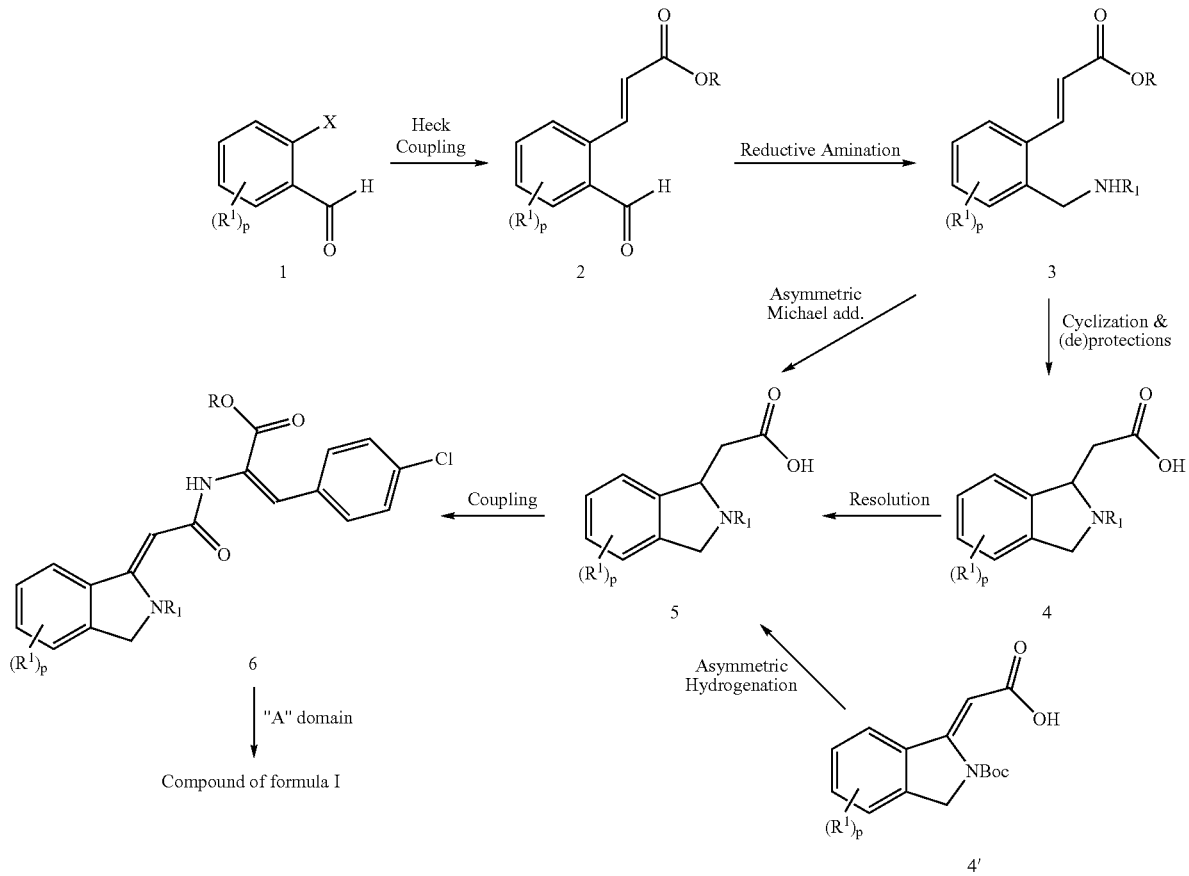

As shown in Reaction Scheme 3, a convergent synthesis of a key intermediate isoindoline (5) via a Heck coupling, followed by a reductive amination, a ring cyclization and a resolution has been developed. Also, alternate asymmetric approaches including asymmetric Michael addition and asymmetric hydrogenation have also been developed to prepare compounds of the invention and/or intermediates thereof.

As shown in Reaction Scheme 3, the isoindoline compounds of the present invention may be prepared from 2-halobenzaldehyde 1 or substituted analog thereof. Preferred starting material is 2-bromobenzaldehyde or substituted analog thereof. Pd-mediated Heck coupling of 2-bromobenzaldehydes 1 with for example, methyl acrylate, provided alpha,beta-unsaturated methyl esters 2, which undergoes reductive amination to give amines, 3 (or carbamates where $R_1$ is for example, Boc). Various Heck coupling reagents and conditions were found suitable to effect the coupling reaction. Suitable catalysts and ligands include $Pd(OAc)_2/PPh_3$, $Pd(OAc)PPh_3/BU_4NBr$, $Pd(PPH_3)_2Cl_2/CUI$, $Pd(OAC)_2/P(O-Tol)_3$. Suitable solvent or solvent systems for the Heck coupling reaction include DMF, toluene and ethyl acetate. More preferred base is triethylamine.

Reductive amination of the aldehyde functionality of 2 to amines is accomplished in good yields by reaction with benzylamine or alpha-methylbenzylamine in acidic conditions, followed by in situ reduction of the incipient imines with $NaCNBH_3$ at about pH 5. Other reducing agents including $Na(OAc)_3BH$ and $NaBH/H$ may also be used to effect reduction of the incipient imines. Interestingly, the resulting amines immediately cyclized to the isoindoline compounds under the same acidic conditions for the reduction. Direct preparation of compound 4 may also be effected by use of $BocNH_2$ instead of benzylamine in the reductive amination step. Screening of various reducing agents demonstrated that the combination of $Et_3SiH$ and TFA in $CH_3CN$ represents the preferred method for effecting reductive amination using $BocNH_2$.

The N-Boc isoindolinecarboxylic acid 5 may also be prepared from 3 as the carbamate, by an intra-molecular Michael addition and ester hydrolysis. The resolution of the isoindolinecarboxylic acids 4 by crystallization afforded enantio-pure compounds 5.

Two alternate asymmetric approaches have also been developed for the synthesis of isoindolinecarboxylic acid 5 i.e., asymmetric Michael additions and asymmetric hydrogenation. In the asymmetric Michael addition approach, alpha-methylbenzyl amine is used as a chiral auxiliary to induce the enantio-selectivity. In the asymmetric hydrogenation approach, compound 4' could be converted to 5 stereoselectively in the presence of chiral ligands.

Finally the coupling of the isoindolines 5 with the "B" domain piece, i.e., D-Cl-Phe to afford compound 6 ("BC" piece) is accomplished by standard amino acid coupling reactions such as, for example, by the use of EDC or EDCI or other activating agents in the presence of suitable is dimethylaminopyridine (DMAP). The product (6) is then coupled with an "A" domain piece as discussed herein to afford the target MC4R agonist compound of formula I by coupling reactions known to one of skill in the art.

Preferably, the isoindole or other "C" domain piece is coupled to an "AB" coupled domain piece to form the compound of formula I.

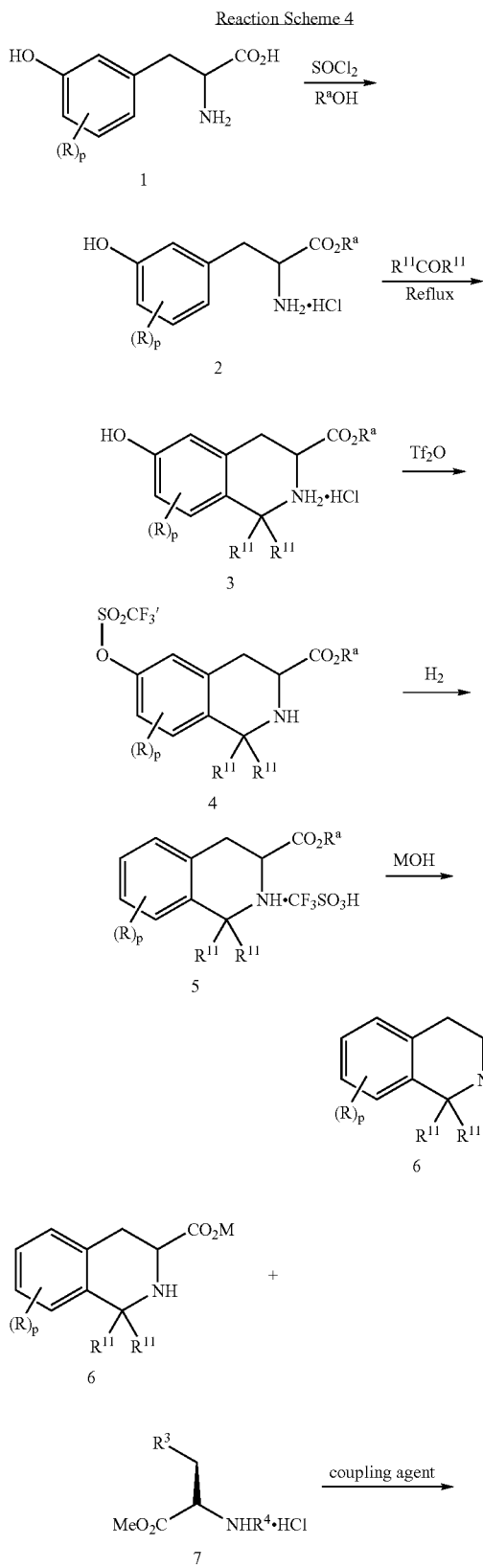

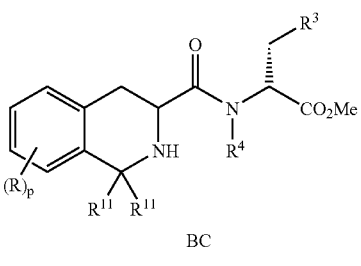

$M = Li^+, K^+, Na^+$

As shown in Reaction Scheme 4, m-tyrosine ester or analogs, including substituted analogs thereof, may be esterified by forming the acid halide followed by nucleophilic displacement of halide by the alkoxy group from an alcohol, i.e., methanol or ethanol. Where thionyl chloride or other halide source is used the product may be isolated as the acid addition salt (2). The resulting ester (2) is subjected to a Pictet-Spengler reaction by heating with a suitable ketone or aldehyde in refluxing conditions. For example, an unsubstituted isoquinoline backbone (3) may be formed by employing formaldehyde in the pictet-Spengler reaction. On the other hand, a gem-dimethyl substituted isoquinoline wherein $R^{11}$ is methyl, may be formed by using acetone as the ketone source and solvent. Other less reactive substituents may be substituted as the $R^{11}$ group for the practice of the present invention.

The product isoquinoline (3) may be isolated preferably as the acid addition salt. Where m-tyrosine is used as the starting material, the free hydroxyl group is removed first by protection/activation with a good leaving group such as, for example, reaction with triflic anhydride (trifluoromethane sulfonic anhydride) or methanesulfonic acid to form the triflate or mesylate in the presence of a base. The triflate is a preferred group used to set up the compound (3) for deoxygenation because of the extra electron withdrawing effect of the trifluoromethane substituent. The deoxygenation reaction is effected by hydrogenation at pressures of about 50 psi. The product (4) may be isolated as the acid addition salt. The product (4) is hydrolyzed under basic conditions to afford the acid salt. Suitable bases for the above hydrolysis include aqueous sodium hydroxide, potassium hydroxide and sodium lithium hydroxide. The reaction is preferably performed in a mixture of aqueous and organic solvents. An exotherm during addition of base may be regulated (i.e., less than about 35° C.) to avoid overheating or "runaway reactions." The reaction product may be isolated by aqueous work up. Alternatively, the entire mixture may be concentrated and washed with organic solvents to afford the desired product (6) after crystallization.

The product (6) is then reacted with a "B" domain substrate such as, for example, 4-chloro-D-phenylalanine as described previously and in the experimental section. The resulting "BC" combination product is then reacted with an "A" domain piece to form the respective compound of formula I. Alternatively, the product (6) may be reacted with an "AB" domain combination product to afford a compound of formula I.

One of skill is aware that certain protections and deprotections of intermediates in Reaction Scheme 4, to form the carbamate, substituted amine or free amine at the isoquinolinyl nitrogen are possible and contemplated as within the scope of this invention. Unless otherwise specified, reagents and procedures for effecting the reactions described herein are known to one of skill in the art and may be found in general reference texts such as *Advanced Organic Chemistry* by J. March, 5th edition, Wiley Interscience Publishers, New York, N.Y., and references therein.

In an alternate procedure, the isoquinoline product i.e., compound (3) or (5) including their N-protected analogs may be resolved by reaction with a resolving agent such as for example, L-tartaric acid, dehydroabietylamine or other resolving agents known to one of skill in the art.

Alternatively, asymmetric analogs of product (6) may be prepared by using asymmetric starting materials. For example, L-DOPA may be used in place of m-tyrosine ester in reactions essentially similar to those described and illustrated in Reaction Scheme 4 and in the examples, to afford the asymmetric analog of compound (6).

Tetrahydroisoquinoline acetic acid derivatives may be prepared and utilized as shown in Reaction Scheme 5 below:

then reacted with an A-domain piece to afford a compound of formula I. The details of the specific reaction steps are similar to or analogous to reactions taught herein, and in the experimental section. Furthermore, one of skill in the art is aware of that such intermediate reactions as hydrolysis and deprotection may be necessary to achieve optimum yields in certain steps of the scheme as shown. One of skill in the art is also aware of further common manipulations such as N-alkylation, or N-acylation, and alkylations on the benzene ring to afford other compounds of formula I.

The following describes the detailed examples of A Domain preparation.

Reaction Scheme 5

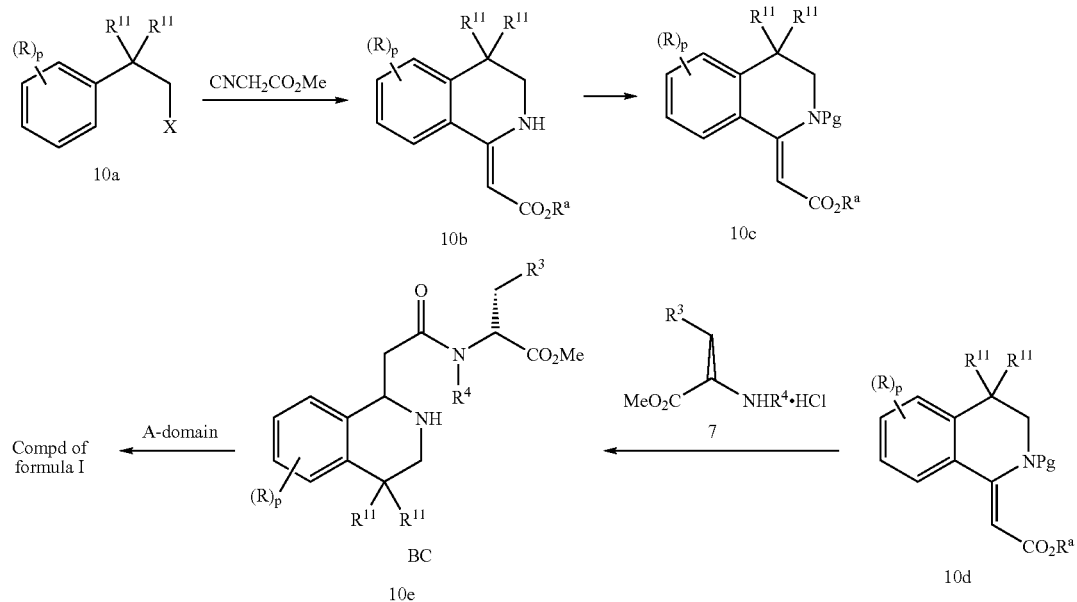

As shown in Reaction Scheme 5, a compound of formula 10a wherein X is halogen, preferably bromo or chloro, and R and $R^{11}$ are as defined previously, and which is obtained commercially or prepared from commercial starting materials is reacted with cyanomethylethylacetate to afford a compound of formula 10b. The compound of formula 10b may be protected as the compound 10c with a suitable protecting group (Pg) and then subjected to hydrogenation conditions including for example asymmetric hydrogenation to form a compound of formula 10d, which may be chiral (depending on hydrogenation conditions, i.e., asymmetric versus non-asymmetric hydrogenation). The compound of formula 10d or stereoisomer thereof, is reacted with a B-domain piece such as, for example, 4-chloro-D-phe to afford a BC piece (10e). The compound of formula 10e is Preparation of 1A Dimethyl-[1-methyl-2-(2-piperazin-1-yl-phenoxy)-R-ethyl]-amine

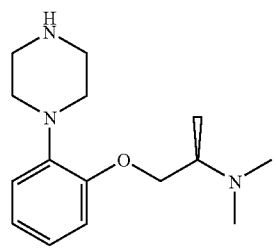

Step 1:

[2-(2-Bromo-phenoxy-1-R-methyl-ethyl]-carbamic acid tert-butyl ester

The o-bromophenol (1.98 g, 11.4 mmol) and R-2-hydroxy-1-methyl-ethyl-carbamic acid tert-butyl ester (2 g, 9.92 mmol) were placed in THF (60 mL) with triphenylphosphine (4.5 g, 17.1 mmol), and the system was cooled to about 0° C. DIAD (3.37 mL, 17.1 mmol) was added portion-wise over 30 minutes. The mixture was warmed to r.t. and stirred for about 16 hours. The mixture was diluted with ether (200 mL) and water was added (100 mL). The mixture was washed with 5N NaOH (100 mL) and extracted with ether and concentrated. A solution ethyl acetate/hexanes was added, and the triphenylphosphine oxide was crystallized and filtered away. Chromatography on silica gel (ethyl acetate/hexanes) afforded about 2.78 g of the product (74%) as clear oil. MS found: 230.0 (M-Boc)

Step 2:

2-(2-bromo-phenoxy)-1-R-methyl-ethylamine

The compound of Step 1 (2.78 g, 8.42 mmol) was placed in DCM (10 mL) and TFA (10 mL) was added. The mixture was stirred at r.t. for about 16 hours and then concentrated and subjected to SCX anion exchange chromatography for purification. About 1.84 g of the title compound was obtained as clear oil (95%). MS found 230.0

Step 3:

[2-(2-Bromo-phenoxy)-1-R-methyl-ethyl]-dimethyl amine

The compound of Step 2 (1.84 g, 7.99 mmol), formaldehyde (1.7 mL of 37% aq.), sodium triacetoxy borohydride (9.5 g, 44.7 mmol), and acetic acid (5.5 mL) were mixed together and stirred in dichloroethane (36 mL) at r.t. for about 4 hours. The mixture was diluted with DCM, quenched with 1N NaOH (100 mL), and then the layers separated. The aqueous layer was back extracted with ether (50 mL) and the organic phases were combined, which was then dried, filtered and concentrated. Chromatography on silica gel afforded about 714 mg of the product (35%).

MS found 258.0

Step 4: The compound of Step 3 (714 mg, 2.72 mmol), piperazine (283 mg, 3.26 mmol), Pd$_2$(dba)$_3$ (126 mg, 0.14 mmol), BINAP (255 mg, 0.41 mmol), and sodium tert-butoxide (368 mg, 3.81 mmol) were mixed together, degassed and toluene(20 mL) was added. The mixture was heated to 100° C. for about 16 hours. The mixture was cooled to r.t., diluted with ether (50 mL), filtered through celite and concentrated. The residue was subjected to SCX purification, and the resultant oil was chromatographed on silica gel (MeOH (NH$_3$2M)/DCM) to give the final compound (243 mg, 34%) as yellow oil. MS found 264.2, M+1

Preparation of 2A

Dimethyl-[1-methyl-2-(2-piperazin-1-yl-phenoxy)-S-ethyl]-amine

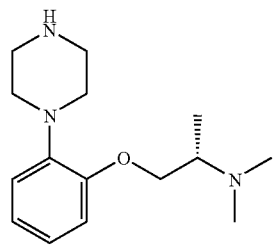

The title compound was prepared in a manner similar to Preparation 1A except that S-2-hydroxy-1-methyl-ethyl-carbamic acid tert-butyl ester was used.

MS found 264.2, M+1

Preparation of 3A

4-[1-Methyl-2-(2-piperazin-1-yl-phenoxy)-R-ethyl]-morpholine

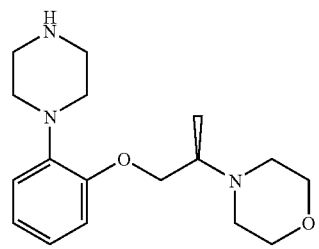

Step 1:
4-[2-(2-Bromo-phenoxy-1-R-methyl-ethyl]morpholine

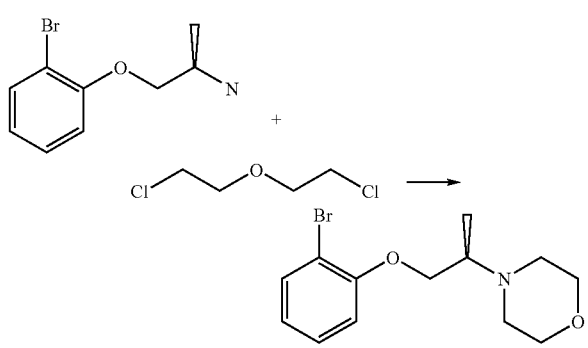

2-(2-Bromo-phenoxy)-1-R-methyl-ethylamine (Preparation 1, Step 2)(1 g, 4.35 mmol), 1-chloro-2-(2-chloroethoxy)-ethane (809 mg, 5.66 mmol), potassium iodide (145 mg, 0.87 mmol), potassium carbonate (2.4 g, 17.4 mmol) and ethanol (40 mL) were mixed together and heated at reflux for about 4 days. The mixture was concentrated to an oil, and the oil was taken up in DCM and washed with water.

The organic fraction was dried and concentrated. Chromatography on silica gel (MeOH/DCM) yielded the product (792 mg, 61%) as clear oil. MS found: 300.0 (M+1)

Step 2: The title compound was prepared by using Buchwald condition from piperazine and 4-[2-(2-Bromo-phenoxy-1-R-methyl-ethyl]morpholine. MS found 306.2, M+1

Preparation of 4A (R)-Ethyl-[1-methyl-2-(2-piperazin-1-yl-phenoxy)-ethyl]-amine

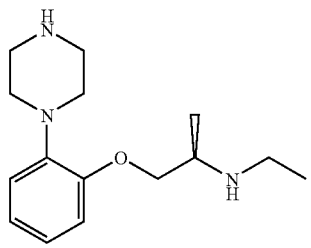

Step 1: (R)-[2-(2-Bromo-phenoxy)-1-methyl-ethyl]-ethyl-amine (R)-2-(2-bromophenoxy)-1-methylethylamine, (Preparation 1A, Step 2) (1.68 g, 7.3 mmol) was dissolved in DMF (16 ml). The mixture was stirred with bromoethane (3.18 ml, 43 mmol) and K$_2$CO$_3$ (7.60 g, 55 mmoles) at r.t. under N$_2$ for about 3 days. The mixture was concentrated, dissolved in EtOAc, washed with water and brine, dried over Na$_2$SO$_4$, and filtered. Solvent was removed and the residue was purified by flash chromatography (silica gel, 5% 2M NH$_3$ in MeOH/CH$_2$Cl$_2$) to give about 2.08 g of a mixture of diethyl and monoethyl amine compounds with the mono ethyl as the minor product.

MS ES MH+286/288 (1:1) (di) and MH+258/260 (1:1) (mono)

Step 2: (R)-Ethyl-[1-methyl-2-(2-piperazin-1-yl-phenoxy)-ethyl]-amine

The compounds of Step 1 (0.88 mg, 3.1 mmoles) was dissolved in dry toluene (8 ml) and then piperazine (0.34 g, 4.0 mmoles), Pd$_2$(dba)$_3$ (0.140 g, 0.15 mmol), BINAP (0.29 g, 0.46 mmol) and sodium tert-butoxide (0.41 g, 4.3 mmol) were added. The mixture was degassed and heated to about 85° C. for about 16 hours. The mixture was allowed to cool to r.t., and diluted with THF. The mixture was filtered through celite and then concentrated. The residue was purified by flash chromatography (silica gel, 5% 2N NH$_3$ in MeOH/CH$_2$Cl$_2$) to give a mixture (0.34 g) of mono- and di-ethyl compound, mono ethyl being as the minor product.

MS ES MH+ 292 (1:1) (di) and MH+ 264 (1:1) (mono)

Preparation of 5A

N-Ethyl-N-[1-methyl-2-(2-piperazin-1-yl-phenoxy)-R-ethyl]-Methanesulfonamide

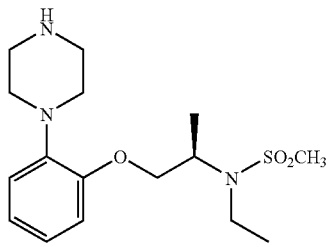

Step 1: N-[2-(2-Bromo-phenoxy)-1-R-methyl-ethyl]-acetamide 2-(2-bromo-phenoxy)-1-R-methyl-ethylamine (Preparation 1A, Step 2) (1.44 g, 6.26 mmoles) was mixed with acetic anhydride (10 ml) and stirred at r.t. for an hour and then stirred another hour at 40–45° C. The mixture was concentrated and water was added. The mixture was extracted with EtOAc, washed with NaHCO$_3$ and brine, and then dried over Na$_2$SO$_4$ and filtered. Removal of solvent gave a residue, which was purified by flash chromatography (silica gel, EtOAc) to give the acetamide, (1.55 g, 91%).

MS ES MH+ 272/274 (1:1)

Step 2: [2-(2-Bromo-phenoxy)-1-R-methyl-ethyl]-ethyl-amine

N-[2-(2-Bromo-phenoxy)-1-R-methyl-ethyl]-acetamide (0.50 g, 1.8 mmol) was dissolved in THF (10 ml). BH$_3$-THP (1.5 M in THF, 3.6 ml, 5.4 mmol) was added and the mixture was heated at 60° C. for about an hour. The mixture was cooled to r.t., and then DIEA (1.2 ml) in MeOH (2.4 ml) was added followed by the addition of I$_2$ (0.91 g) in THF (5 ml). The mixture was stirred for about 30 minutes and diluted with EtOAc. It was washed with 1N Na$_2$S$_2$O$_3$, and brine, and then dried over Na$_2$SO$_4$ and filtered. Removal of solvent gave the crude ethylamine(0.54 g).

MS ES MH+ 258/260(1:1)

Step 3: N-[2-(2-Bromo-phenoxy)-1-R-methyl-ethyl]-N-ethyl-methanesulfonamide

[2-(2-Bromo-phenoxy)-1-R-methyl-ethyl]-ethyl-amine (0.54 g, 1.8 mmol) was dissolved in CH$_2$Cl$_2$ (10 ml). DIEA (0.63 ml, 3.6 mmol) and MsCl (0.17 ml, 2.2 mmol) were added and the mixture was stirred at r.t. overnight. Additional MsCl (0.51 ml, 6.6 mmol) and DIEA (1.26 ml, 7.2 mmol) were added and the mixture was stirred at r.t. overnight. Additional MsCl (0.34 ml, 4.4 mmol) and DIEA (0.63 ml, 3.6 mmol) were added and then stirred for another 9 hours. The mixture was diluted with EtOAc, washed with diluted NaHCO$_3$ and brine, and then dried over Na$_2$SO$_4$ and filtered. Removal of solvent gave a residue, which was purified by flash chromatography (silica gel, EtOAc/hexane, ⅓) to give the sulfonamide (0.39 g, 64%, in two steps).

MS ES MH+ 336/338 (1:1)

Step 4: The final compound was prepared from piperazine and N-[2-(2-Bromo-phenoxy)-1-R-methyl-ethyl]-N-ethyl-methanesulfonamide using Buchwald condition. MS ES MH+ 342

Preparation of 6A

Dimethyl-[2-(2-piperazin-1-yl-phenoxy)-R,S-propyl]-amine

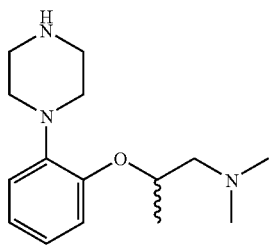

The title compound was prepared in a manner similar to Preparation 1A except that o-bromophenol was coupled with racemic 1-dimethylamino-propan-2-ol.
MS found 264.2, M=+1

Preparation of 7A 3-(2-Piperazin-1-yl-phenoxy)-S-pyrrolidine-1-carboxylic acid tert-butyl ester:

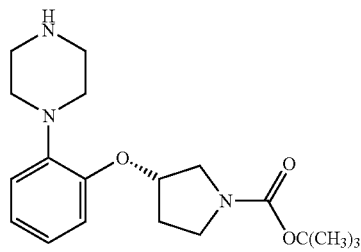

The title compound was prepared in a manner similar to Preparation 1A except that o-bromophenol was coupled with R-3-hydroxy-pyrrolidine-1-carboxylic acid tert-butyl ester. MS found 348.2, M+1

Preparation of 8A 3-(2-Piperazin-1-yl-phenoxy)-R-pyrrolidine-1-carboxylic acid tert-butyl ester

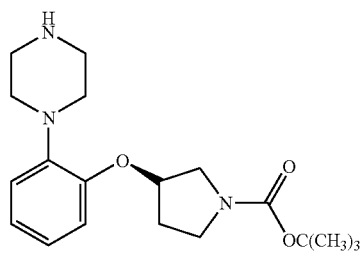

The title compound was prepared in a manner similar to Preparation 7A except that o-bromophenol was coupled with S-3-Hydroxy-pyrrolidine-1-carboxylic acid tert-butyl ester. MS found 348.1 M+1

Preparation of 9A 2-(2-Piperazin-1-yl-phenoxymethyl)-S-pyrrolidine-1-carboxylic acid tert-butyl ester

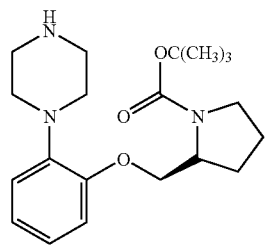

The title compound was prepared in a manner similar to Preparation 1A except that o-bromophenol was coupled with Boc-L-prolinol. MS found 362.3, M+1

Preparation 10A 2-(2-Piperazin-1-yl-phenoxymethyl)-R-pyrrolidine-1-carboxylic acid tert-butyl ester

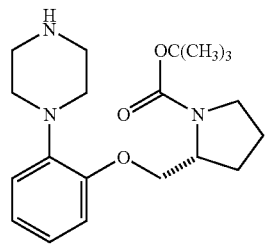

The title compound was prepared in a manner similar to Preparation 1A except that o-bromophenol was coupled with Boc-D-prolinol. MS found 362.2, M+1

Preparation of 11A

4-[2-(1-tert-butoxycarbonyl-S-pyrrolidin-3-yloxy)-5-methyl-phenyl]piperazine

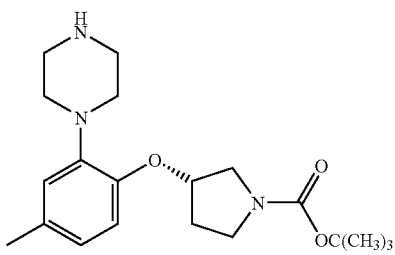

The title compound was prepared in a manner similar to Preparation 1A except that 2-bromo-4-methyl phenol was coupled with N-boc-3-(R)-hydroxy-pyrrolidine.
LRMS (electrospray): 362.3 (M+1)

Preparation of 12A

1-[5-Isopropyl-2-S-(pyrrolidin-3-yloxy)-phenyl]-piperazine

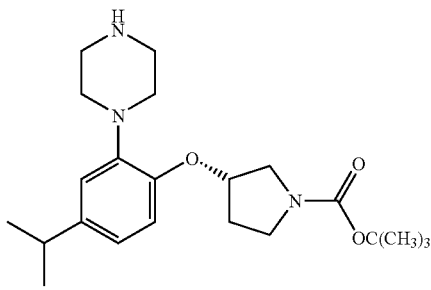

The title compound was prepared in a manner similar to Preparation 11A except that 2-Bromo-4-isopropyl-phenol was coupled with N-boc-3-(R)-hydroxy-pyrrolidine.

Preparation of 13A

1-[2-(1-Methyl-S-piperidin-3-yloxy)-phenyl]-piperazine

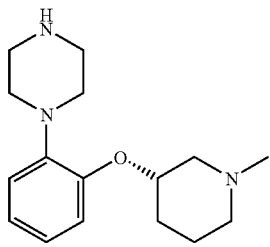

Step 1: R-piperidin-3-ol HCl salt (15 g, 109 mmol) was placed in DCM/water (500 mL of 1/1 mixture) with potassium carbonate (30.1 g, 218 mmol), and di-t-butyl dicarbonate (26.2 g, 120 mmol) was added with off gassing. The mixture was stirred at r.t. overnight and then diluted with DCM (400 mL) and washed with water (2×200 mL). The organic fraction was dried and concentrated to give white crystalline solids (23.2 g).

Step 2: The compound obtained in Step 1 (10 g, 49.68 mmol), ortho bromophenol (7.14 g, 41.4 mmol) and triphenylphosphine (19.55 g, 74.5 mmol) were placed in THF (100 mL), and the mixture was cooled to 0° C. DIAD (14.7 mL, 74.5 mmol) was added dropwise for about 30 minutes, and the mixture was warmed to r.t. and stirred for about 16 hours. The mixture was diluted with ether (500 mL) and water was added (50 mL). Then the organic portion was washed with 5N NaOH (500 mL), and the aqueous phase was extracted with ether (500 mL) and concentrated. The concentrated oil was taken up in EtOAc/hexanes and the triphenylphosphine oxide crystallized. The slurry was filtered, and the filtrate was concentrated and chromatograped on silica gel to give the product (6.65 g, 45%) as a clear oil.

Step 3: The compound obtained in Step 2 (1 g, 2.81 mmol) was placed in DCM/TFA (20 mL of 1/1 mixture), and the mixture was stirred at r.t. for about 16 hours. The mixture was concentrated and subjected to SCX anion exchange chromatography to give the product (775 mg) as a clear oil. MS found 256.

Step 4: The compound of Step 3 (8.63 g, 33.7 mmol), formaldehyde (7.06 mL of 37% aq.), sodium triacetoxy borohydride (40 g, 188.72 mmol) and glacial acetic acid (23.1 mL, 404.4 mmol) were mixed in dichloroethane (153 mL), and the mixture was stirred at r.t. for about 24 hours. The mixture was diluted with DCM (200 mL) and quenched with 1N NaOH (200 mL), and then the layers were separated. The aqueous layer was back extracted with ether (200 mL), and the organic phases were combined, dried, filtered and concentrated. Chromatography gave the product (8.18 g, 90%) as a clear oil. MS found 270.02

Step 5: The compound of Step 4 (4.28 g, 15.84 mmol), piperazine (1.64 g, 19.01 mmol), Pd$_2$(dba)$_3$ (725 mg, 0.792 mmol), BINAP (1.48 g, 2.38 mmol) and sodium tert-butoxide (2.13 g, 22.22 mmol) were mixed together and toluene (100 mL) was added. The mixture was heated to 100° C. for about 5 hours. The mixture was cooled to r.t., diluted with ether (100 mL), filtered through celite and concentrated. The residue was subjected to SCX purification, and the resultant oil was chromatographed to give the final compound (2.12 g, 49%) as a yellow oil. MS found 276.2

Preparation of 14A

1-{2-[1-(2,2,2-Trifluoro-ethyl)-S-piperidin-3-yloxy]-phenyl}-piperazine

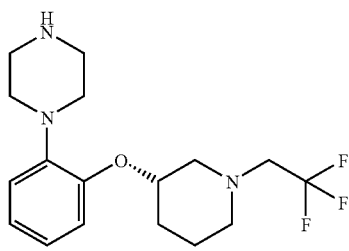

Step 1: 1-[3-(2-Bromo-phenoxy)-S-piperidin-1-yl]-2,2,2-trifluoro-ethanone

About 1.0 g (3.9 mmol) of 3-(2-Bromo-phenoxy)-piperidine was dissolved in 20 ml THF under nitrogen and 1.7 ml (12.0 mmol) trifluoracetic anhydride was added dropwise. The mixture was stirred for about 30 minutes and concentrated in vacuo followed by the addition of ethyl acetate. The mixture was washed with water and brine, and then dried with sodium sulfate and concentrated to dryness. The resulting oil was chromatographed on silica by eluting with 10% ethyl ethyl acetate/90% hexane to afford about 1.25 g of the title compound. Mass MH$^+$ 353

Step 2: 3-(2-Bromo-phenoxy)-1-(2,2,2-trifluoro-ethyl)-S-piperidine

About 1.25 g (2.13 mmol) of compound from Step 1 was dissolved in 14 ml THF under nitrogen and 0.45 ml (2.13 mmol) borontrifluoride etherate was added. The mixture was heated to reflux and 5.3 ml of (6.39 mmol) borane dimethylsulfide was added dropwise over 10 minutes. The mixture was stirred for about 45 minutes and the sulfide was allowed to boil off. After cooling, about 6–7 ml 6N HCl was added and the flask was heated to about 40° C. The mixture was made basic with 2N NaOH and then ethyl acetate was added. The organic layer was separated, washed with brine, dried with sodium sulfate and concentrated to dryness. The resulting oil was chromatographed on silica by eluting with 20% ethyl ethyl acetate/80% hexane to afford about 1.13 g of the title compound. Mass MH+ 339

Step 3: The final compound was prepared by coupling the compound of Step 2 with piperazine under Buchwald condition.

Preparation of 15A 3-(2-Piperazin-phenoxy)-R-piperidine-1-carboxylic acid tert-butyl ester

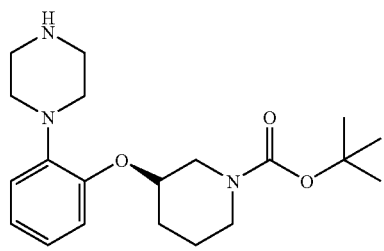

Step 1:

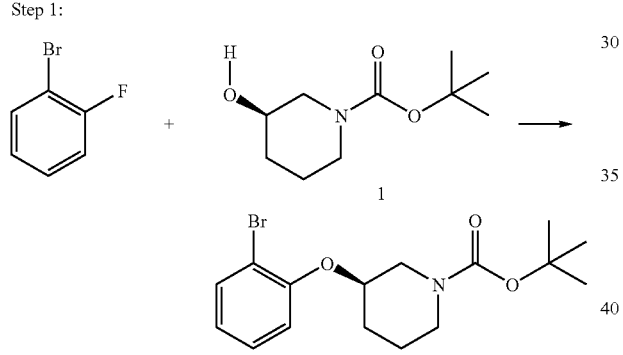

Sodium hydride (2.99 g, 74.55 mmol) (60% in mineral oil) was slurred in DMF (20 mL) and heated to 65° C. To the slurry was added 1 (5 g, 24.85 mmol) in DMF (25 mL) dropwise over 30 minutes. The mixture was stirred at 65° C. for about an hour. Bromofluorobenzene (5.5 mL, 49.7 mmol) in DMF (5 mL) was added dropwise, and the mixture was stirred at 65° C. for about 16 hours. The reaction was diluted with water and concentrated to an oily solid, which was then extracted between water (200 mL) and 1/1 EtOAc/hexanes (200 mL). The organic layer was dried, filtered and concentrated. Chromatography gave the compound 2 (6.35 g, 72%) as a clear oil.

Step 2: Compound 2 (2 g, 5.61 mmol), piperazine (581 mg, 6.74 mmol), Pd$_2$(dba)$_3$ (256 mg, 0.28 mmol), BINAP (523 mg, 0.84 mmol), and sodium tert-butoxide (755 mg, 7.85 mmol) were mixed together and toluene (50 mL) was added. The mixture was heated to 100° C. for about 5 hours. The mixture was allowed to cool to r.t, which was then diluted with ether (100 mL), filtered through celite and concentrated. The residue was subjected to SCX purification, and the resultant oil was chromatographed to give the final compound (1.56 g, 77%) as a yellow oil. MS found 362.2, M+1

Preparation of 16A

1-[2-(1-methyl-R-piperidin-3-yloxy)-phenyl]-phenyl]-piperazine

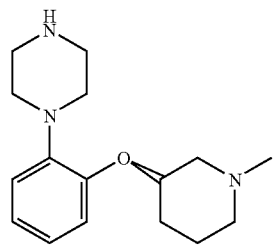

The title compound was prepared in a manner similar to Preparation 13A except that R-3-(2-Bromo-phenoxy)-piperidine was used.

Preparation of 17A

Synthesis of 4-[2-(N-boc-piperidin-4-yloxy)-phenyl]-piperazine

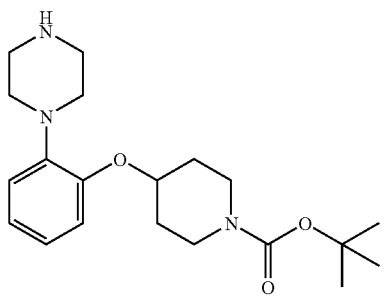

Step 1: N-boc-4(2-bromo-phenoxy)-piperidine

To a slurry of NaH (60% dispersion in oil, 5.9 g, 148.5 mmol, 3.0 eq.) in DMP (40 mL) at 65° C. under N$_2$ was added a solution of N-boc-4-hydroxy piperidine (10 g, 49.5 mmol, 1.0 eq.) in DMF (50 mL). After stirring for about 2 hours, a solution of 1-bromo-2-fluoro benzene (11.0 mL, 99.0 mmol, 2.0 eq.) in DMF (10 mL) was added dropwise. The resulting mixture was stirred at 65° C. overnight. The mixture was diluted with EtOAc (250 mL) and washed with water (100 mL) and brine (100 mL). The aqueous layer was extracted with EtOAc (3×). The combined organic extracts were dried (Na$_2$SO$_4$), filtered and concentrated. Purification by flash chromatography (250 g SiO$_2$, linear gradient, 40 mL/min, 0% to 30% EtOAc/Hexane over 20 minutes and 30% EtOAc for 13 minutes) afforded title compound (14.2 g, 39.8 mmol, 81%). LRMS (electrospray): 358.0.

Step 2: To a solution of N-boc-4-(2-bromo-phenoxy)-piperidine (13.4 g, 39.6 mmol, 1.0 eq.), piperazine (9.73 g, 113 mmol, 3.0 eq.), Pd$_2$dba$_3$ (1.72 g, 1.88 mmol, 0.05 eq.), BINAP (3.5 g, 5.65 mmol, 0.15 eq.) in toluene (150 mL) was added NaOtBu (5.1 g, 52.6 mmol, 1.4 eq.). The mixture was heated to 95° C. and stirred at that temperature overnight. The slurry was diluted with EtOAc and filtered through a pad of celite. The filtrate was concentrated and purified by ion exchange (SCX, 10 g) column. Further purification by flash chromatography (250 g SiO₂, 40 ml/min, linear gradient 0–10% 2.0 M NH₃ in MeOH/CH₂Cl₂ for 20 minutes and 10% 2.0 M NH₃ in MeOH/CH₂Cl₂ for 73 minutes) afforded the final compound (12.65 g, 93%). LRMS (electrospray): 362.7 (M+1).

Preparation of 18A 3-(2-Piperazin-1-yl-phenoxy)-S-piperidine-1-carboxylic acid tert-butyl ester

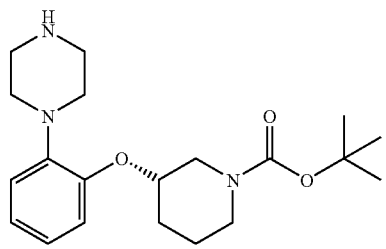

Step 1:
3-(2-Bromo-phenoxy)-S-piperidine-1-carboxlic acid tert-butyl ester

The o-bromophenol (1.72 g, 9.92 mmol) and Boc-R-3-hydroxypiperidine (2 g, 9.92 mmol) were placed in THF (60 mL) with triphenylphosphine (3.9 g, 14.9 mmol), and the system was cooled to 0° C. DIAD (2.94 mL, 14.9 mmol) was added portion wise over 30 minutes and the mixture was warmed to r.t. and stirred for about 16 hours. The mixture was diluted with ether (200 mL) and water was added (100 mL). The mixture was washed with 5N NaOH (100 mL), extracted with ether and concentrated. Ethyl acetate/hexanes was added and the triphenylphosphine oxide was crystallized and filtered away. The residue was chromatographed on silica gel (ethyl acetate/hexanes) afforded the product (588 mg, 17%) as a clear oil. MS found: 256.0 (M-Boc)

Step 2: The compound of Step 1 (588 mg, 1.65 mmol), piperazine (171 mg, 1.98 mmol), Pd₂(DBA)₃ (76 mg, 0.083 mmol), BINAP (154 mg, 0.248 mmol), and sodium tert-butoxide (222 mg, 2.31 mmol) were mixed together and degassed followed by the addition of toluene (15 mL). The mixture was heated to 100° C. for about 16 hours. The mixture was cooled to r.t., and diluted with ether (50 mL), filtered through celite and concentrated. The residue was subjected to SCX purification, and the resultant oil was chromatographed on silica gel (10% MeOH (NH₃ 2M)/DCM) to afford the final compound (103 mg, 17%) as a yellow oil.

MS found 362.2, M=+1

Preparation of 19A 3-(2-Piperazin-1-yl-phenoxy)-piperidine-1-carboxylic acid tert-buyl ester

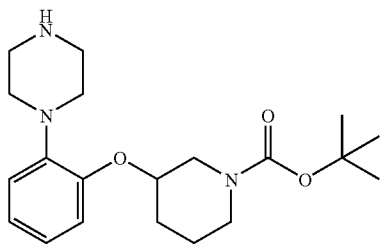

Step 1:
3-(2-Bromo-phenoxy)-piperidine-1-carboxylic acid tert-butyl ester

Ortho-bromophenol (1.72 g, 9.92 mmol) and racemic Boc-3-hydroxypiperidine (2 g, 9.92 mmol) were placed in THF (60 mL) with triphenylphosphine (3.9 g, 14.9 mmol), and the mixture was cooled to 0° C. DIAD (2.94 mL, 14.9 mmol) was added portion wise over 30 minutes, and the mixture was warmed to r.t. and stirred for about 16 hours. The mixture was diluted with ether (200 mL) and water was added (100 mL). The mixture was washed with 5N NaOH (100 mL), extracted with ether and concentrated. Ethyl acetate/hexanes was added, and the triphenylphosphine oxide was crystallized and filtered away. The residue was chromatographed on silica gel (ethyl acetate/hexanes) to afford the product (1.2 g, 34%) as a clear oil. MS found: 256.0 (M-Boc)

Step 2: The compound of Step 1 (600 mg, 1.68 mmol), piperazine (174 mg, 2.02 mmol), Pd₂(dba)₃ (77 mg, 0.084 mmol), BINAP (157 mg, 0.252 mmol), and sodium tert-butoxide (226 mg, 2.35 mmol) were mixed together and degassed followed by the addition of toluene (20 mL). The mixture was heated to 100° C. for about 16 hours. The mixture was cooled to r.t, and then diluted with ether (50 mL), filtered through celite and concentrated. The residue was subjected to SCX purification, and the resultant oil was chromatographed on silica gel (MeOH (NH₃ 2M)/DCM) to give the final compound (311. mg, 51%) as a yellow foam. MS found 362.3, M+1

Preparation of 20A

1-[3-(2-piperazin-1-yl-phenoxy)-R-piperdin-1-yl]-ethanone

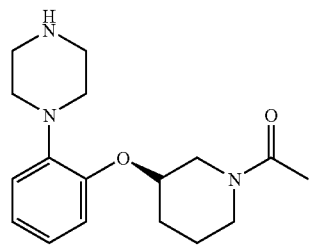

Step 1: 2,2,2-trifluoro-1-{4-[2-(R-piperidin-3-yloxy)-phenyl]-piperazin-1-yl}-ethanone 3-(2-piperazin-1-yl-phenoxy)-R-piperidin-1-carboxylic acid tert-butyl ester (1.56 g, 4.32 mmol) was dissolved in DCM (20 mL). Pyridine (1.37 g, 17.28 mmol) and trifluoroacetic anhydride (1.81 g, 8.63 mmol) were added to the mixture and then stirred at r.t. for about 12 h. The mixture was subjected to an aqueous work up, and then dissolved in DCM/TFA (1/1, 20 mL), which was stirred at r.t. for about 4 hours. The material was concentrated and chromatographed to afford the final compound (1.34 g, 86%) as a yellow foam. MS found: 358.1 M+1

Step 2: The compound of Step 1 was dissolved in acetic anhydride (10 mL) and triethyl amine (3 mL) was added. The mixture was stirred at r.t. for about 6 hours and concentrated to dryness, which was then taken up in DCM (50 mL). The mixture was washed with 1N NaOH (50 mL), and the organic fraction was dried and concentrated. The material was placed in 7N NH3/MeOH (50 mL) and aged for about 48 hours. The resulting material was subjected to SCX purification and purified on silica gel to give the final compound (613 mg, 92%) as a pale yellow oil. MS found 304.2, M+1

Preparation of 21A

1-[3-(2-piperazin-1-yl-phenoxy)-S-piperdin-1-yl]-ethanone

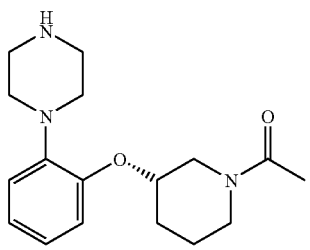

The title compound was prepared in a manner similar to Preparation 20A except that 3-(2-piperazin-1-yl-phenoxy)-S-piperidin-1-carboxylic acid tert-butyl ester was used.

Preparation of 22A

1-[3-(2-Piperazin-1-yl-phenoxy)-piperidin-1-yl]-propan-1-one

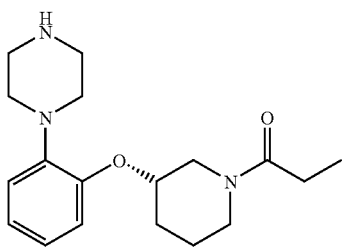

To 2,2,2-trifluoro-1-{4-[2-(S-piperidin-3-yloxy)-phenyl]-piperazin-1-yl}-ethanone (prepared by following substantially similar procedure as described in Preparation 20A) (0.198 g, 0.552 mmol), TEA (0.085 ml, 0.608 mmol) in DCM (2 mL) at 0° C. and propionyl chloride (0.053 ml, 0.608 mmol) was added. The mixture was stirred at r.t. for about 2 hours. The mixture was concentrated and DCM was added. The resulting solution was washed with 1N NaOH, separated, dried over sodium sulfate, and concentrated to give yellow oily material. MS M+1 414.3.

The resulting amide was mixed with 7N $NH_3$ (10 ml) and aged at r.t. for three (3) days. The solution was concentrated and purified through SCX column and chromatographed on silica to afford about 94 mg of the final compound (54%). MS M+1 318.2.

Preparation of 23A

2-Methyl-1-[3-(2-piperazin-1-yl-phenoxy)-piperidin-1-yl]-propan-1-one

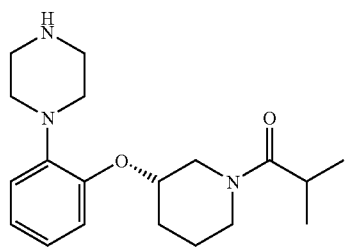

The title compound was prepared in a manner similar to Preparation 22A. MS 332.2, M+H

Preparation of 24A 3-(2-Piperazin-1-yl-phenoxy)-piperidine-1-carboxylic acid methyl ester

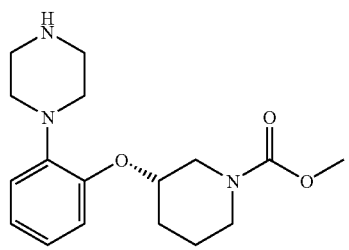

The title compound was prepared in a manner similar to Preparation 22A except that methyl chloroformate was used. MS 320.2, M+H

Preparation of 25A 3-(2-Piperazin-1-yl-phenoxy)-piperidine-1-carboxylic acid ethyl ester

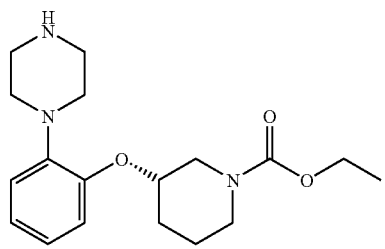

The title compound was prepared in a manner similar to Preparation 22A except that ethyl chloroformate was used. MS 334.2, M+H

Preparation of 26A 3-(2-Piperazin-1-yl-phenoxy)-piperidine-1-carboxylic acid isopropyl ester

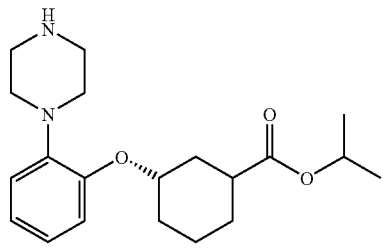

The title compound was prepared in a manner similar to Preparation 22A except that isopropyl chloroformate was used.
MS 348.2, M+H

Preparation of 27A

1-[2-(1-Methanesulfonyl-piperidin-3-yloxy)-phenyl]-piperazine

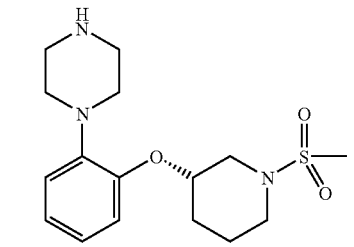

The title compound was prepared in a manner similar to Preparation 22A except that methanesulfonyl chloride was used.
MS 340.2, M+H

Preparation of 28A

1-[2-(1-Ethanesulfonyl-piperidin-3-yloxy)-phenyl]-piperazine

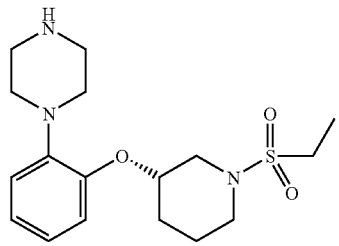

The title compound was prepared in a manner similar to Preparation 22A except that ethanesulfonyl chloride was used.
MS 354.2, M+H

Preparation of 29A

1-{2-[1-(Propane-2-sulfonyl)-piperidin-3-yloxy]-phenyl}-piperazine

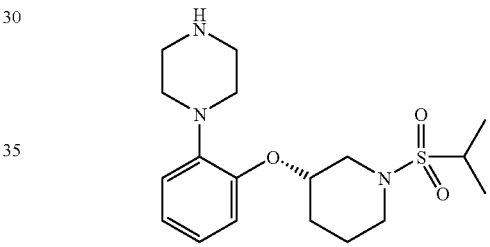

The title compound was prepared in a manner similar to Preparation 22A except that isopropanesulfonyl chloride was used.
MS 368.2, M+H

Preparation of 30A 3-(6-Fluoro-2-piperazin-1-yl-phenoxy)-piperidine-1-carboxylic acid tert-butyl ester

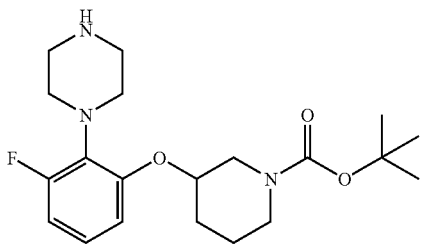

Step 1: 2-Bromo-3-fluoro-anisole

The 3-fluoro anisole (15 g, 119 mmol) was placed in THF (300 mL) and cooled to about −78° C., and then n-BuLi (89 mL 1.6 M in hexanes) was added while maintaining the temperature at around −70° C. The mixture was stirred for about 15 minutes, and bromine (18.9 g, 119 mmol) was added over 10 minutes. The mixture was warmed to r.t. and stirred overnight. The mixture was quenched with water, diluted with ether (500 mL) and partitioned between water/ether (1/1 300 mL). The water layer was back extracted with ether (250 mL), and the combined organic fractions were dried, filtered and concentrated. The dark residue was distilled under house vacuum (product 115–130° C.) to recover about 13.8 g of the product as a gray oil (57%).

Step 2: 2-bromo-3-fluorophenol

2-Bromo-3-fluoro anisole (10 g, 48.77 mmol) was dissolved in DCM (200 mL) and cooled to about −78° C. To the solution was added BBr$_3$ (11.53 mL, 121.9 mmol) in one portion. The mixture was warmed to r.t. and stirred overnight. The mixture was partitioned between water and DCM (50 mL), and the aqueous layer was back extracted with DCM (200 mL). The combined organics were dried (NaSO$_4$), filtered and concentrated to give about 9.32 g of the product as a dark oil. MS found 188.9 (M−1)

Step 3: The final compound was prepared by using Mitsunobu followed by Buchwald condition from 2-bromo-3-fluorophenol and racemic N-boc-3-hydroxypiperidine.

MS found 380.3 M+1

Preparation of 31A

2-Fluoro-5-(2-piperazin-1-yl-phenoxy)-piperidine-1-carboxylic acid tert-butyl ester

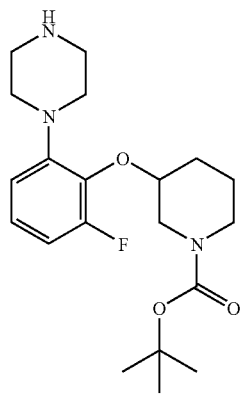

Step 1: 2-Chloro-6-fluoro phenol

2-Chloro-6-fluoro anisole (5 g, 31.13 mmol) was dissolved in DCM (300 mL) and cooled to about −78° C. To the solution was added BBr$_3$ (7.35 mL, 77.8 mmol) in one portion. The reaction was warmed to r.t, stirred for about 16 hours and poured over ice to quench remaining BBr$_3$. The material was partitioned between water and DCM (500 mL each). The aqueous layer was back extracted with DCM (200 mL), and the combined organics were dried (NaSO$_4$), filtered and concentrated to give the product (4.60 g) as a dark oil.

MS found 145.0 M−1

Step 2: The title compound was prepared using Mitsunobu followed by Buchwald condition from 2-chloro-6-fluoro phenol and racemic N-boc-3-hydroxypiperidine.

MS found 380.3 M+1

Preparation of 32A 3-(2-Bromo-4-fluoro-phenoxy)-piperidine-1-carboxylic acid tert-butyl ester

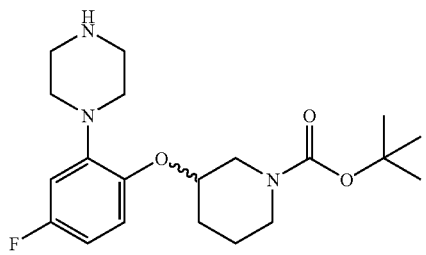

The title compound was prepared by using Mitsonobu followed by Buchwald condition from 2-bromo-4-fluorophenol and racemic N-boc-3-hydroxypiperidine.

MS found: 380.3 M=+1

Preparation of 33A 3-(5-Fluoro-2-piperazin-1-yl-phenoxy)-piperidine-1-carboxylic acid tert-butyl ester

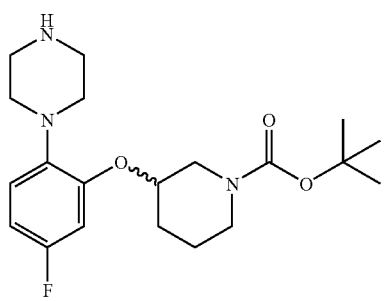

The title compound was prepared by using Mitsunobu followed by Buchwald condition from 2-bromo-5-fluorophenol and racemic N-boc-3-hydroxypiperidine.

Preparation of 34A 3-(2-Piperazin-1-yl-trifluoromethyl-phenoxy)-S-pyrrolidine-1-carboxylic acid tert-butyl ester

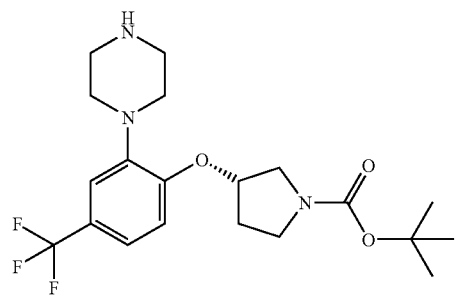

The title compound was prepared by using Mitsunobu followed by Buchwald condition from 2-bromo-4-trifluoromethyl phenol and N-boc-R-3-pyrrolidinol. MS 416.3 (M+1)

Preparation of 35A

4-[2-(2-Morpholin-4-yl-ethoxy)-phenyl]-piperazine-1-carboxylic acid tert-butyl ester

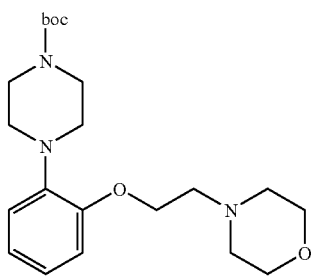

Diisopropyl azodicarboxylate (0.48 mL, 2.4 mmol) was added dropwise to a stirred solution of 4-(2-hydroxy-phenyl)-piperazine-1-carboxylic acid tert-butyl ester (0.56 g, 2 mmol), 2-morpholin-4-yl-ethanol (0.24 mL, 2 mmol) and triphenylphosphine (0.63 g, 2.4 mmol) in THF (20 mL) cooled to 0° C. The resulting solution was warmed to r.t. and stirred for about 16 hours. The solvent was removed in vacuo and the residue purified by silica gel chromatography (ethyl acetate) to afford the final compound (0.50 g, 64%) as a clear oil $^1$H NMR (CDCl$_3$) δ 6.80–7.05 (m, 4H), 4.10–4.15 (m, 2H), 3.55–3.80 (m, 8H), 3.00–3.10 (m, 4H), 2.75–2.85 (m, 2H), 2.60–2.70 (m, 4H), 1.55 (s, 9H); TLC (SiO$_2$): R$_f$=0.25 (ethyl acetate)

Preparation of 36A

4-[2-(1-Methyl-piperidin-4-yloxy)-phenyl]-piperazine-1-carboxylic acid tert-butyl ester

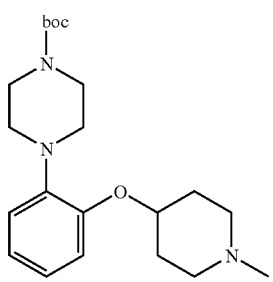

The title compound was prepared by using Mitsunobu condition from 4-(2-hydroxyphenyl)-piperazine-1-carboxylic acid-tert-butyl ester and N-methylpiperidinol.

Preparation of 37A

4-[2-(1-tert-Butoxycarbonyl-piperidin-4-yloxy)-phenyl]-piperazine-1-carboxylic acid benzyl ester

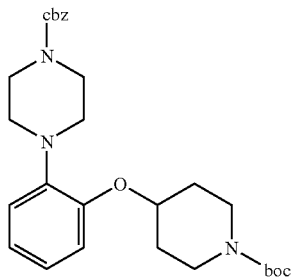

Diisopropyl azodicarboxylate (0.70 mL, 3.55 mmol) was added dropwise to a stirred solution of 4-(2-hydroxy-phenyl)-piperazine-1-carboxylic acid benzyl ester (0.74 g, 2.4 mmol), 4-hydroxy-piperidine-1-carboxylic acid tert-butyl ester (0.48 g, 2.4 mmol) and triphenylphosphine (0.93 g, 3.6 mmol) in THF (25 mL) cooled to 0° C. The resulting solution was warmed to r.t. and stirred for about 16 hours. The solvent was removed in vacuo and the residue purified by silica gel chromatography (20% ethyl acetate in hexanes) to afford the final compound (0.50 g, 43%) as a clear oil.

$^1$H NMR (CDCl$_3$) δ 6.80–7.35 (m, 9H), 5.25 (s, 2H), 4.45–4.55 (s, 1H), 2.80–3.80 (m, 12H), 1.75–2.5 (m, 4H), 1.50 (s, 9H) TLC (SiO$_2$): R$_f$=0.30 (20% ethyl acetate in hexanes)

Preparation of 38A

4-[2-(1-Methyl-piperidin-3-yloxy)-phenyl]-piperazine-1-carboxylic acid tert-butyl ester

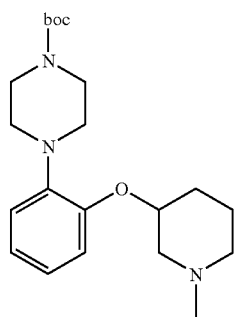

The title compound was prepared in a manner similar to 4-[2(2-Morpholin-4-yl-ethoxy)-phenyl]-piperazine-1-carboxylicacid tert-butyl ester except that 4-(2-hydroxy-phenyl)-piperazine-1-carboxylic acid tert-butyl ester was coupled to 1-methyl-piperidin-3-ol.

Preparation of 39A

4-[2-(1-Methyl-piperidin-2-ylmethoxy)-phenyl]-piperazine-1-carboxylic acid tert-butyl ester

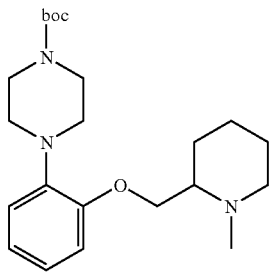

The title compound was prepared by using Mitsunobu condition from 4-(2-hydroxy-phenyl)-piperazine-1-carboxylic acid tert-butyl ester and 1-Methyl-2-piperidinemethanol.

Preparation of 40A

4-[2-(1-Ethyl-pyrrolidin-3-yloxy)-phenyl]-piperazine-1-carboxylic acid tert-butyl ester

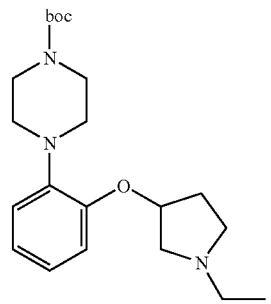

The title compound was prepared by using Mitsunobu condition from 4-(2-hydroxy-phenyl)-piperazine-1-carboxylic acid tert-butyl ester and 1-Ethyl-3-pyrrolidinol.

Preparation of 41A

4-[2-(1-Methanesulfonyl-piperidin-3-yloxy)-phenyl]-piperazine-1-carboxylic acid tert-butyl ester

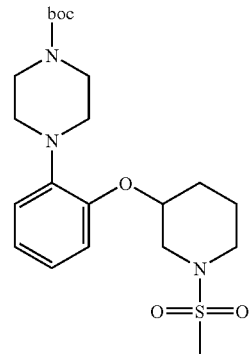

Step 1: 1-Methanesulfonyl-piperidin-3-ol

Piperidin-3-ol (5.0 g, 49.4 mmol) was dissolved in 1/1 THF/methylene chloride (100 mL). Triethylamine (17 mL, 123 mmol) was added, and the solution was cooled to 0° C. Methanesulfonyl chloride (4.0 mL, 52 mmol) was added dropwise. The mixture was warmed to r.t. and stirred overnight. The reaction was diluted with ethyl acetate (800 mL), washed with 1 N HCl (100 mL), water (75 mL), saturated aqueous sodium bicarbonate (75 mL) and brine (75 mL), and then dried over anhydrous sodium sulfate. The solvent was concentrated under reduced pressure and purified via silica gel chromatography (ethyl acetate) to afford the title compound as a clear oil.

$^1$H NMR (CDCl$_3$) δ 3.83–3.96 (m, 1H), 3.40–3.53 (m, 1H), 3.23–3.37 (m, 1H), 2.96–2.19 (m, 2H), 2.80 (s, 3H), 1.78–2.02 (m, 3H), 1.48–1.75 (m, 1H).

Step 2: The title compound was prepared by using Mitsunobu condition from 4-(2-Hydroxy-phenyl)-piperazine-1-carboxylic acid tert-butyl ester and 1-methanesulfonyl-piperidin-3-ol.

Preparation of 42A

4-[2-(1-Acetyl-piperidin-4-yloxy)-phenyl]-piperazine-1-carboxylic acid tert-butyl ester

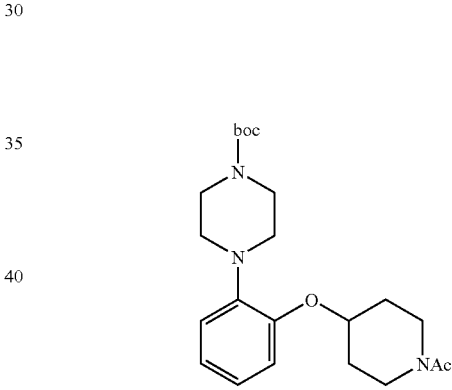

Step 1: 1-(4-Hydroxy-piperidin-1-yl)-ethanone 4-hydroxypiperidine (0.534 g, 5.3 mmol) was dissolved in methylene chloride (50 mL). The solution was cooled to −78° C. and triethylamine (1.10 mL, 7.95 mmol) was added. Acetyl chloride (0.33 mL, 4.77 mmol) was added dropwise to the mixture. The mixture was warmed to r.t., concentrated under reduced pressure and purified using silica gel chromatography (50% ethyl acetate in hexanes) to give the title compound (0.540 g, 80%) as an oil.

$^1$H NMR (CDCl$_3$) δ 4.05–3.90 (m, 2H), 3.75–3.65 (m, 1H), 3.25–3.05 (m, 2H), 2.25 (s, 1H), 2.05 (s, 3H), 1.90–1.75 (m, 2H), 1.60–1.40 (m, 2H).

Step 2: The title compound was prepared by using Mitsunobu condition from 4-(2-hydroxy-phenyl)-piperazine-1-carboxylic acid tert-butyl ester and 1-(4-Hydroxy-piperidin-1-yl)-ethanone.

Preparation of 43A

4-[2-(2-Pyrrolidin-1-yl-ethoxy)-phenyl]-piperazine-1-carboxylic acid tert-butyl ester

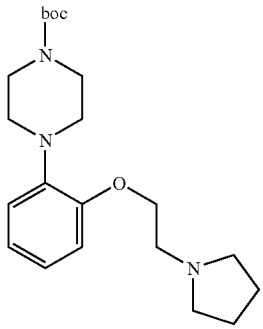

The title compound was prepared by using Mitsunobu condition from 4-(2-hydroxy-phenyl)-piperazine-1-carboxylic acid tert-butyl ester and 2-hydroxyethyl pyrrolidine.

Preparation 44A

4-[2-(1-Methyl-pyrrolidin-3-yloxy)-phenyl]-piperazine-1-carboxylic acid tert-butyl ester

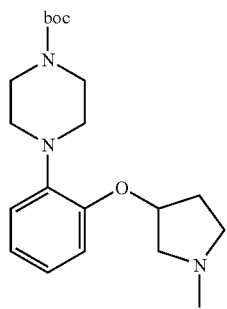

The title compound was prepared using Mitsunobu condition from 4-(2-hydroxy-phenyl)-piperazine-1-carboxylic acid tert-butyl ester and 1-Methyl-3-pyrrolidinol.

Preparation 45A

4-[2-(1-Acetyl-piperidin-3-yloxy)-phenyl]-piperazine-1-carboxylic acid tert-butyl ester

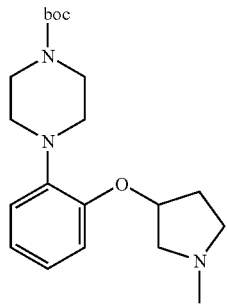

Step 1: 1-(3-Hydroxy-piperidin-1-yl)-ethanone

3-Hydroxypiperidine (3.0 g, 30.0 mmol) was dissolved in THF (40 mL) and methylene chloride (40 mL). Triethylamine (7.47 g, 74.0 mmol) was added. The mixture was cooled to −78° C. and acetyl chloride (2.35 g, 30.0 mmol) was added drop wise. The mixture was warmed to r.t. and stirred under nitrogen for 1 about an hour. The solvents were removed under reduced pressure, and the resulting oil was purified using silica chromatography (2% methanol in ethyl acetate) to afford the title compound (3.57 g, 83%) as an oil.

$^1$H NMR (CDCl$_3$) δ 3.90–3.55 (m, 3H), 3.50–3.15 (m, 3H), 2.10 (s, 3H), 1.95–1.60 (m, 2H), 1.55–1.25 (m, 2H).

Step 2: The title compound was prepared by using mitsonobu condition from 4-(2-hydroxy-phenyl)-piperazine-1-carboxylic acid tert-butyl ester and 1-(3-Hydroxy-piperidin-1-yl)-ethanone.

$^1$H NMR (CDCl$_3$) δ 7.05–6.95 (m, 4H), 3.75–3.70 (m, 3H), 3.60–3.50 (m, 4H), 3.35–3.30 (m, 2H), 3.05–3.00 (m, 4H), 1.90–0.185 (m, 2H), 2.00 (s, 3H), 1.50 (s, 9H), 1.45–1.40 (m, 2H).

Preparation 46A

4-{2-[2-(4-Methanesulfonyl-piperazin-1-yl)-ethoxy]-phenyl}-piperazine-1-carboxylic acid tert-butyl ester

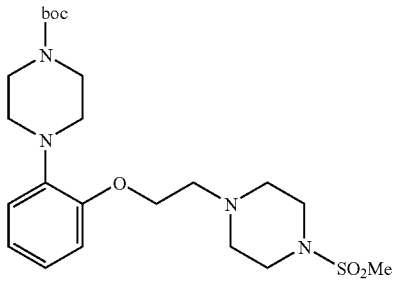

Step 1: 2-(4-Methanesulfonyl-piperazin-1-yl)-ethanol

2-Piperazin-1-yl-ethanol (1.30 g, 1.0 mmol) and triethylamine (2.8 mL, 2 mmol) were dissolved in methylene chloride (20 mL). The solution was cooled to 0° C. and methanesulfonyl chloride (0.78 mL, 1 mmol) was added dropwise. The mixture was warmed to r.t., and the solvent was removed under reduced pressure. The residue was purified via silica gel chromatography (10% methanol in ethyl acetate) to afford the title compound (1.0 g, 48%).

$^1$H NMR (CDCl$_3$) δ 3.62–3.75 (m, 2H), 3.23–3.38 (m, 4H), 2.82 (s, 3H), 2.57–2.74 (m, 6H). TLC (SiO$_2$): R$_f$=0.16 (5% methanol in ethyl acetate)

Step 2: The title compound was prepared by using Mitsunobu condition from 4-(2-hydroxy-phenyl)-piperazine-1-carboxylic acid tert-butyl ester and 2-(4-Methanesulfonyl-piperazin-1-yl)-ethanol.

Preparation 47A

4-[2-(1-Methanesulfonyl-azetidin-3-yloxy)-phenyl]-piperazine-1-carboxylic acid tert-butyl ester

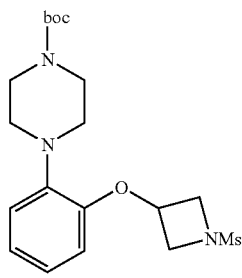

Step 1: 1-Benzhydryl-3-(2-bromo-phenoxy)-azetidine

Bromophenol (3.8 mL, 32.6 mmol), benzhydrylazetidinol (7.8 g, 32.6 mmol) and triphenylphosphine (12.8 g, 28.9 mmol) were dissolved in THF (200 mL) under nitrogen and cooled to 0° C. Diisopropyl azodicarboxylate (9.7 mL, 48.9 mmol) was added dropwise over 30 minutes, and the mixture was stirred for about 96 hours at r.t. Diethyl ether (400 mL) was added, and the solution was washed with 5 N NaOH (2×50 mL) and brine (50 mL), and then dried over magnesium sulfate and concentrated to a colorless oil. Purification by silica gel chromatography (4:1 hexanes/ethyl acetate) gave the title compound as a colorless oil (7.0 g, 55%).

$^1$H NMR (CDCl$_3$) δ 7.51 (dd, J=7.8, 1.6 Hz, 1H) 7.40–7.43 (m, 4H), 7.11–7.33 (m, 8H), 6.79 (td, J=7.7, 1.3 Hz, 1H), 6.58 (dd, 1H, J=8.2, 1.3 Hz) 4.78–4.84 (m, 1H,), 4.45 (s, 1H), 3.72–3.77 (m, 2H), 3.13–3.18 (m, 2H)

Step 2: 1-[2-(1-Benzhydryl-azetidin-3-yloxy)-phenyl]-piperazine

1-Benzhydryl-3-(2-bromo-phenoxy)-azetidine (3.6 g, 9.16 mmol), piperazine (946 mg, 11 mmol), BINAP (427 mg, 1.38 mmol), Pd$_2$dba$_3$ (410 mg, 0.46 mmol) and sodium tert-butoxide (1.23 g, 12.8 mmol) were dissolved into toluene (100 mL). The solution was degassed under vacuum and bubbled with nitrogen. The vessel was sealed under nitrogen and heated to 90° C. for about 24 hours. Diethyl ether (500 ml) was added, and the solution was filtered through a bed of celite. The solution was concentrated to an orange oil. Purification by silica gel chromatography [1% NH$_3$ in methanol/ethyl acetate (1 L), 5% NH$_3$ in methanol/ethyl acetate (1 L), and 10% NH$_3$ in methanol/ethyl acetate (1L)] gave the title compound as an orange powder (2.0 g, 65%).

$^1$H NMR (CDCl$_3$) δ 7.40–7.43 (m, 4H), 7.25–7.37 (m, 4H), 7.15–7.21 (m, 2H), 6.83–6.92 (m, 3H), 6.55 (dd, J=6.5, 1.7 Hz, 11) 4.79–4.87 (m, 1H,), 4.44 (s, 1H), 3.71–3.77 (m, 2H), 3.12–3.16 (m, 2H), 3.04 (s, 8H), 1.86 (bs, 1H).

Step 3: 4-[2-(1-Benzhydryl-azetidin-3-yloxy)-phenyl]-piperazine-1-carboxylic acid tert-butyl ester 4-[2-(1-Benzhydryl-azetidin-3-yloxy)-phenyl]-piperazine-1-carboxylic acid tert-butyl ester (610 mg, 1.53 mmol) and di-tert-butyl dicarbonate (0.883 g, 4.05 mmol) were dissolved into dioxane (3 mL) and water (5 mL) at 0° C. Sodium bicarbonate (340 mg, 4.05 mmol) was added, and the mixture was warmed to r.t. and stirred for about 2 hours. Ethyl acetate (100 mL) was added, and the solution was washed with H$_2$O (3×20 mL), saturated sodium bicarbonate (20 mL)and brine (20 mL) and then dried over magnesium sulfate. Purification by silica gel chromatography (hexanes/ethyl acetate 4:1) gave the title compound as a colorless oil (770 mg, 100%).

$^1$H NMR (CDCl$_3$) δ 7.40–7.43 (m, 4H), 7.16–7.34 (m, 6H), 6.85–6.91 (m, 3H), 6.55–6.58 (m, 1H), 4.80–4.87 (m, 1H), 4.44 (s, 1H), 3.72–3.77 (m, 2H), 3.55–3.59 (m, 4H), 3.13–3.19 (m, 2H), 2.99–3.02 (m, 4H), 1.49 (s, 9H). TLC (SiO$_2$): R$_f$=0.90 (1:1 hexanes/ethyl acetate)

Step 4: 4-[2-(Azetidin-3-yloxy)-phenyl]-piperazine-1-carboxylic acid tert-butyl ester 4-[2-(1-Benzhydryl-azetidin-3-yloxy)-phenyl]-piperazine-1-carboxylic acid tert-butyl ester (750 mg, 1.5 mmol) and ammonium formate (1.8 g, 30 mmol) were dissolved into methanol (50 mL) at r.t. The solution was added slowly to 10% palladium on carbon (750 mg) in methanol (20 mL) under nitrogen atmosphere. The mixture was stirred for about 48 hours and filtered through a bed of celite. The solvent was removed under reduced pressure to afford the title compound as a colorless oil (380 mg, 60%).

$^1$H NMR (CDCl$_3$) δ 6.98–7.04 (m, 3H), 6.72–6.75 (m, 1H), 5.17–5.21 (m, 1H,), 4.53 (dd, J=12.4, 6.5 Hz, 2H), 4.18 (dd, J=12.3, 5.0 Hz, 2H), 3.57–3.61 (m, 4H), 2.99–3.02 (m, 4H), 1.48 (s, 9H)

Step 5: 4-[2-(Azetidin-3-yloxy)-phenyl]-piperazine-1-carboxylic acid tert-butyl ester (137 mg, 0.41 mmol) and triethylamine (97 µL, 0.7 mmol) were dissolved into THF (2 mL) at 0° C. Mesityl chloride (45 µL, 0.57 mmol) was added, and the solution was stirred for about 16 hours. The solution was concentrated and filtered through a silica gel plug with 1:1 hexanes/ethyl acetate. The final compound was isolated as a colorless oil (120 mg, 71%)

$^1$H NMR (CDCl$_3$) δ 6.90–7.10 (m, 3H), 6.65–6.75 (m, 1H), 4.95–5.01 (m, 1H,), 4.25–4.35 (m, 2H), 4.05–4.15 (m, 2H), 3.55–3.65 (m, 4H), 2.97–3.02 (m, 4H), 2.91 (s, 3H), 1.48 (s, 9H). TLC (SiO$_2$): R$_f$=0.38 (1:1 hexanes/ethyl acetate)

Preparation 48A

4-[2-(1-Methyl-azetidin-3-yloxy)-phenyl]-piperazine-1-carboxylic acid tert-butyl ester

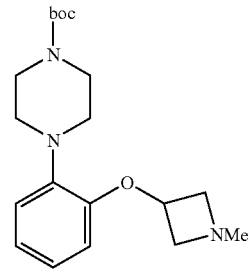

4-[2-(Azetidin-3-yloxy)-phenyl]-piperazine-1-carboxylic acid tert-butyl ester (Preparation 47A, Step 4) (140 mg, 0.42 mmol) was dissolved in CH$_2$Cl$_2$ (2 mL). Acetic acid (0.15 mL) and formalin (85 µL, 1.05 mmol) were added, and the mixture was cooled to 0° C. Sodium triacetoxyborohydride (249 mg, 1.17 mmol) was added, and the solution was stirred for about 16 hours. Methylene chloride (15 mL) was added, and the solution was washed with saturated NaHCO$_3$ (5 mL) and brine (5 mL) and then dried over magnesium sulfate and concentrated to a colorless oil (300 mg, 21%).

¹H NMR (CDCl₃) δ 6.91–6.98 (m, 3H), 6.58–6.61 (m, 1H), 4.72–4.79 (m, 1H), 3.83–3.88 (m, 2H), 3.60 (t, J=5.1 Hz, 2H), 3.12–3.17 (m, 2H), 3.01 (t, J=5.1 Hz, 4H), 2.72 (s, 3H), 1.48 (s, 9H)

Preparation 49A

4-{2-[1-(Propane-2-sulfonyl)-piperidin-3-yloxy]-phenyl}-piperazine-1-carboxylic acid tert-butyl ester

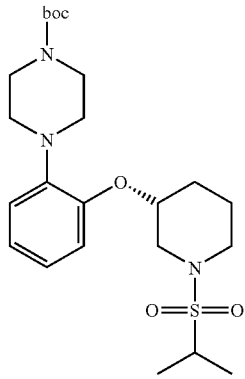

Step 1: 4-[2-(1-Benzyloxycarbonyl-piperidin-3-yloxy)-phenyl]-piperazine-1-carboxylic acid tert-butyl ester (S)-3-Hydroxy-piperidine-1-carboxylic acid benzyl ester (2.34 g, 8.6 mmol) was dissolved in THF (40 mL) at room temperature. 4-(2-Hydroxy-phenyl)-piperazine-1-carboxylic acid tert-butyl ester (2.4 g, 8.6 mmol) and triphenylphosphine (2.7 g, 10.32 mmol) were added. Diisopropyl azodicarboxylate (2.05 mL, 10.32 mmol) was added dropwise to the solution. The reaction was stirred overnight, concentrated under reduced pressure, and purified using silica gel chromatography (100% ethyl acetate) to afford the title compound (2.5 g, 55%).

¹H NMR (CDCl₃) δ 7.30–7.20 (m, 5H), 6.65–6.50 (m; 4H), 5.35 (s, 2H), 3.75–3.70 (m, 3H), 3.65–3.60 (m, 4H), 3.35–3.30 (m, 2H), 3.25–3.20 (m, 4H), 1.85–1.60 (m, 4H), 1.50 (s, 9H)

Step 2: 4-{2-[1-(Propane-2-sulfonyl)-piperidin-3-yloxy]-phenyl}-piperazine-1-carboxylic acid tert-butyl ester 4-[2-(1-Benzyloxycarbonyl-piperidin-3-yloxy)-phenyl]-piperazine-1-carboxylic acid tert-butyl ester (2.5 g, 4.7 mmol) was dissolved in methanol (20 mL). Palladium on carbon (50% water, 2.1 g) was added. A hydrogen atmosphere was established using balloons, and the mixture was stirred at r.t. for about 4 hours. The catalyst was removed by filtration with ethyl acetate through a bed of celite. The compound was isolated by running a silica gel plug with a gradient of 100% ethyl acetate (200 mL) to triethylamine in ethyl acetate (10%). The isolated product (0.382 g, 0.96 mmol) was dissolved in methylene chloride (10 mL) at 0° C., and triethylamine (0.4 mL, 2.9 mmol) was added. Isopropylsulfonyl chloride (0.13 mL, 1.15 mmol) was added dropwise, and the mixture was warmed to r.t. for about 30 minutes, which was then concentrated under reduced pressure and purified using silica gel chromatography (75% ethyl acetate in hexanes) to afford the final compound (0.39 g, 80%).

¹H NMR (CDCl₃) δ 7.25–6.85 (m, 4H), 3.55–3.50 (m, 4H), 3.05–2.95 (m, 4H), 2.15–1.60 (m, 4H), 1.50 (s, 9H), 1.45–1.40 (m, 6H), 1.30–1.25 (m, 5H)

Preparation 50A

4-[2-(1-Benzoyl-piperidin-3-yloxy)-phenyl]-piperazine-1-carboxylic acid tert-butyl ester

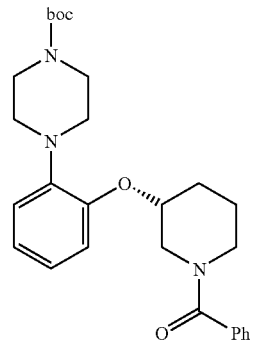

4-[2-(Piperidin-3-yloxy)-phenyl]-piperazine-1-carboxylic acid tert-butyl ester (Preparation 49A) (311 mg, 0.86 mmol) was dissolved in CH₂Cl₂ (15 mL) under nitrogen and cooled to 0° C. Benzoyl chloride (0.3 mL, 2.58 mmol) was added followed by dropwise addition of triethylamine (0.48 mL, 3.44 mmol). The mixture was warmed to r.t. and stirred for about 16 hours. Methylene chloride (20 mL) was added, and the solution was washed with saturated NaHCO₃ (20 mL) and brine (20 mL), and then dried over magnesium sulfate. The solvents were removed under reduced pressure, and the residue was purified by flash column chromatography on silica to afford the final compound as a white solid (330 mg, 83%).

¹H NMR (CDCl₃) δ 7.25–7.45 (m, 5H), 6.90–7.10 (m, 3H), 6.82–6.90 (m, 1H), 4.15–4.30 (m, 1H), 3.42–3.85 (m, 8H), 2.86–3.20 (m, 4H), 1.85–2.10 (m, 3H), 1.51–1.69 (m, 1H), 1.48 (s, 9H) TLC (SiO₂): R_f=0.2 (1:1 ethyl acetate/hexanes)

Preparation 51A

4-[2-(1-Isobutyryl-piperidin-3-yloxy)-phenyl]-piperazine-1-carboxylic acid tert-butyl ester

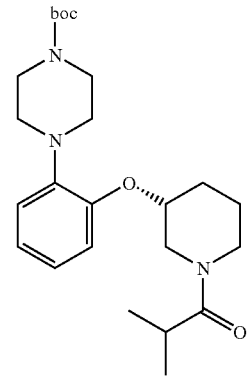

4-[2-(Piperidin-3-yloxy)-phenyl]-piperazine-1-carboxylic acid tert-butyl ester (Preparation 49A, Step 2) (340 mg, 0.94 mmol) was dissolved in CH$_2$Cl$_2$ (15 mL) under nitrogen and cooled to 0° C. Isobutyryl chloride (0.29 mL, 2.82 mmol) was added followed by dropwise addition of triethylamine (0.52 mL, 3.76 mmol). The mixture was warmed to r.t. and stirred for about 16 hours. Methylene chloride (20 mL) was added, and the solution was washed with saturated NaHCO$_3$ (20 mL) and brine (20 mL), and then dried over magnesium sulfate. The solvents were removed under reduced pressure, and the residue was purified by flash column chromatography on silica gel, eluting with ethyl acetate/hexanes (1:1), to afford the final compound as a white solid (322 mg, 80%). TLC (SiO$_2$): R$_f$=0.42 (1:1 ethyl acetate/hexanes)

Preparation 52A

4-[2-(1-Benzenesulfonyl-piperidin-3-yloxy)-phenyl]-piperazine-1-carboxylic acid tert-butyl ester

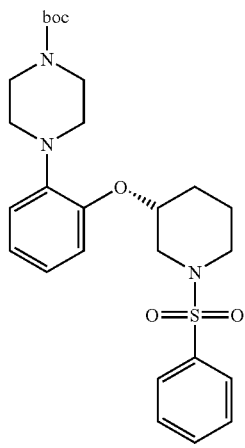

Step 1: 4-[2-(1-Benzyloxycarbonyl-piperidin-3-yloxy)-phenyl]-piperazine-1-carboxylic acid tert-butyl ester 3-Hydroxy-piperidine-1-carboxylic acid benzyl ester (2.34 g, 8.6 mmol) was dissolved in THF (40 mL) at r.t. 4-(2-Hydroxy-phenyl)-piperazine-1-carboxylic acid tert-butyl ester (2.4 g, 8.6 mmol) and triphenylphosphine (2.7 g, 10.32 mmol) were added. Diisopropyl azodicarboxylate (2.05 mL, 10.32 mmol) was added dropwise to the solution. The mixture was stirred overnight, and then concentrated under reduced pressure and purified using silica gel chromatography (100% ethyl acetate) to afford the title compound (2.5 g, 55%).

$^1$H NMR (CDCl$_3$) δ 7.30–7.20 (m, 5H), 6.65–6.50 (m, 4H), 5.35 (s, 2H), 3.75–3.70 (m, 3H), 3.65–3.60 (m, 4H), 3.35–3.30 (m, 2H), 3.25–3.20 (m, 4H), 1.85–1.60 (m, 4H), 1.50 (s, 9H)

Step 2: The compound of Step 1 (2.5 g, 4.7 mmol) was dissolved in methanol (20 mL). Palladium on carbon (50% water, 2.1 g) was added. A hydrogen atmosphere was established using balloons, and the mixture was stirred at r.t. for about 4 hours. The catalyst was removed by filtration with ethyl acetate through a bed of celite. The compound was isolated by running scrub-plug with a gradient of 100% ethyl acetate (200 mL) to triethylamine in ethyl acetate (10%). The isolated product (0.36 g, 0.9 mmol) was dissolved in methylene chloride (10 mL) at 0° C., and triethylamine (0.38 mL, 2.7 mmol) was added. Benzenesulfonyl chloride (0.15 mL, 1.1 mmol) was added drop wise to the reaction mixture. The solution warmed to r.t., concentrated under reduced pressure and purified using silica gel chromatography (75% ethyl acetate in hexanes) to afford the final compound (0.400 g, 82%).

$^1$H NMR (CDCl$_3$) δ 7.95–7.85 (m, 2H), 7.55–7.30 (m, 3H), 6.65–6.50 (m, 4H), 3.75–3.70 (m, 1H), 3.65–3.60 (m, 4H), 3.25–3.20 (m, 4H), 3.15–3.10 (m, 2H), 2.75–2.70 (m, 2H), 1.90–1.80 (m, 2H), 1.65–1.55 (m, 2H), 1.50 (s, 9H)

Preparation 53A

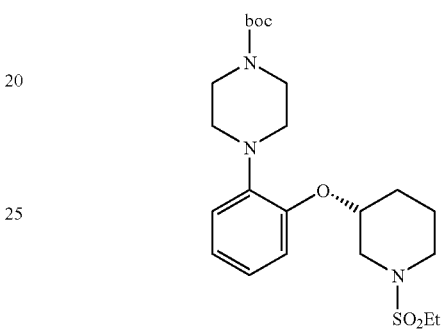

Step 1: 4-[2-(1-benzyl-piperidin-3-yloxy)-phenyl]-piperazine-1-carboxylic acid tert-butyl ester was s prepared by using Mitsunobu condition from 4-(2-hydroxy-phenyl)-piperazine-1-carboxylic acid tert-butyl ester and (S)-1-benzyl-piperidin-3-ol.

Step 2: 4-[2-(Piperidin-3-yloxy)-phenyl]-piperazine-1-carboxylic Acid tert-butyl ester A solution of the compound from Step 1 (2.07 g, 4.59 mmol) in ethanol (50 mL) was treated with palladium on carbon (50% by weight with water, 1.0 g), and the mixture was shaken on a Parr hydrogenation apparatus for about 48 hours. The solution was filtered through celite and, the solvent was removed under reduced pressure to yield the title compound as a clear oil (1.10 g, 66%).

$^1$H NMR (CD$_3$OD) δ 6.93–7.10 (m, 4H), 4.35–4.47 (m, 1H), 4.52–4.68 (m, 5H), 3.03–3.18 (m, 2H), 2.64–3.02 (m, 6H), 1.77–2.15 (m, 3H), 1.53–1.66 (m, 1H), 1.48 (s, 9H)

Step 3: Triethylamine (0.26 g, 2.53 mmol) was added to a solution of the compound from Step 2 (0.37 g, 1.01 mmol) in methylene chloride (10 mL)/THF (10 mL) at −78° C. under nitrogen. Methanesulfonyl chloride was added dropwise, and the reaction was allowed to warm to r.t. and stirred for about 2 hours. The mixture was diluted with diethyl ether (200 mL), filtered, and the solvent was removed under reduced pressure. The residue was purified by flash column chromatography on silica gel by eluting with ethyl acetate/hexanes (1:1) to afford the final compound as a clear oil (0.26 g, 56%).

$^1$H NMR (CDCl$_3$) δ 6.82–7.05 (m, 4H), 4.34–4.50 (m, 1H), 3.73–3.89 (m, 1H), 3.45–3.67 (m, 5H), 2.87–3.24 (m, 8H), 2.03–2.21 (m, 1H), 1.87–2.01 (m, 1H), 1.64–1.72 (m, 2H), 1.55 (m, 3H), 1.52 (s, 9H)

Preparation 54A

4-[2-(1-Propionyl-piperidin-3-yloxy)-phenyl]-piperidine-1-carboxylic Acid tert-Butyl Ester

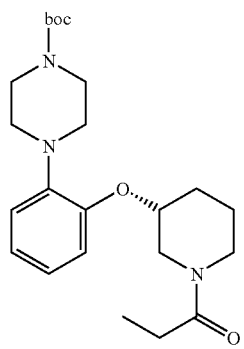

Propionyl chloride (0.11 g, 1.21 mmol) was added dropwise to a solution of 4-[2-(piperidin-3-yloxy)-phenyl]-piperazine-1-carboxylic acid tert-butyl ester (Preparation 53A) (0.37 g, 1.01 mmol) and DIPEA (0.20 g, 1.52 mmol) in methylene chloride (20 mL) at 0° C. under nitrogen. The mixture was warmed to r.t. and stirred overnight. The solution was diluted with ethyl acetate (400 mL) and washed with water (45 mL), saturated aqueous sodium bicarbonate (45 mL) and brine (45 mL), which was then dried over anhydrous sodium sulfate. The solvent was removed, and the residue was purified by flash column chromatography on silica gel by eluting with ethyl acetate/hexanes (1:1) to provide the final compound as a clear oil (0.26 g, 61%).

$^1$H NMR (CDCl$_3$) δ 6.81–7.02 (m, 4H), 4.20–4.52 (m, 2H), 3.45–3.65 (m, 6H), 3.25–3.42 (m, 1H), 2.86–3.12 (m, 4H), 2.30–2.47 (m, 1H), 2.08–2.25 (m, 1H), 1.77–2.03 (m, 2H), 1.61 (s, 2H), 1.51 (s, 9H), 1.01–1.23 (m, 3H)

Preparation 55A

4-[2-(2-Methanesulfonylamino-propoxy)-phenyl]-piperazine-1-carboxylic acid tert-butyl ester

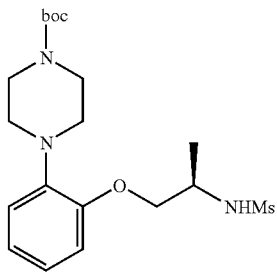

Step 1: 4-[2-(2-Amino-propoxy)-phenyl]-piperazine-1-carboxylic acid tert-butyl ester 4-[2-(2-Benzyloxycarbonylamino-propoxy)-phenyl]-piperazine-1-carboxylic acid tert-butyl ester (5.7 g, 12.15 mmol) and 10% wet palladium on carbon (5.0 g) were dissolved in methanol (200 mL) at r.t. The solution was stirred under hydrogen for about 4 hours. The mixture was filtered through a bed of celite. The solvent was removed under reduced pressure to afford the title compound as a colorless oil (4.2 g, 100%).

$^1$H NMR (CDCl$_3$) δ 6.89–7.05 (m, 4H), 4.01 (dd, J=9.6, 4.1 Hz, 1H), 3.86 (t, J=7.8 Hz, 1H), 3.56–3.86 (m, 6H), 3.36–3.45 (m, 1H), 1.47 (s, 9H), 1.25 (d, J=6.5 Hz, 3H)

Step 2: The compound of Step 1 (750 mg, 2.24 mmol) and triethylamine (0.52 mL, 3.7 mmol) were dissolved in THF (10 mL) at 0° C. Mesityl chloride (0.24 mL, 3.14 mmol) was added, and the solution was stirred for about 16 hours. Ethyl acetate (50 mL) was added, and the solution was washed with saturated NaHCO$_3$ (2×10 mL) and brine (10 mL) and then dried over magnesium sulfate. The solution was concentrated to afford the final compound as a colorless oil (930 mg, 100%).

$^1$H NMR (CDCl$_3$) δ 6.91–7.01 (m, 4H), 6.27 (d, J=7.9 Hz, 1H), 4.01–4.19 (m, 2H), 3.77–3.86 (m, 1H), 3.63 (s, 4H), 3.09–3.16 (m, 2H), 2.87–2.94 (m, 2H), 2.82 (s, 3H), 1.48 (s, 9H), 1.41 (d, J=6.9 Hz, 3H). TLC (SiO$_2$): R$_f$=0.80 (3:1 ethyl acetate/hexanes)

Preparation 56A

4-{2-[2-(Methanesulfonyl-methyl-amino)-propoxy]-phenyl}-piperazine-1-carboxylic acid tert-butyl ester

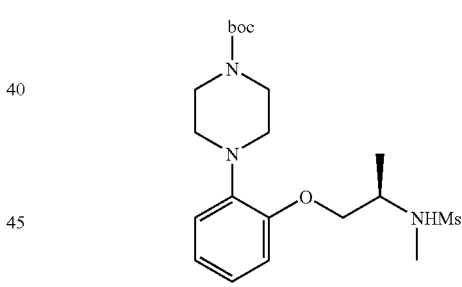

4-[2-(2-Methanesulfonylamino-propoxy)-phenyl]-piperazine-1-carboxylic acid tert-butyl ester (470 mg, 1.14 mmol) was dissolved in THF (20 mL) and cooled to 0° C. Sodium hydride (29 mg of 60% dispersion in oil, 1.2 mmol) was added followed by dropwise addition of methyl iodide (78 µL, 1.25 mmol). The mixture was warmed to r.t. and stirred for about 36 hours. Ethyl acetate (20 mL) was added, and the solution was washed with saturated NaHCO$_3$ (5 mL), H$_2$O (5 mL) and brine (5 mL) and then dried over magnesium sulfate. The solvents were removed under reduced pressure to afford the final compound as a clear oil (486 mg, 100%).

$^1$H NMR (CDCl$_3$) δ 6.85–7.03 (m, 4H), 4.06–4.15 (m, 1H,), 3.89 (dd, J=10.0, 4.5 Hz, 1H), 3.50–3.62 (m, 4H), 2.85–3.05 (m, 4H), 2.98 (s, 3H), 2.85–3.05 (m, 4H), 2.88 (s, 3H), 1.48 (s, 9H), 1.32 (d, J=7.0 Hz, 3H)

Preparation 57A

4-[2-(2-Piperidin-1-yl-propoxy)-phenyl]-piperazine-1-carboxylic acid tert-butyl ester

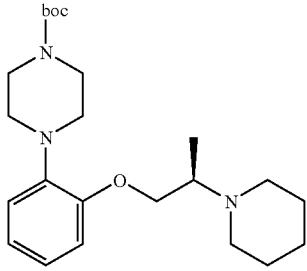

Step 1: 4-[2-(2-Benzyloxycarbonylamino-propoxy)-phenyl]-piperazine-1-carboxylic acid tert-butyl ester (3-Hydroxy-2-methyl-propyl)-carbamic acid benzyl ester (5.0 g, 24.0 mmol) was dissolved in THF (175 mL) at 0° C. 4-(2-hydroxy-phenyl)-piperazine-1-carboxylic acid tert-butyl ester (6.7 g, 24.0 mmol) and triphenylphosphine (7.6 g, 29.0 mmol) were added. Diisopropyl azodicarboxylate (5.75 mL, 29.0 mmol) was added dropwise, and the mixture was stirred overnight. The mixture was concentrated under reduced pressure and purified using silica gel chromatography (25% ethyl acetate in hexanes) to afford the title compound (5.33 g, 47%).

$^1$H NMR (CDCl$_3$) δ 7.30–7.20 (m, 5H), 7.00–6.80 (m, 4H), 5.75 (s, 1H), 5.05 (s, 2H), 4.10–4.00 (m, 3H), 3.95–3.90 (m, 1H), 3.55 (s, 4H), 3.10–3.00 (m, 2H), 2.90–2.80 (m, 2H), 2.05 (s, 1H)

Step 2: The compound of Step 1 (5.33 g, 11.36 mmol) was dissolved in methanol (200 mL), and palladium on carbon (50% water, 5.0 g) was then added. A hydrogen atmosphere was established using balloons and the reaction stirred at r.t. for about 4 hours. The catalyst was removed by filtration with ethyl acetate (200 mL) through a bed of celite. Compound was isolated, and the residue (1.0 g, 2.13 mmol) was dissolved in acetonitrile (55 mL). Potassium carbonate (1.18 g, 8.52 mmol) was added, and the mixture was heated to reflux and then diiodopentane (0.76 g, 2.34 mmol) in acetonitrile (10 mL) was added dropwise. The reaction was stirred overnight and cooled to r.t., filtered and concentrated under reduced pressure. The compound was purified by using silica gel chromatography (1% ammonium hydroxide in ethyl acetate) to afford the final compound (0.95 g, 83%).

$^1$H NMR (CDCl$_3$) δ 6.95–6.80 (m, 4H), 4.10–4.00 (m, 1H), 3.85–3.80 (m, 1H), 3.60–3.55 (m, 4H), 3.35–3.30 (m, 1H), 3.00 (s, 4H), 2.75–2.50 (m, 4H), 1.50 (s, 9H), 1.45–1.30 (m, 6H), 1.10 (s, 3H)

Preparation 58A

4-[2-(2-Diethylamino-propoxy)-phenyl]-piperazine-1-carboxylic acid tert-butyl ester

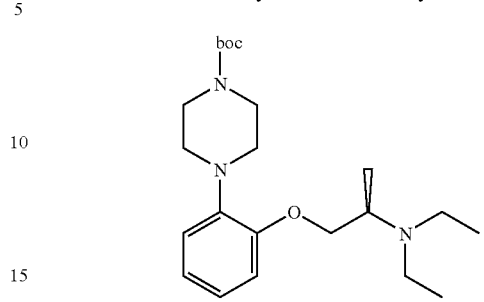

4-[2-(2-Amino-propoxy)-phenyl]-piperazine-1-carboxylic acid tert-butyl ester (0.35 g, 0.75 mmol) was dissolved in methanol (25 mL), and the reaction was cooled to 0° C. Acetaldehyde (0.363 g, 8.25 mmol) and sodium triacetoxyborohydride (0.795 g, 3.75 mmol) were added. A reflux condenser was fitted and the flask was stirred at r.t. for about 24 hours. The solution was extracted with diethyl ether (3×50 mL) and then concentrated under reduced pressure to afford the final compound (0.360 g, 90%).

$^1$H NMR (CDCl$_3$) δ 6.95–6.80 (m, 4H), 4.10–4.00 (m, 1H), 3.85–3.80 (m, 1H), 3.60–3.55 (m, 4H), 3.35–3.30 (m, 1H), 3.00 (s, 4H), 2.75–2.50 (m, 4H), 1.50 (s, 9H), 1.20–1.15 (m, 4H), 1.10–1.00 (m, 5H)

Preparation 59A

4-[2-(N-methyl-piperidin-4-yloxy)-phenyl]-piperazine

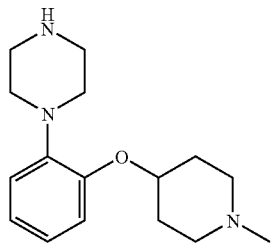

Step 1: N-Cbz-4-[2-(N-boc-piperidin-4-yloxy)-phenyl]-piperazine

To a solution of 4-[2-(N-boc-piperidin-4-yloxy)-phenyl]-piperazine (1.5 g, 4.1 mol, 1.0 eq.) in DCM (20 mL) was added Et$_3$N (0.8 mL, 5.74 mmol, 1.4 eq.), di-carbobenzoyloxy anhydride (1.4 g, 4.9 mmol, 1.2 eq.) and DMAP (25 mg, 0.2 mmol, 0.5 eq.). The mixture was stirred at r.t. overnight. The solution was diluted with DCM (100 mL) and washed with saturated aqueous NaHCO$_3$ (50 mL) and brine (50 mL). The organic layer was dried (Na$_2$SO$_4$), filtered and concentrated to afford the title compound (2.03 g, 4.1 mmol, 100%).

LRMS (electrospray): 496.4 (M+1).

Step 2: N-Cbz-4-[2-(piperidin-4-yloxy)-phenyl]-piperazine

To a solution of Step 2 (2.03 g, 4.1 mmol) in CH$_2$Cl$_2$ (10 mL) and DMS (2 mL) was added TFA (10 mL). After stirring for about 2 hours, the solution was diluted with heptane and concentrated (2×). The residue were dissolved in CH$_2$Cl$_2$ and washed with saturated aqueous sodium bicarbonate. The aqueous solution was extracted with CH$_2$Cl$_2$ (3×). The combined organic extracts were dried (Na$_2$SO$_4$), filtered and concentrated. The product was purified by SCX (10 g) ion exchange chromatography. Further purification by flash chromatography (125 g SiO$_2$, linear gradient, 40 mL/min, 0%–10% 2.0M NH$_3$ in MeOH/CH$_2$Cl$_2$ for 20 minutes and then 10% 2.0M NH$_3$ in MeOH/CH$_2$Cl$_2$ for 46 minutes) afforded title compound (1.05 g, 2.65 mmol, 65%). LRMS (electrospray): 396.3 (M+1).

Step 3: To a solution of the compound obtained from Step 2 (1.0 g, 2.5 mmol, 1.0 eq.) in EtOH (8 mL) was added formaldehyde (37 wt % in H$_2$O, 1.0 mL, 12.5 mmol, 5.0 eq.) and formic acid (0.5 mL, 12.5 mmol, 5.0 eq.). The mixture was heated at 70° C. and stirred at that temperature overnight. The mixture was cooled to r.t. and concentrated. Purification by SCX (10 g) ion-exchange chromatography afforded Cbz-protected title compound (1.0 g, 2.44 mmol, 98%). LRMS (electrospray): 410.1(M+1).

Step 4: To a solution of Cbz-protected title compound made above (480 mg, 1.17 mmol, 1.0 eq.) in IPA (15 mL) was added 10% Palladium on carbon (96 mg, 20 wt %). The reaction mixture was stirred at r.t. under H$_2$ (1 atm) over night. The reaction mixture was filtered through a pad of celite and concentrated to afford final compound (315 mg, 1.14 mmol, 98%). LRMS (electrospray): 276.1 (M+1).

Preparation 60A

Dimethyl-[2-(2-piperazin-1-yl-phenoxy)-ethyl]-amine

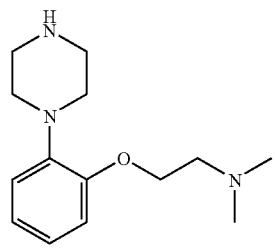

To a solution of 1-Boc-4(2-hydroxyphenyl)-piperazine (300 mg, 1.08 mmol), 2-dimethylaminoethyl chloride hydrochloride (233 mg, 1.62 mmol), K$_2$CO$_3$ (450 mg, 3.26 mmol), and KI (357 mg, 2.15 mmol) in DMF (10 mL) was added 18-crown-6 (1.42 g, 5.37 mmol). After stirring overnight, water was added and the solution extracted with CH$_2$Cl$_2$ (3×). The combined organic extracts were concentrated to an oil. The oil was loaded onto a 10 g SCX ion exchange column equilibrated with MeOH. The column was flushed with 20 mL of MeOH, 20 mL of 0.2 M NH$_3$ in MeOH, and 20 mL of 2 M NH$_3$ in MeOH. The fractions containing desired product were combined and concentrated to an oil. To a solution of the oil in MeOH (2 mL) was added 1M HCl (6 mL) in Et$_2$O. After stirring overnight the solution was concentrated to an oil to obtain the final compound. MS: 250.2 (M+1).

Preparation 61A

N-boc-4-{2-[2-(ethyl-methanesulfonyl-amino)-2-methyl-propoxy]-phenyl}-piperazine

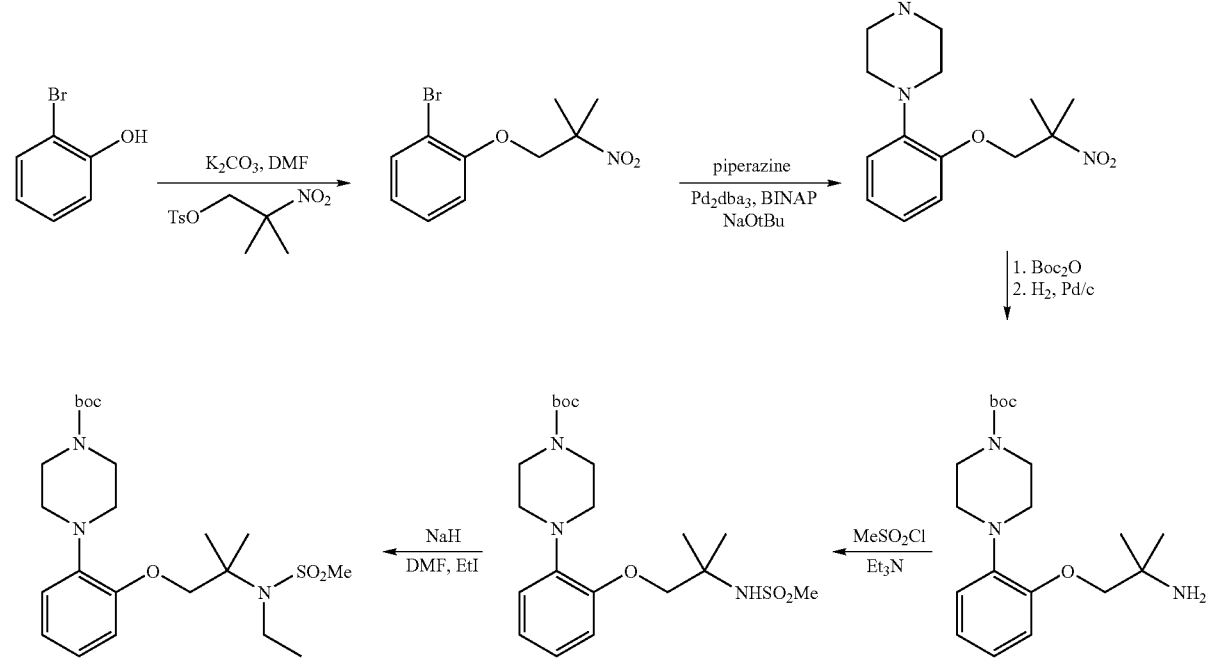

Step 1: To a solution of N-boc-1-[2-(2-methyl-2-nitro-propoxy)-phenyl]-piperazine (1.22 g) in 50 mL of DMF was added K₂CO₃ (3.5 g, 25 mmol). After stirring for about an hour, 2-methyl-2-nitropropyl-p-toluenesulfonate (3 g, 11 mmol) was added. After stirring overnight at 100° C., the solution was cooled to r.t. and diluted with EtOAc. The mixture was washed with water (2×) and brine, and then dried (Na₂SO₄), filtered and concentrated. Purification by silica gel chromatography (4×20 cm SiO₂, 10 to 20% EtOAc/hexanes, over 45 minutes at 35 mL/min) afforded about 2.43 g (8.86 mmol, 89%) of 1-bromo-2-(2-methyl-2-nitro-propoxy)-benzene as a white solid. GCMS (EI): 273 [M].

Step 2: A solution of 1-bromo-2-(2-methyl-2-nitro-propoxy)-benzene (2.30 g, 8.4 mmol), piperazine (1.8 g, 20 mmol), Pd₂dba₂ (384 mg, 0.4 mmol), BINAP (784 mg, 1.26 mmol), and NaOtBu (1.13 g, 12 mmol) in 34 mL of toluene was heated to 90° C. for 5 hrs. The solution was concentrated, dissolved in CH₂Cl₂ and filtered through celite. Purification by silica gel chromatography (4×20 cm SiO₂, 0,1,2,3,4,5,7,9,11% 2M NH₃ in MeOH/CH₂Cl₂ step gradient, 12 min each at 35 mL/min) afforded 1.72 g (6.15 mmol, 73%) of 1-[2-(2-methyl-2-nitro-propoxy)-phenyl]-piperazine as a yellow oil. LRMS (electrospray): 280.1 [M+1].

Step 3: To a solution of compound from Step 2 (1.68 g, 6.01 mmol), DMAP (40 mg, 0.33 mmol), Et₃N (1.84 mL, 13.2 mmol) in 60 mL of CH₂Cl₂ was added Boc₂O (1.44 g, 6.60 mmol). After stirring overnight, the solution was washed with 1 M HCl, water, saturated aqueous sodium bicarbonate and brine, and then dried (Na₂SO₄), filtered and concentrated to afford about 2.0 g (5.28 mmol, 88%) N-boc-1-[2-(2-methyl-2-nitro-propoxy)-phenyl]-piperazine as a yellow oil. LRMS (electrospray): 380.2 [M+1].

Step 4: To a solution of N-boc-1-[2-(2-methyl-2-nitro-propoxy)-phenyl]-piperazine (1.22 g, 3.22 mmol) and ammonium formate (2.0 g, 32 mmol) in 15 mL of MeOH and 5 mL of THF was added 10% Pd/c (500 mg). After stirring for about 3 days under 60 psi of H₂, the solution was filtered through celite and concentrated. The residue was partitioned between water and EtOAc. The aqueous solution was extracted with EtOAc (3×). The combined organic solutions were washed with brine and then dried (Na₂SO₄), filtered and concentrated to afford about 1.17 g (3.35 mmol, 100%) of N-boc-4-[2-(2-amino-2-methyl-propoxy)-phenyl]-piperazine as an off white solid. LRMS (electrospray): 350.2 [M+1].

Step 5: To a solution of compound from Step 4 (175 mg, 0.5 mmol) and Et₃N (210 uL, 1.5 mmol) in 5 mL of CH₂Cl₂ at 0° C. was added MsCl (41 uL, 0.53 mmol) at 10 uL increment until starting material was no longer present by TLC. The mixture was quenched with saturated aqueous sodium bicarbonate, diluted with EtOAc and washed with 1 M HCl, water and brine, which was then dried (Na₂SO₄), filtered and concentrated to afford about 155 mg (0.36 mmol, 73%) of N-boc-4-[2-(2-methanesulfonylamino-2-methyl-propoxy)-phenyl]-piperazine as a yellow solid. LRMS (electrospray): 428.1 [M+1].

Step 6: To a solution of N-boc-4-[2-(2-methanesulfonylamino-2-methyl-propoxy)-phenyl]-piperazine (197 mg, 0.46 mmol) in 4 mL of DMF was added NaH (55 mg of a 60% dispersion in oil, 1.38 mmol). After stirring for about 30 minutes, EtI (550 uL, 6.88 mmol) was added. After stirring at 45° C. for about an hour, the mixture was quenched with saturated aqueous sodium bicarbonate. The mixture was diluted with EtOAc, washed with water and brine, and then dried (Na₂SO₄), filtered and concentrated. The material was combined with 0.36 mmol of crude material from a previous reaction and purified by silica gel chromatography (35 g SiO₂, 10 to 30% EtOAc/hexanes, over 30 minutes at 35 mL/min.) to afford about 323 mg (0.71 mmol, 86% combined yield) of the final compound. LRMS (electrospray): 456.2 [M+1]

Preparation 62A

4-[2-(2-Morpholin-4-yl-ethoxy)-phenyl]-piperazine

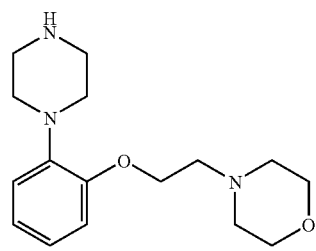

To a solution of 2-bromophenol (50 g, 0.289 mol), K₂CO₃ (175 g, 1.27 mol) and DMF (1500 mL) was added chloroethyl morpholine-HCl (59 g, 0.317). After stirring for about 4 hours at 100° C., 2-bromophenol (4 g, 0.023 mol) was added. After stirring for about 3 hours at 100° C., the solution was cooled to r.t. and diluted with 4L of EtOAc. The solution was washed with water, 5 M NaOH, water and brine, and then dried (Na₂SO₄), filtered, and concentrated to afford about 78 g (0.273 mol, 94%) of a colorless oil. The product was coupled with piperazine under Buchwald condition to afford the final compound. LRMS (electrospray): 292.29 [M+1]

Preparation 63A

1-[2-(2-Morpholin-4-yl-ethoxy)-phenyl]-[1,4]diazepan

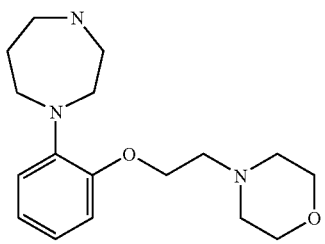

The title compound was prepared in a manner similar to Preparation 63A except that 4-[2-(2-bromo-phenoxy)-ethyl] morpholine was coupled to homopiperazine.

Preparation 64A

4-(2-Diethylcarbamoylmethoxy-phenyl)-piperazine-1-carboxylic acid tert-butyl ester

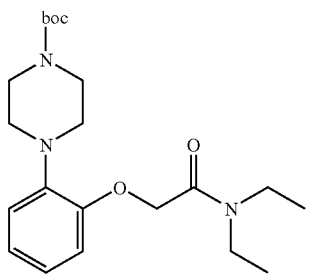

4-(2-hydroxy-phenyl)-piperazine-1-carboxylic acid tert-butyl ester (500 mg, 1.8 mmol) was dissolved in DMF (2 mL), and sodium hydride (1.98 mmol) was added. The mixture was stirred for about 10 minutes and 2-chloro-N,N-diethyl-acetamide (269 mg, 1.8 mmol) was added. The mixture was heated to 80° C. for about 2 hours. The mixture was concentrated and deprotected, which was then chromatographed to give about 395 mg of the final compound as a clear oil (75%). MS found 292.2

Preparation 65A

2,2,2-Trifluoro-1-[3-(2-piperidin-4-yl-phenoxy)-S-pyrrolidin-1-yl]-ethanone

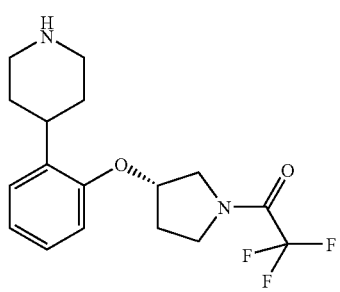

Step 1: 4-(4,4,5,5-Tetramethyl-[1,3,2]dioxoborolan-2-yl)-3,6-dihydro-2H-pyridine-1-carboxylic acid tert-butyl ester 4-Trifluoromethanesulfonyloxy-3,6-dihydro-2H-pyridine-1-carboxylic acid tert-butyl ester [*Synthesis* 1991 (11), 993–995, 8.2 g, 24.7 mmol], bis(pinacolat)diboran(6.93 g, 27.3 mmol), dichloro(1,1-bisdiphenyl-phosphino(ferrocene) Pd(II) dichloromethane adduct (0.54 g, 0.738 mmol), 1,1'-bis(diphenylphosphino)ferrocene (0.410 g, 0.738 mmol) and potassium acetate (6.6 g, 66.8 mmol) were mixed in dioxane (150 ml) and degassed. The mixture was heated to 80° C. for about 4 hours and then stirred at r.t. overnight. The mixture was diluted with CH$_2$Cl$_2$, filtered through celite, and concentrated to an oil. Oil was chromatographed on silica by eluting with 1:3 ethylacetate/hexane to afford the title compound (6.5 g). MS: 310 (M+1)

Step 2: 4-{2-[1-(2,2,2-Trifluoro-acetyl)-S-pyrrolidin-3-yloxy]phenyl}-3,6-dihydro-2H-pyridine-1-carboxylic acid tert-butyl ester 1-[3-(2-bromo-phenoxy)-S-pyrrolidin-1-yl]-2,2,2-trifluoro-ethanone (1.19 g, 3.52 mmol), the compound of Step 1 (1.31 g, 4.22 mmol), potassium carbonate (1.46 g, 10.56 mmol), and dichloro(1,1'-bis (diphenylphosphino) ferrocene) palladium (II) dichloromethane adduct (154 mg, 0.22 mmol) were combined and placed in DMF (12 mL), degassed and heated at 90° C. for about 16 hours. The mixture was cooled to r.t. and diluted with DCM (100 mL). The mixture was filtered over celite and DCM was removed by vacuum. The mixture was partitioned between 500 mL 1/1 EtOAc/hexane and 300 mL water, and the aqueous phase was washed with (200 mL) of the 1/1 EtOAc/hexane. The organic phase was washed with water (200 mL), concentrated and chromatographed on silica gel to afford the product (486 mg, 31%) as a yellow oil.

Step 3: N-Boc-2,2,2-Trifluoro-1-[3-(2-piperidin-4-yl-phenoxy)-S-pyrrolidin-1-yl]-ethanone The compound of Step 2 (486 mg, 1.10 mmol) was added to a slurry of Pt/C 10% (500 mg) in the solvent system (EtOAc/IPA 50 mL). The mixture was pressurized to 50 psi hydrogen for 2 days. The mixture was filtered through celite and concentrated to give a clear oil (467 mg, 96%).

MS found 343.2

Step 4: The compound of Step 3 (467 mg, 1.06 mmol) was placed in the solvent system (TFA/DCM 1/1 10 mL) and stirred for about 3 hours at r.t. The mixture was quenched with sodium bicarbonate solution and extracted, and the organic phase was concentrated to afford about 286 mg of the final compound (84%).

MS found 343.2 (M+1)

Preparation 66A

4-[2-(2-Piperidin4-ylphenoxy)-ethyl]-morpholine

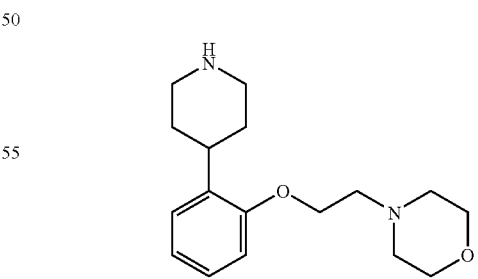

The title compound was prepared by following a substantially similar procedure as described in Preparation 65A except that 4-(4,4,5,5-Tetramethyl-[1,3,2]dioxoborolan-2-yl)-3,6-dihydro-2H-pyridine-1-carboxylic acid tert-butyl ester was coupled with 1-[3-(2-bromo-phenoxy)-morpholin-1-yl]-ethanone. MS found 291.2

Preparation 67A 2,2,2-Trifluoro-1-[3-(2-R-piperidin-4-yl-phenoxy)-piperidin-1-yl]-ethanone

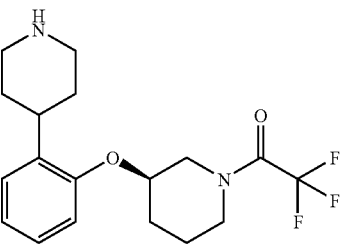

The title compound was prepared by following a substantially similar procedure as described in Preparation 65A except that 4-(4,4,5,5-Tetramethyl-[1,3,2]dixoaborolan-2-yl)-3,6-dihydro-2H-pyridine-1-carboxylic acid tert-butyl ester was coupled with 1-[3-(2-Iodo-phenoxy)-1-R-methyl-piperidin-1-yl]-2,2,2-trifluoro-ethanone.

MS found 357.1

Preparation 68A

1-[2-(1-Methyl-S-piperidin-3-yloxy)-phenyl-piperidine

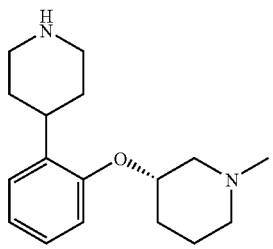

The title compound was prepared by following a substantially similar procedure as described in Preparation 65A except that 4-(4,4,5,5-Tetramethyl-[1,3,2]dioxoborolan-2-yl)-3,6-dihydro-2H-pyridine-1-carboxylic acid tert-butyl ester was coupled with 3-(2-Bromo-phenoxy)-1-S-methyl-piperidine. MS found 375.2

Preparation 69A

Diethyl-[1-methyl-2-(2-piperidin-4-yl-phenoxy)-ethyl]-amine

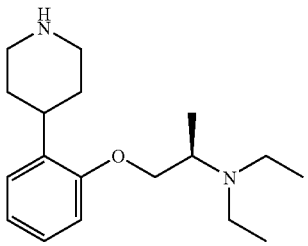

The title compound was prepared by following a substantially similar procedure as described in Preparation 65A except that 4(4,4,5,5-Tetramethyl-[1,3,2]dixoaborolan-2-yl)-3,6-dihydro-2H-pyridine-1-carboxylic acid tert-butyl ester was coupled with[2-(2-Bromo-phenoxy)-1-methyl-ethyl]-diethyl-amine. MS 291 (M+1)

C Domain Preparations:

The protected amino acid derivatives corresponding to the B and C domains are, in many cases, commercially available. Other protected amino acid derivatives can be prepared by following known literature method (See Williams, R. M. *Synthesis of Optically Active α-Amino Acids,* Pergamon Press: Oxford, 1989). The following provides the preparation of C domains.

Preparation 1C

1-Methoxycarbonylmethyl-1,3-dihydro-isoindole-2-carboxylic acid tert-butyl ester

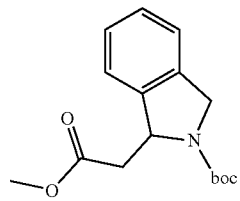

Step A: (2-Bromo-benzyl)-carbamic acid tert-butyl ester

To a mixture of 125.0 g (561.8 mmol) of 2-bromobenzylamine hydrochloride and 170.7 g (1236.0 mmol) of potassium carbonate in 300 mL of 50% THF/water was added 134.9 g (618.0 mmol) of di-tert-butyl dicarbonate in four portions over 20 minutes. The mixture was stirred at r.t. for about 16 hours and then diluted with 300 mL of ethyl acetate and 300 mL of water. The organic portion was separated and the aqueous portion was extracted three times with 200 mL each of ethyl acetate. The combined ethyl acetate portions were washed once with 250 mL of 10% aqueous sodium bisulfate. The organic portion was dried (MgSO$_4$), filtered and concentrated to dryness to afford about 161 g of Step A compound.

Step B: 3-[2-(tert-Butoxycarbonylamino-methyl)-phenyl]-acrylic acid methyl ester To compound of Step A (161.0 g, 561.8 mmol) in DMF (800 mL) was added methyl acrylate (58.0 g, 674.2 mmol), TEA (170.5 g, 1685.4 mmol) and dichlorobis(triphenylphosphine) palladium(II) (7.9 g, 11.2 mmol). The mixture was heated at 80° C. for about 32 hours. The mixture was cooled, diluted with 1000 mL of EtOAc and washed with 10% aqueous sodium bisulfate. The aqueous portion was extracted three times with EtOAc and the combined organics were dried ($Na_2SO_4$) and concentrated to dryness. The residue was dissolved in a small amount of DCM and filtered through 7 inches of silica gel in a 2 L sintered glass funnel eluting with 25% EtOAc/hexanes. The eluent was concentrated to dryness and recrystallized from EtOAc/hexanes to afford about 116.9 g (71%) of Step B compound.

Step C: To a 0° C. solution of (116.9 g, 401.2 mmol) material from Step B in DCM (800 mL) was added 200 mL of TFA dropwise over 15 minutes. After removing the cooling bath, the mixture was stirred for about 2.5 hours and then concentrated to dryness. The residue was dissolved in 500 mL of DCM and saturated aqueous sodium bicarbonate is slowly added until the mixture was slightly basic. The organic portion was separated and the aqueous portion is extracted two times with DCM. The combined organic portions were dried ($Na_2SO_4$) and concentrated to dryness. The residue was dissolved in 800 mL of DCM and DIPEA (57.0 g, 441.4 mmol) was added. To the mixture was added di-tert-butyl dicarbonate (96.3 g, 441.4 mmol) in five portions over 45 minutes and then stirred at r.t. for 16 hours. The mixture was washed with 10% aqueous sodium bisulfate, and the organic portion was separated and the aqueous portion is extracted two times with DCM. The combined organic extracts were dried (($Na_2SO_4$) and concentrated to dryness. The resulting residue was dissolved in a small amount of DCM and filtered through 7 inch silica gel in a 2L sintered glass funnel eluting with 25% EtOAc/hexanes. The eluent was concentrated to dryness and the enantiomers were separated by chiral chromatography. The first eluting isomer was labeled as isomer #1 and the second eluting is labeled as isomer #2, which afforded about 52.6 g (45%) of the final compound (isomer 2). EIS-MS 292 [M+1].

Preparation 2C

1-Carboxymethyl-1,3-dihydro-isoindole-2-carboxylic acid tert-butyl ester

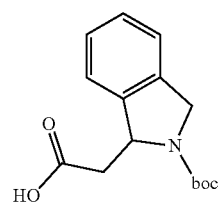

To 1-methoxycarbonylmethyl-1,3-dihydro-isoindole-2-carboxylic acid tert-butyl ester (52.6 g, 180.5 mmol) in MeOH (500 mL) was added 1 N NaOH (199 mL, 199.0 mmol). The mixture is stirred at r.t. for about 48 hours and then concentrated to dryness. The resulting residue was dissolved in water (300 mL) and extracted with diethyl ether (2×). The aqueous portion was acidified to pH 2 with 10% aqueous sodium bisulfate and extracted with EtOAc. The combined organic extracts were dried ($MgSO_4$) and concentrated to dryness to afford about 49.8 g of the final compound (99%). EIS-MS 276 [M−1].

Preparation 3C (2-isopropyl-2,3-dihydro-1H-isoindol-1-yl)-acetic acid

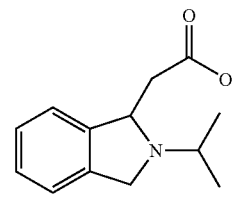

Step A: (2,3-dihydro-1H-isoindol-1-yl)-acetic acid methyl ester

To the compound prepared in Preparation C1 (11.75 g., 40.41 mmol) in DCM (50 mL) was added TFA (50 mL) dropwise. After about 2 hours, the mixture was concentrated to dryness and the resulting residue was partitioned with saturated aqueous sodium bicarbonate (200 mL) and EtOAc (300 mL). The organic portion was separated and the aqueous layer was extracted with DCM (4×500 mL). The combined DCM extracts were combined, dried ($Na_2SO_4$), and concentrated to dryness to afford about 3.97 g (51%).

Step B: (2-isopropyl-2,3-dihydro-1H-isoindol-1-yl)-acetic acid methyl ester

To the compound obtained from Step A (0.50 g, 2.61 mmol) in dichloroethane (46 mL) was added acetone (1.76 mL, 24.01 mmol) and sodium triacetoxyborohydride (2.48 g., 11.74 mmol). After 6 hours, the mixture was diluted with 1.0N NaOH (100 mL), and the organic portion was separated. The aqueous layer was extracted with DCM (3×100 mL). The combined DCM extracts were dried ($MgSO_4$) and concentrated to dryness to afford about 0.60 g (99%). EIS-MS 235 [M+1].

Step C: To the compound of Step B (0.53 g., 2.30 mmol) in MeOH (5.1 mL) was added 1.0N NaOH (2.53 mL, 2.53 mmol). After two days, the solution was concentrated to dryness. The resulting residue was diluted with 1.0N HCl and water was loaded onto a strong cation exchange resin. The resin was washed with water, THF/water (1:1) and then water. The product was then eluted from the resin with pyridine/water (1:9). The eluent was concentrated to dryness to afford about 0.43 g (85%) of the final compound. EIS-MS 220 [M+1].

95

Preparation 4C (2-Methyl-2,3-dihydro-1H-isoindol-1-yl)-acetic acid

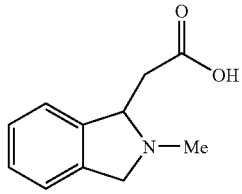

Step A:
(2-Methyl-2,3-dihydro-1H-isoindol-1-yl)-acetic acid methyl ester

The compound from preparation C1 was deprotected with TFA in a manner similar to preparation 3C of Step A. To the deprotected compound (0.50 g, 2.61 mmol), in dichloroethane (46 mL), was added 37% aqueous formaldehyde solution (1.80 mL, 24.01 mmol) and sodium triacetoxyborohydride (2.48 g., 11.74 mmol). After 3 days, the mixture was diluted with 1.0N NaOH (100 mL). The organic portion was separated and the aqueous layer was extracted with DCM (3×100 mL). The combined DCM extracts were dried ($Na_2SO_4$) and concentrated to dryness. The resulting residue was purified by flash chromatography ($SiO_2$, eluting with 100% EtOAc) affording about 0.43 g (79%) of the alkylated isoindole. EIS-MS 206 [M+1].

Step B: To the compound of Step A (0.34 g., 1.66 mmol) in MeOH (3.7 ML) was added 1.0N NaOH (1.82 mL, 1.82 mmol). After 2 days, the solution was concentrated to dryness. The resulting residue was diluted with 1.0N HCl and water was then loaded onto a strong cation exchange resin. The resin was washed with water, THF/water(1:1) and water, and the product was eluted from the resin with pyridine/water(1:9). The eluent was concentrated to dryness to afford about 0.31 g (98%) of the final compound. EIS-MS 192 [M+1].

Preparation 5C

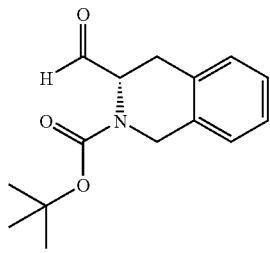

The above compound was prepared from Boc-L-Tic-OH as described in Preparation 6C below, except that the Weinreb amide was made by a similar procedure to that described in *Synthesis*, 676, 1983.

96

Preparation 6C

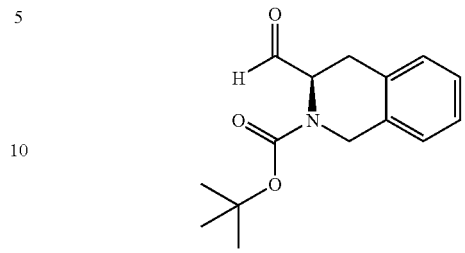

Boc-D-Tic-OH (14.9 g, 53.7 mmol), methoxymethylamine hydrochloride (5.24 g, 53.7 mmol), EDC (11.3 g, 59.1 mmol), HOBT (7.98 g, 59.1 mmol), DIEA (9.83 ml, 59.1 mmol) and THF (500 ml) were combined, and the resulting mixture was stirred for about 18 hours at r.t. under nitrogen. The reaction mixture was concentrated and the residue was taken up in ethyl acetate. The resulting mixture was washed with 1M HCl, saturated $NaHCO_3$ and brine, which was then dried via filtration through phase separator paper. Removal of solvent gives a residue, which was chromatographed on silica gel using (1:1 ethylacetate/hexane) to give about 12.3 g of Boc-D-Tic-NMeOMe (Weinreb amide).

Lithium aluminum hydride (1.0M in THF, 5.1 ml, 5.00 mmol) was slowly added to the Weinreb amide prepared above (1.28 g, 4.00 mmol) in THF (35 ml) at 0° C. The reaction mixture was stirred at 0° C. for about 15 minutes. Aqueous $KHSO_4$ (970 mg in 20 ml $H_2O$) was slowly added followed by diethylether. The organic layer was separated and the aqueous layer was extracted with diethylether. The organic phases were combined and washed with aqueous 1M HCl, saturated aqueous $NaHCO_3$ and brine, which was then dried over $Na_2SO_4$. Removal of solvent afforded about 780 mg of the final compound. MS: MH+262.

Preparation 7C (2-Butyl-2,3-dihydro-1H-isoindol-1-yl)-acetic acid methyl ester

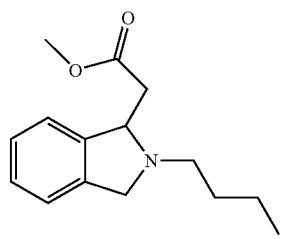

The compound from preparation C1 was deprotected with TFA in a manner similar to preparation 3C of Step A. To the deprotected compound (0.50 g, 2.61 mmol) and butryaldehyde (2.16 mL, 24.01 mmol) in dichloroethane (46 mL) was added sodium triacetoxyborohydride (2.48 g., 11.74 mmol). After reacting about 3 hours, the mixture was diluted with 1.0 N NaOH (100 mL) and partitioned. The aqueous layer was extracted with DCM (3×75 mL). The DCM layers were combined, dried over sodium sulfate, filtered and concentrated under reduced pressure to give a brown residue. The residue was purified via silica gel chromatography (eluent: ethyl acetate/hexanes (1:3). The purified fractions were combined and concentrated to give the title compound as a brown oil (0.51 g, 77%). MS ES 249.2 (M+H)

Preparation 8C (2-Butyl-2,3-dihydro-1H-isoindol-1-yl)-acetic acid

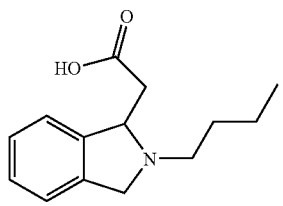

To a solution containing the compound 7C (0.47 g, 1.89 mmol) in methanol (4.2 mL) was added 1.0 N NaOH (2.08 mL, 2.08 mmol). After reacting about 2 hours, the solution was concentrated under reduced pressure. The residue was diluted with 1.0 N HCl, and water was loaded onto a strong cation exchange resin. The resin was washed with water and THF/water (1:1), and the product was eluted from the resin with pyridine/water (1:9). The pyridine washes were concentrated under reduced pressure, and azeotroped with acetone to give the title compound as brown solids (0.28 g.,(64%)) MS ES 234.19 (M+H)

Preparation 9C

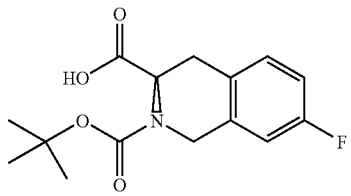

Step A: To a solution of N-Boc-4-Fluoro-D-Phe (2.37 g, 8.366 mmol) in methanol, 3 mL of concentrated sulfuric acid was added. The mixture was heated to reflux overnight and then concentrated in vacuo. MS M+1 198.1

Step B: To an ice cold mixture of 1.65 g (8.367 mmol) of compound from Step A, 1.353 mL of pyridine and ethyl chloroformate (0.848 mL, 8.869 mmol) is added slowly with stirring for about 30 minutes giving white solid. The mixture was partitioned between water and ethyl acetate. The aqueous layer was extracted with EtOAc (2×). The combined organic solution was dried over MgSO₄, filtered, and concentrated in vacuo to give about 2.17 g of yellow oil (96%). MS M+1 270.1.

Step C: A mixture containing 2.17 g (8.06 mmol) of the compound from Step B, paraformaldehyde (0.254 g, 8.46 mmol), and 10 mL of 3:1 glacial acetic acid/conc. sulfuric acid was stirred at r.t. for about 48 hours. The mixture was partitioned between water and ethyl acetate. The aqueous layer was extracted with EtOAc (3×). The combined EtOAc solution was dried over magnesium sulfate, filtered, and concentrated in vacuo. The desired product was purified by column chromatography eluting with 25% EtOAc in Hexane to give about 1.31 g (58%) of colorless oil. MS: M+1 282.1

Step D: A solution of 1.31 g (4.656 mmol) of material from Step C in 20 mL of 5N HCl was heated to reflux for about 24 hours. The solution was concentrated in vacuo. The resulting white solid was washed with ether to afford about 0.87 g (81%). MS M+1 196.1.

Step E: To a solution of 0.87 g (3.755 mmol) of material from Step D in 20 ml of 1:1 dioxane/water, di-t-butyl-dicarbonate (0.901 g, 4.131 mmol) and 2.355 mL (16.90 mmol) of TEA were added. The mixture was allowed to stir at r.t. overnight. The mixture was diluted with EtOAc, and the separated aqueous layer was extracted with EtOAc (3×). The combined organic solution was dried over magnesium sulfate, filtered and concentrated in vacuo to give about 0.64 g (58%)of the final compound. MS M−1 294.1.

Preparation 10C

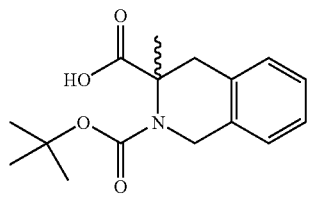

Step A: By following a procedure of Preparation 28C, Step A and 1.0 g(5.58 mmol) of α-methyl-DL-phenylanaline, about 1.4 g of ester was prepared. MS M+1 194.1

Step B: By following a procedure of Preparation 28C, Step B and 1.08 g (5.59 mmol) of material from Step A, about 1.48 g (100%) of product was prepared. MS M+1 266.1

Step C: By following a procedure of Preparation 28C, Step C and 1.48 g (5.59 mmol) of material from Step B, about 1.55 g (100%) of product was prepared. MS M+1 278.1

Step D: By following a procedure of Preparation 28C, Step D and 1.55 g (5.59 mmol) of material from Step C, about 1.33 g of product was prepared. MS M+1 192.1

Step E: By following a procedure of Preparation 28C, Step E and 1.33 g (5.84 mmol) of material from Step D, about 1.70 g (100%) of the final compound was prepared. MS M+1 292.2

Preparation 11C

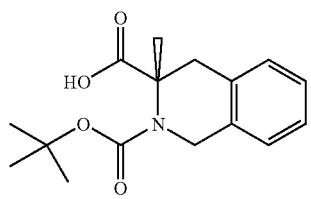

Step A: By following a procedure of Preparation 28C, Step A and 2.0 g(11.16 mmol) of □-methyl-D-phenylanaline, about 2.15 g of ester was prepared. MS M+1 194.1

Step B: By following a procedure of Preparation 28C, Step B and 2.15 g (11.16 mmol) of material from Step A, about 1.46 g (49%) of product was prepared. MS M+1 266.1

Step C: By following a procedure of Preparation 28C, Step C and 1.46 g (5.503 mmol) of material from Step B, about 0.74 g (48%) of product was prepared. MS M+1 278.1

Step D: By following a procedure of Preparation 28C, Step D and 0.74 g (2.67 mmol) of material from Step C, about 0.54 g (89%) of product was prepared. MS M+1 192.1

Step E: By following a procedure of Preparation 28C, Step E and 0.54 g (2.37 mmol) of material from Step D, about 0.54 g (78%) of the final compound was prepared. MS M+1 292.2

Preparation 12C

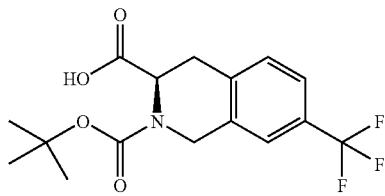

Step A: By following a procedure of Preparation 28C, Step A and 0.65 g (1.95 mmol) of N-Boc-4-trifluoromethyl-D-phenylanaline, about 0.48 g of ester was prepared. MS M+1 248.0

Step B: By following a procedure of Preparation 28C, Step B and 0.48 g (1.95 mmol) of material from Step A, about 0.60 g (96%) of product was prepared. MS M+1 320.1

Step C: By following a procedure of Preparation 28C, Step C and 0.6 g (1.879 mmol) of material from Step B, about 0.37 g (59%) of product was prepared. MS M+1 332.1

Step D: By following a procedure of Preparation 28C, Step D and 0.37 g (1.117 mmol) of material from Step C, about 0.11 g (35%) of product was prepared. MS M+1 246.1

Step E: By following a procedure of Preparation 28C, Step E and 1.11 g (0.391 mmol) of material from Step D, about 0.234 g (>100%) of the final compound is prepared. MS M−1 344.1

Preparation 13C

Lithium; (2-tert-butoxycarbonyl-1,2,3,4-tetrahydro-isoquinolin-1-yl)-acetate

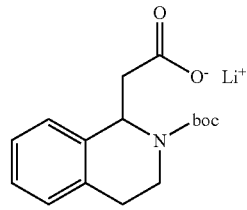

Step 1: (1,2,3,4-tetrahydro-isoquinolin-1-yl)-acetic acid methyl ester

To a solution 100.4 g (52 mol) of Boc-tetrahydo isoquinoline-1-acetic (100.4 g, 520.0 mmol) in 200 mL methanol was added 400 mL of 2.3 M HCl in methanol. The mixture was stirred overnight and concentrated in vacuo. The residue was dissolved in ethyl acetate and washed with saturated sodium bicarbonate, brine, and then dried (Na$_2$SO$_4$) and concentrated in vacuo to afford about 109.5 g (100%) of the title compound. EIS-MS: 206 (M+1).

Step 2: 1-methoxycarbonylmethyl-3,4-dihydro-1H-isoguinoline-2-carboxylic acid tert-butyl ester To a 0° C. solution of material from Step 1 (50.5 g, 240.0 mmol) in 250 mL dry THF was added di-tert-butyl dicarbonate (59.3 g, 270.0 mmol) in 50 mL dropwise. After siring for about 45 minutes, the mixture was concentrated in vacuo. The residue was dissolved in ethyl acetate, washed with saturated sodium bicarbonate and brine, and then dried (Na$_2$SO$_4$) and concentrated in vacuo. Chromatography of the residue afforded both enantiomers of the title compound. EIS-MS: 306 (M+1).

Step 3: To a solution of material from Step 2 (10.2 g, 33.4 mmol) in 220 mL of dioxane was added a solution of lithium hydroxide monohydrate (1.67 g, 39.8 mmol) in 110 mL water in portions to maintain a temperature below 30° C. The mixture was stirred for about 16 hours and concentrated in vacuo to afford about 11.2 g of the final compound. EIS-MS: 292 (M+1).

Preparation 14C lithium; (2-methyl-1,2,3,4-tetrahydro-isoquinolin-1-yl)-acetate

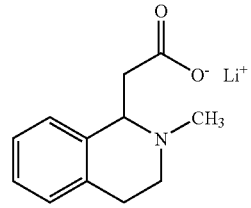

Step 1: (1,2,3,4-Tetrahydro-isoquinolin-1-yl)-acetic acid methyl ester

The material from Preparation of 13C Step 2 (9.98 g, 32.7 mmol) was mixed with 500 mL cold 4M HCl/dioxane and stirred at r.t. for about an hour. The mixture was concentrated in vacuo. The residue was dissolved in ethyl acetate and then washed with saturated sodium bicarbonate and brine. The organic portion was dried (Na$_2$SO$_4$), filtered and concentrated in vacuo to afford about 6.9 g (100%) of the title compound. EIS-MS: 206 (M+1).

Step 2: (2-methyl-1,2,3,4-tetrahydro-isoquinolin-1-yl)-acetic acid methyl ester

To a solution of material from Step 1 (6.71 g, 32.0 mmol) in 175 mL of dichloroethane was added 37% aqueous formaldehyde (22.6 mL, 300 mmol). After about 10 minute, sodium triacetoxyborohydride (31.2 g, 147.0 mmol) was added in 2 to 3 g portions with some cooling to maintain ambient temperature. The mixture was stirred for about 16 hours and DCM and water was added. The mixture was adjusted to pH 9–10 with 5N sodium hydroxide. The organic layer was separated, washed with brine, and then dried (Na$_2$SO$_4$) and concentrated in vacuo. Chromatography (silica gel, 5%(2N ammonia in methanol)/DCM) of the residue afforded about 6.9 g (96%) of the title compound. EIS-MS: 220 (M+1).

Step 3: To a solution of material from Step 2 (4.45 g, 18.9 mmol) in 120 mL dioxane was added lithium hydroxide monohydrate (1.02 g, 22.7 mmol) in 65 mL water in portions keeping the temperature below 30° C. After about 16 hours, the mixture was concentrated in vacuo to afford about 8.12 g of the final compound. EIS-MS: 206 (M+1).

Preparation 15C 1,1-Dimethyl-6-methoxy-1,2,3,4-tetrahydroisoquinoline-3-carboxylic acid ethyl ester

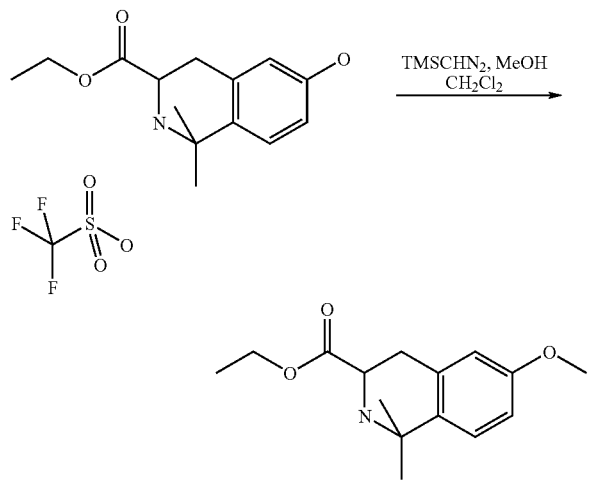

To a solution of the triflate salt of 1,1-dimethyl-1,2,3,4-tetrahydroisoquinoline-3-carboxylic acid ethyl ester (1.5 g, 3.76 mmol, 1.0 eq.) in MeOH (20 mL) and $CH_2Cl_2$ (2 mL) at 0° C. was added a solution of (trimethylsilyl)diazomethane (2.0 M in hexane, 3.7 mL, 2.0 eq.). The resulting mixture was warmed to r.t. and stirred overnight, and then the solution was concentrated. Purification by flash chromatography (125 g $SiO_2$ linear gradient, 40 mL/min, 1:1 EtOAc/hexane for 33 minutes) afforded about 900 mg of the final compound (96%).

LRMS (electrospray): 250:2 (M+1).

"B Domain" and "C Domain" Combination

Preparation 1BC

3-[2-(4-Chloro-phenyl)-1-methoxycarbonyl-ethyl-carbamoyl]-3,4-dihydro-1H-isoquinoline-2-carboxylic acid tert-butyl ester (N-Boc-D-Tic-4-Cl-D-phe-OH)

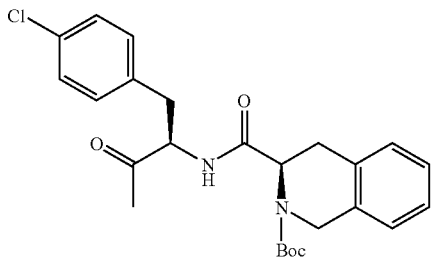

Step 1: The HCl salt of H-D-p-Cl-Phe-OMe (35.8 g, 129 mmol) was dissolved in water (200 mL). Ethyl acetate (200 mL) was added followed by addition of a saturated sodium bicarbonate solution. The mixture was stirred for about 5 minutes, and then the organic layer was separated, washed with water (200 mL) and dried over magnesium sulfate. Concentration of the mixture under reduced pressure produces a white solid (32.2 g). The solid was then dissolved in methylene chloride (200 mL), D-Boc-Tic (35.8 g, 129 mmol) and 4-dimethylaminopyridine (75 mg). The mixture was cooled to 0° C. and JEDC (24.7 g, 129 mmol) was added in two portions. After stirring for about 20 minutes, the ice bath was removed and the solution was allowed to warm to r.t. The solution was stirred for about 4 hours and then diluted with water (400 mL). The organic layer was washed with water (3×), dried over magnesium sulfate and concentrated under reduced pressure to give a clear oil (70 g). Column chromatography (35% ethyl acetate/heptane) afforded about 55.6 g of the intermediate Boc-D-p-Cl-Phe-OMe (85%).

$^1$H NMR(DMSO) (Two rotomers observed) δ8.26(d, 1H), 8.19(d, 0.5 H), 7.24(d, 2H), 7.00–7.19(m, 8H), 4.68(m, 0.5H), 4.20–4.60(m, 4.5H), 3.58(s, 3H), 3.51(s, 1.5H), 2.77–3.10(m, 6H), 1.42(s, 3H), 1.21(s, 9H). MS(ES) 473.0 (M$^+$), 471.1(M$^-$).

Step 2: The compound of Step 1 (54.3 g, 114 mmol) was dissolved in methanol (170 mL). The solution was cooled to 0° C. with an ice bath and 1N NaOH (290 mL) is added dropwise. After vigorous stirring for about 20 minutes, the mixture was warmed to about 25° C. The solution was concentrated under reduced pressure to give yellow oil. The oil was dissolved in water (200 mL) and the pH is adjusted to about 1. Ethyl acetate (200 mL) was added, and the organic layer was separated and dried over magnesium sulfate. Concentration of the organics produced about 46.3 g of the final compound.

$^1$H NMRDMSO) (Two rotomers observed) δ7.98(d, 1H), 7.82(d, 0.5 H), 6.90–7.41(m, 16H), 4.20–4.70(m, 8.5H), 2.60–3.20(m, 8.5H), 1.32–1.41(m, 19H). MS(ES) 459.1 m/z(M$^+$), 457.1(M$^-$).

Preparation 2BC

Boc-L-Tic-4-Cl-D-phe-OH

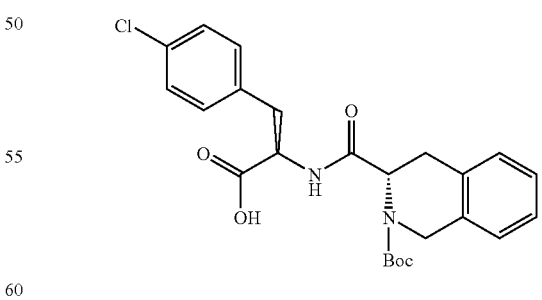

The above compound was prepared using N-Boc-Tic-OH as described in Preparation 1BC.

$^1$H NMR(DMSO) (Two rotomers observed) δ7.98(d, 1H), 7.72(d, 0.5 H), 6.90–7.41(m, 16H), 4.0–4.70(m, 8.5H), 2.60–3.20(m, 8.5H), 1.32–1.41(m, 19H). MS (ES) 459.1 m/z(M$^+$), 457.1(M$^-$).

Preparation 3BC

Lithium; 2-[(2-tert-butoxycarbonyl-1,2,3,4-tetrahydro-isoquinolin-3-ylmethyl)-amino]-3-(4-chlorophenyl)-propionate

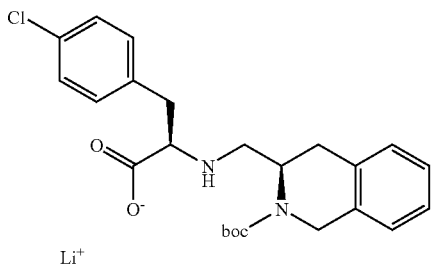

Step A: 3-(Methoxy-methyl-carbamoyl)-3,4-dihydro-1H isoquinoline-2-carboxylic acid tert-butyl ester To Boc-D-1,2,3,4-tetrahydroisoquinoline carboxylic acid (14.9 g, 53.7 mmol), in THF (500 mL), was added N,O-dimethylhydroxylamine hydrochloride (5.24 g, 53.7 mmol), EDC (11.3 g, 59.1 mmol), HOBT (7.98 g, 59.1 mmol) and DIPEA (9.83 ml, 56.4 mmol). The mixture was stirred for about 16 hours at r.t. and under nitrogen, and then concentrated to dryness. The resulting residue was taken up in EtOAc, washed with 1M HCl, saturated sodium bicarbonate and brine, and then dried (Na$_2$SO$_4$). After concentrating to dryness, the resulting residue was purified by flash chromatography (SiO$_2$, eluting with 1:1 EtOAc/hexane) to give about 12.3 g (71%) of the ester. EIS-MS 321 [M+1]

Step B: 3-Formyl-3,4-dihydro-1H-isoquinoline-2-carboxylic acid tert-butyl ester To a 0° C. solution of material from Step A (1.28 g, 4.00 mmol) in THF (30 mL) was slowly added 1.0 M LAH (in THF, 5.1 ml, 5.1 mmol). The reaction mixture was stirred at 0° C. for another 15 minutes. To the mixture was slowly added 20 mL of 5% aqueous potassium hydrogensulfate and the mixture extracted with Et$_2$O (2×). The combined organic portions were washed with 1M HCl, saturated sodium bicarbonate and brine, and then dried (Na$_2$SO$_4$) and concentrated to dryness affording 0.78 g (75%).
EIS-MS 262 [M+1]

Step C: 3-{[2-(4-Chloro-phenyl)-1-methoxycarbonyl-ethylamino]-methyl}-3,4-dihydro-1H-isoguinoline-2-carboxylic acid tert-butyl ester To a 0° C. solution of 4-Cl-D-Phe-OMe (6.27 g, 25.1 mmol) and sodium acetate (8.23 g, 100.0 mmol), in 850 ml dry MeOH, was added material from Step B (9.8 g, 37.6 mmol) in 50 ml MeOH. The mixture was stirred for about 15 minutes and then sodium cyanoborohydride (2.37 g, 37.6 mmol) was added. The cooling bath was removed and the reaction stirred for 16 hours at r.t. The mixture was concentrated to dryness and the resulting residue taken up in water and 1 ml of 1M HCl. The mixture was extracted with EtOAc, and the organics were washed with saturated sodium bicarbonate and brine, and then dried (Na$_2$SO$_4$) and concentrated to dryness. The resulting residue was purified by flash chromatography (SiO$_2$, eluting with 2:1 hexane/EtOAc) affording about 8.62 g (75%). EIS-MS 459 [M+1]

Step D: To a 12° C. solution of material from Step C (1.11 g, 2.42 mmol) in dioxane (15 ml) was added a solution of lithium hydroxide (0.10 g, 2.42 mmol) in water (7.5 mL). The mixture was stirred for about 16 hours and then concentrated to dryness affording about 1.08 g (100%) of the final compound. EIS-MS 445 [M+1].

Preparation 4BC lithium; 2-[(2-tert-butoxycarbonyl-1,2,3,4-tetrahydro-isoquinolin-3-ylmethyl)-amino]-3-(4-chlorophenyl)-propionate

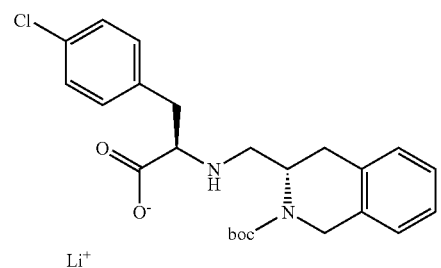

The above compound was Prepared in a manner similar to the preparation 3BC above except Boc-L-1,2,3,4-tetrahydroisoquinoline carboxylic acid was used.

Preparation 5BC

Preparation of Lithium 2-[(2-tert-butoxycarbonyl-1,2,3,4-tetrahydro-isoquinolin-3-ylmethyl)-methylamino]-3-(4-chloro-phenyl)-propionate

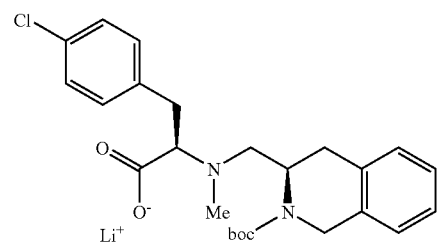

Step A: To a solution of 3-{[2-(4-Chloro-phenyl)-1-methoxycarbonyl-ethylamino]-methyl}-3,4-dihydro-1H-isoquinoline-2-carboxylic acid tert-butyl ester from preparation 3BC Step C (0.60 gm, 1.31 mmol) in anhydrous methanol, was added sodium acetate (0.54 gm, 6.54 mmol). The solution was brought to pH 5–6 with 3–4 drops of glacial acetic acid. Aqueous formaldehyde (37% by wt., 0.49 mL)

was added. The solution was put under a nitrogen atmosphere and cooled to 0° C. After about 15 minutes, sodium cyanoborohydride (0.25 gm, 3.92 mmol) was added and rinsed into the reaction with anhydrous methanol (5 mL). The mixture was stirred at r.t. overnight, and then concentrated in vacuo and reconstituted in aqueous sodium bicarbonate and ethyl acetate. After separation of phases, the aqueous phase was extracted with ethyl acetate (2×), and all organics were combined, dried (magnesium sulfate), filtered, and concentrated to an opaque white oil (0.64 gm). Chromatography (0 to 20% ethyl acetate in hexane) gave about 0.6 g of methylated product as a clear oil (97%). MS (m/z, ES+): 473.2.

Step B: A solution of LiOH.H$_2$O (0.05 gm, 1.27 mmol) in distilled water (4 mL) was added to a solution of the material from Step A in 1,4-dioxane (8 mL), and the reaction was cooled slightly in an ice water bath. The mixture was stirred under a nitrogen atmosphere at r.t. overnight. An additional 1.5 eq. of LiOH.H$_2$O (0.08 gm) were added as an aqueous solution (4 mL), and the mixture was stirred at r.t. over the weekend. The mixture was concentrated, and then combined with THF and concentrated (3×) to help dry the material. The resulting foam was dried at r.t. overnight in a vacuum oven to give about 0.67 g of final compound as a white foam (114%). MS (m/z, ES+): 459.2

Preparation 6BC lithium 2-[(2-tert-butoxycarbonyl-1,2,3,4-tetrahydro-isoquinolin-3-ylmethyl)-(2-methoxy-ethyl)-amino]-3-(4-chloro-phenyl)-propionate

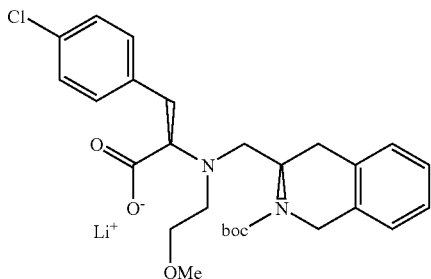

Step A: To a solution of methoxyacetaldehyde (0.15 gm, 2.03 mmol), 3-{[2-(4-Chloro-phenyl)-1-methoxycarbonyl-ethylamino]-methyl}-3,4-dihydro-1H-isoquinoline-2-carboxylic acid tert-butyl ester from preparation 3BC Step C (0.31 gm, 0.68 mmol) in acetonitrile was added sodium triacetoxyborohydride (0.72 gm, 3.38 mmol). After stirring overnight under a nitrogen atmosphere at r.t., additional acetaldehyde (0.25 gm) dissolved in acetonitrile and sodium triacetoxyborohydride (0.21 gm) was added, and the mixture was stirred for about 8.5 hours. The mixture was quenched at r.t. with 5N NaOH (5 mL). The aqueous phase was separated from the organic and extracted with ethyl acetate (4×). The combined organics were washed with a brine solution, and then dried, filtered and concentrated. Chromatography (gradient of ethyl acetate in hexane, 0 to 12%) gives about 0.23 g of 3-{[[2-(4-Chloro-phenyl)-1-methoxycarbonyl-ethyl]-(2-methoxy-ethyl)-amino]-methyl}-3,4-dihydro-1H-isoquinoline-2-carboxylic acid tert-butyl ester as a yellow oil (70%). MS (m/z, ES+): 517.2.

Step B: To a solution of the material from Step A in 1,4-dioxane was added a solution of lithium hydroxide monohydrate (0.05 gm, 1.11 mmol) in distilled water (2 mL). The mixture was stirred overnight at r.t. and then concentrated to a white residue. Addition of THF and concentration (3×) gives the lithium carboxylate as a foam. The foam was dried overnight under vacuum to afford about 0.25 g of crude solids (109%). MS (m/z, ES+): 503.3

Preparation 7BC

1-{[1-Carboxy-2-(4-chloro-phenyl)-ethylcarbamoyl]-methyl}-1,3-dihydro-isoindole-2-carboxylic acid tert-butyl ester

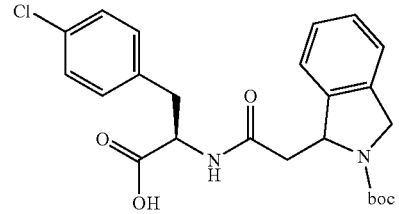

Step A: To a suspension of 4-Cl-D-Phe-OMe hydrochloride (40.4 g, 161.5 mmol) in DCM (250 mL) was added saturated aqueous sodium bicarbonate (250 mL), and the mixture was stirred at r.t. for about 1 hour. The organic portion was separated and the aqueous portion was extracted with DCM (2×). The combined organic portions were dried (Na$_2$SO$_4$) and concentrated to dryness. To the free amine, in DCM (400 mL) at 0° C., was added 1-Carboxymethyl-1,3-dihydro-isoindole-2-carboxylic acid tert-butyl ester from preparation 2C (isomer 2, 44.8 g, 161.5 mmol), EDC (31.0 g, 161.5 mmol) and 4-DMAP (2.0 g, 16.1 mmol). The mixture was stirred at 0° C. for about 30 minutes whereupon the cooling bath was removed and the mixture was stirred for another 5 hours at r.t. The mixture was then washed with saturated aqueous sodium bicarbonate (200 mL) and 10% aqueous sodium bisulfate (200 mL), and then dried (Na$_2$SO$_4$) and concentrated to dryness to afford about 76.4 g (100%) of the ester. EIS-MS 471 [M−1]

Step B: To the ester from Step A (76.4 g, 161.5 mmol) in MeOH (760 mL) was added 1 N NaOH (242.0 mL, 242.0 mmol), and the mixture was heated at 50° C. for 4 hours and then stirred for another 16 hours at r.t. After concentrating to dryness, the resulting residue was taken up in 500 mL of water and washed with diethyl ether (2×). The aqueous portion was acidified to pH 2 with 10% aqueous sodium bisulfate and extracted with EtOAc (4×200 mL). The combined organic extracts were dried (MgSO$_4$) and concentrated to dryness. The resulting solid was suspended in hexanes, filtered, and dried to afford about 67.7 g (91%) of the final compound. EIS-MS: 457 [M−1]

Preparation 8BC 3-(4-Chloro-phenyl)-2-[(1,1-dimethyl-1,2,3,4-tetrahydro-isoquinoline-3-carbonyl)-amino]-propionic acid methyl ester

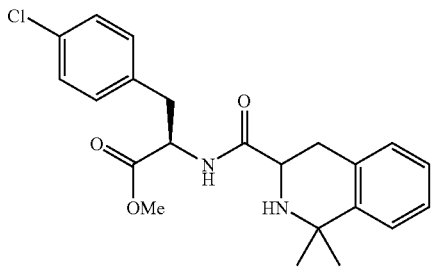

To a solution of 1,1-dimethyl Tic (240 mg, 1.17 mmol), 4-Cl-D-Phe-OMe (322 mg, 1.28 mmol), HOBT (197 mg, 1.46 mmol), and DIPEA (0.81 mL, 44.68 mmol) in DCM/DMF (1:1) was added EDC (280 mg, 1.46 mmol). The resulting mixture was stirred at r.t. overnight. The mixture was then diluted with EtOAc (100 mL), washed with saturated aqueous NaHCO$_3$ and brine, and then dried (Na$_2$SO$_4$) and concentrated to dryness. Purification and separation of diastereomers by flash chromatography (35 g SiO$_2$, linear gradient, 40 mL/min 10–50% EtOAc/hexane for 25 minutes and 50% EtOAc/hexane for 7 minutes) afforded the final compound. LRMS (ESI+): 401.1 (M+H)

Preparation 9BC 3-(4-Chloro-phenyl)-2-[(1,1-dimethyl-1,2,3,4-tetrahydro-isoquinoline-3-carbonyl)-amino]-propionic acid

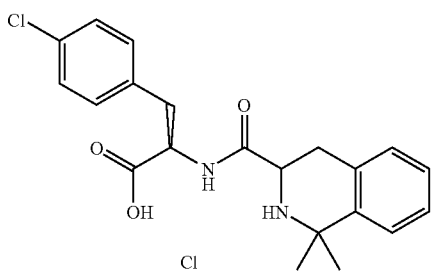

To the compound from preparation 8BC (5.95 g, 14.88 mmol) in a 1:1 mixture of THF/H$_2$O (50 mL) was added lithium hydroxide hydrate (0.75 g, 17.87 mmol). The mixture was stirred at r.t. for about 18 hours. The mixture was then concentrated to dryness. The resulting residue was dissolved in water (50 mL), made acidic with 1N HCl (25 mL) and washed with Et$_2$O (100 mL). The aqueous layer was evaporated to dryness to afford about 6.18 g of the final compound (98%). LRMS(EIS+): 387 [M+1]

Preparation 10BC

1-{[1-Carboxy-2-(4-methoxy-phenyl)-ethylcarbamoyl]-methyl}-1,3-dihydro-isoindole-2-carboxylic acid tert-butyl ester

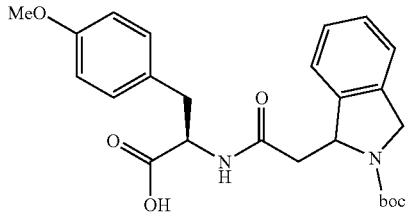

Step 1: To a solution of p-methoxy-D-Phe-OMe (1.72 g, 8.23 mmol) dissolved in THF (45 mL) and 1-carboxymethyl-1,3-dihydro-isoindole-2-carboxylic acid tert-butyl ester (2.51 g, 9.05 mmol) was added HOBT (1.22 g, 9.05 mmol), EDC (1.73 g, 9.05 mmol) and DIPEA (1.6 mL, 9.05 mmol). The reaction was stirred overnight at r.t. and then concentrated. The mixture was washed with 1M HCl, dilute NaHCO$_3$ and brine, and then dried with sodium sulfate. The mixture was chromatographed on silica gel eluting with 3% 2M NH$_3$ in MeOH/CH$_2$Cl$_2$ giving about 2.58 g as white solids. Mass MH$^+$ 469

Step 2: The white solid from Step 1 (2.58 g, 5.5 mmol) was dissolved in dioxane (37 mL) and lithium hydroxide hydrate (0.35 g, 8.3 mmol) in H$_2$O (19 mL) was added. The mixture was stirred for about 2.5 hours at r.t. and then concentrated. Ethyl acetate was added and the mixture was washed with 1M HCl and brine, and then concentrated to afford about 2.56 g of the final free acid. LRMS(ESI+): 455 (M+1)

Preparation 11BC

1-[1-Carboxy-2-(4-chloro-phenyl)-ethylcarbamoyl]-1,3-dihydro-isoindole-2-carboxylic acid tert-butyl ester

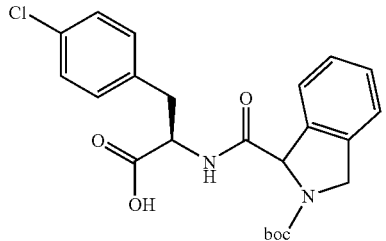

Step 1: About 2.0 g (7.60 mmol) of (R,S)-Boc-1,3-dihydro-2H isoindole carboxylic acid was dissolved in 100 ml THF and about 2.28 g (9.12 mmol) of 4-Cl-D-phe-methylester HCl, 1.25 g (9.12 mmol) of HOBT, 1.75 g (9.12 mmol) of EDC, and 1.6 ml (9.12 mmol) of DIEA were added. The mixture was stirred overnight at r.t., concentrated to dryness, washed with 1M HCl, dilute NaHCO$_3$ and brine, and then dried over sodium sulfate. The material was chromatographed on silica gel by eluting with ethyl acetate/ hexane 1:2 to give about 1.05 g of isomer 1 and about 0.82 g of isomer 2, and about 1.61 g mixture of isomers 1 and 2. Mass MH+ 459

Step 2: About 0.82 g (1.79 mmol) of the isomer 2 obtained in Step 1 was dissolved in 11 ml of dioxane and 0.11 g (2.68 mmole) of LiOH-hydrate in 5.5 ml of H$_2$O was added. The mixture was stirred for about 4 hours at r.t. and then concentrated to dryness. Ethyl acetate was added, and the solution was washed with 1M HCl and brine, and then concentrated to dryness affording about 0.75 g of the free acid. Mass: 445 (MH+)

EXAMPLE

Example 1

Coupling Procedure 1

6-Methoxy-1,1-dimethyl-1,2,3,4-tetrahydro-isoguinoline-3-carboxylic acid (1-(4-chloro-benzyl)-2-{4-[2-(2-morpholin-4-yl-ethoxy)-phenyl]-piperazin-1-yl}-2-oxo-ethyl)-amide dichloride

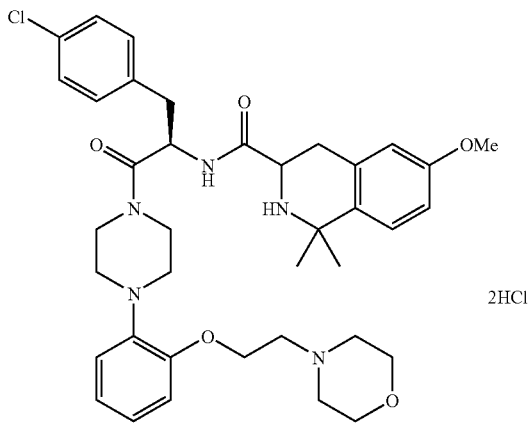

Step 1: To a 3000 mL flask containing 4-[2-(2-Piperazin-1-yl-phenoxy)-ethyl]-morpholine (25.3 g, 0.0868 mol), Boc-D-p-Cl-Phe (28.6 g, 0.0954 mol), HOBT (13.5 g, 0.10 mol), iPr$_2$NEt (30.2 mL, 0.173 mol), 800 mL of CH$_2$Cl$_2$, and 200 mL of DMF was added EDC (19.1 g, 0.10 mol). After stirring overnight, the solution was concentrated to remove the CH$_2$Cl$_2$ and divided into two equal portions which were each diluted with 1000 mL of EtOAc. The organic solutions were washed with saturated sodium bicarbonate, water (2×) and brine, and then dried (Na$_2$SO$_4$), filtered and concentrated. Half of the material was subjected to silica gel chromatography (0 to 5% MeOH/CH$_2$Cl$_2$) to afford a white solid. The other half was dissolved in Et$_2$O and precipitated by adding 1 M HCl in Et$_2$O. The precipitate was washed with Et$_2$O, transferred to a flask as a slurry in Et$_2$O, and concentrated to afford a white solid. The Boc protected product purified by flash chromatography was deprotected as described in Step 2 below. The Boc protected product purified by precipitation was deprotected in a similar manner. The purity of the two batches of material were identical by HPLC (>99%). Combined yield: 38.4 g, 0.070 mol, 81%.

Step 2: To a solution of (1-(4-chloro-benzyl)-2-{4-[2-(2-morpholin-4-yl-ethoxy)-phenyl]-piperazin-1-yl}-2-oxo-ethyl)-carbamic acid tert-butyl ester (23.57 g, 41.1 mmol) in MeOH (225 mL) was added 1.0 M HCl in Et$_2$O. The mixture is stirred at r.t. overnight. The solid was filtered, washed with Et$_2$O and dried under vacuum overnight to afford 2-amino-3-(4-chloro-phenyl)-1-{4-[2-(2-morpholin-4-yl-ethoxy)-phenyl]-piperazine-1-yl}-propan-1-one (19.6 g, 36 mmol, 88%).

Step 3: To a solution of compound from Step 2 (2.0 g, 3.69 mmol, 1.1 eq.), 1,1-dimethyl-6-methoxy-1,2,3,4-tetrahydroisoquinoline-3-carboxylic acid (810 mg, 3.36 mmol, 1.0 eq.), HOBT (567 mg, 4.2 mmol, 1.25 eq.), DIPEA (2.35 mL, 13.44 mmol, 4.0 eq.), CH$_2$Cl$_2$ (20 mL), and DMF (20 mL) was added 1-(3-dimethylaminopropyl)-3-ethylcarbodiimide hydrochloride (805 mg, 4.2 mmol, 1.25 eq.). The mixture was stirred at r.t. overnight and diluted with ethyl acetate. The mixture was washed with saturated aqueous sodium bicarbonate and brine, and then dried over Na$_2$SO$_4$, filtered, and concentrated. Purification by flash chromatography (125 g SiO$_2$, linear gradient, 40 mL/minute, 0 to 10% MeOH/CH$_2$Cl$_2$ over 20 minutes and 10% MeOH/CH$_2$Cl$_2$ for 13 minutes) afforded the final compound (1.68 g, 2.4 mmol, 73%) as a mixture of diastereomers. The final compound was converted to chloride salt by adding 1.0 M HCl in Et$_2$O. The two diastereomers were separated by reversed-phase chromatography.

Isomer-1 (667463): HRMS (electrospray) calcd for C$_{38}$H$_{48}$N$_5$O$_5$Na Cl: 712.3242. Found: 712.3253.

Isomer-2: HRMS (electrospray) calcd for C$_{38}$H$_{48}$N$_5$O$_5$ Na Cl: 712.3242. Found: 712.3278.

Example 2

Coupling Procedure 2

N-[1-(4-Chloro-benzyl)-2-oxo-2-(4-{2-[1-(2,2,2-trifluoro-ethyl)-piperidin-3-yloxy]-phenyl}-piperazin-1-yl)-ethyl]-2-(2,3-dihydro-1H-isoindol-1-yl)-acetamide tristrifluoroacetic Acid

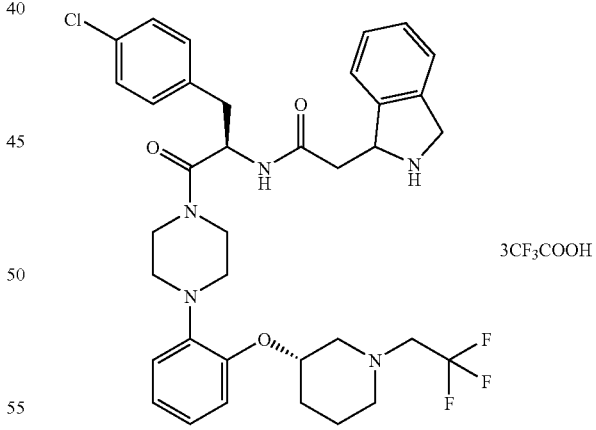

Step 1: To a solution of 208 mg (0.455 mmol, 1.2 eq.) 1-{[1-carboxy-2-(4-chloro-phenyl)-ethylcarbamoyl]-methyl}1–1,3-dihydro-isoindole-2-carboxylic acid tert-butyl ester, 0.13 mL, (0.758 mmol, 2.0 eq.) of DIPEA, and 173 mg (0.455 mmol, 1.2 eq.) of HATU in 8 mL of DCM and 1 mL of DMF was added a solution of 130 mg (0.379 mmol, 1.0 eq.) of 1-{2-[1-(2,2,2-trifluoro-ethyl)-piperidin-3-yloxy]-phenyl}-piperazine in 2 mL of DCM. The solution was stirred at r.t. for about 3 hours and then concentrated to an oil. Ethyl acetate was added and the solution was washed

Example 3

Coupling Procedure 3

[3R, 3(1R)]-1,2,3,4-Tetrahydro-isoquinoline-3-carboxylic acid (1-(4-chloro-benzyl)-2-{4-[2-(1-methyl-piperidin-3-yloxy)-phenyl]-piperazin-1-yl}-2-oxo-ethyl)-amide tristrifluoroacetate

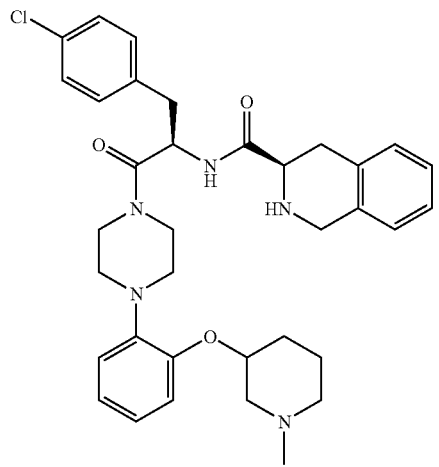

Step 1: 1-[2-(1-Methyl-piperidin-3-yloxy)-phenyl]-piperazine(0.20 g, 0.73 mmol) was taken up in methylene chloride (30 mL) and treated with HOBT (0.10 g, 0.73 mmol), 3-[1-carboxy-2-(4-chloro-phenyl)-ethylcarbamoyl]-3,4-dihydro-1H-isoquinoline-2-carboxylic acid tert-butyl ester (0.37 g, 0.80 mmol), and 1,3-dicyclohexylcarbodiimide (0.17 g, 0.80 mmol). The mixture was stirred at r.t. for about 30 minutes. The precipitate was filtered off, and the solution was diluted with ethyl acetate (400 mL) and washed with water (60 mL), saturated aqueous sodium bicarbonate (60 mL) and brine (60 mL), and then dried over anhydrous sodium sulfate. The solvent was concentrated under reduced pressure, and the resulting residue was purified via silica gel chromatography (5% methanol in ethyl acetate).

Step 2: The resulting product was dissolved in methylene chloride (5 mL), and TFA(5 mL) was added. The mixture was stirred for about 2 hours. The solvent was concentrated under reduced pressure and the residue was purified via preparatory HPLC to afford the final compound (0.80 g, 10%) as a white solid.

with saturated sodium bicarbonate solution, water (4×) and brine, and then dried with sodium sulfate, filtered, and concentrated to an oil. Purification by flash chromatography eluting with 3% NH$_3$ (2M) in methanol/DCM afforded about 120 mg of oily residue. MS: (M+1) 784

Step 2: The residue was dissolved in 1 mL of DCM, cooled with an ice bath, and 2 mL of cooled TFA/DCM (1/1) was added. The mixture was stirred for about 1 hour with an ice bath in place. The mixture was concentrated and purified as the TFA salt via reverse phase HPLC giving about 10.6 mg of the final compound (7%). HRMS (electrospray) calculated for C$_{36}$H$_{41}$ClF$_3$N$_5$O$_3$3C$_2$HF$_3$O$_2$: 684.2928. Found: 684.2932.

$^1$H NMR (CD$_3$OD) δ 7.24–7.47 (m, 8H), 6.88–7.18 (m, 4H), 5.17–5.30 (m, 1H), 4.404–4.51 (s, 2H), 4.17–4.30 (m, 1H), 3.57–3.83 (m, 5H), 3.38–3.55 (m, 3H), 2.95–3.18 (m, 7H), 2.92 (s, 3H), 1.63–1.85 (m, 6H). MS (ESI): m/z=616 [C$_{35}$H$_{42}$ClN$_5$O$_3$+H]$^+$

Example 4

Coupling Procedure 4

N-(1-(4D-chloro-benzyl)-2-oxo-2-{4-[2-R-(piperidin-3-yloxy)-phenyl]-piperazin-1-yl}-ethyl)-2-(1,2,3,4-tetrahydro-isoquinolin-1-yl)-acetamide trihydrochloride

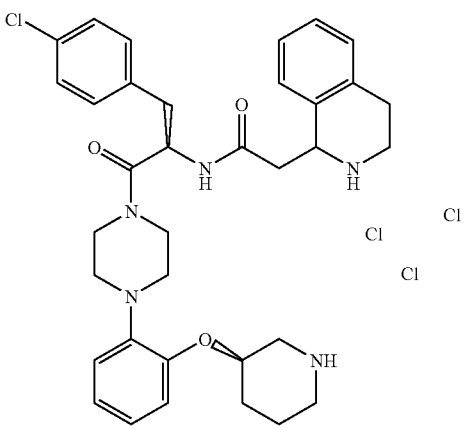

Step 1: 1-[2-(1-Boc-R-piperidin-3-yloxy)-phenyl piperazine (3.91 g, 10.82 mmol, 1 eq.), HOBT (1.46 g, 10.82 mmol, 1 eq.), DIPEA (5.67 mL, 10.82 mmol, 1 eq.) and FMOC D-Cl Phe (4.57 g, 10.82 mmol) were mixed together in DCM (180 mL) and DMP (20 mL). EDC (2.08 g, 10.82 mmol, 1 eq.) was added, and the mixture was stirred at r.t. for about 16 hours. The mixture was concentrated to a yellow foam. Chromatography on silica gel gave an off white foam (6.68 g, 80%).

MS found: 765.2 M+1

Step 2: The material from Step 1 (6.62 g, 8.65 mmol) was dissolved in TBF (300 mL), and TBAF (17.3 mL of 1 M solution in THF, 17.3 mmol) was added at 0° C. while stirring. The mixture was stirred for about an hour and concentrated to a thick oil. The material was dissolved in ethyl acetate (200 mL) and washed with water (2×200 mL). The organic fraction was dried over sodium sulfate, filtered and concentrated. Silica gel chromatography gave 2-amino-3D-(4-chloro-phenyl)-1-{4-[2R-(piperidin-3-yloxy)-phenyl]-piperazine-1-yl}-propan-1-one (4.5 g, 97%) as a yellow foam.

MS found 543.2 M+1

Step 3: To a solution of the compound from Step 2 (130 mg, 0.21 mmol, 1.0 eq.), lithium salt of 1-carbomethyl-3,4-dihydro-1H-isoquinoline-2-carboxylic acid tert-butyl ester (75 mg, 0.25 mmol, 1.2 eq.), HOBT (38 mg, 0.25 mmol, 1.2 eq.), DIPEA (0.11 mL, 0.63 mmol, 3.0 eq.), CH$_2$Cl$_2$ (4 mL) and DMF (2 mL) was added EDC (48 mg, 0.25 mmol, 1.2 eq.). The mixture was stirred at r.t. overnight. The mixture was diluted with ethyl acetate and washed with saturated aqueous sodium bicarbonate and brine, and then dried over $Na_2SO_4$, filtered and concentrated. Purification by flash chromatography (10 g $SiO_2$, linear gradient, 40 mL/minute, 0 to 10% $MeOH/CH_2Cl_2$ over 25 minutes and 10% $MeOH/CH_2Cl_2$ for 7 minutes) afforded boc-protected title compound (168 mg, 0.2 mmol, 98%).

Step 4: To a solution of boc-protected title compound (155 mg, 0.19 mmol) in $CH_2Cl_2$ (2 mL) was added TFA (2 mL) and DMS (0.25 mL). The mixture was stirred at r.t. for about 2 hours. The mixture was concentrated and purified using SCX (10 g) ion-exchange chromatography to afford final compound (121 mg, 0.16 mmol, 88%), which was converted to chloride salt by adding 1.0 M HCl in $Et_2O$.

HRMS (electrospray) calculated for $C_{35}H_{43}N_5O_3Cl$: 616.3054. Found: 616.3073.

Example 5

Coupling Procedure 5

3-D-(4-chloro-phenyl)-1-{4-[5-trifluoromethyl-2-S-(pyrrolidin-3-yloxy)-phenyl]-piperazin-1-yl}2-D-[(1,2,3,4-tetrahydro-isoquinoline-3-ylmethyl)-amino]-propan-1-one 3HCl Salt

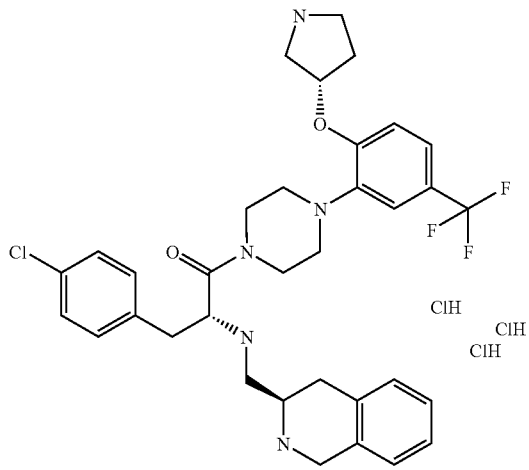

Step 1: To a solution of lithium; 2-[(2-tert-butoxycarbonyl-1,2,3,4-tetrahydro-isoquinolin-3-ylmethyl)-amino]-3-(4-chloro-phenyl)-propionate(359 mg, 0.79 mmol, 1.2 eq), 3-(2-piperazin-1-yl-trifluoromethyl-phenoxy)-S-pyrrolidine-1-carboxylic acid tert-butyl ester (275 mg, 0.66 mmol, 1.0 eq.), DIPEA (0.576 mL, 3.3 mmol, 5 eq.), $CH_2Cl_2$ (18 mL), HOBT (107 mg, 0.79 mmol, 1.2 eq.), and DMF (2 mL), was added EDC (151 mg, 0.79 mmol, 1.2 eq.). The solution was stirred at r.t. for about 16 hours and then was concentrated to an oil.

Step 2: The residue was taken up in DCM/TFA 1/1 (10 mL) and stirred at r.t. for about 16 hours. The mixture was concentrated and free based via SCX ion exchange chromatography. The product containing fractions was concentrated to give an oily residue. Chromatography on silica gel followed by addition of excess HCl in diethyl ether gave the final compound (395 mg, 84%) as an off white solid. MS found 643.3

Example 6

Coupling Procedure 6

1,2,3,4-tetrahydro-isoquinoline-3-D-carboxylic acid (1-D-(4-chloro-benzyl)2-oxo-2-S-{4-[2-NH-(piperidin-3-yloxy)-phenyl]-piperadin-1-yl}-ethyl)-amide 2HCl Salt

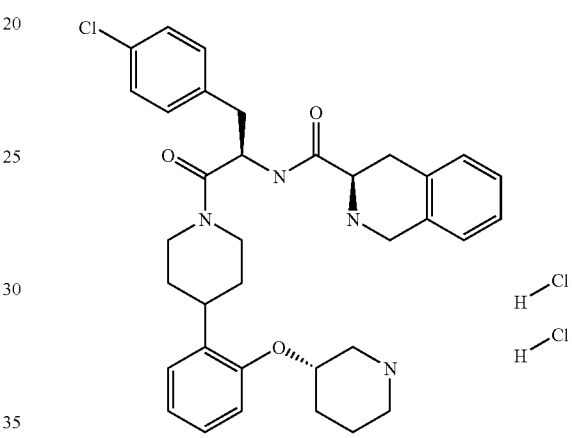

Step 1: To a solution of 3-[1-carboxy-2-(4-chloro-phenyl)-ethylcarbamoyl]-3,4-dihydro-1H-isoquinoline-2-carboxylic acid tert-butyl ester (693 mg, 1.51 mmol, 1.1 eq.), 2,2,2-trifluoro-1-[3-(2-S-piperidin-4-y1-phenoxy)-piperidin-1-yl]-ethanone (489 mg, 1.37 mmol, 1.0 eq.), DIPEA (0.79 mL, 4.52 mmol, 3.3 eq.) and $CH_2Cl_2$ (10 mL) was added HATU (574 mg, 1.51 mmol, 1.1 eq.). The solution was stirred at r.t. for about 16 hours and concentrated to an oil. Purification by flash chromatography afforded an oily residue.

Step 2: The residue was taken up in 7 N $NH_3$/MeOH (15 mL) and stirred at r.t. for about 12 hours. The mixture was concentrated, and the residue was dissolved in TFA/DCM (1/1) 15 mL) and stirred at r.t. for about 12 hours. The residue was freebased via SCX ion exchange chromatography. The product containing fractions was concentrated to give an oily residue. Chromatography on silica gel followed by addition of excess HCl in diethyl ether gave the final compound (358 mg, 53%) as an off white solid.

MS found 601.1

Examples 7–48

The Examples 7–48 are prepared from an appropriate A domain piperazine by following a substantially similar coupling procedure as described in Procedures 1–6 (Examples 1–6).

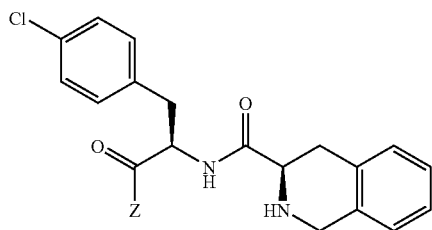
| Example | Z | Coupling Procedure | MS (ESI) |
|---|---|---|---|
| 7 | (piperazinyl-phenoxy-CH2-CH(CH3)-N(CH3)2) | 2 | 604.3 (M + H) |
| 8 | (piperazinyl-phenoxy-CH2-CH(CH3)-N(CH3)2) | 2 | 604.3 (M + H) |
| 9 | (piperazinyl-phenoxy-CH2-CH(CH3)-morpholine) | 2 | 646.3 (M + H) |
| 10 | (piperazinyl-phenoxy-CH-CH2-N(CH3)2) | 2 | 604.3 (M + H) |
| 11 | (piperazinyl-phenoxy-(N-methylpiperidin-3-yl)) | 2 | 616.3 M + H) |

-continued
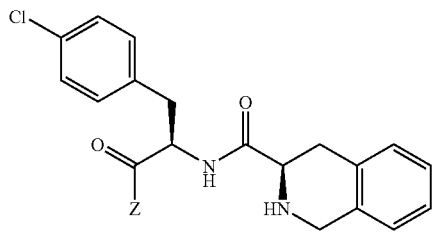
| Example | Z | Coupling Procedure | MS (ESI) |
|---|---|---|---|
| 12 | | 5 | 602.3 (M + H) |
| 13 | | 5 | 602.3 (M + H) |
| 14 | | 1 | 604.3 (M + H) |
| 15 | | 2 | 632.0 (M + H) |
| 16 | | 3 | 616.0 (M + H) |

-continued
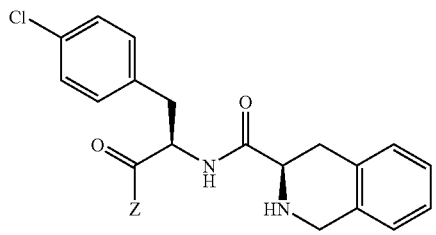
| Example | Z | Coupling Procedure | MS (ESI) |
|---|---|---|---|
| 17 | 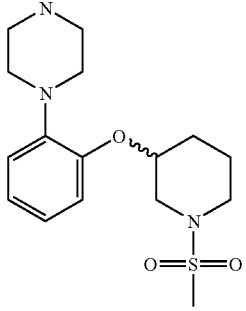 | 2 | 680.0 (M + H) |
| 18 | 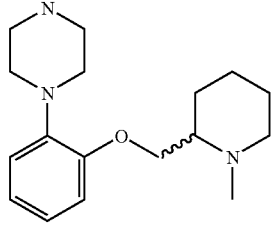 | 2 | 630.0 (M + H) |
| 19 | 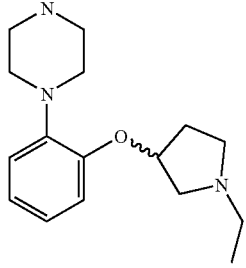 | 2 | 616.0 (M + H) |
| 20 | 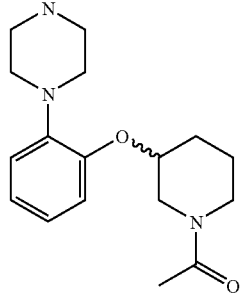 | 2 | 644.0 (M + H) |

-continued
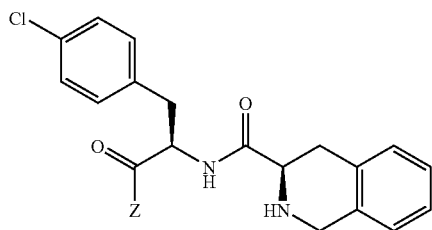
| Example | Z | Coupling Procedure | MS (ESI) |
|---|---|---|---|
| 21 | [piperazinyl-phenyl-O-CH2-CH(Me)-N(H)-S(O)2-Me] | 2 | 655.0 (M + H) |
| 22 | [piperazinyl-phenyl-O-CH2-CH(Me)-N(Me)Ms] | 2 | 668.0 (M + H) |
| 23 | [piperazinyl-phenyl-O-CH2CH2-N(piperazinyl-NSO2Me)] | 2 | 709.0 (M + H) |
| 24 | [piperazinyl-phenyl-O-azetidinyl-NMs] | 2 | 652.0 (M + H) |
| 25 | [piperazinyl-phenyl-O-CH2-CH(Me)-NEt2] | 2 | 632.0 (M + H) |

-continued
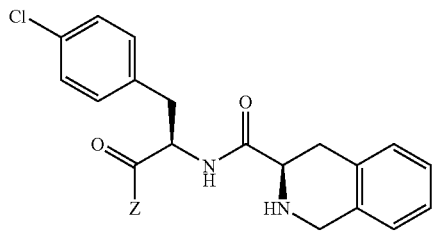
| Example | Z | Coupling Procedure | MS (ESI) |
|---|---|---|---|
| 26 | | 2 | 588.0 (M + H) |
| 27 | | 2 | 706.0 (M + H) |
| 28 | | 2 | 672.0 (M + H) |
| 29 | | 2 | 742.0 (M + H) |

-continued
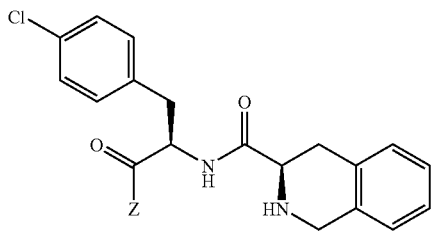
| Example | Z | Coupling Procedure | MS (ESI) |
|---|---|---|---|
| 30 | piperazinyl-phenoxy-(R)-piperidine-N-SO2-iPr | 2 | 708.0 (M + H) |
| 31 | piperazinyl-phenoxy-CH2-(N-methylpiperidine) | 2 | 630.0 (M + H) |
| 32 | piperazinyl-phenoxy-CH2-(N-methylpiperidine) | 2 | 630.0 (M + H) |
| 33 | piperazinyl-phenoxy-(R)-piperidine-N-SO2-Et | 2 | 694.0 (M + H) |

-continued
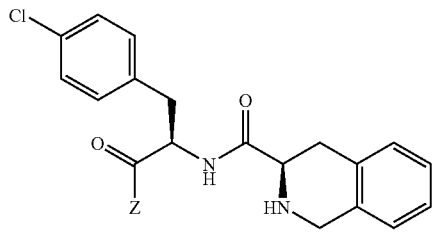
| Example | Z | Coupling Procedure | MS (ESI) |
|---------|---|--------------------|----------|
| 34 | piperazine-phenyl-O-(piperidine-N-propionyl) | 2 | 658.0 (M + H) |
| 35 | piperazine-phenyl-O-(N-methylpiperidine) | 2 | 616.0 (M + H) |
| 36 | piperazine-phenyl-O-piperidine | 5 | 602.0 (M + H) |
| 37 | piperazine-phenyl-O-(N-acetylpiperidine) | 2 | 644.0 (M + H) |
| 38 | piperazine-phenyl-O-CH₂CH₂-NMe₂ | 2 | 590.3 (M + H) |

-continued
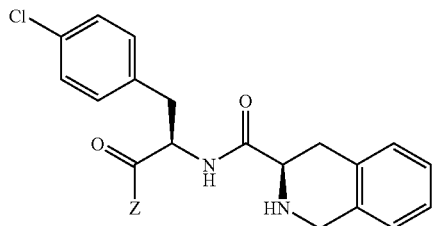
| Example | Z | Coupling Procedure | MS (ESI) |
|---------|---|--------------------|----------|
| 39 | 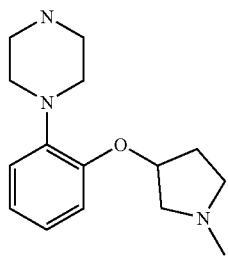 | 2 | 602.0 (M + H) |
| 40 | 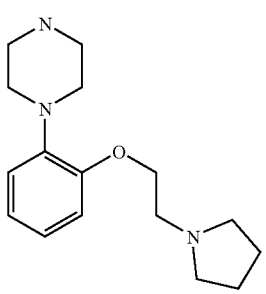 | 2 | 617.0 (M + H) |
| 41 | 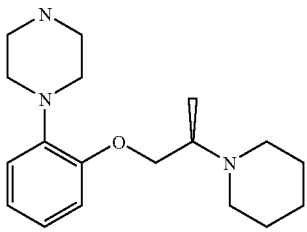 | 2 | 644.0 (M + H) |
| 42 | 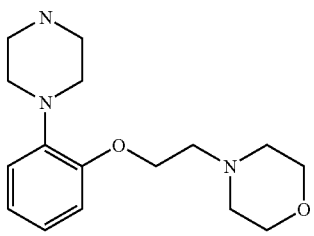 | 2 | 630.3 (M + H) |
| 43 | 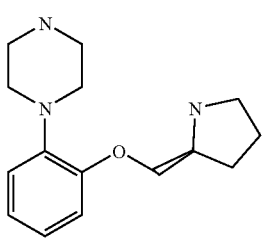 | 2 | 602.3 (M + H) |

-continued
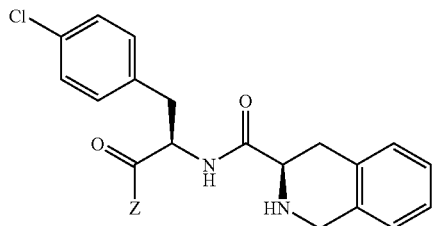
| Example | Z | Coupling Procedure | MS (ESI) |
|---|---|---|---|
| 44 | piperazinyl-phenyl-O-CH2-(S)-pyrrolidine | 2 | 602.3 (M + H) |
| 45 | piperazinyl-phenyl-O-(S)-pyrrolidin-3-yl | 5 | 588.3 (M + H) |
| 46 | piperazinyl-phenyl-O-(R)-pyrrolidin-3-yl | 5 | 588.3 (M + H) |
| 47 | piperazinyl-phenyl-O-(S)-1-methylpiperidin-3-yl | 2 | 616.3 (M + H) |
| 48 | homopiperazinyl-phenyl-O-CH2CH2-morpholine | 2 | 646.3 (M + H) |

Examples 49–50

The compounds of Examples 49–50 are prepared from an appropriate A domain piperazine by following a substantially similar coupling procedure as described in Procedures 1–6 (Examples 1–6).

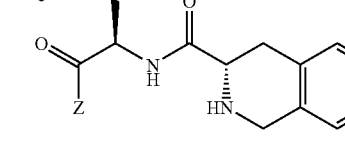

| Example | Z | Coupling Procedure | MS (M + H) |
|---|---|---|---|
| 49 | 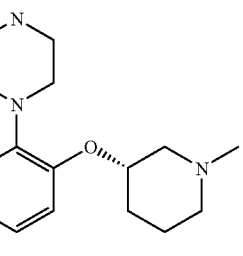 | 1 | 616.3 |
| 50 | 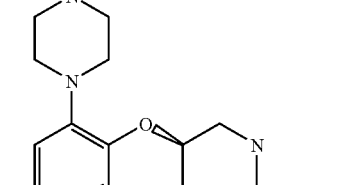 | 4 | 602.3 |

Examples 51–57

Examples 51–57 are prepared from an appropriate A domain piperazine by following a substantially similar coupling procedure as described in Procedures 1–6 (Examples 1–6).

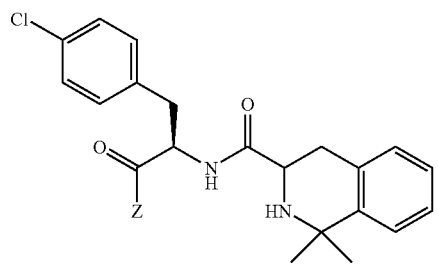

| Example | Z | Coupling Procedure | MS (M + H) |
|---|---|---|---|
| 51 | 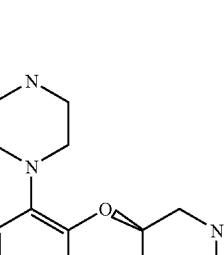 | 5 | 630.3 |
| 52 | 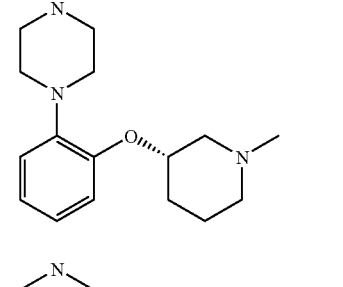 | 2 | 644.3 |
| 53 | 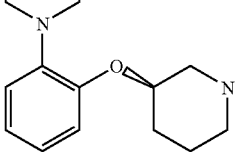 | 2 | 644.3 |
| 54 | 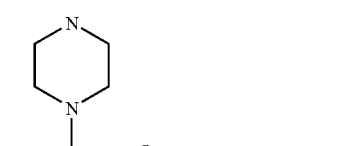 | 5 | 630.3 |
| 55 |  | 5 | 682.3 |

-continued

[Structure: 4-chlorophenyl-CH2-CH(C(=O)Z)-NH-C(=O)-[1,1-dimethyl-tetrahydroisoquinoline-3-yl]]

| Example | Z | Coupling Procedure | MS (M + H) |
|---------|---|--------------------|-----------| 
| 56 | 4-(1-methylpiperidin-4-yloxy)-2-(piperazin-1-yl)phenyl | 2 | 643.3 |
| 57 | 2-(piperazin-1-yl)phenyl 4-(piperidin-4-yloxy) | 5 | 630.3 |

Examples 58–66

Examples 58–66 are prepared from an appropriate A domain piperazine by following by following a substantially similar coupling procedure as described in Procedure 5 (Example 5).

[Structure: 4-chlorophenyl-CH2-CH(C(=O)Z)-NH-C(=O)-[tetrahydroisoquinoline-3-yl]]

| Example | Z | Coupling Procedure | MS (ESI) |
|---------|---|--------------------|----------|
| 58 | 2-(piperazin-1-yl)phenyl (piperidin-3-yloxy) | 5 | 588.3 (M + H) |

-continued

[Structure: 4-chlorophenyl-CH2-CH(C(=O)Z)-NH-C(=O)-[tetrahydroisoquinoline-3-yl]]

| Example | Z | Coupling Procedure | MS (ESI) |
|---------|---|--------------------|----------|
| 59 | 3-fluoro-2-(piperidin-3-yloxy)-6-(piperazin-1-yl)phenyl | 5 | 606.3 (M + H) |
| 60 | 3-fluoro-2-(piperidin-3-yloxy)-6-(piperazin-1-yl)phenyl | 5 | 606.3 (M + H) |
| 61 | 4-trifluoromethyl-2-(piperazin-1-yl)-(pyrrolidin-3-yloxy)phenyl | 5 | 642.3 (M + H) |
| 62 | 4-fluoro-2-(piperidin-3-yloxy)-6-(piperazin-1-yl)phenyl | 5 | 606.3 (M + H) |
| 63 | 5-fluoro-2-(piperidin-3-yloxy)-6-(piperazin-1-yl)phenyl | 5 | 606.3 (M + H) |

-continued
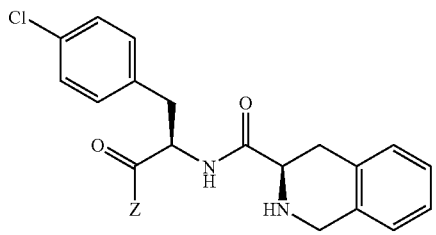
| Example | Z | Coupling Procedure | MS (ESI) |
|---|---|---|---|
| 64 | ![structure] | 5 | 588.3 (M + H) |
| 65 | ![structure] | 5 | 616.3 (M + H) |
-continued
| Example | Z | Coupling Procedure | MS (ESI) |
|---|---|---|---|
| 66 | ![structure] | 5 | 608.3 (M + H) |
Examples 67–85
Examples 67–85 are prepared from an appropriate A domain piperazine by following a substantially similar coupling procedure as described in Procedures 1–6 (Examples 1–6).
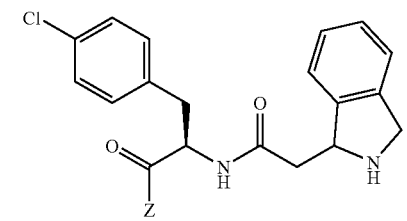
| Example | Z | Coupling Procedure | MS (ESI) |
|---|---|---|---|
| 67 |  | 1 | 682.3 (M + H) |

-continued
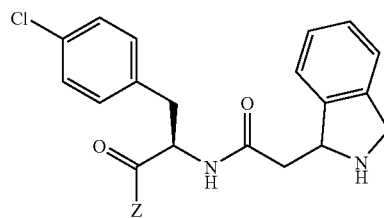
| Example | Z | Coupling Procedure | MS (ESI) |
|---|---|---|---|
| 68 | piperazinyl-phenyl-O-CH2CH2-morpholine | 1 | 633.0 (M + H) |
| 69 | piperazinyl-phenyl-O-CH2-C(CH3)2-N(Et)(SO2Me) | 1 | 696.3 (M + H) |
| 70 | piperazinyl-phenyl-O-(3R)-piperidinyl | 5 | 602.4 (M + H) |
| 71 | piperazinyl-phenyl-O-CH2-C(=O)-N(Et)2 | 2 | 632.2 (M + H) |
| 72 | piperazinyl-phenyl-O-(3R)-(1-acetyl)piperidinyl | 2 | 644.3 (M + H) |

-continued
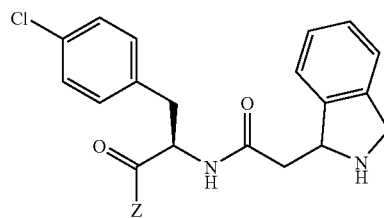
| Example | Z | Coupling Procedure | MS (ESI) |
|---|---|---|---|
| 73 | (piperazinyl-phenyl-O-piperidinyl-acetyl) | 2 | 644.3 (M + H) |
| 74 | (piperazinyl-phenyl-O-N-methylpiperidinyl) | 2 | 308.7 (M + 2H)/2 |
| 75 | (piperazinyl-phenyl-O-N-methylpiperidinyl) | 1 | 638.3 (M + H) |
| 76 | (piperazinyl-phenyl-O-piperidinyl) | 4 | 602.3 (M + H) |
| 77 | (piperazinyl-phenyl-O-piperidinyl-propionyl) | 2 | 658.5 (M + H) |

-continued
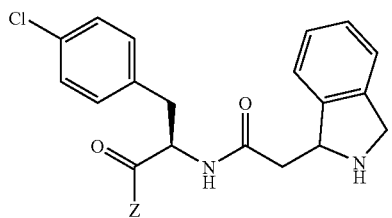
| Example | Z | Coupling Procedure | MS (ESI) |
|---|---|---|---|
| 78 | piperazinyl-phenoxy-piperidine-isobutyryl | 2 | 672.4 (M + H) |
| 79 | piperazinyl-phenoxy-piperidine-methyl carbamate | 2 | 660.3 (M + H) |
| 80 | piperazinyl-phenoxy-piperidine-ethyl carbamate | 2 | 674.3 (M + H) |
| 81 | piperazinyl-phenoxy-piperidine-isopropyl carbamate | 2 | 688.3 (M + H) |

-continued
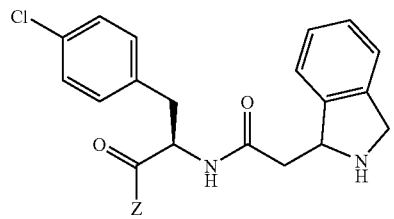
| Example | Z | Coupling Procedure | MS (ESI) |
|---|---|---|---|
| 82 | | 2 | 680.3 (M + H) |
| 83 | | 2 | 694.3 (M + H) |
| 84 | | 2 | 708.3 (M + H) |
| 85 | | 2 | 684.3 (M + H) |

Examples 86–88
Examples 86–88 are prepared from an appropriate A domain piperazine by following a substantially similar coupling procedure as described in Procedures 1–6 (Examples 1–6).
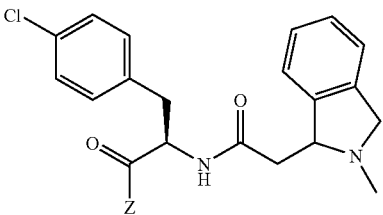
| Example | Z | Coupling Procedure | MS (ESI) |
|---|---|---|---|
| 86 | (1-methylpiperidin-3-yloxy)-2-(piperazin-1-yl)phenyl | 1 | 630.3 (M + H) |
| 87 | (piperidin-3-yloxy)-2-(piperazin-1-yl)phenyl | 4 | 616.3 (M + H) |
| 88 | 2-(2-morpholinoethoxy)-phenyl piperazine | 1 | 646.4 (M + H) |

Examples 89–90

Examples 89–90 are prepared from an appropriate A domain piperazine by following a substantially similar procedure as described in Coupling Procedure 1 (Example 1).

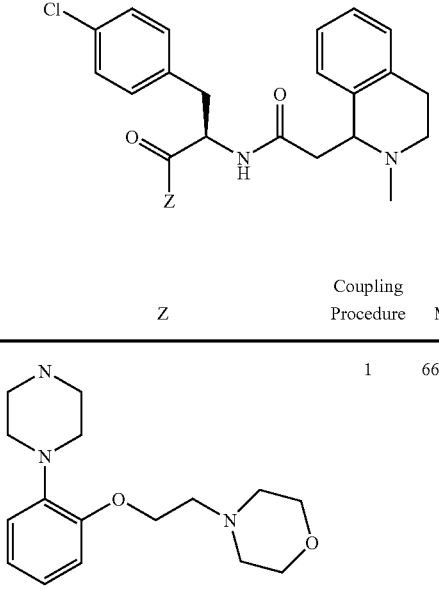

| Example | Z | Coupling Procedure | MS (ESI) |
|---|---|---|---|
| 89 | 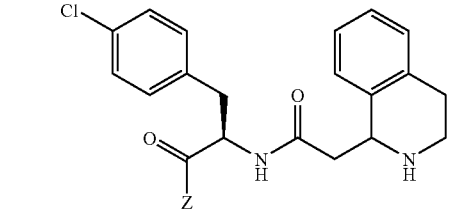 | 1 | 660 (M + H) |
| 90 | 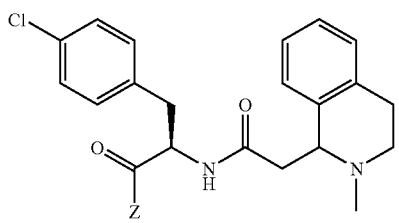<br>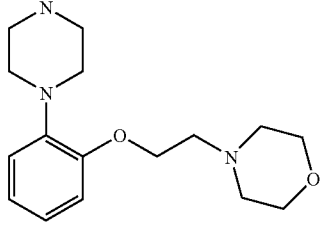 | 1 | 660 (M + H) |

Examples 91–98

Examples 91–98 are prepared from an appropriate A domain piperazine by a substantially similar procedure as described in Coupling Procedures 1–6 (Examples 1–6).

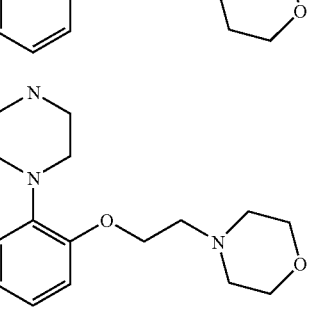

| Example | Z | Coupling Procedure | MS (ESI) |
|---|---|---|---|
| 91 | | 1 | 646.4 (M + H) |
| 92 | | 1 | 646.4 (M + H) |

-continued
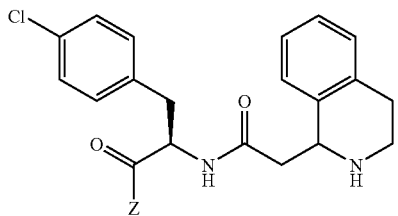
| Example | Z | Coupling Procedure | MS (ESI) |
|---|---|---|---|
| 93 | piperazine-phenyl-O-(3S)-1-methylpiperidine | 1 | 652.3 (M + H) |
| 94 | piperazine-phenyl-O-(3R)-1-methylpiperidine | 1 | 630.3 (M + H) |
| 95 | piperazine-phenyl-O-(3S)-piperidine | 4 | 616.3 (M + H) |
| 96 | piperazine-phenyl-O-(3R)-piperidine | 4 | 616.3 (M + H) |
| 97 | piperazine-phenyl-O-4-piperidine | 5 | 616.2 |

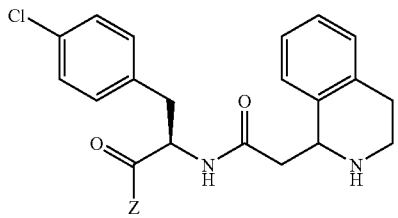

| Example | Z | Coupling Procedure | MS (ESI) |
|---|---|---|---|
| 98 | 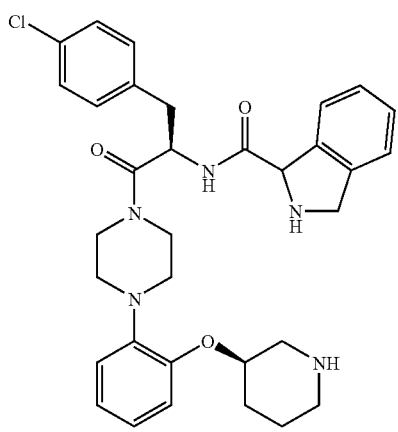 | 5 | 616.2 |

Examples 99

Example 99 is prepared from an appropriately substituted A domain piperazine by following a substantially similar coupling procedure as described in Coupling Procedure 5 (Example 5).

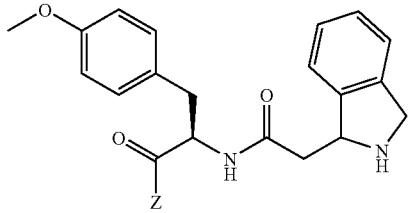

| Example | Z | Coupling Procedure | Found HRMS (electrospray) |
|---|---|---|---|
| 100 | | 5 | 598.3412 (M + H) |
| 101 | | 2 | 612.3570 (M + H) |

Found HRMS (electrospray): 588.2763 (M+H)

Examples 100–101

Examples 101–102 are prepared from an appropriately substituted A domain piperazine by following a substantially similar coupling procedure as described in Coupling Procedures 1–6 (Examples 1–6).

Example 102

Example 103 is prepared from an appropriately substituted A domain piperazine by following a substantially similar coupling procedure as described in Coupling Procedure 5 (Example 5).

155

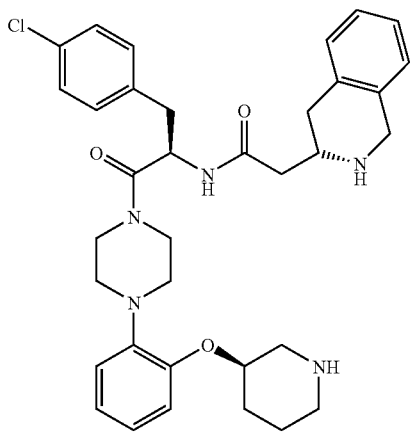

Found HRMS (electrospray): 616.3037 (M+H)

Example 103

Example 103 is prepared from an appropriately substituted A domain piperazine by following substantially similar coupling procedure as described in Coupling Procedure 1 (Example 1).

156

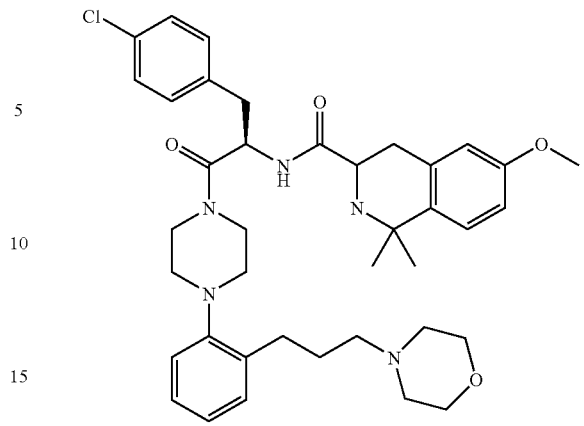

Found HRMS (electrospray): 588.3253 (M+H)

Examples 104–107

Examples 104–107 are prepared from an appropriately substituted A domain piperidine by following a substantially similar coupling procedure as described in Coupling Procedures 1–6 (Examples 1–6).

| Example | Z | Coupling Procedure | MS (ESI) |
|---|---|---|---|
| 104 | | 6 | 601.3 (M + H) |
| 105 | | 2 | 615.3 (M + H) |
| 106 | | 2 | 631.3 (M + H) |

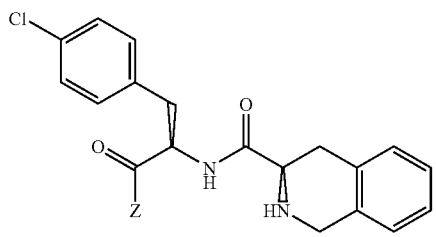

| Example | Z | Coupling Procedure | MS (ESI) |
|---|---|---|---|
| 107 | (piperidinyl-phenyl-O-pyrrolidine) | 6 | 587.3 (M + H) |

Examples 108–109

Examples 108–109 are prepared from an appropriately substituted A domain piperidine by following a substantially similar coupling procedure as described in Coupling Procedures 1–6 (Examples 1–6).

| Example | Z | Coupling Procedure | MS (ESI) |
|---|---|---|---|
| 108 | (piperidinyl-phenyl-O-CH₂-C(=N-Et₂)) | 2 | 631.3 (M + H) |
| 109 | (piperidinyl-phenyl-O-piperidine) | 6 | 601.2 (M + H) |

Examples 110–111

Examples 110–111 are prepared from an appropriately substituted A domain piperidine by following a substantially similar coupling procedure as described in Coupling Procedures 1–6 (Examples 1–6).

| Example | Z | Coupling Procedure | MS (ESI) |
|---|---|---|---|
| 110 | (piperidinyl-phenyl-O-piperidine) | 6 | 629.3 (M + H) |
| 111 | (piperidinyl-phenyl-O-N-methylpiperidine) | 2 | 643.2 (M + H) |

Examples 112–115

The compounds of Examples 112–115 are prepared from an appropriately substituted A domain piperazine by following a substantially similar coupling procedure as described in Coupling Procedures 1–5.

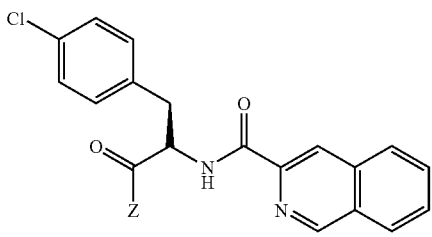

| Example | Z | Coupling Procedure | MS (ESI) |
|---|---|---|---|
| 112 | | 4 | 598.3 (M + H) |
| 113 | | 1 | 628.6 (M + H) |
| 114 | | 2 | 628.1 (M + H) |

Preparation of Novel C-Domain Pieces

Heck Coupling

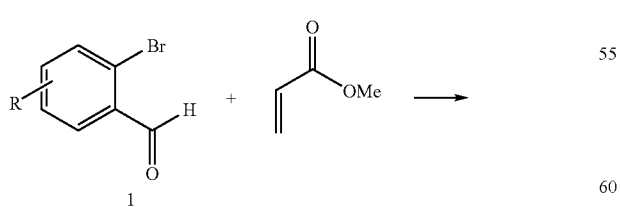

1
1a R = H
1b R = 5-OMe
1c R = 4,5-OMe
1d R = 5-NO$_2$

-continued

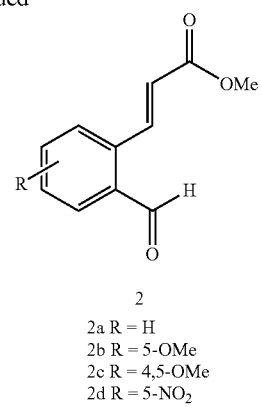

2
2a R = H
2b R = 5-OMe
2c R = 4,5-OMe
2d R = 5-NO$_2$

Preparation PP1

Synthesis of Compound (2a) by a Heck Coupling of 2-bromobenzaldehyde (1a) with methyl acrylate (Pd(OAc)$_2$/PPh$_3$ as the catalyst): A mixture of 2-bromobenzaldehyde (1a) (24.5 g, 132 mmol), methyl acrylate (17.9 mL, 199 mmol), Pd(OAc)$_2$ (590 mg, 2.65 mmol, 2 mol %), PPh$_3$ (1.39 g, 5.30 mmol, 4 mol %) and Et$_3$N (46 mL, 331 mmol) was stirred at 80° C. for 15 h. Large amount of yellow solid was formed after the reaction was done. The mixture was cooled to rt, concentrated, and mixed with H$_2$O (200 mL). The organic solid was collected by filtration, and then applied to a plug of silica gel (25 g) (EtOAc/hexane 1:1) to give a dark yellow solid. The solid was purified by crystallization (100 mL EtOAc bottom layer, 120 mL hexane top layer) to provide 17.57 g (70%) (100% pure by NMR) of the first crop and 5.23 g (21%) (95% by NMR) of the second crop of 2a.

Preparation PP2

Synthesis of Compound (2a) by a Heck Coupling of 2-bromobenzaldehyde (1a) with Methyl Acrylate (R=H) (Pd(OAc)$_2$/P(O-Toyl)$_3$ as the catalyst): The compound 1a (9.998 g, 54.04 mmol) was dissolved in toluene (20 mL) at r.t. Methylacrylate (5.996 g, 69.65 mmol, 1.29 eq.), NEt$_3$ (15 mL), Pd(OAc)$_2$ and P(O-Tolyl)$_3$ were successively added and the mixture was stirred under reflux. After 2 hours, the reaction mixture was allowed to cool to RT. Then the precipitated yellow catalyst was removed by filtration. The catalyst was rinsed with toluene (2×10 mL) and the filtrates were concentrated to dryness under reduced pressure. The residual oil was dried under vacuum over the weekend to give a crude solid (11.449 g). The solid was taken-up with isopropanol (25 mL) and stirred overnight at RT. Then, the precipitate was filtered and rinsed with isopropanol (5 mL). The wet cake (8.240 g) was dried overnight at RT affording the highly pure 2-carboxaldehyde-methyl-cinnamate with 74% yield (7.627 g, 40.1 mmol).

Preparation PP3

Heck Coupling of 1b and methyl acrylate to form 2b (R=5-OMe): A mixture of 2-bromo-5-methoxybenzaldehyde (1b) (4.5 g, 20.9 mmol, Aldrich), methyl acrylate (2.7 g, 1.5 eq, 2.83 mL), Et$_3$N (7.4 g, 3.5 eq, 10.2 mL), Pd(OAc)$_2$ (93 mg, 0.02 eq), and P(O-Tol)$_3$ was stirred and heated to 80° C. over 2–3 days. The reaction mixture was cooled to r.t., partitioned between EtOAc (50 mL) and brine (50 mL). The aqueous was extracted with EtOAc (2×50 mL). The combined organic was washed with brine (1×50 mL), dried over MgSO$_4$, filtered, concentrated to yield a yellow brown oil (5.01 g, 109%). This crude oil was purified in a hot solvent Hex/EtOAc (80 mL/15 mL) to yield 2b as a pale yellow solid (3.5 g, 76%).

Preparation PP4

Heck Coupling of 1c and Methyl Acrylate to Form 2c (R=4,5-OMe): To a solution of 1c (906 mg, 3.70 mmol) in toluene (2 mL) was added Pd(OAc)$_2$ (17 mg, 0.074 mmol, 2 mol %), P(O-Tolyl)$_3$ (45 mg, 0.148 mmol, 4 mol %), methyl acrylate (0.5 mL, 5.55 mmol) and Et$_3$N (1.5 mL, 11.1 mmol). The mixture was stirred at 80° C. for 21 h, cooled to rt, and mixed with H$_2$O (40 mL). The organic compounds were extracted with EtOAc (50 mL), washed with brine (40 mL), dried (Na$_2$SO$_4$), and concentrated. The residue was purified by flash chromatography to provide 466 mg (47%) of recovered 1c followed by 450 mg (49%) of 2c (4,5-Ome).

Preparation PP5

Heck Coupling of 1d and Methyl Acrylate to Form 2d (R=5-NO$_2$): The procedure is same as that of 2c, yielding 82% of 2d after purification.

Preparation PP6

Reductive Amination

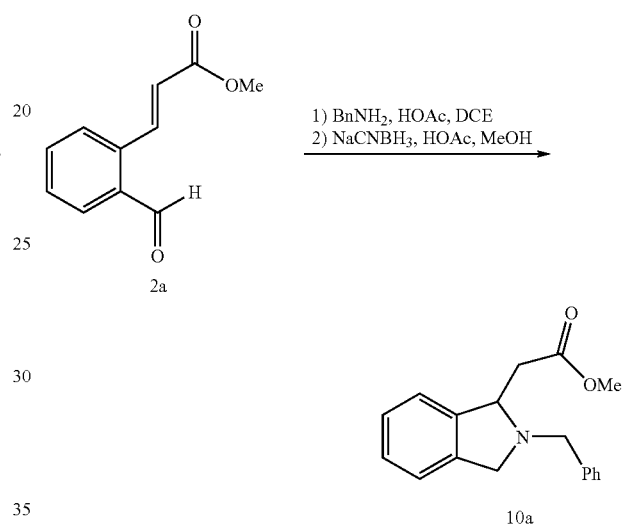

Reductive amination of (2a) with benzyl amine to form isoindoline (10a). To a solution of 2a (11.27 g, 59.2 mmol) in ClCH$_2$CH$_2$Cl (60 mL) was added BnNH$_2$ (6.47 mL, 59.2 mmol), followed by HOAc (5.1 mL, 89 mmol). The mixture was stirred at rt for 1 h. NaCNBH$_3$ (5.58 g, 88.8 mmol) and MeOH (30 mL) were then added to the above solution. The resulting mixture was stirred at rt for another 2 h and quenched with sat. NaHCO$_3$ solution (150 mL). The mixture was extracted with EtOAc (2×100 mL) and the combined organic layers were washed with brine (150 mL), dried (Na$_2$SO$_4$), and concentrated to provide 15.3 g of crude product of 10a which was carried out for the next hydrogenolysis reaction.

Preparation PP7

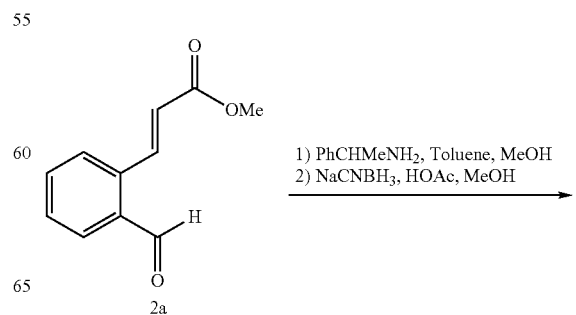

-continued

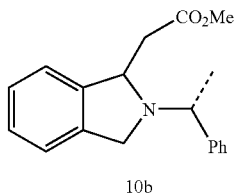

10b

One-pot process from 2-carboxaldehyde-methyl-cinnamate to target cyclized isoindoline product using NaBH₃CN. 2-carboxaldehyde-methyl-cinnamate 2a (3.254 g, 17.1 mmol) was dissolved in a 1:1 MeOH: PhCH₃ mixture (20 mL) at RT. R-(+)-phenethylamine (2.073 g, 17.1 mmol) was added and the solution was heated under reflux for 2 hours. HPLC in process control indicated that the imine formation was completed. Then, AcOH (2.055 g, 34.2 mmol) and NaBH₃CN (2.15 g, 34.2 mmol) were successively added at RT, the reaction mixture being cooled with a water-bath. The reaction mixture was post-agitated overnight. Water (10 mL), MeOH (20 mL) and 37% HCl (2.8 mL) were successively added and the organic layer was extracted. The aqueous layer was washed with PhCH₃ (10 mL). Then, the aqueous layer was made basic with 5N NaOH (20 mL) and MeOH was concentrated to partly remove MeOH. Extraction with EtOAc (2×25 mL) was performed. The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b with 92% yield (4.642 g, 15.7 mmol). HPLC % area indicated that the 2 diastereomers were produced in a 55:45 ratio. ¹H NMR confirmed this result by integration of the methyl group of the phenethyl substituent. Note: The Heck or Heck-type coupling was performed in toluene with a slight excess of methylacrylate which was removed by distillation before the MeOH and the R-(+)-phenethylamine addition.

Preparation PP8

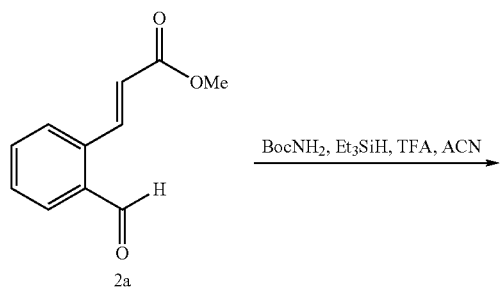

Reductive amination of (2a) with t-butyl carbamate to form (11a): To a solution of aldehyde 2a (238 mg, 1.25 mmol) in CH₃CN (8 mL) was added t-butyl carbamate (439 mg, 3.75 mmol), followed by triethylsilane (0.6 mL, 3.75 mmol) and TEA (0.19 mL, 2.5 mmol). The mixture was stirred at rt overnight, quenched with sat. NaHCO₃ solution (20 mL) and extracted with EtOAc (2×30 mL). The combined organic layers were washed with brine (30 mL), dried (Na₂SO₄) and concentrated. The residue was purified by flash chromatography (hexane/EtOAc 3:1) to provide 317 mg (87%) of 11a.

Preparation PP9

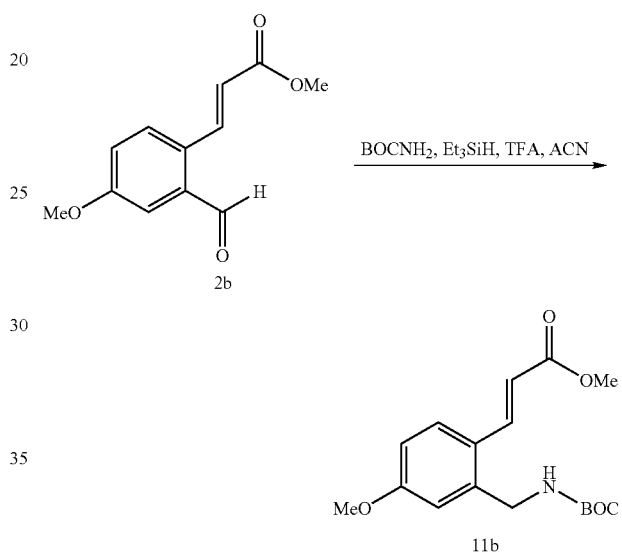

Reductive amination of 2b with t-butyl carbamate to form 11b: A mixture of aldehyde 2b (600 mg, 2.72 mmol) Et₃SiH (955 mg, 3 eq, 1.31 mL), TFA (620 mg, 2 eq, 420 uL), t-butyl carbamate (980 mg, 3 eq) in acetonitrile (15 mL) was stirred at room temperature over 2 days. Removed the solvent on a Rotary evaporator and purified the crude residue on a flash column (100 g SiO₂, 7:1→6:1 Hex/EtOAc). Collected 307 mg good desired product 11b (35%); 195 mg product contaminated with aldehyde SM (22%).

Preparation PP10

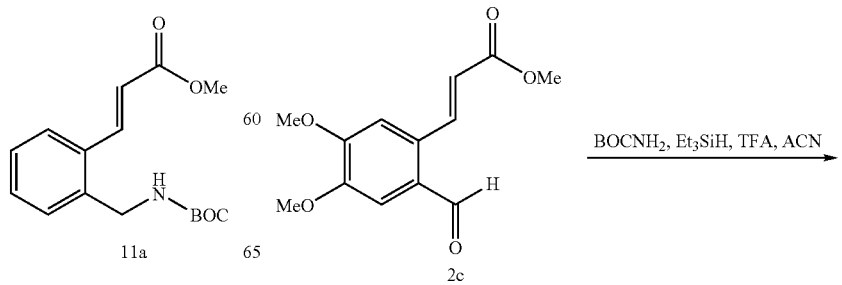

-continued

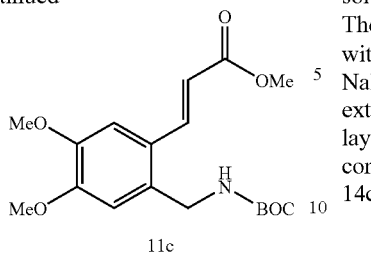
11c

Reductive amination of (2c) with t-butyl carbamate to form (11c): To a solution of aldehyde 2c (411 mg, 1.64 mmol) in CH₃CN (10 mL) was added t-butyl carbamate (580 mg, 4.93 mmol), followed by triethylsilane (0.8 mL, 4.93 mmol) and TFA (0.25 mL, 3.28 mmol). The mixture was stirred at rt overnight, quenched with sat. NaHCO₃ solution (30 mL) and extracted with EtOAc (2×30 mL). The combined organic layers were washed with brine (30 mL), dried (Na₂SO₄) and concentrated. The residue was purified by flash chromatography (hexane/EtOAc 3:1, hexane/EtOAc 1:1) to provide 535 mg (93%) of 11c.

Preparation PP11

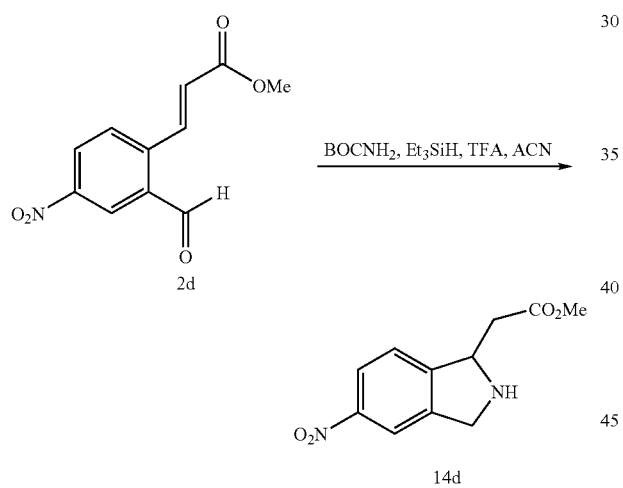

To a solution of 2d (1.02 g, 4.34 mg) in CH₂Cl₂/CH₃CN (1:1 24 mL) was added BocNH₂ (1.5 g, 13.02 mmol), Et₃SiH (2.1 mL, 13.02 mmol), and TFA (0.67 mL, 8.67 mmol). The mixture was stirred at rt for 7 h. A precipitate was formed during the reaction. The reaction mixture was quenched with sat. NaHCO₃ solution (30 mL), and diluted with CH₂Cl₂ (40 mL). The organic layer was washed with brine (30 mL), dried (Na₂SO₄), and concentrated. The residue was purified by flash chromatography (hexane/EtOAc 3:1, then CH₂Cl₂/EtOAc 10:1) to provide 2.08 g yellow solid which still containing BocNH₂. The product is not the desired Boc-carbamate 14c. LC-MS result showed that the product is the Schiff base intermediate.

To the above product (420 mg) in CH₂Cl₂ (10 mL) was added Et₃SiH (1 mL) and TFA (0.4 mL). The mixture was stirred at rt for 1 h and small amount of sample was taken for NMR. NMR analysis demonstrated that the starting material was consumed and the product was 14c. TFA (0.7 mL) was then added to the above mixture and the resultant solution was stirred at rt for another 5 h and concentrated. The residue was dissolved in EtOAc (20 mL) and washed with H₂O (10 mL). The aqueous layer was basified with sat. NaHCO₃ (30 mL) and the organic compounds were extracted with CH₂Cl₂ (2×25 mL). The combined organic layers were washed with brine (20 mL), dried (Na₂SO₄) and concentrated to provide 218 mg of the cyclized compound 14c.

Preparation PP12

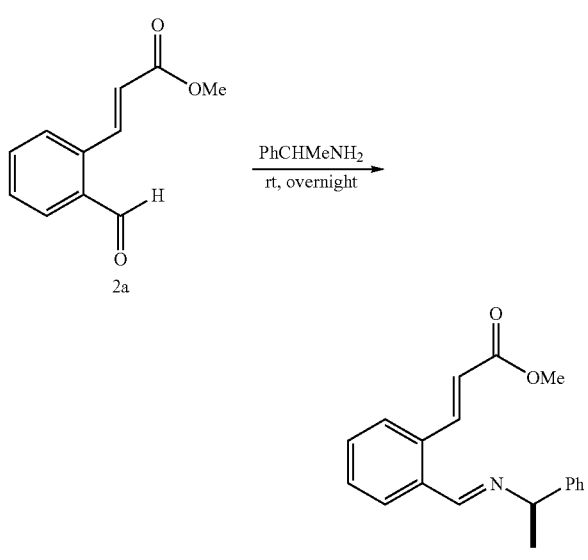

Condensation of 2a with α-Methylbenzylamine to Form Imine 9. 2-carboxaldehyde-methyl-cinnamate 2a (0.897 g, 4.72 mmol) was dissolved in MeOH (10 mL) at RT. R-(+)-phenethylamine (0.577 g, 4.76 mmol) was added and the solution was heated under reflux for 2 hours. HPLC in process control indicated that the imine formation was completed. The solvent was stripped on a rotary evaporator and the resulting oil was dried at RT under vacuum overnight. The Schiff base 9 was obtained almost quantitatively (1:412 g, 4.81 mmol).

Preparation PP13

Michael Addition

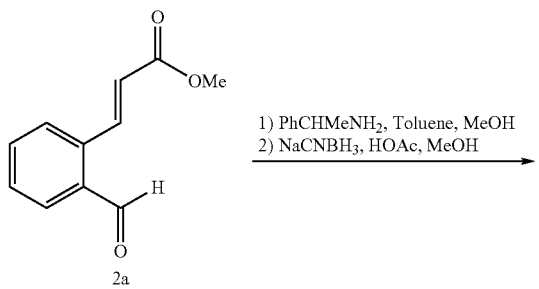

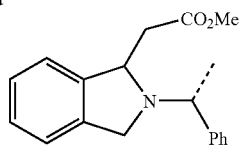

10b
(1.2:1)

The compound of α-Methyl benzylamine was applied as the auxiliary. As shown above, the one-pot reaction of aldehyde 2a and α-Methyl benzylamine gave 90% of 10b with a ratio of 1.2:1.

Step-wise Reduction, Amination, and Cyclization

Condensation of aldehyde 2a with α-methylbenzylamine in acetonitrile, methanol, methanol/toluene(1:1) or toluene afforded imine 9 in excellent yield. Reduction of the imine was initially carried out at RT with NaCNBH₃/HOAc. As a result, a poor ee ratio (1.2:1) was obtained, similarly to the previous described one-pot procedure. But when the reaction was carried out with NABH A at RT, the ratio was elevated to 2:1. By lowering the reaction temperature to −78° C., the ratio was increased to 5 to 6:1.

Preparation PP14

Cyclization of t-Butyl carbamate (11a): The N-Boc isoindoline methyl ester 12 was originally synthesized from 11a via deprotection of Boc with TFA, followed by basic workup, and protection with a Boc group. This procedure has been greatly improved by a one-step procedure.

Preparation PP15

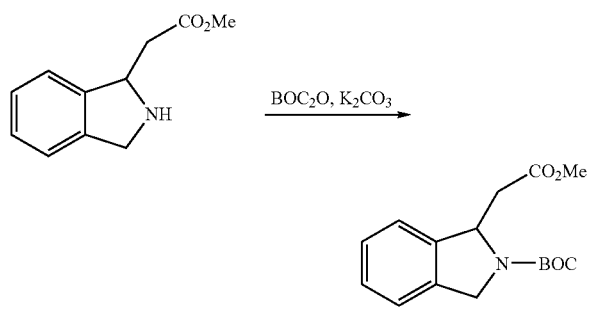

In a 3 L 3-neck round bottom flask equipped with a nitrogen inlet, thermocouple and mechanical stirrer, a solution of 160 g (1.15 moles) of K₂CO₃ in 180 mL of water was stirred at rt. Solid BOC anhydride 120 g (0.55 moles) was added in one portion forming a semi-solution. To the reaction mixture, a solution of the crude amino ester starting material, 87 g (0.46 moles) in 120 mL of TBF was added slowly at such a rate to keep the internal temperature below 35° C. A mild effervescence was observed. The reaction mixture was stirred for 18 hours at rt. Analysis of a reaction aliquot via NMR (DMSO₆) indicates the desired product. The reaction was diluted with brine and the product extracted with EtOAc. The organic layer was dried over Na₂SO₄, filtered, and concentrated to yield a dark oil, 150.1 g, >100% yield. The crude material was taken on to the next step.

Preparation PP16

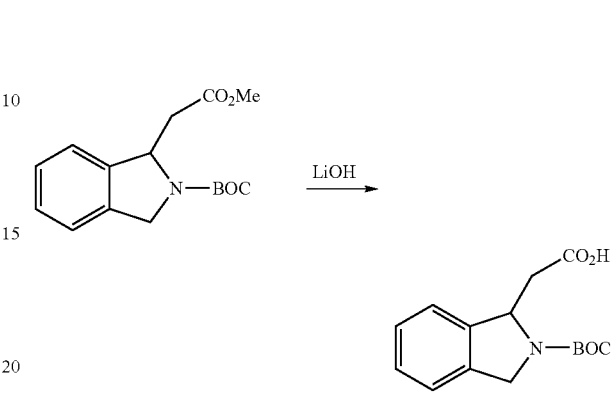

In a 3-L 3-neck round bottom flask equipped with a mechanical stirrer, thermocouple, and reflux condenser, a solution of 150 g (approx. 0.46 moles) of crude N-BOC ester starting material in 750 mL of methanol was stirred at rt. To the solution, 750 mL of water was added and the cloudy mixture was stirred vigorously. Solid LiOH 25 g (1.03 moles) was added in small portions at such a rate to maintain the internal temperature below 45° C. Upon completion of addition, the reaction was stirred overnight at rt becoming a dark green color. After 18 hours the reaction was concentrated to yield a thick semisolid. The crude product was dissolved in EtOAc and washed with 1 N HCl quickly, followed by two brine washes. The organic layer was dried with Na₂SO₄, filtered and concentrated to yield 81 g of a dark green solid. The aqueous layers were combined and back extracted with methylene chloride, dried over Na₂SO₄, filtered, and concentrated to yield 6 g of a dark green solid. Both solids were combined to yield 87 g of desired product confirmed via NMR (DMSO₆).

Preparation PP17

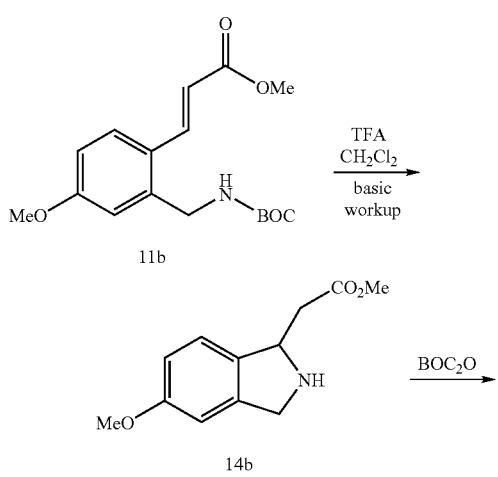

11b

14b

-continued

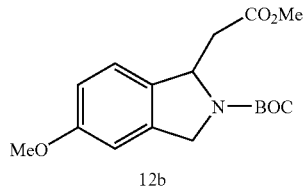

12b

Synthesis of 14b: Dissolved the N-boc compound 11b (200 mg, 0.62 mmol) in CH$_2$Cl$_2$ (1.0 mL). Cooled the clear light yellow solution to 0° C. Added slowly TFA (~710 mg, 10 eq, ~500 microliter) via a syringe. Removed the cooling bath and stirred the clear light brown solution at RT overnight. TLC (3:1 Hex/EtOAc, UV) confirmed a complete reaction. Removed the TFA on a rotavapor. Added EtOAc and concentrated again (twice). The crude residue was partitioned between EtOAc (10–15 mL) and a sat. NaHCO$_3$ (10–15 mL). The aqueous was extracted with EtOAc (2×10 mL). The combined organic was dried over MgSO$_4$, filtered, and concentrated to yield a light brown wet solid (212 mg, 138%). NMR (CD$_3$OD) confirmed the desired isoindoline 14b. This crude isoindoline was used in the next protection step without purification.

Preparation PP18

Synthesis of 12b: To a mixture of the isoindoline 14b (190 mg, 0.859 mmol), K$_2$CO$_3$ (189 mg, 1.5 eq) in a solvent 1:1 THF/H$_2$O (1.0 mL) at RT was added BOC$_2$O (210 mg, 1.1 eq). The reaction mixture was stirred at RT overnight. TLC (3:1 Hex/EtOAc, UV) confirmed a complete reaction. Diluted the mixture with EtOAc (15 mL), and washed with H$_2$O (1×20 mL). The aqueous was extracted with EtOAc (1×20 mL). The combined organic was washed with brine (1×20 mL), dried over MgSO$_4$, filtered, concentrated to yield a clear brown oil (340 mg, 123%). This crude oil was purified on a prep TALC plate (2×1,000 micron, solvent 2:1.5:0.5 CHCl$_3$/Hex/EtOAc) to yield 12b a clear yellow oil (190 mg, 69%). $^1$H and $^{13}$C NMR (CDCl$_3$) were obtained.

Procedure PP19

Synthesis of 12d (5-NO$_2$) by Boc-protection. The compound was prepared by following the same procedure as described for 12b.

Preparation PP20

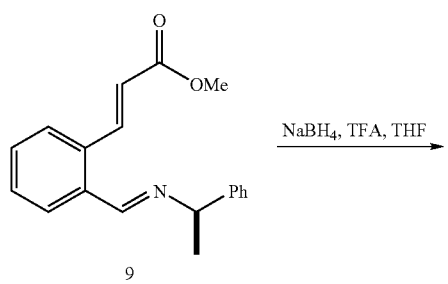

9

-continued

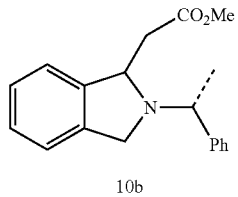

10b

The imine 9 (1.412 g, 4.81 mmol) was dissolved in anhydrous THF (10 mL) at RT and TFA (5 mL) was added. The black solution was then cooled to −78° C. (dry ice bath) and NaBH$_4$ (0.893 g, 23.6 mmol, 5 eq.) was added in 2 portions over 5 minutes. Then, the reaction mixture was post-agitated at −78° C. for 3 hours and allowed to gently warm at RT overnight. Water (20 mL), cyclohexane (10 mL) and EtOH (20 mL) were successively added and the organic layer was extracted and discarded. The aqueous layer was made basic with 5N NaOH (20 mL) and extracted two times with a 2:1 EtOAC/PhCH$_3$ mixture (30 mL). The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b (1.273 g, 4.31 mmol) with 91.4% yield. HPLC % area indicated that the 2 diastereomers were produced in a 84:16 ratio (de 68%). $^1$H NMR confirmed this result by integration of the methyl group of the phenethyl substituent.

Preparation PP20

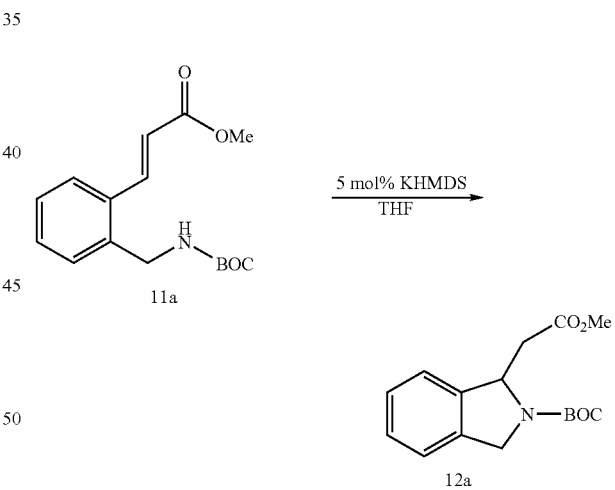

11a

12a

N-Boc methyl ester 11a (36.3 g, 0.125 mol) was dissolved in THF (250 mL), and the solution was cooled to about 0° C. A solution of potassium bis(trimethylsilyl) amide (1.24 g, 0.05 mol. eq.) was added slowly via a syringe under nitrogen atmosphere. The temperature was raised about 8 degrees during the addition. The cooling bath was removed and the solution was stirred at r.t. for 30–45 min. The clear brown solution was poured into a separation funnel containing about 100 mL of a saturated NH$_4$Cl. The layers were separated. The aqueous layer was extracted with EtOAc (2×50 mL). The combined organic was washed with brine (1×100 mL), dried over Na$_2$SO$_4$, filtered, concentrated on a Rotary evaporator to a clear yellow oil (37.3 g). This crude oil was purified on a flash column (600 g SiO$_2$), with a gradient solvent 6:1 Hex/EtOAc (2.13 L), 5:1 Hex/EtOAc (1.2 L), 4:1 Hex/EtOAc (1.5 L) to yield 12a as a clean yellow oil (34.5 g, 95%).

Preparation PP21

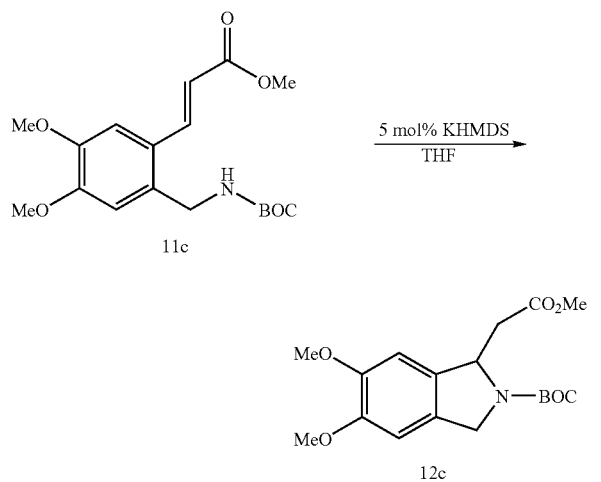

To a solution of 11c (535 mg, 1.52 mmol) in THF (10 mL) was added KHMDS (0.5 M in toluene, 0.1 mL, 0.05 mmol, 2 mol %). The mixture was stirred at r.t. for 20 min, quenched with sat. NH$_4$Cl solution (20 mL), and diluted with EtOAc (20 mL). The organic layer was separated, washed with brine (20 mL), dried (Na$_2$SO$_4$) and concentrated. The residue was filtered through a plug of silica gel (EtOAc/CH$_2$Cl$_2$ 1:10) to give 530 mg (99%) of 12c as an off white solid.

Preparation PP22

Deprotections:

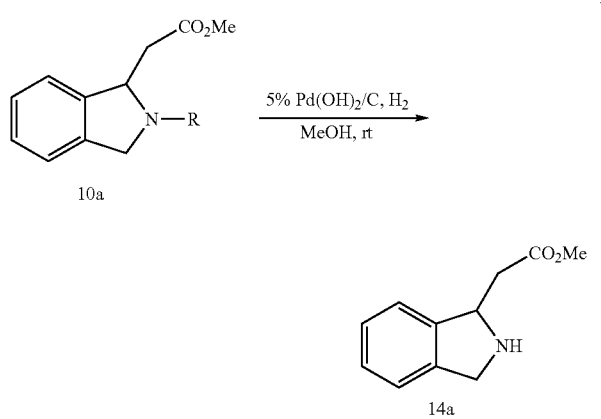

Hydrogenolysis of 10a (R=Bn) to Form (14a): To a solution of crude 10a (15.3 g, 54.4 mmol) in MeOH (100 mL) was added Pd(OH)$_2$/C (Pearlman's catalyst, 1.02 g, 6 mol %) in a par-shaker bottle. The suspension was shaken under 30 psi H$_2$ pressure overnight in the par-shaker, and filtered through a plug of celite. The filtrate was concentrated to provide 10.1 g of crude 14a as brown oil. (The procedure is same for the methyl benzylamine isoindoline substrate 10b).

Preparation PP23

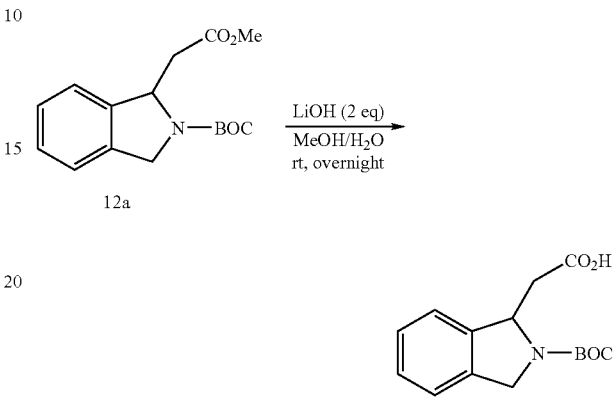

In a typical reaction a mixture of the isoindoline ester 12a (92 mg, 0.316 mmol) in 1:1 MeOH/H$_2$O (2 ml) was treated with LiOH (15 mg, 2 eq) at RT overnight. Diluted the mixture with CH$_2$Cl$_2$ (5 ml) and water (5 ml). Adjusted the pH of the reaction mixture to 1–3 with a 10% NaHSO$_4$ solution. Separated the layers. The aqueous was extracted with CH$_2$Cl$_2$ (1×10 ml). The combined organic was dried over Na$_2$SO$_4$, filtered, concentrated to yield 16a as a pale yellow foam (76 mg, 87%). NMR (CDCl$_3$) showed a clean desired acid product.

It is noted that he reaction time must be more than 6 hours. The crude foam can be purified by slurry in warm hexane and then filter to yield a tan solid. Hydrolysis using KOH (2–5 eq) in 1:1 MeOH/H$_2$O overnight would give the same result.

Preparation PP24

Resolution

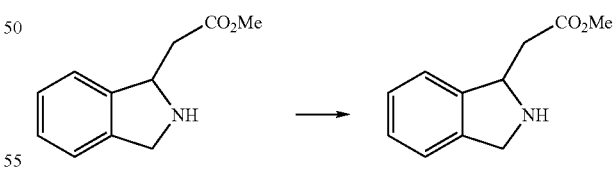

Purification of Partially Resolved Isoindoline-caboxylic acid methyl ester: A solution of the crude material (97.62 g) isoindolinecaboxylic acid methyl ester in CH$_2$Cl$_2$ (350 mL) was extracted with 1M HCl (400 mL, 200 mL). The combined aqueous portions were washed with CH$_2$Cl$_2$ (4×250 mL) and then made basic with K$_2$CO$_3$ solution (85 g in 150 mL of water). The mixture was extracted with CH$_2$Cl$_2$ (6×100 mL) and the combined organic extracts were dried (Na$_2$SO$_4$) and concentrated to give partially resolved Isoindolinecaboxylic acid methyl ester as an oil (33.2 g). 60% ee by chiral CE.

Preparation PP25

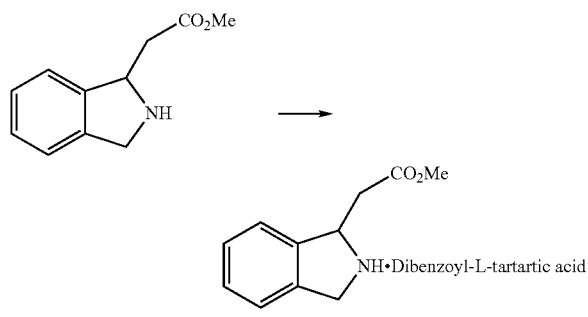

Resolution of Partially Resolved Isoindoline-caboxylic acid methyl ester: A solution of partially resolved isoindoline-caboxylic acid methyl ester (33.24 g, 0.174 mol) in EtOH (130 mL) was treated slowly with a solution of dibenzoyl-L-tartaric acid (56.06 g, 0.156 mol) in EtOH (200 mL). The solution was seeded with seeded with product and stirred at RT for 4 hours. Pure product was collected by filtration, washed with EtOH (30 mL) and dried to off-white crystals (60.49 g). 96.5% ee by chiral CE.

Preparation PP26

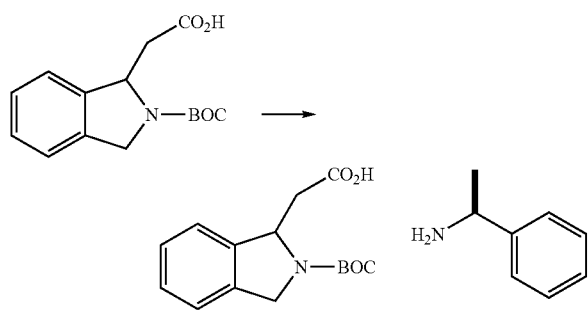

Resolution of N-BOC Isoindolinecaboxylic acid: A solution/slurry of racemic N-BOC Isoindolinecaboxylic acid (114.5 g, 0.413 mol) in EtOAc (1000 mL) was treated slowly with triethylamine (28.8 mL, 0.206 mol), followed by (S)-(−)-α-methylbenzylamine. The solution was seeded with product and stirred at RT overnight. The product was collected by filtration, washed with EtOAc (200 mL) and dried to a white powder (62.98 g). 97.6% ee by chiral CE.

Asymmetric Hydrogenation Routes

Part I: Synthesis of the Z-isomer (Precursor of Asymmetric Hydrogenation)

Scheme P1

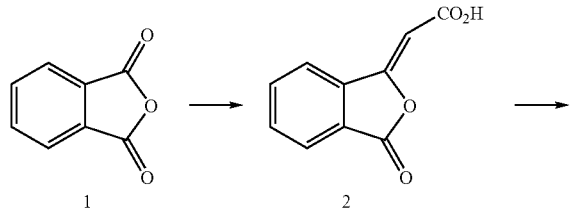

Preparation PP27

Z-isomer 5 was synthesized as outlined in Scheme P1. Compound 5 was shown to be a single isomer by HPLC and H-1 nmr. The double bond stereochemistry was derived from comparative NOE data using the purported E-isomer (Scheme P1). The best chiral induction was achieved using compound 8/Ferrotane/MeOH-THF. With regard to the conversion of 9 to 10, which would constitute a formal asymmetric synthesis of isoindolene 10, this has been achieved using Super hydride-$BF_3$.$OEt_2$. However, the product was a mixture of 10 and the corresponding de-BOC (deprotected) compound.

Preparation PP28

Compound 2 (Scheme P1)

Phthalic anhydride (751.5 g, 5.014 mole), potassium acetate (498 g, 5.014 mole) and acetic anhydride (1 L) were stirred together under nitrogen. The mixture was slowly warmed to 145–150° C. and stirred for 10 minutes, then at 140° C. for 20 minutes. The mixture was allowed to slowly cool to 80° C. over 1 hour. Three volumes of water were added causing precipitation of a solid. After filtration, the filtered solid was washed with warm water and pulled as dry as possible for 30 minutes. The solid was then washed with ethanol and acetone respectively. If required further purification could be achieved by slurring the solid in acetone, at room temperature, for 15 minutes, then filtration. Drying in vacuo at 50° C. for 20 hours gave compound 2 as an off-white solid, 470 g (48%) with an NMR purity of approx. 90%.

Preparation PP29

Compound 3 (Scheme P1)

Compound 2 (470 g, 2.47 mole) was added to stirred aqueous ammonia (470 ml conc. NH₃ in 4.7 L water). The resultant mixture was stirred at room temperature for 1 hour then filtered. The filtered solid was washed with water. The combined aqueous filtrate and washings were carefully acidified with 6M aq. HCl,(2.35 L). The precipitate was removed by filtration and dried in vacuo at 50° C. to give compound 3 as a yellow solid, 259 g (52%).

Preparation PP30

Compound 4 (Scheme P1)

Compound 3 (511 g, 2.7 mole) was slurred in toluene (10 vol). Thionyl chloride (385 g, 3.24 mole) was added over 10 minutes to the stirred mixture, which was then heated to reflux for 1.5 hours. H-1 NMR analysis indicated approx. 80% conversion to acid chloride). DMF (3.7 ml) was added and the mixture refluxed an additional 3 hours. The resultant mixture was allowed to cool to 35° C. and methanol (1.27 L) added at such a rate that the reaction temperature was maintained at 30–35° C. The reaction mixture was kept at this temperature a further 15 minutes then concentrated in vacuo to give compound 4 as a brown solid, 536 g (quantitative).

Preparation PP31

Compound 5 (Scheme P1)

Compound 4 (750 g, 3.65 mole) was dissolved in acetonitrile (15 L). The stirred mixture was cooled to 0–5° C. and DMAP (624 g, 5.11 mole) added in one portion. After 10 minutes BOC anhydride (1115 g, 5.11 mole) was added in one portion: there was a slight exotherm accompanied by gas evolution. The mixture was stirred at room temperature for 5 hours, and then concentrated in vacuo. The residue was dissolved in EtOAc and washed with 10% aqueous citric acid, satd. aq. Na₂CO₃ and water respectively. After drying, concentration of the organics gave a thick syrup. This material was run through a plug of silica gel (1.5 kg) eluting with 1:1 EtOAc-hexane. Compound 5 was isolated as a dark solid, 619 g (55%). Careful chromatography on silica gel eluting with 20% EtOAc-hexane gave 5 as a fluffy white solid.

Scheme P2

Part II: Synthesis of the E-isomer (Precursor of Asymmetric Hydrogenation)

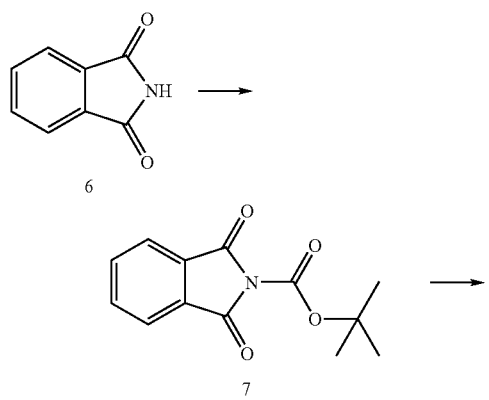

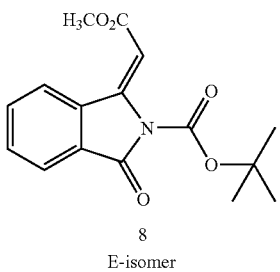

Preparation PP32

The E-isomer of Compound 8 (Scheme P2) was prepared as shown in Scheme P2.

Preparation PP33

Compound 7 (Scheme P2)

The compound 7 was prepared according to the procedure of Einhorn et al, *Synth. Commun.* 2001, 31(5), 741–748.

Preparation PP34

Compound 8 (Scheme P2)

Compound 7 (15.00 g, 60.7 mmole) and methyl(triphenyl phosphoranylidene) acetate (41.40 g, 121.3 mmole) were slurred in toluene (150 ml). The mixture was stirred at reflux and monitored for reaction of 7 by GC. After 1.5 hours the reaction appears complete by GC. After cooling to room temperature, the mixture was filtered. The solid on the filter was washed with toluene until colorless. The combined filtrate/washings were concentrated in vacuo to leave a tan solid. This material was coated on silica gel and chromatographed on silica gel (1 kg) eluting with 10% EtOAc-hexane. Compound 8 was isolated as a white or pale yellow powder, 5.52 g (30%).

Scheme P3

Asymmetric hydrogenation:

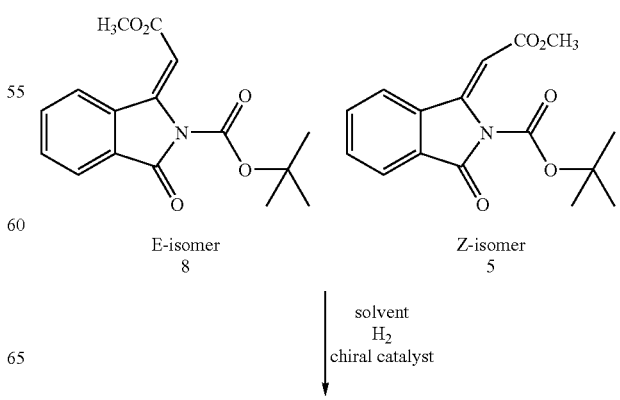

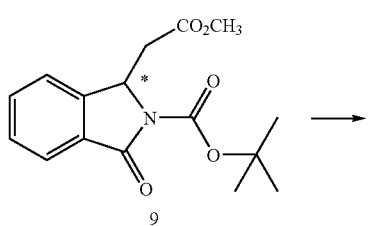

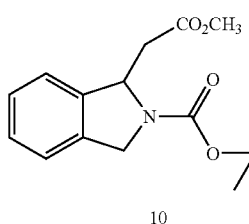

Preparation PP35

Screening of chiral hydrogenation conditions indicated that the best chiral induction was achieved using compound 8/Ferrotane/MeOH-THF. With regard to the conversion of 9 to 10, which would constitute a formal asymmetric synthesis of isoindolene 10, this has been achieved using Super hydride-BP$_3$.OEt$_2$. However, the product was a mixture of 10 and the corresponding de-BOC (deprotected) compound.

Scheme P4

Coupling of Chiral Isoindoline with d-4-chloro-Phenyl-alanine Using Tartrate Salt

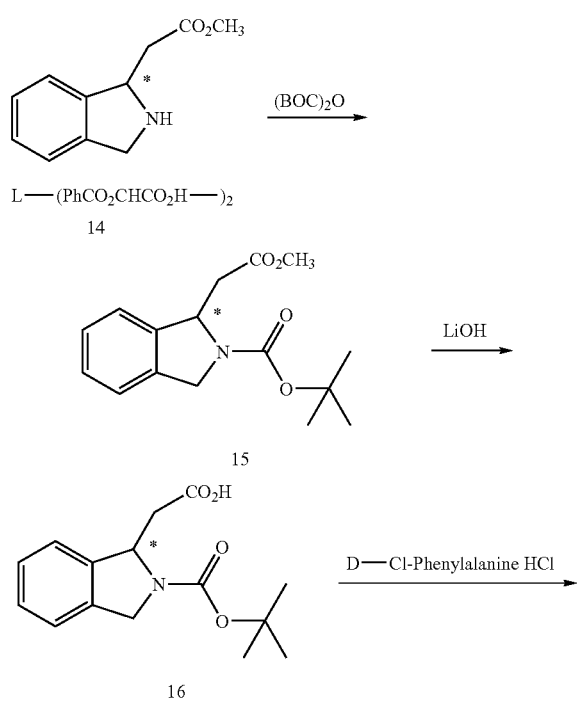

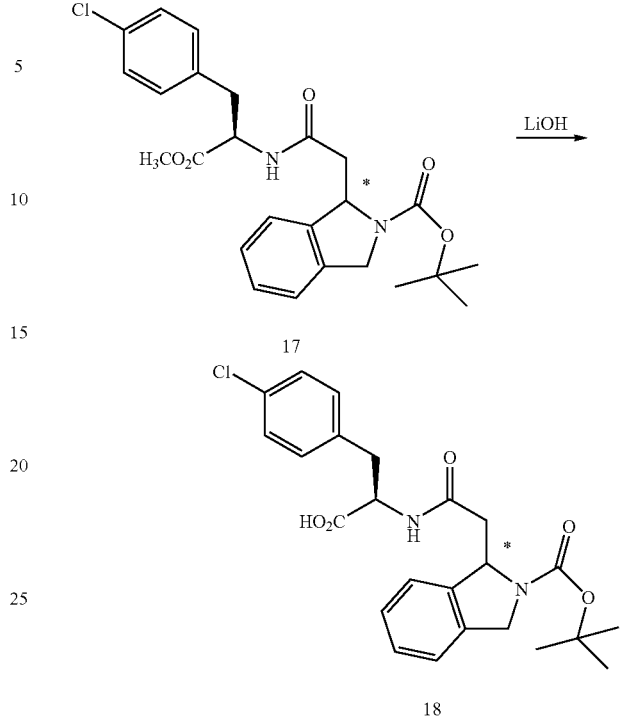

Preparation PP36

Compound 15 (Scheme P4)

Tartrate salt 14 (58.00 g, 100.27 mmole) was slurred in water (580 ml). Solid NaHCO$_3$ (25.27 g, 300.8 mmole) was carefully added BOC anhydride (22.98 g, 105.28 mmole) was in one portion and the progress of the reaction monitored by reverse phase HPLC. After 1 hour additional BOC anhydride (2.18 g, 10.00 mmole) was added. The reaction was complete (by HPLC) after 3 hours. The mixture was extracted with EtOAc (2×250 ml.) The combined organic extracts were washed with water (250 ml) and dried (MgSO$_4$). Filtration and concentration in vacuo gave 15 as a clear light brown oil (31.33 g) contaminated with a small amount of t-BuOH and BOC anhydride. This material was used directly in the next reaction.

Preparation PP37

Compound 16 (Scheme P4)

Ester 15 (29.21 g) 100.26 mmole) was dissolved in 3:1 TBF-water (100 ml). LiOH (6.00 g, 250.65 mmole) was added in 1 portion to the stirred solution. After 17 hours, the mixture was stripped to dryness and the residue was dissolved in water (500 ml.) EtOAc (250 ml) was added and solid NaHSO$_4$ added to the stirred mixture until the pH=3. The organic layer was separated and the aqueous layer extracted with EtOAc (250 ml.) The combined EtOAc layers were dried (MgSO4). Filtration and concentration in vacuo gave acid 16 as a light tan solid, 27.10 g (97%).

Scheme P5

Rrom alpha-methyl benzylamine salt:

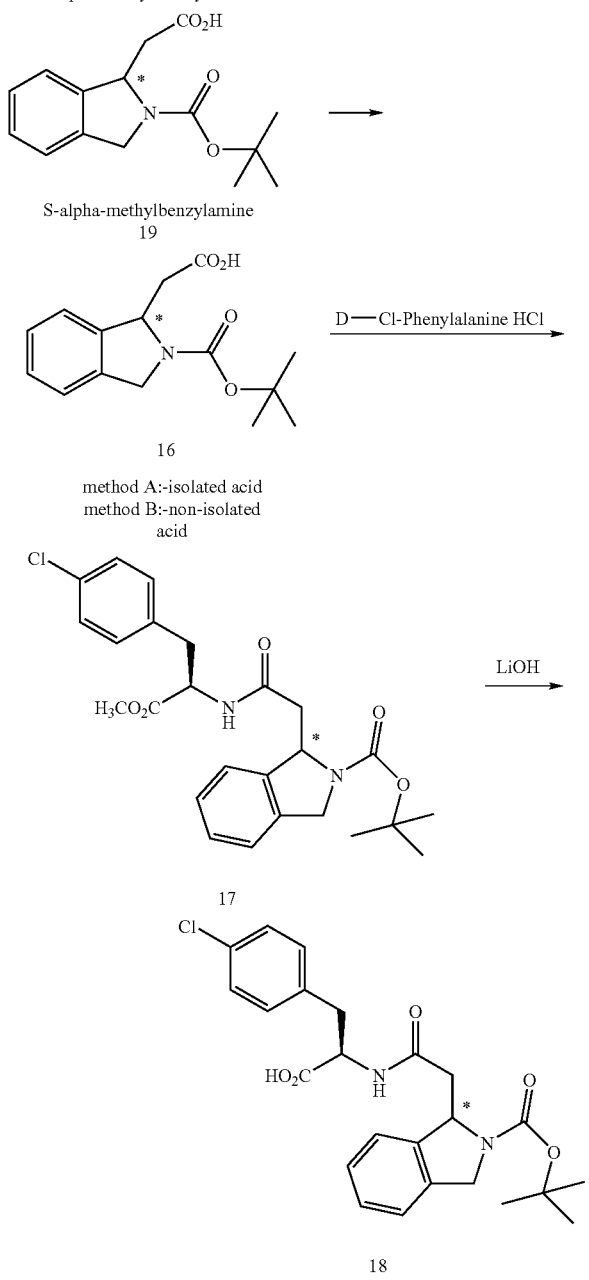

S-alpha-methylbenzylamine
19

16
method A:-isolated acid
method B:-non-isolated acid

17

18

The chemistry used is shown in Scheme P5. Two protocols were used: method A used isolated 16, method B used a solution of 16 derived from resolved salt 19.

Preparation PP38

Compound 17 (Scheme P5, Method A)

Acid 16 (24.18 g, 87.2 mmole) and D-chloro-phenylalanine hydrochloride (21.81 g, 87.2 mmole) were dissolved in $CH_2Cl_2$ (100 ml) and DMF (25 ml). The mixture was stirred at ambient temperature. HOBT (13.55 g, 100.3 mmole) and Hunig's base (45.6 ml, 33.81 g, 261.6 mmole) were added. HATU (38.13 g, 100.3 mmole) was added in 1 portion (there was a rapid exotherm to 50° C.). The mixture was stirred for 90 minutes then diluted with EtOAc (750 ml). The resulting mixture was washed with water, 5% $KHSO_4$, brine and satd. $NaHCO_3$ respectively, then dried. Filtration and concentration in vacuo gave crude 17 as a brown foam. The product was purified by chromatography on silica gel (1 kg) eluting with 1:1 EtOAc-hexane. Ester 17 was isolated as a tan powder, 38.85 g (94%).

Preparation PP39

Compound 17 (Scheme P5, Method B)

Resolved salt 19 (96.27 g, 232.5 mmole) was partitioned between water (500 ml) and $CH_2Cl_2$ (250 ml) Solid $KHSO_4$ was added portion wise until pH=2.5. Separate the organic layer and extract the aqueous layer with $CH_2Cl_2$ (150 ml). The combined organic layers were dried ($MgSO_4$) then filtered. To this solution was added 4-chloro-D-phenylalanine (58.16 g, 232.5 mmole), HOBT (34.57 g, 255.8 mmole), Hunig's base (93.2 ml, 69.13 g, 534.9 mmole) and finally HATU (97.26 g, 255.8 mmole). The resultant mixture was stirred at room temperature for 18.5 hours, and then poured onto a plug of silica gel (1 kg). This was washed with 1:1 EtOAc-hexane until no more product elutes. Ester 17 was isolated as a pink foam, 101.79 g (93%): contains about 1% unreacted 16.

Preparation PP40

Compound 18 (Scheme P5)

Ester 17 (38.64 g, 81.7 mmole) was dissolved in 3:1 THF-water (200 ml). LiOH (2.15 g, 89.9 mmole) was added to the mixture, which was stirred at room temperature for 2 hours. The solvent was then removed in vacuo and the residual solid taken up in water (600 ml). This was extracted with MTBE (250 ml). The aqueous layer was separated and stirred with EtOAc (250 ml), and solid $KHSO_4$ was added portion wise until pH=3. The layers were separated and the aqueous extracted with EtOAc (250 ml). The combined organic layers were dried over MgSO4. Filtration and concentration in vacuo gave acid 18 as a light pink foam, 38.41 g (35.71 g corrected for residual solvent, 95%).

Preparation PP41

Step 1: Esterification

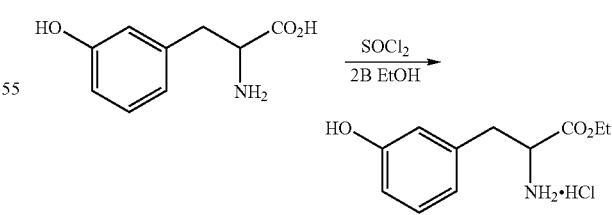

In a 22 L 4-neck round bottom flask equipped with a reflux condenser, thermocouple and nitrogen inlet, a slurry of 1000 g (5.4 moles) of m-tyrosine in 10 L of 2B-3 EtOH was cooled to 5° C. To the slurry, 350 ML (12.4 moles) of thionyl chloride were added dropwise via an addition funnel at such a rate to maintain the reaction temperature below 20°

C. Upon completion of addition, the reaction was heated to reflux temperature and stirred for 18 hrs. The reaction was concentrated to one-third the volume and 8 L of MTBE were charged. The resulting thick slurry was stirred for 14 hrs in a rotary evaporator at r.t. The resulting solid was isolated on a filter pad and dried at 40° C. for 48 hrs yielding 1288 g (95%). NMR (MSOd$_6$) indicated desired material.

Preparation PP42

Step 2: Pictet-Spengler

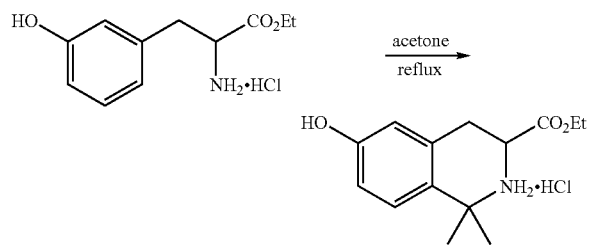

In a 22 L 4 neck round bottom flask equipped with a mechanical stirrer, thermocouple, and reflux condenser placed on top of a Soxhlet extractor charged with 4° A sieves, a semi-solution of m-tyrosine ethyl ester hydrochloride 1288 g (5.26 moles) in 13 L of acetone was heated to reflux temperature. The condensate was filtered through the sieves to remove water. The reaction was stirred vigorously at reflux for 48 hrs. An NMR sample in DMSOd$_6$ indicated the absence of starting material. The reaction was cooled to r.t. and concentrated to yield an off-white solid, 1411 g (94%).

Preparation PP43

Step 3: Triflation

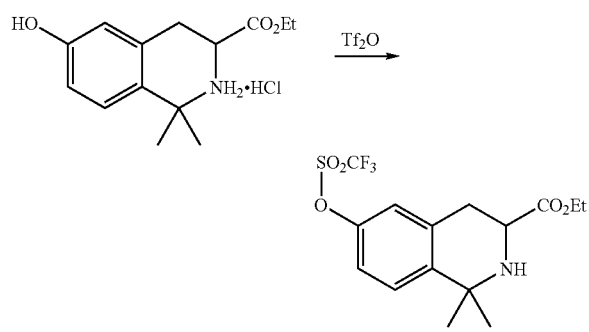

In a 22 L 4 neck round bottom flask equipped with a reflux condenser, mechanical stirrer, nitrogen inlet, and a thermocouple, 1240 g (4.35 moles) of the starting material salt in 12.4 L of methylene chloride was cooled to 4° C. To the mixture, 1452 mL (10.4 moles) of triethylamine were added and stirred into solution. Triflic anhydride, 1472 mL (5.22 moles) was added dropwise to the reaction at such a rate to maintain the internal temperature below 10° C. The ice bath was removed and the reaction warmed to rt. and stirred for 18 hrs. The reaction was concentrated to a oil then dissolved in 4 L of EtOAc and concentrated again to an oil in an effort to remove excess triflic anhydride The crude residue was dissolved in 4 L of EtOAc and washed with water and saturated sodium bicarbonate solution. The organic layer was isolated and dried with sodium sulfate, filtered and concentrated to yield 1720 g (>100%) of a crude dark oil which was used without further purification.

Preparation PP44

Step 4: Deoxygenation

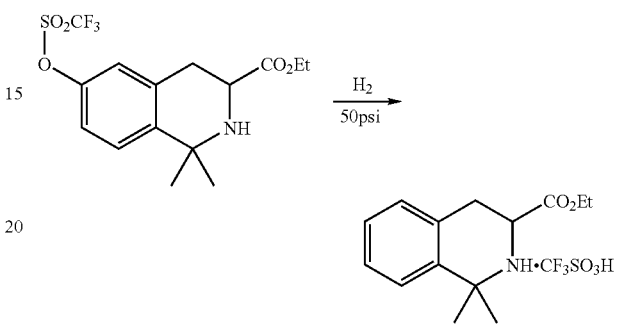

A solution of 1720 g (4.35 moles) of crude starting material in 14 L of acetone was charged to a 10 gallon stainless steel autoclave. To the solution, a slurry of 5% Pd/C in 1.2 L of toluene was added. The reaction mixture was evacuated and purged with H$_2$ gas at 50 psi two times. The reaction was stirred overnight at 50° C. with H$_2$ at 50 psi. A sample aliquot indicated no reaction had occurred. The mixture was filtered and concentrated to a thick oil and resubjected to reaction conditions. After 18 hrs, NMR of a sample aliquot indicated absence of starting material. The reaction mixture was filtered and the filtrate concentrated to yield 1581 g of an off-white solid (95%).

Preparation PP45

Step 5: Hydrolysis/Salt Formation

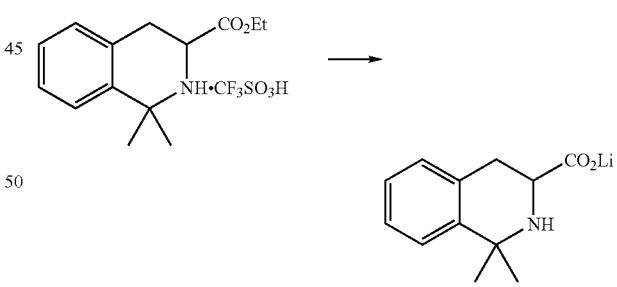

To a 2 L 3 neck round bottom flask equipped with a mechanical stirrer, thermocouple, and nitrogen inlet, a mixture of 700 g (1.83 moles) of the triflate salt starting material was charged. A solution of 427 g (1.83 moles) of the starting material free base in 13.3 L of THF was added followed by 700 mL of water. The semi-solution was stirred vigorously at r.t. To the reaction flask, 43.7 g (1.83 moles) of solid LiOH were added in small portions at such a rate to maintain the internal temperature below 35° C. The reaction was stirred for 18 hrs at r.t. and concentrated to yield a thick oil. THF (4 L) was added and the semi-solution was concentrated. This was repeated with toluene and the semi-solid was placed under house vacuum on the roto vap with stirring for 18 hrs to yield 650 g of a crude solid. The solid was reslurried in EtOAc, filtered, isolated and dried to yield 525 g (68%) of the lithium salt as an off-white solid.

Preparation PP46

Step 6: Coupling

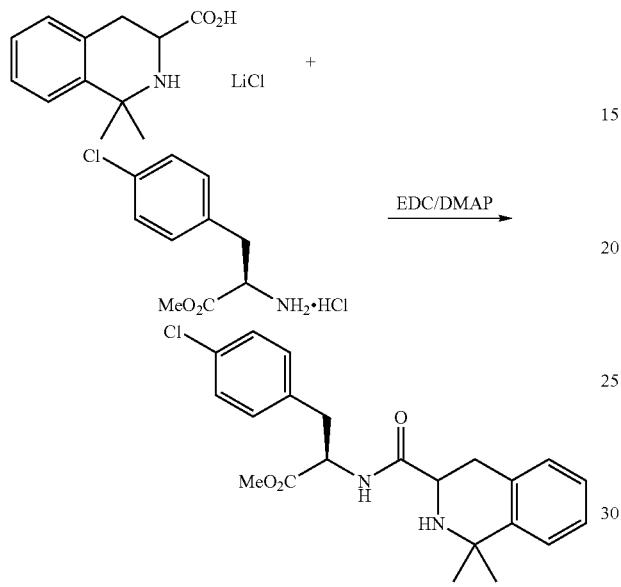

Solid d-chloro-phenylalanine 446 g (1.78 moles) was added to the semi-solution followed by 20 g (0.162 moles) of DMAP. The resulting mixture was stirred for 15 minutes then solid EDCl (1-(3-dimethylaminopropyl)-3-ethylcarbodiimide hydrochloride) 390 g (2.03 moles) was added. The reaction mixture was heated to 80° C. and stirred for 18 hours. Thin layer chromatography (1:1 EtOAc:Hex) indicated very little starting material present. The reaction was cooled to r.t. and concentrated to yield a thick oil. The crude oil was dissolved in EtOAc and washed with water, and brine. The solution was dried with sodium sulfate, filtered and concentrated to yield a thick oil, 426 g. The crude oil was chromatographed in several lots using a Waters Prep 500 chromatography apparatus. The eluent consisted of a gradient system, 5%–80% EtOAc in heptane at a flow rate of 240 ml/min over 38 minutes. The two diasteromers were separated and isolated to yield 119.04 g for the top spot and 111.3 g for the bottom spot. Conformation of both desired diastereomers was achieved via NMR (DMSO$_6$).

Preparation PP47

Resolution of Tetrahydroisoquinolinecarboxylic Acid Ethyl Ester to Prepare l-tartaric Acid Salt

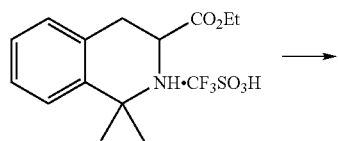

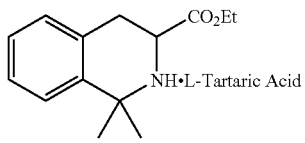

Preparation of free-base: A racemic mixture of tetrahydroisoquinolinecarboxylic acid (7.43 g) in EtOAc (60 mL) was treated with saturated NaHCO$_3$ solution (60 mL) and saturated Na$_2$CO$_3$ solution (10 mL). The mixture was agitated and the layers were separated. The organic phase was dried (Na$_2$SO$_4$) and concentrated to give the corresponding free-base as an oil (4.85 g)

Resolution: A mixture of the above free base (467 mg, 2.0 mmol), and L-tartaric acid (300 mg, 2.0 mmol) in acetone (4 mL) was stirred at r.t. overnight. The title L-tartaric acid salt was collected by filtration, washed with acetone (about 2 mL) and dried to a white powder (367 mg). 100% ee by chiral CE.

Preparation PP48

Resolution of N-BOC Tetrahydroisoquinolinecarboxylic Acid

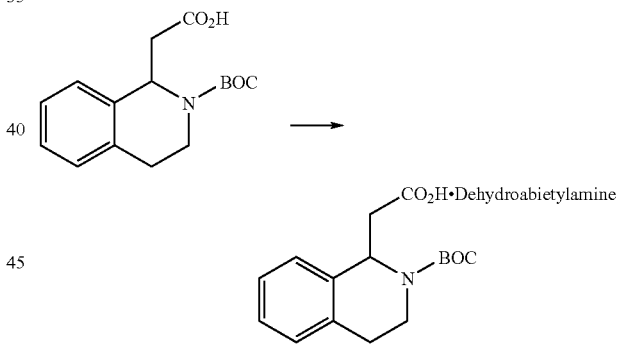

2-{2-[(tert-butyl)oxycarbonyl]-1,2,3,4-tetrahydroisoquinolyl}acetic acid dehydroabietylamine salt: Racemic 2-{2-[(tert-butyl)oxycarbonyl]-1,2,3,4-tetrahydroisoquinolyl}acetic acid (30.15 g, 103.5 mmol) was dissolved in i-PA (300 mL). Dehydroabietylamine (22.11 g, 52.7 mmol of a 68 weight % mixture) was added to the solution, which was then agitated on a multi-arm shaker for 63 h. The resultant thick paste was filtered and rinsed with i-PA (50 mL, 25 mL). Dried in a 50° C. vacuum oven to obtain a white solid (27.73 g, 52% ee by chiral CE analysis). The product was reslurried in i-PA (266 mL) and agitated on a multi-arm shaker for 23.5 h. Filtered the thick slurry and rinsed with cold i-PA (50 mL, 30 mL). Dried the cake in a 50° C. vacuum oven and obtained the product as a white solid (23.63 g, 40% yield, 94% ee by chiral CE analysis).

Scheme P6

Asymmetric Hydrogenation:

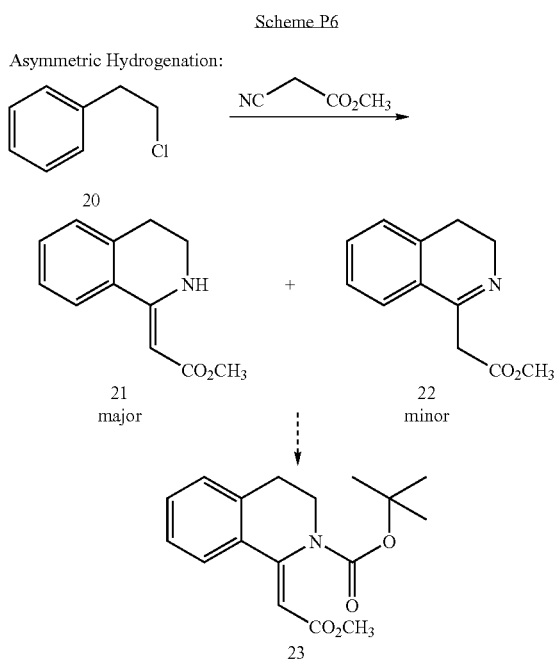

Preparation PP49

Enamine 21 (Scheme P6) was prepared as a substrate for asymmetric hydrogenation screening studies. It is formed as an approx. 10:1 mixture with imine 22. The enamine (21) may be NH-protected i.e., by a Boc protecting group. The resulting compound 23 may be subjected to asymmetric hydrogenation to afford the acetic acid or methylacetate substituted isoquinoline, which may be processed into a compound of formula I as demonstrated previously.

Preparation PP50

Compound 21 (Scheme P6)

Prepared as Published W Sobotka et al, *J. Org. Chem.*, 1965, 30, 3667

Scheme P7

Synthesis of Gem-dimethyl TIC:

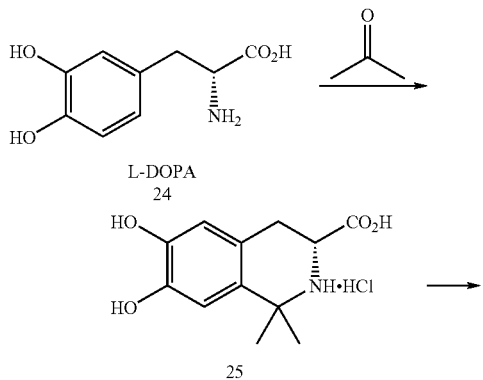

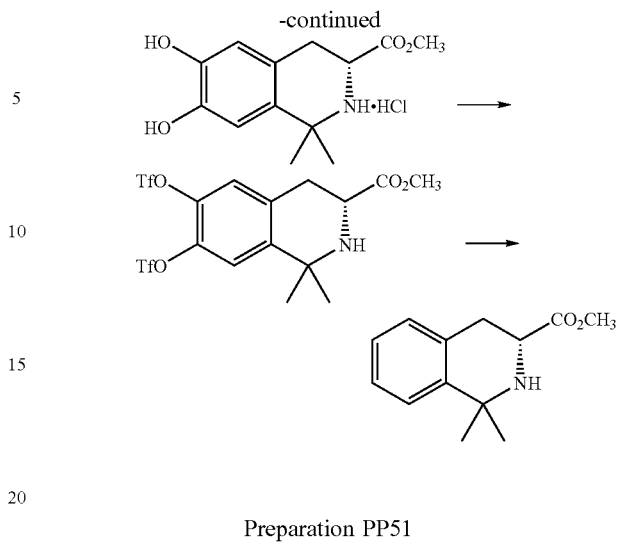

Preparation PP51

The chiral synthesis of gem-dimethyl TIC using L-Dopa as the starting material instead of tyrosine was successfully demonstrated up to the Pictet-Spengler reaction with L-DOPA and acetone. The product is a mixture of starting material 24 and product 25 (major component). The product was isolated by using common isolation procedures. An alternative isolation method is to react the mixture (24 and 25) with BOC anhydride wherein the less hindered N—H in 24 leads to preferential BOC protection of 24, allowing for ready separation of 25. Chemistry for the rest of the sequence i.e., deoxygenation reaction, has been demonstrated herein.

What is claimed is:

1. A compound of formula I:

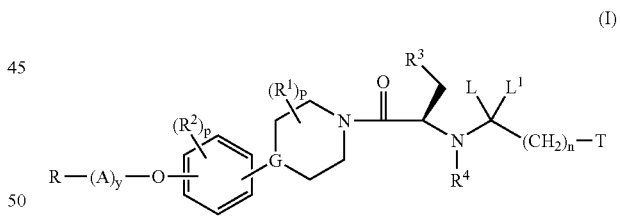

(I)

or a pharmaceutically acceptable salt or steroisomer thereof, wherein

G is N;
A is $C_1$–$C_8$ alkyl or $C_3$–$C_7$ cycloalkyl;
L and $L^1$ are independently: hydrogen or together oxo;
T is:

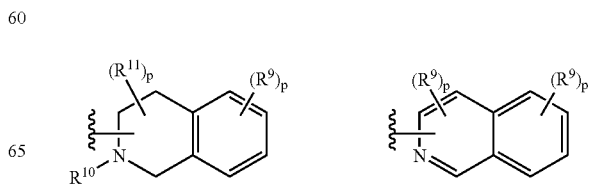

-continued

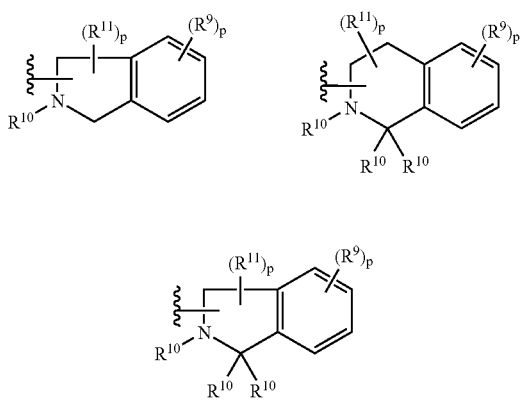

R is: when y is 1;
N(R$^8$)$_2$,
NR$^8$COR$^8$,
NR$^8$CON(R$^8$),
NR$^8$C(O)OR$^8$,
NR$^8$SO$_2$R$^8$ or R is: when y is 0 or 1;
heterocyclyl, provided that when y is 0, a heteroatom is not directly connected to oxygen or adjacent to a carbon that is connected to oxygen; and
wherein the heterocyclyl having at least one nitrogen in the heterocyclic ring and is optionally substituted with one to five substituents independently selected from R$^8$;

R$^1$ is independently:
hydrogen, CONH(C$_1$–C$_8$ alkyl), C$_1$–C$_8$ alkyl, (D)phenyl, (D)C$_3$–C$_7$ cycloalkyl or oxo, provided that oxo is not attached to the ring carbon adjacent to G;

R$^2$ is independently:
hydrogen,
halo
C$_1$–C$_8$ alkyl,
C$_1$–C$_8$ alkylsulfonyl,
(D)C$_3$–C$_7$ cycloalkyl or
C$_1$–C$_4$ haloalkyl;

R$^3$ is independently: aryl or thienyl;
wherein aryl and thienyl are optionally substituted with one to three substituents selected from the group consisting of:
cyano, halo, C$_1$–C$_8$ alkyl, (D)C$_3$–C$_7$ cycloalkyl, C$_1$–C$_4$ alkoxy, C$_1$–C$_4$ haloalkyl, benzyloxy, and C$_1$–C$_4$ haloalkyloxy;

R$^4$ is independently:
hydrogen, C$_1$–C$_8$ alkyl, C(O)R$^8$, C(O)OR$^8$, C$_3$–C$_7$ cycloalkyl or (CH$_2$)$_n$O(C$_1$–C$_8$ alkyl),
wherein n is 2–8;

each R$^8$ is independently:
hydrogen,
phenyl
C$_1$–C$_8$ alkyl,
C$_1$–C$_8$ alkylsulfonyl,
C(O)C$_1$–C$_8$ alkyl,
C(O)aryl, wherein aryl being phenyl or naphthyl,
SO$_2$-aryl, wherein aryl being phenyl or naphthyl,
(D)C$_3$–C$_7$ cycloalkyl or
(CH$_2$)$_n$C$_1$–C$_4$ haloalkyl, wherein n is 1–8;

each R$^9$ is independently:
hydrogen,
hydroxy,
(D)cyano,
halo,
C$_1$–C$_8$ alkyl,
C$_1$–C$_8$ alkoxy,
C$_3$–C$_7$ cycloalkyl,
C$_1$–C$_4$ haloalkyl,
(D)C(O)R$^8$,
(D)OR$^8$,
(D)OCOR$^8$,
(D)NR$^8$SO$_2$R$^8$, each R$^{10}$ is independently:
hydrogen, (C$_1$–C$_8$)alkyl, C(O)C$_1$–C$_8$ alkyl, aryl or C$_3$–C$_7$ cycloalkyl;

each R$^{11}$ is independently:
hydrogen,
C$_1$–C$_8$ alkyl,
(CH$_2$)$_n$N(R$^8$)$_2$,
(CH$_2$)$_n$NR$^8$C(O)C$_1$–C$_4$ alkyl, and
(CH$_2$)$_n$NR$^8$SO$_2$C$_1$–C$_4$ alkyl,
wherein n is 2–8;

D is a bond or —(CH$_2$)$_n$—;
n is 0–8;
p is 0–4;
q is 0–1;
y is 0–1.

2. The compound of claim 1, wherein the R heterocyclyl is a 4-, 5- or 6-membered ring having one nitrogen atom.

3. The compound of claim 2, wherein the R heterocyclyl is a 6-membered ring having one nitrogen and one oxygen atom.

4. The compound of claim 3, wherein R$^3$ is phenyl optionally para-substituted with fluoro, chloro, bromo, iodo, benzyloxy, methoxy or methyl.

5. The compound of claim 4, wherein R$^3$ is phenyl para-substituted with chloro, fluoro or methoxy.

6. The compound of claim 5, wherein R$^4$ is hydrogen.

7. The compound of claim 6, wherein —(CH$_2$)$_n$—T is:

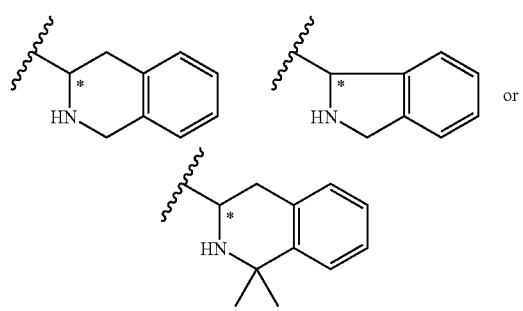

where * denotes a chiral carbon atom having a R or S configuration.

8. The compound of claim 7, wherein L and L$^1$ are together oxo and the chiral carbon has R configuration.

9. A compound of formula II,

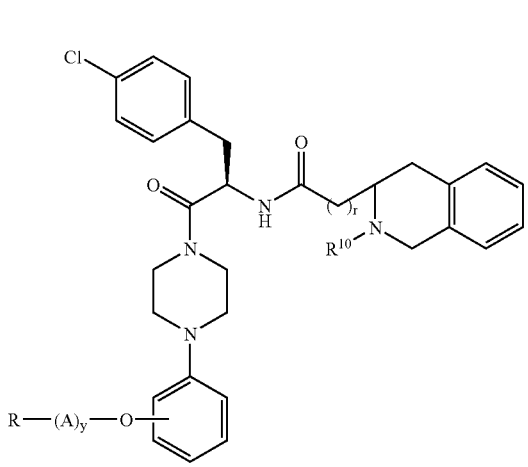

(II)

or a pharmaceutically acceptable salt or steroisomer thereof, wherein
  A is $C_1$–$C_8$ alkyl or $C_3$–$C_7$ cycloalkyl;
  r is 0 or 1;
  y is 0 or 1;
  D is a bond or —$(CH_2)_n$—;
  n is 0–8;
  R is: when y is 1;
    $N(R^8)_2$,
    $NR^8COR^8$,
    $NR^8CON(R^8)_2$,
    $NR^8C(O)OR^8$,
    $NR^8SO_2R^8$ or
  R is: when y is 0 or 1;
    heterocyclyl, provided that when y is 0, a heteroatom is not directly connected to oxygen or adjacent to a carbon that is connected to oxygen; and
    wherein the heterocyclyl has at least one nitrogen in the heterocyclic ring and is optionally substituted with one to five substituents independently selected from $R^8$;
  each $R^8$ is independently:
    hydrogen,
    phenyl
    $C_1$–$C_8$ alkyl,
    $C_1$–$C_8$ alkylsulfonyl,
    $C(O)C_1$–$C_8$ alkyl,
    C(O)aryl, wherein aryl being phenyl or naphthyl,
    $SO_2$-aryl, wherein aryl being phenyl or naphthyl,
    (D)$C_3$–$C_7$ cycloalkyl or
    $(CH_2)_nC_1$–$C_4$ haloalkyl, wherein n is 1–8;
  each $R^{10}$ is independently:
    hydrogen, $(C_1$–$C_8)$alkyl, $C(O)C_1$–$C_8$ alkyl, aryl or $C_3$–$C_7$ cycloalkyl.

10. The compound of claim 9, wherein O—$(A)_y$—R is attached to the ortho position of the phenyl ring.

11. The compound of claim 10, wherein the R heterocyclyl is a 4-, 5- or 6-membered ring having one nitrogen atom.

12. The compound of claim 11, wherein the nitrogen is substituted with one substituent selected from $R^8$ when y is 0.

13. The compound of claim 11, wherein the R heterocyclyl is a 6-membered ring having one nitrogen and one oxygen atom.

14. A compound of formula IV,

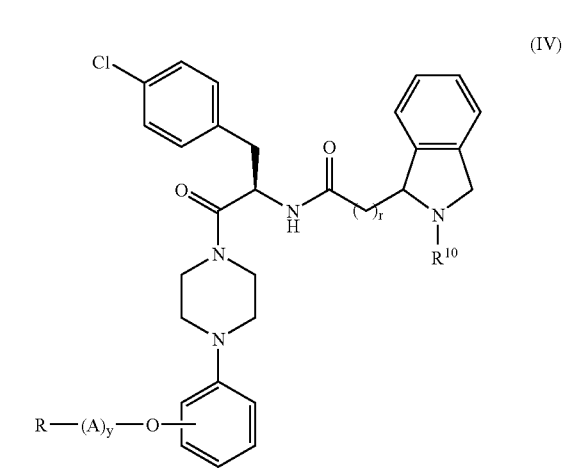

(IV)

or a pharmaceutically acceptable salt or steroisomer thereof, wherein
  A is $C_1$–$C_8$ alkyl or $C_3$–$C_7$ cycloalkyl;
  r is 0 or 1;
  y is 0 or 1;
  D is a bond or —$(CH_2)_n$—;
  n is 0–8;
  R is: when y is 1;
    $N(R^8)_2$,
    $NR^8COR^8$,
    $NR^8CON(R^8)_2$,
    $NR^8C(O)OR^8$,
    $NR^8SO_2R^8$ or
  R is: when y is 0 or 1;
    heterocyclyl, provided that when y is 0, a heteroatom is not directly connected to oxygen or adjacent to a carbon that is connected to oxygen; and
    wherein the heterocyclyl has at least one nitrogen in the heterocyclic ring and is optionally substituted with one to five substituents independently selected from $R^8$;
  each $R^8$ is independently:
    hydrogen,
    phenyl
    $C_1$–$C_8$ alkyl,
    $C_1$–$C_8$ alkylsulfonyl,
    $C(O)C_1$–$C_8$ alkyl,
    C(O)aryl, wherein aryl being phenyl or naphthyl,
    $SO_2$-aryl, wherein aryl being phenyl or naphthyl,
    (D)$C_3$–$C_7$ cycloalkyl or
    $(CH_2)_nC_1$–$C_4$ haloalkyl, wherein n is 1–8;
  each $R^{10}$ is independently:
    hydrogen, $(C_1$–$C_8)$alkyl, $C(O)C_1$–$C_8$ alkyl, aryl or $C_3$–$C_7$ cycloalkyl.

15. The compound of claim 14, wherein O—$(A)_y$—R is attached to the ortho position of the phenyl ring.

16. The compound of claim 15, wherein the R heterocyclyl is a 4-, 5- or 6-membered ring having one nitrogen atom.

17. The compound of claim 16, wherein the nitrogen is substituted with one substituent selected from $R^8$ when y is 0.

18. The compound of claim 16, wherein the heterocyclyl is a 6-membered ring having one nitrogen and one oxygen atom.

19. A compound of formula V,

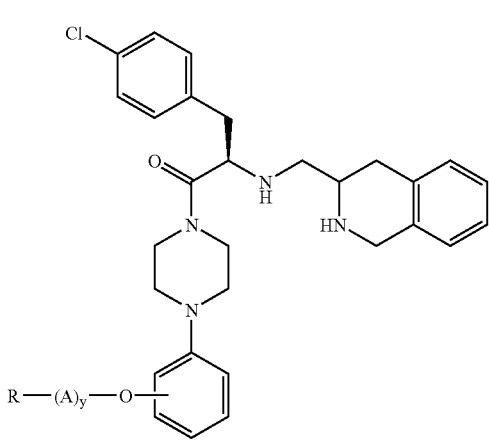

(V)

or a pharmaceutically acceptable salt or steroisomer thereof, wherein

A is $C_1$–$C_8$ alkyl or $C_3$–$C_7$ cycloalkyl;
y is 0 or 1;
D is a bond or —$(CH_2)_n$—;
n is 0–8;
R is: when y is 1;
  $N(R^8)_2$,
  $NR^8COR^8$,
  $NR^8CON(R^8)_2$,
  $NR^8C(O)OR^8$,
  $NR^8SO_2R^8$ or
R is: when y is 1 or 1;
  heterocyclyl, provided that when y is 0, a heteroatom is not directly connected to oxygen or adjacent to a carbon that is connected to oxygen; and
  wherein the heterocyclyl has at least one nitrogen in the heterocyclic ring and is optionally substituted with one to five substituents independently selected from $R^8$;
each $R^8$ is independently:
  hydrogen,
  phenyl
  $C_1$–$C_8$ alkyl,
  $C_1$–$C_8$ alkylsulfonyl,
  $C(O)C_1$–$C_8$ alkyl,
  C(O)aryl, wherein aryl being phenyl or naphthyl,
  $SO_2$-aryl, wherein aryl being phenyl or naphthyl,
  $(D)C_3$–$C_7$ cycloalkyl or
  $(CH_2)_nC_1$–$C_4$ haloalkyl, wherein n is 1–8.

20. The compound of claim 19, wherein O—$(A)_y$—R is attached to the ortho position of the phenyl ring.

21. The compound of claim 20, wherein the R heterocyclyl is a 4-, 5- or 6-membered ring having one nitrogen atom.

22. The compound of claim 21, wherein the nitrogen is substituted with one substituent selected from $R^8$ when y is 0.

23. The compound of claim 21, wherein the heterocyclyl is a 6-membered ring having one nitrogen and one oxygen atom.

24. A compound of formula VI,

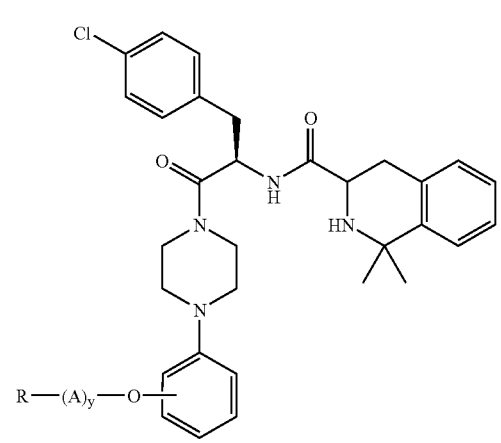

(VI)

or a pharmaceutically acceptable salt or steroisomer thereof, wherein

A is $C_1$–$C_8$ alkyl or $C_3$–$C_7$ cycloalkyl;
y is 0 or 1;
D is a bond or —$(CH_2)_n$—;
n is 0–8;
R is: when y is 1;
  $N(R^8)_2$,
  $NR^8COR^8$,
  $NR^8CON(R^8)_2$,
  $NR^8C(O)OR^8$,
  $NR^8SO_2R^8$ or
R is: when y is 0 or 1;
  heterocyclyl, provided that when y is 0, a heteroatom is not directly connected to oxygen or adjacent to a carbon that is connected to oxygen; and
  wherein the heterocyclyl has at least one nitrogen in the heterocyclic ring and is optionally substituted with one to five substituents independently selected from $R^8$;
each $R^8$ is independently:
  hydrogen,
  phenyl
  $C_1$–$C_8$ alkyl,
  $C_1$–$C_8$ alkylsulfonyl,
  $C(O)C_1$–$C_8$ alkyl,
  C(O)aryl, wherein aryl being phenyl or naphthyl,
  $SO_2$-aryl, wherein aryl being phenyl or naphthyl,
  $(D)C_3$–$C_7$ cycloalkyl or
  $(CH_2)_nC_1$–$C_4$ haloalkyl, wherein n is 1–8.

25. The compound of claim 24, wherein O—$(A)_y$—R is attached to the ortho position of the phenyl ring.

26. The compound of claim 25, wherein the R heterocyclyl is a 4-, 5- or 6-membered ring having one nitrogen atom.

27. The compound of claim 26, wherein the nitrogen is substituted with one substituent selected from $R^8$ when y is 0.

28. The compound of claim 26, wherein the heterocyclyl is a 6-membered ring having one nitrogen and one oxygen atom.

29. A compound selected from the group consisting of:

| Name of Compound | Compound |
|---|---|
| (N-(1-(4-R-chlorobenzyl)-2-{4-[2-(1-methyl-S-piperidin-3-yloxy)-phenyl]-piperazin-1-yl}-2-oxo-ethyl)-2-(2,3-dihydro-1H-isoindol-1-yl)-aceamide, trihydrochloride | 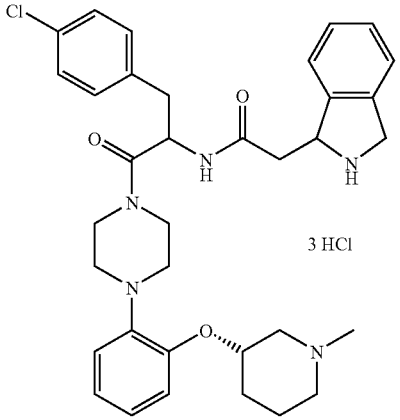 3 HCl |
| (N-(1-(4-R-chlorobenzyl)-2-oxo-2-{4-[2-(R-piperidin-3-yloxy)-phenyl]-piperazin-1-yl}ethyl)-2-(2,3-dihydro-1H-isoindol-1-yl)-aceamide, trihydrochloride | 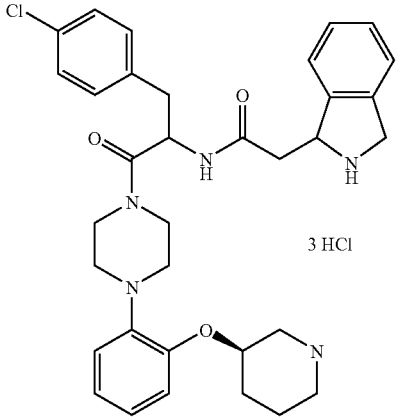 3 HCl |
| 2-(2,3-dihydro-1H-isoindol-1-yl)-N-(1-(4-methoxy-benzyl)-2-{4-[2-(1-methyl-piperidin-3-yloxy)-phenyl]-piperazin-1-yl)-2-oxo-ethyl)-acetaimde, trihydrochloride | 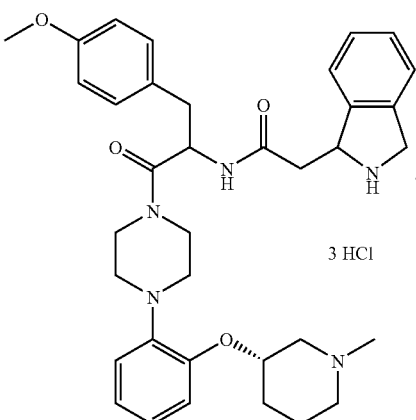 3 HCl |

60

30. A pharmaceutical composition which comprises a pharmaceutical carrier and at least one compound of formula I or its pharmaceutically acceptable salts or stereoisomer thereof as recited in claim 1.

31. A process of making a pharmaceutical composition comprising a compound of formula I or a pharmaceutically acceptable salt or stereoisomers thereof as recited in claim 1 and a pharmaceutically acceptable carrier.

32. A method of treating obesity in a mammal comprising the administration of a therapeutically effective amount of the compound of formula I as recited in claim 1.

33. A process for preparing a compound of formula I:

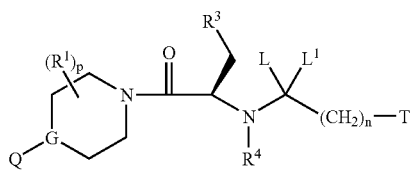
(I)

or a pharmaceutically acceptable salt or stereoisomer thereof, wherein
G is N;
A is $C_1-C_8$ alkyl or $C_3-C_7$ cycloalkyl;
—$CLL^1$—$(CH_2)_n$—T is:

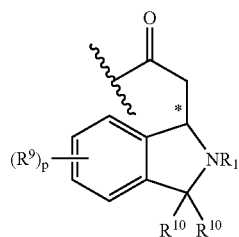

wherein $R^1$ is hydrogen, $C_1-C_8$ alkyl, Boc, CBZ, FMOC, phenyl or $(C_1-C_8$ alkyl)phenyl;
Q represents a moiety:

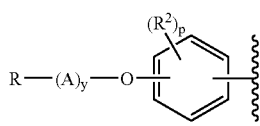

R is: when y is 1;
$N(R^8)_2$,
$NR^8COR^8$,
$NR^8CON(R^8)_2$,
$NR^8C(O)OR^8$,
$NR^8SO_2R^8$ or
R is: when y is 0 or 1;
heterocyclyl, provided that when y is 0, a heteroatom is not directly connected to oxygen or adjacent to a carbon that is connected to oxygen; and
wherein the heterocyclyl has at least one nitrogen in the heterocyclic ring and is optionally substituted with one to five substituents independently selected from $R^8$;
$R^1$ is independently:
hydrogen, $CONH(C_1-C_8$ alkyl), $C_1-C_8$ alkyl, (D)phenyl, (D)$C_3-C_7$ cycloalkyl or oxo, provided that oxo is not attached to the ring carbon adjacent to G;
$R^2$ is independently:
hydrogen,
halo
$C_1-C_8$ alkyl,
$C_1-C_8$ alkylsulfonyl,
(D)$C_3-C_7$ cycloalkyl or
$C_1-C_4$ haloalkyl;
$R^3$ is independently: aryl or thienyl;
wherein aryl and thienyl are optionally substituted with one to three substituents selected from the group consisting of:
cyano, halo, $C_1-C_8$ alkyl, (D)$C_3-C_7$ cycloalkyl, $C_1-C_4$ alkoxy, $C_1-C_4$ haloalkyl, benzyloxy, and $C_1-C_4$ haloalkyloxy;

$R^4$ is independently:
hydrogen, $C_1-C_8$ alkyl, $C(O)R^8$, $C(O)OR^8$, $C_3-C_7$ cycloalkyl or $(CH_2)_nO(C_1-C_8$ alkyl),
wherein n is 2–8;
each $R^8$ is independently:
hydrogen,
phenyl
$C_1-C_8$ alkyl,
$C_1-C_8$ alkylsulfonyl,
$C(O)C_1-C_8$ alkyl,
C(O)aryl, wherein aryl being phenyl or naphthyl,
$SO_2$-aryl, wherein aryl being phenyl or naphthyl,
(D)$C_3-C_7$ cycloalkyl or
$(CH_2)_nC_1-C_4$ haloalkyl, wherein n is 1–8;
each $R^9$ is independently:
hydrogen,
hydroxy,
(D)cyano,
halo,
$C_1-C_8$ alkyl,
$C_1-C_8$ alkoxy,
$C_3-C_7$ cycloalkyl,
$C_1-C_4$ haloalkyl,
(D)$C(O)R^8$,
(D)$OR^8$,
(D)$OCOR^8$,
each $R^{10}$ is independently:
hydrogen, $(C_1-C_8)$alkyl, $C(O)C_1-C_8$ alkyl, aryl or $C_3-C_7$ cycloalkyl;
D is a bond or —$(CH_2)_n$—;
n is 0–8;
p is 0–4;
q is 0–1; and
y is 0–1;
comprising the steps of:
a) reacting a compound having a structural formula 1,

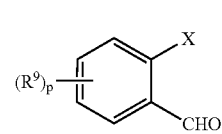
(1)

with $CH_2CH=C(O)OR^a$ wherein $R^a$ is hydrogen or $C_1-C_8$ alkyl and X is halo, in the presence of a catalyst and a base in a suitable organic solvent to give the compound of formula 2,

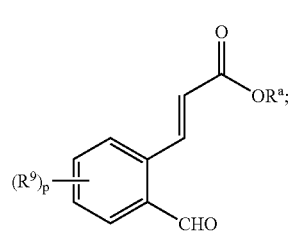
(2)

b) reductively aminating the compound of formula 2 in the presence of amine in an acidic condition to give a compound of formula 3,

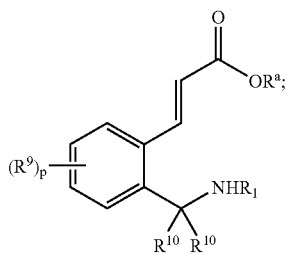

c) cyclizing the compound of formula 3 by Michael addition to give a compound of formula 4 or stereoisomers thereof,

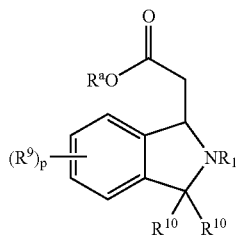

d) coupling the compound of formula 4 or stereoisomers thereof, wherein $R^a$ of compound 4 is H, with a compound of formula 5,

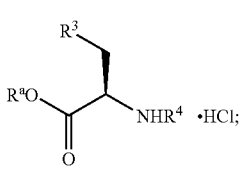

wherein $R^a$ of compound 5 is $C_1$–$C_8$ alkyl, to give a compound of formula 6;

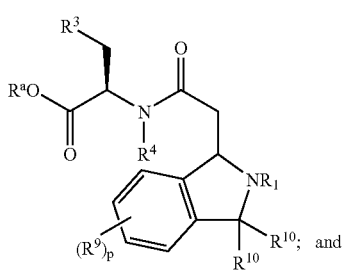

e) coupling the compound of formula 6, wherein $R^a$ is H, with a compound having a structural,

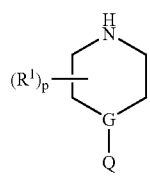

to afford the compound of formula 1.

34. The process of claim 33, wherein

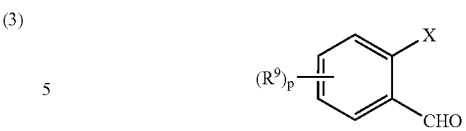

in Step (a) is 2-bromobenzaldehydes.

35. The process of claim 33, wherein $CH_2CH{=}C(O)OR^a$ in Step (a) is methylacrylate.

36. The process of claim 35, wherein the catalyst in Step (a) is selected from the group consisting of: $Pd(Ph_3P)_2Cl_2$, $Pd(Ph_3P)_4Cl_2$, $Pd(Ph_3P)_4$, $Pd(Ph_3\ P)_2Cl_2/CuI$, $Pd(OAc)_2/Ph_3P$—$Bu_4NBr$, $Pd(Ph_3P)_4Cl_2/H_2$ and $Pd(OAc)_2/P(O\text{-tol})_3$; and wherein the base in Step (a) is $NR_3$ wherein R is hydrogen or $C_1$–$C_8$ alkyl.

37. The process of claim 36, wherein the amine in Step (b) is selected from the group consisting of: benzylamine, alpha-methylbenzylamine and $BocNH_2$.

38. The process of claim 36, wherein the Step (b) further comprises reducing an incipient imine compound in the presence of reducing agent, the reducing agent being selected from the group consisting of: $NaCNBH_3$, $Na(OAc)_3BH$, $NaBH_4/H+$, and a combination of $Et_3SiH$ and TFA in $CH_3CN$ or $CH_2Cl_2$.

39. The process of claim 38, wherein the stereoisomer of compound of formula 4 in Step (c) is a compound of formula 4a

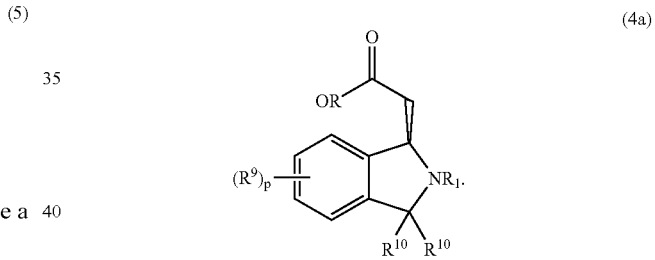

40. The process of claim 38, wherein the compound of formula 4a is prepared by asymmetric hydrogenation of a compound having structural formula,

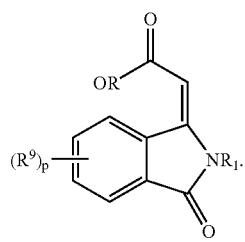

41. The process of claim 40, wherein the Michael addition in Step (c) is carried out in a basic workup condition.

42. The process of claim 33, wherein the Step (e) further comprises deprotecting or protecting of the compound of formula (6) at $NR_1$.

* * * * *